US011634691B2

(12) United States Patent
Schaffer et al.

(10) Patent No.: US 11,634,691 B2
(45) Date of Patent: Apr. 25, 2023

(54) COMPOSITIONS AND METHODS OF TREATMENT

(71) Applicant: The Regents of the University of California, Oakland, CA (US)

(72) Inventors: David V. Schaffer, Danville, CA (US); Melissa A. Kotterman, Berkeley, CA (US); Bum-Yeol Hwang, Moraga, CA (US); James T. Koerber, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 17/725,289

(22) Filed: Apr. 20, 2022

(65) Prior Publication Data

US 2022/0389390 A1    Dec. 8, 2022

Related U.S. Application Data

(63) Continuation of application No. 17/468,290, filed on Sep. 7, 2021, which is a continuation of application No. 14/774,972, filed as application No. PCT/US2014/040083 on May 29, 2014, now Pat. No. 11,136,557.

(60) Provisional application No. 61/829,735, filed on May 31, 2013.

(51) Int. Cl.
| | |
|---|---|
| *C12N 15/86* | (2006.01) |
| *A01N 63/00* | (2020.01) |
| *C07H 21/04* | (2006.01) |
| *C12N 7/00* | (2006.01) |
| *C12N 15/113* | (2010.01) |
| *C07K 14/00* | (2006.01) |
| *A61K 48/00* | (2006.01) |
| *C12N 5/071* | (2010.01) |

(52) U.S. Cl.
CPC ............ *C12N 7/00* (2013.01); *A61K 48/0008* (2013.01); *C07K 14/001* (2013.01); *C12N 5/0686* (2013.01); *C12N 15/113* (2013.01); *C12N 15/86* (2013.01); *C12N 2310/14* (2013.01); *C12N 2750/14122* (2013.01); *C12N 2750/14142* (2013.01)

(58) Field of Classification Search
CPC ................ C12N 15/86; C12N 2510/00; C12N 2750/14122; C07H 21/04
See application file for complete search history.

(56) References Cited

U.S. PATENT DOCUMENTS

| | | | |
|---|---|---|---|
| 5,773,700 | A | 6/1998 | Grinsven et al. |
| 6,096,548 | A | 8/2000 | Stemmer |
| 6,482,634 | B1 | 11/2002 | Wilson et al. |
| 6,491,907 | B1 | 12/2002 | Rabinowitz et al. |
| 6,596,539 | B1 | 7/2003 | Stemmer et al. |
| 6,703,237 | B2 | 3/2004 | Samulski et al. |
| 6,710,036 | B2 | 3/2004 | Kurtzman et al. |
| 6,733,757 | B2 | 5/2004 | Patel et al. |
| 6,855,314 | B1 | 2/2005 | Chiorini et al. |
| 6,943,153 | B1 | 9/2005 | Manning, Jr. et al. |
| 6,962,815 | B2 | 11/2005 | Bartlett |
| 7,172,893 | B2 | 2/2007 | Rabinowitz et al. |
| 7,252,997 | B1 | 8/2007 | Hallek et al. |
| 7,254,489 | B2 | 8/2007 | Mossel |
| 7,285,381 | B1 | 10/2007 | Hallek et al. |
| 7,314,912 | B1 | 1/2008 | Hallek et al. |
| 7,368,428 | B2 | 5/2008 | Serrero |
| 7,427,396 | B2 | 9/2008 | Arbetman et al. |
| 7,556,965 | B2 | 7/2009 | Hallek et al. |
| 7,629,322 | B2 | 12/2009 | Kleinschmidt et al. |
| 7,749,492 | B2 | 7/2010 | Bartlett et al. |
| 7,968,340 | B2 | 6/2011 | Hallek et al. |
| 8,524,446 | B2 | 9/2013 | Gao et al. |

(Continued)

FOREIGN PATENT DOCUMENTS

| | | |
|---|---|---|
| AU | 2014331708 | 5/2016 |
| CA | 2379220 | 1/2001 |

(Continued)

OTHER PUBLICATIONS

Schaffer et al., 2014, Geneseq Accession No. BBR00471, computer printout, pp. 1-2, (Schaffer B).*
Kotin et al., 2017, Geneseq Accession No. BDN88104, computer printout pp. 1-2, (Kotin B).*
Schaffer et al., 2016, US 20160017295 A1, Schaffer ('295).*
Adachi, et al.; "A New Recombinant Adeno-Associated Virus (AAV)-Based Random Peptide Display Library System: Infection-Defective AAV1.9-3 as a Novel Detargeted Platform for Vector Evolution"; Gene Therapy and Regulation; vol. 5, No. 1, pp. 31-55 (Oct. 2010).

(Continued)

*Primary Examiner* — Shin Lin Chen
(74) *Attorney, Agent, or Firm* — Shweta Chandra; Bozicevic, Field & Francis LLP

(57) ABSTRACT

The present disclosure provides infectious recombinant adeno-associated virus (rAAV) virions that comprise a variant capsid protein and a heterologous nucleic acid. The present disclosure further provides the variant adeno-associated virus (AAV) capsid proteins (and/or a nucleic acid encoding the variant AAV capsid proteins), which confer to an infectious rAAV virion an increased resistance to human AAV neutralizing antibodies. The present disclosure further provides host cells comprising an infectious rAAV virion and/or a nucleic acid encoding a subject variant AAV capsid protein. The present disclosure further provides methods of delivering a heterologous nucleic acid to a target cell where the target cell is contacted with a subject infectious rAAV virion. The present disclosure further provides methods of delivering a gene product to an individual, the methods generally involving administering an effective amount of a subject rAAV virion to an individual in need thereof.

20 Claims, 37 Drawing Sheets

Specification includes a Sequence Listing.

(56) References Cited

U.S. PATENT DOCUMENTS

| | | |
|---|---|---|
| 8,574,583 B2 | 11/2013 | Kay et al. |
| 8,632,764 B2 | 1/2014 | Xiao et al. |
| 8,663,624 B2 | 3/2014 | Schaffer et al. |
| 9,193,956 B2 | 11/2015 | Schaffer et al. |
| 9,233,131 B2 | 1/2016 | Schaffer et al. |
| 9,441,244 B2 | 9/2016 | Schaffer et al. |
| 9,587,282 B2 | 3/2017 | Schaffer et al. |
| 11,021,519 B2 | 6/2021 | Chalberg et al. |
| 11,167,041 B2 | 11/2021 | Kim et al. |
| 2002/0136710 A1 | 9/2002 | SamulskI et al. |
| 2002/0155610 A1 | 10/2002 | Colosi |
| 2002/0192823 A1 | 12/2002 | Bartlett |
| 2003/0138772 A1 | 7/2003 | Gao et al. |
| 2003/0143732 A1 | 7/2003 | Fosnaugh et al. |
| 2003/0171254 A1 | 9/2003 | Sasaki et al. |
| 2003/0228284 A1 | 12/2003 | McCown et al. |
| 2004/0180440 A1 | 9/2004 | Zolotukhin |
| 2005/0019927 A1 | 1/2005 | Hildinger et al. |
| 2005/0053922 A1 | 3/2005 | Schaffer |
| 2005/0089973 A1 | 4/2005 | Yocum et al. |
| 2005/0106558 A1 | 5/2005 | Perabo et al. |
| 2005/0148069 A1 | 7/2005 | Gage et al. |
| 2005/0220766 A1 | 10/2005 | Amalfitano et al. |
| 2005/0287122 A1 | 12/2005 | Bartlett et al. |
| 2006/0051333 A1 | 3/2006 | Arbetman et al. |
| 2006/0292117 A1 | 12/2006 | Loiler et al. |
| 2007/0020624 A1 | 1/2007 | Rubenfield et al. |
| 2007/0036760 A1 | 2/2007 | Wilson et al. |
| 2007/0172460 A1 | 7/2007 | Kleinschmidt et al. |
| 2007/0196338 A1 | 8/2007 | Samulski et al. |
| 2008/0269149 A1 | 10/2008 | Bowles et al. |
| 2009/0202490 A1 | 8/2009 | Schaffer et al. |
| 2010/0166729 A9 | 7/2010 | Madison et al. |
| 2010/0172871 A1 | 7/2010 | Flannery et al. |
| 2011/0104120 A1 | 5/2011 | Xiao et al. |
| 2011/0171262 A1 | 7/2011 | Bakker et al. |
| 2011/0236353 A1 | 9/2011 | Wilson et al. |
| 2012/0093772 A1 | 4/2012 | Horsager et al. |
| 2013/0323302 A1 | 12/2013 | Constable et al. |
| 2014/0242031 A1 | 8/2014 | Schaffer et al. |
| 2014/0294771 A1 | 10/2014 | Schaffer et al. |
| 2014/0364338 A1 | 12/2014 | Schaffer et al. |
| 2015/0118201 A1 | 4/2015 | Xiao et al. |
| 2015/0152142 A1 | 6/2015 | Asokan et al. |
| 2015/0225702 A1 | 8/2015 | Schaffer et al. |
| 2015/0232953 A1 | 8/2015 | Schaffer et al. |
| 2015/0315610 A1 | 11/2015 | Nishie et al. |
| 2016/0017295 A1 | 1/2016 | Schaffer et al. |
| 2016/0102324 A1 | 4/2016 | Duchateau et al. |
| 2016/0184394 A1 | 6/2016 | Schaffer et al. |
| 2017/0096683 A1 | 4/2017 | Scaria et al. |
| 2019/0255192 A1 | 8/2019 | Kirn et al. |
| 2019/0300579 A1 | 10/2019 | Dudman et al. |

FOREIGN PATENT DOCUMENTS

| | | |
|---|---|---|
| CN | 1325451 A | 12/2001 |
| CN | 1826414 A | 8/2006 |
| CN | 1966082 A | 5/2007 |
| CN | 101484005 A | 7/2009 |
| CN | 101532024 A | 9/2009 |
| CN | 103561774 A | 2/2014 |
| CN | 106232618 A | 10/2014 |
| WO | WO 1997/038723 | 10/1997 |
| WO | WO 1999/067393 | 12/1999 |
| WO | WO 2000/028004 | 5/2000 |
| WO | WO 2001/070276 | 9/2001 |
| WO | WO 2002/053703 | 7/2002 |
| WO | WO 2003/018820 | 3/2003 |
| WO | WO 2003/023032 | 3/2003 |
| WO | WO 2003/054197 | 7/2003 |
| WO | WO 2003/093436 | 11/2003 |
| WO | WO 2004/083441 | 9/2004 |
| WO | WO 2004/108922 | 12/2004 |
| WO | WO 2004/112727 | 12/2004 |
| WO | WO 2005/005610 | 1/2005 |
| WO | WO 2005/033321 | 4/2005 |
| WO | WO 2006/066066 | 6/2006 |
| WO | WO 2006/110689 | 10/2006 |
| WO | WO 2007/120542 | 10/2007 |
| WO | WO 2008/131951 | 11/2008 |
| WO | WO 2009/137006 | 11/2009 |
| WO | WO 2009/154452 | 12/2009 |
| WO | WO 2010/093784 | 8/2010 |
| WO | WO 2010/138263 | 12/2010 |
| WO | WO 2011/117258 | 9/2011 |
| WO | WO 2012/145601 | 10/2012 |
| WO | WO 2013/029030 | 2/2013 |
| WO | WO 2013/170078 | 11/2013 |
| WO | WO 2013/173512 | 11/2013 |
| WO | WO 2014/124282 | 8/2014 |
| WO | WO 2014/194132 | 12/2014 |
| WO | WO 2014/194132 A1 * | 12/2014 |
| WO | WO 2014/207190 | 12/2014 |
| WO | WO 2015/048534 | 4/2015 |
| WO | WO 2015/054653 | 4/2015 |
| WO | WO 2015/121501 | 8/2015 |
| WO | WO 2015/142941 | 9/2015 |
| WO | WO 2015/191693 | 12/2015 |
| WO | WO 2016/134375 | 8/2016 |
| WO | WO 2016/141078 | 9/2016 |
| WO | WO 2016/144892 | 9/2016 |
| WO | WO 2017/023724 | 2/2017 |
| WO | WO 2017/023724 A1 * | 2/2017 |
| WO | WO 2017/197355 | 11/2017 |
| WO | WO 2019/046069 | 3/2019 |

OTHER PUBLICATIONS

Akiyama, et al.; "Intraocular Injection of an Aptamer that Binds PDGF-B: A Potential Treatment for Proliferative Retinopathies"; Journal of Cellular Physiology; vol. 207, pp. 407-412 (2006).

Ali, et al.; "Restoration of photoreceptor ultrastructure and function in retinal degeneration slow mice by gene therapy"; Nature Genetics; vol. 25, pp. 306-310 (Jul. 2000).

Allocca, et al.; "Novel adeno-associated virus serotypes efficiently transduce murine photoreceptors"; Journal of Virology; vol. 81, No. 20, pp. 11372-11380 (Oct. 2007).

Asokan, et al., "Reengineering a receptor footprint of adeno-associated virus enables selective and systemic gene transfer to muscle"; Nat Biotechnol; vol. 28, No. 1, pp. 79-82 (Jan. 2010).

Asuri, et al.; "Directed Evolution of Adena-associated Virus for Enhanced Gene Delivery and Gene Targeting in Human Pluripotent Stem Cells"; Molecular Therapy, vol. 20, No. 2, pp. 329-338 (Feb. 1, 2012).

Attached Score Report Result Per SEQ ID No. 17 per US2002/0192823 to Bartlett Published Dec. 19, 2002.

Bichsel, et al.; "Bacterial delivery of nuclear proteins into pluripotent and differentiated cells"; PLoS One; vol. 6, No. 1, pp. 1-9 (Jan. 2011).

Blacklow, et al.; "A Seroepidemiologic Study of Adenovirus-Associated Virus Infection in Infants and Children"; Am J Epidemiol.; vol. 94, No. 4, pp. 359-366 (Oct. 1971).

Boucas, et al.; "Engineering adeno-associated virus serotype 2-based targeting vectors using a new insertion site-position 453-and single point mutations"; J Gene Med.; vol. 11, No. 12, pp. 1103-1113 (Dec. 2009).

Buch, et al., "in Contrast to AAC-Mediated Cntf Expression, AAV-Mediated Gdnf Expression Enhances Gene Replacement Therapy in Rodent Models of Retinal Degeneration"; Molecular Therapy; vol. 14, No. 5, pp. 700-709 (Nov. 2006).

Buning, et al., "Receptor targeting of adeno-associated virus vectors"; Gene Therapy; vol. 10, pp. 1142-1151 (2003).

Chadderton, et al.; "Improved Retinal Function in a Mouse Model of Dominant Retinitis Pigmentosa Following AAV-delivered Gene Therapy"; Molecular Therapy; vol. 17, No. 4, pp. 593-599 (Apr. 2009).

Choi, et al.; "AAV Hybrid Serotypes: Improved Vectors for Gene Delivery."; Current Gene Therapy; vol. 5, No. 3, pp. 299-310 (Jun. 2005).

(56) References Cited

OTHER PUBLICATIONS

Cronin, et al.; "Efficient transduction and optogenetic stimulation of retinal bipolar cells by a synthetic adeno-associated virus capsid and promoter"; EMBO Molecular Medicine; 16 pages (2014).
Dalkara, et al.; "In Vivo-Directed Evolution of a New Adeno-Associated Virus for Therapeutic Outer Retinal Gene Delivery from the Vitreous"; Science Translational Medicine; vol. 5, Issue 187, 11 pages (Jun. 12, 2013).
Dalkara, et al.; "Developing Photoreceptor Targeted AAV Variant by Directed Evolution"; ARVO Annual Meeting Abstract Search and Program Planner; vol. 2011, pp. 4381 (May 2011).
Database Geneseq [Online] Oct. 16, 2008 (Oct. 16, 2008), "Modified Adeno-associated virus (hu.44) capsid protein, VP1, hu.44R2.", retrieved from EBI accession No. GSP:AEL63853, Database accession No. AEL63853.
Database Geneseq [Online] Oct. 16, 2008 (Oct. 16, 2008), "Modified Adeno-associated virus (hu.44) capsid protein, VP1, hu.44R3.", retrieved from EBI accession No. GSP:AEL63854, Database accession No. AEL63854.
Davidson, et al.; "Recombinant adeno-associated virus type 2, 4, and 5 vectors: transduction of variant cell types and regions in the mammalian central nervous system."; Proc Natl Acad Sci USA.; vol. 97, No. 7, pp. 3428-3432 (Mar. 28, 2000).
Day, et al.; "Advances in AAV Vector Development for Gene Therapy in the Retina"; Adv. Exp. Med. Biol.; vol. 801, pp. 687-693 (2014).
Den Dunnen, et al.; "Mutation nomenclature extensions and suggestions to describe complex mutations: a discussion."; Human Mutation; vol. 15, pp. 7-12 (2000).
Diprimio, et al.; "Surface loop dynamics in adeno-associated virus capsid assembly"; Journal of Virology; vol. 82, No. 11, pp. 5178-5189 (Jun. 2008).
Erles, et al.; "Update on the prevalence of serum antibodies (IgG and IgM) to adeno-associated virus (AAV)."; J Med Virol.; vol. 59, No. 3, pp. 406-411 (Nov. 1999).
Excoffon, et al.; "Directed evolution of adeno-associated virus to an infectious respiratory virus"; Proc Natl Acad Sci USA; vol. 106, No. 10, pp. 3865-3870 (Mar. 10, 2009).
Flotte, et al.; "Gene expression from adeno-associated virus vectors in airway epithelial cells"; Am J Respir Cell Mol Biol.; vol. 7, No. 3, pp. 349-356 (Sep. 1992).
Gen Bank accession No. AAZ79678; rat AAV1 VP3 capsid protein sequence downloaded from NCBI; downloaded on Nov. 3, 2008.
GenBank accession No. ABZ10812; AAV13 capsid protein sequence downloaded from NCBI; downloaded on Nov. 3, 2008.
Girod, et al.; "Genetic capsid modifications allow efficient re-targeting of adeno-associated virus type 2"; Nat. Med.; vol. 5, No. 9, pp. 1052-1056 (Sep. 1999).
Gray, et al.; "Directed Evolution of a Novel Adeno-associated Virus (AAV) Vector That Crosses the Seizure-compromised Blood-Brain Barrier (BBB)"; Molecular Therapy; vol. 18, No. 3, pp. 570-578 (2010).
Gregory-Evans, et al.; "Ex vivo Gene Therapy Using Intravitreal Injection of GDNF-secreting Mouse Embryonic Stem Cells in a Rat Model of Retinal Degeneration"; Molecular Vision; vol. 15, pp. 962-973 (May 13, 2009).
Grieger, et al.; "Separate basic region motifs within the adeno-associated virus capsid proteins are essential for infectivity and assembly"; Journal of Virology; vol. 80, No. 11, pp. 5199-5210 (2006).
Grifman, et al.; "Incorporation of tumor-targeting peptides into recombinant adeno-associated virus capsids"; Molecular Therapy; vol. 3, No. 6, pp. 964-975 (Jun. 2001).
Grimm, et al.; "In Vitro and In Vivo Gene Therapy Vector Evolution via Multispecies Interbreeding and Retargeting of Adeno-Associated Viruses"; Journal of Virology; vol. 82, No. 12, pp. 5887-5911 (Jun. 2008).
Halbert, et al.; "Repeat transduction in the mouse lung by using adeno-associated virus vectors with different serotypes." J. Virol.; vol. 74, No. 3, pp. 1524-1532 (Feb. 2000).

Hellstrom, et al.; "Cellular tropism and transduction properties of seven adeno-associated viral vector serotypes in adult retina after intravitreal injection"; Gene Therapy; vol. 16, pp. 521-532 (2009).
Hirsch, et al.; "Directed Evolution of the AAV Capsid for Human Embryonic Stem Cell Transduction"; Molecular Therapy; vol. 17, Supp. 1, S177-S178 (May 2009).
Huttner, et al "Genetic Modifications of the Adeno-Associated Virus Type 2 Capsid Reduce Affinity to Human Serum Antibodies and Overcome Potential Limitations of Neutralizing Antibodies for the Used in Human Gene Therapy"; Blood; vol. 100, No. 11, pp. Abstract No. 5548 (Nov. 16, 2002).
Huttner, et al.; "Genetic modifications of the adeno-associated virus type 2 capsid reduce the affinity and the neutralizing effects of human serum antibodies."; Gene Ther; vol. 10, pp. 2139-2147 (Dec. 2003).
Jang, et al.; "An evolved adeno-associated viral variant enhances gene delivery and gene targeting in neural stem cells"; Mol Ther.; vol. 19, No. 4, pp. 667-675 (Apr. 2011).
Jeune, et al.; "Pre-existing Anti-Adeno-Associated Virus Antibodies as a Challenge in AAV Gene Therapy"; Human Gene Therapy Methods; vol. 24, pp. 59-67 (Apr. 2013).
Karp, et al.; "An in vitro model of differentiated human airway epithelia, Methods for establishing primary cultures"; Methods Mol Biol.; vol. 188, pp. 115-137 (2002).
Kotin et al., 2017, Geneseq Accession No. BDN88104, computer printout pp. 1-2.
Kern, et al.; "Identification of a heparin-binding motif on adeno-associated virus type 2 capsids"; Journal of Virology; vol. 77, No. 20, pp. 11072-11081 (Oct. 2003).
Khabou, et al.; "Insight Into the Mechanisms of Enhanced Retinal Transduction by the Engineered AAV2 Capsid Variant-7m8"; Biotechnology and Bioengineering; vol. 113, No. 12, pp. 2712-2724 (Dec. 2016).
Khani, et al.; "AAV-Mediated Expression Targeting of Rod and Cone Photoreceptors with a Human Rhodopsin Kinase Promoter"; Investigative Ophthalmology & Visual Science; vol. 48, No. 9, pp. 3954-3961 (Sep. 2007).
Klimczak, et al al.; "A Novel Adeno-Associated Viral Variant for Efficient and Selective Intravitreal Transduction of Rat Muller Cells"; PLoS ONE; vol. 4, No. 10, pp. 1-10 (Oct. 2009).
Klimczak; "Molecular Evolution of Adeno-associated Virus for Improved Retinal Gene Therapies"; Dissertation submitted in partial fulfillment of the requirements for the degree of Doctor of Philosophy in Molecular and Cell Biology in the Graduate Division of University of California, Berkeley; 116 pages (2010).
Koerber, et al.; "DNA Shuffling of Adeno-associated Virus Yields Functionally Diverse Viral Progeny"; Molecular Therapy; vol. 16, No. 10, pp. 1703-1709 (Oct. 2008).
Koerber, et al.; "Engineering of a Novel AAV Vector in a Human Airway Model System for Cystic Fibrosis Gene Therapy"; AIChE Annual Meeting Abstract, 3 pages (Nov. 29, 2008).
Koerber, et al.; "Molecular Evolution of Adeno-associated Virus for Enhanced Glial Gene Delivery", Molecular Therapy; vol. 17, No. 12, pp. 2088-2095 (Dec. 2009).
Kotterman, et al.; "Engineering adeno-associated viruses for clinical gene therapy"; Nat Rev Genet; vol. 15, No. 7, pp. 445-451 (Jul. 1, 2014).
Kotterman, et al.; "Enhanced selective gene delivery to neural stem cells in vivo by an adeno-associated viral variant"; Development; vol. 142, pp. 1885-1892 (2015).
Kwon, et al.; "Designer gene delivery vectors: molecular engineering and evolution of adeno-associated viral vectors for enhanced gene transfer"; Pharmaceutical Research; vol. 25, No. 3, pp. 489-499 (Mar. 2008).
Lai, et al.; "Long-term evaluation of AAV-mediated sFlt-1 gene therapy for ocular neovascularization in mice and monkeys"; Mol Ther.; vol. 12, No. 4, pp. 659-668 (Oct. 2005).
Lee, at al.; "Adena-associated Virus (AAV) Vectors: Rational Design Strategies for Capsid Engineering"; Current Opinion in Biomedical Engineering; pp. 7:58-63 (2018).
Li, et al.; "Engineering and Selection of Shuffled AAV Genomes: A New Strategy for Producing Targeted Biological Nanoparticles"; Molecular Therapy; vol. 16, No. 7, pp. 1252-1260 (Jul. 2008).

(56) References Cited

OTHER PUBLICATIONS

Li, et al.; "Generation of Novel AAV Variants by Directed Evolution for Improved CFTR Delivery to Human Ciliated Airway Epithelium"; Molecular Therapy; vol. 17, No. 12, pp. 2067-2077 (Dec. 2009).
Limberis, et al.; "Adeno-associated virus serotype 9 vectors transduce murine alveolar and nasal epithelia and can be readministered"; Proc Natl Acad Sci USA; vol. 103, No. 35, pp. 12993-12998 (Aug. 29, 2006).
Loiler, et al.; "Targeting recombinant adeno-associated virus vectors to enhance gene transfer to pancreatic islets and liver"; Gene Ther.; vol. 10, pp. 1551-1558 (2003).
Maguire, et al.; "Directed evolution of adeno-associated virus for glioma cell transduction"; J. Neurooncol.; vol. 96, pp. 337-347 (2010).
Maheshri, et al.; "Directed evolution of adeno-associated virus yields enhanced gene delivery vectors"; Nature Biotechnology; vol. 24, No. 2, pp. 198-204 (Feb. 2006).
McCullum, et al.; "Random Mutagenesis by Error-Prone PCR"; Methods Mol Biol.; vol. 634, pp. 103-109; doi: 10.1007/978-1-60761-652-8_7 (2010).
McGee, et al., "Glial Cell Line Derived Neurotrophic Factor Delays Photoreceptor in a Transgenic Rat Model of Retinitis Pigmentosa"; Molecular Therapy; vol. 4, No. 6, pp. 622-629 (Dec. 2001).
Michelfelder, et al.; "Successful Expansion but Not Complete Restriction of Tropism of Adeno-Associated Virus by In Vivo Biopanning of Random Virus Display Peptide Libraries"; PLoS One; vol. 4, No. 4, pp. 1-13 (Apr. 2009).
Michelfelder, et al.; "Vectors selected from adeno-associated viral display peptide libraries for leukemia cell-targeted cytotoxic gene therapy"; Experimental Hematology; vol. 35, pp. 1766-1776 (2007).
Mitchell, et al.; "AAV's anatomy: Roadmap for optimizing vectors for translational success"; Curr Gene Ther.; vol. 10, No. 5, pp. 319-340 (Oct. 2010).
Miyake, et al.; "Global gene transfer into the CNS across the BBB after neonatal systemic delivery of single-stranded AAV vectors"; Brain Research; vol. 1389, pp. 19-26 (2011).
Moskalenko, et al; "Epitope mapping of human anti-adeno-associated virus type 2 neutralizing antibodies: implications for gene therapy and virus structure."; J. Virol.; vol. 74, No. 4, pp. 1761-1766 (Feb. 2000).
Muller, et al.; "Random peptide libraries displayed on adeno-associated virus to select for targeted gene therapy vectors"; Nat Biotechnol; vol. 21, No. 9, pp. 1040-1046 (Sep. 2003).
Nguyen, et al; "Convection-enhanced delivery of AAV-2 combined with heparin increases TK gene transfer in the rat brain."; Neuroreport; vol. 12, No. 9, pp. 1961-1964 (Jul. 3, 2001).
Nicklin, et al.; "Efficient and selective AAV2-mediated gene transfer directed to human vascular endothelial cells"; Mol. Ther.; vol. 4, No. 2, pp. 174-181 (Aug. 2001).
Office Action dated Mar. 29, 2022, U.S. Appl. No. 16/315,032, 43 pp.
Opie, et al.; "Identification of Amino Acid Residues in the Capsid Proteins of Adeno-Associated Virus Type 2 that Contribute to Heparan Sulfate Proteoglycan Binding"; Journal of Virology; vol. 77, No. 12, pp. 6995-7006 (Jun. 2003).
Ortolano, et al.; "Present and Future of Adeno Associated Virus Based Gene Therapy Approaches"; Recent Patents on Endocrine, Metabolic & Immune Drug Discovery; vol. 6, pp. 47-66 (2012).
Paddison, et al.; "Stable suppression of gene expression by RNAi in mammalian cells"; Proc. Nat'l Acad. Sci. USA; vol. 99, No. 3, pp. 1443-1448 (Feb. 5, 2002).
Padron, et al.; "Structure of adeno-associated virus type 4"; Journal of Virology; vol. 79, No. 8, pp. 5047-5058 (Apr. 2005).
Park, et al.; "Intravitreal delivery of AAV8 retinoschisin results in cell type-specific gene expression and retinal rescue in the Rs1-KO mouse"; Gene Therapy; vol. 16, pp. 916-926 (2009).
Pechan, et al; "Novel anti-VEGF chimeric molecules delivered by AAV vectors for inhibition of retinal neovascularization."; Gene. Ther.; vol. 16, No. 1, pp. 10-16 (Jan. 2009).

Perabo, et al.; "Combinatorial engineering of a gene therapy vector: directed evolution of adeno-associated virus"; The Journal of Gene Medicine; vol. 8, No. 2, pp. 155-162 (Feb. 2006).
Perabo, et al.; "Heparan Sulfate Proteoglycan Binding Properties of Adeno-Associated Virus Retargeting Mutants and Consequences for Their In Vivo Tropism"; Journal of Virology; vol. 80, No. 14, pp. 7265-7269 (Jul. 2006).
Perabo, et al.; "In Vitro Selection of Viral Vectors with Modified Tropism: The Adeno-associated Virus Display"; Molecular Therapy; vol. 8, No. 1, pp. 151-157 (Jul. 2003).
Petrs-Silva, et al.; "High-efficiency transduction of the mouse retina by tyrosine-mutant AAV serotype vectors"; Molecular Therapy; vol. 17, No. 3, pp. 463-471 (Mar. 2009).
Popa-Wagner, et al.; "Impact of VP1-Specific Protein Sequence Motifs on Adeno-Associated Virus Type 2 Intracellular Trafficking and Nuclear Entry"; Journal of Virology; vol. 86, No. 17, pp. 9163-9174 (Sep. 2012).
Rabinowitz, et al.; "Building a Better Vector: The Manipulation of AAV Virions"; Virology; vol. 278, pp. 301-308 (2000).
Rabinowitz, et al.; "Insertional mutagenesis of AAV2 capsid and the production of recombinant virus."; Virology; vol. 265, No. 2, pp. 274-285 (Dec. 20, 1999).
Rayaprolu, et al.; "Comparative Analysis of Adeno-Associated Virus Capsid Stability and Dynamics"; Journal of Virology; vol. 87, No. 24, pp. 13150-13160 (Dec. 2013).
Ried, et al.; "Adeno-associated virus capsids displaying immunoglobulin-binding domains permit antibody-mediated vector retargeting to specific cell surface receptors"; J. Virol.; vol. 76, No. 9, pp. 4559-4566 (May 2002).
Ryals, et al.; "Quantifying transduction efficiencies of unmodified and tyrosine capsid mutant AAV vectors in vitro using two ocular cell lines"; Mol Vision; vol. 17, pp. 1090-1102 (Apr. 2011).
Santiago-Ortiz, et al.; "AAV Ancestral Reconstruction Library Enables Selection of Broadly Infectious Viral Variants"; Gene. Ther.; vol. 22, No. 12, pp. 934-946 (Dec. 2015).
Schaffer et al., 2014, Geneseq Accession No. BBR00471, computer printout, pp. 1-2.
Schaffer, et al.; "Directed evolution of AAV vector mutants for enhanced gene delivery"; Abstracts of Papers American Chemical Society; vol. 227, Part 1, p. U214 (Mar. 2004).
Score result 33 for Arbetman et al. WO2004112727-A2, Dec. 29, 2004.
Shao, et al.; "Gene Transfer to the Gastrointestinal Tract After Peroral Administration of Recombinant Adeno-associated Virus Type 2 Vectors"; Journal of Pediatric Gastroenterology and Nutrition; vol. 43, pp. 168-179 (Aug. 2006).
Shen, et al.; "Characterization of the relationship of AAV capsid domain swapping to liver transduction efficiency"; Mol Ther.; vol. 15, No. 11, pp. 1955-1962 (Aug. 28, 2007).
Shen, et al.; "Multiple Roles for Sialylated Glycansin Determining the Cardiopulmonary Tropism of Adeno-Associated Virus 4"; Journal of Virology; vol. 87, No. 24, pp. 13206-13213 (Dec. 2013).
Shi, et al.; "Capsid modifications overcome low heterogeneous expression of heparan sulfate proteoglycan that limits AAV2-mediated gene transfer and therapeutic efficacy in human ovarian carcinoma"; Gynecol. Oncol.; vol. 103, pp. 1054-1062 (2006).
Shi, et al.; "Insertional mutagenesis at positions 520 and 584 of adeno-associated virus type 2 (AAV2) capsid gene and generation of AAV2 vectors with eliminated heparin-binding ability and introduced novel tropism"; Hum. Gene Ther.; vol. 17, pp. 353-361 (Mar. 2006).
Shi, et al.; "RGD inclusion in VP3 provides adeno-associated virus type 2 (AAV2)-based vectors with a heparan sulfate-independent cell entry mechanism"; Mol. Ther.; vol. 7, No. 4, pp. 515-525 (Apr. 2003).
Shi, W. et al.; "Insertional Mutagenesis of the Adeno-Associated Virus Type 2 (AAV2) Capsid Gene and Generation of AAV2 Vectors Targeted to Alternative Cell-Surface Receptors"; Human Gene Therapy; vol. 12, pp. 1697-1711 (Sep. 20, 2001).
Sonntag, et al.; "Adeno-associated virus type 2 capsids with externalized VP1/VP2 trafficking domains are generated prior to passage

(56) References Cited

OTHER PUBLICATIONS through the cytoplasm and are maintained until uncoating occurs in the nucleus"; Journal of Virology; vol. 80, No. 22, pp. 11040-11054 (Nov. 2006).
Steinbach, et al.; "Assembly of adeno-associated virus type 2 capsids in vitro" J of Gen Virology; vol. 78, pp. 1453-1462 (1997).
Sullivan, et al.; "Rationally designed AAV2 and AAVrh8R capsids provide improved transduction in the retina and brain"; Gene Therapy; vol. 25, pp. 205-219 (2018).
Sun, et al.; "Immune responses to adeno-associated virus and its recombinant vectors"; Gene Therapy; vol. 10, pp. 964-976 (2003).
Surace, et al.; "Delivery of Adeno-Associated Virus Vectors to the Fetal Retina: Impact of Viral Capsid Proteins on Retinal Neuronal Progenitor Transduction"; Journal of Virology; vol. 77, No. 14, pp. 7957-7962 (Jul. 2003).
Takada, et al.; "Synaptic Pathology in Retinoschisis Knockout (Rs1$^{-/y}$) Mouse Retina and Modification by rAAV-Rs1 Gene Delivery"; Investigative Ophthalmology & Visual Science; vol. 49, No. 8, pp. 3677-3678 (Aug. 2008).
Tal; "Adeno-Associated Virus-Based Vectors in Gene Therapy"; Journal of Biomedical Science; vol. 7, No. 4, pp. 279-291 (Jul. 2000).
Tervo, et al.; "A Designer AAV Variant Permits Efficient Retrograde Access to Projection Neurons"; Neuron; vol. 92, pp. 372-382 (2016).
Third-Party Submission dated Mar. 15, 2022, U.S. Appl. No. 16/315,032, 95 pp.
Tomar, et al.; "Use of Adeno-Associated Viral Vector for Delivery of Small Interfering RNA"; Oncogene; vol. 22, No. 36, pp. 5712-5715 (Aug. 28, 2003).
UniProtKB database: B4Y881_9VIRU; "Capsid protein VP1, adeno-associated virus"; 6 pages (Sep. 23, 2008).
Van Vliet, et al.; "Proteolytic mapping of the adeno-associated virus capsid"; Mol Ther.; vol. 14, No. 6, pp. 809-821 (Dec. 2006).
Venkatakrishnan, et al.; "Structure and Dynamics of Adeno-Associated Virus Serotype 1 VP1-Unique N-Terminal Domain and its Role in Capsid Trafficking"; Journal of Virology; vol. 87, No. 9, pp. 4974-4984 (May 2013).
Watanabe, et al.; "Tropisms of AAV for Subretinal Delivery to the Neonatal Mouse Retina and its Application for In Vivo Rescue of Developmental Photoreceptor Disorders"; PLoS ONE; vol. 8, No. 1, 12 pages (Jan. 15, 2013).
Waterkamp, et al.; "Isolation of targeted AAV2 vectors from novel virus display libraries"; J. Gene. Med.; vol. 8, pp. 1307-1319 (Sep. 6, 2006).
White, et al.; "Genetic Modification of Adeno-Associated Viral Vector Type 2 Capsid Enhances Gene Transfer Efficiency in Polarized Human Airway Epithelial Cells"; Human Gene Therapy; vol. 19, pp. 1407-1414 (Dec. 2008).
White, et al.; "Targeted gene delivery to vascular tissue in vivo by tropism-modified adeno-associated virus vectors"; Circulation; vol. 109, pp. 513-519 (Feb. 3, 2004).
Wickham, et al.; "Increased in vitro and in vivo gene transfer by adenovirus vectors containing chimeric fiber proteins"; Journal of Virology; vol. 71, No. 11, pp. 8221-8229 (Nov. 1997).
Willett, et al.; "Immunology of AAV-mediated gene transfer in the eye"; Frontiers in Immunology; vol. 4, No. 261, 8 pages (Aug. 2013).
Wobus, et al.; "Monoclonal antibodies against the adeno-associated virus type 2 (AAV-2) capsid: epitope mapping and identification of capsid domains involved in AAV-2-cell interaction and neutralization of AAV-2 infection."; J. Virol.; vol. 74, No. 19, pp. 9281-9293 (Oct. 2000).
Work, et al.; "Vascular bed-targeted in vivo gene delivery using tropism-modified adeno-associated viruses"; Mol. Ther.; vol. 13, No. 4, pp. 683-693 (Apr. 2006).
Wu, et al.; "Mutational analysis of the adeno-associated virus type 2 (AAV2) capsid gene and construction of AAV2 vectors with altered tropism"; Journal of Virology; vol. 74, No. 18, pp. 8635-8647 (Sep. 2000).
Wu, et al.; "α2,3 and α2,6 N-linked Sialic Acids Facilitate Efficient Binding and Transduction by Adeno-Associated Virus Types 1 and 6"; Journal of Virology; vol. 80, No. 18, pp. 9093-9103 (Sep. 2006).
Xiao, et al.; "Adenovirus-facilitated nuclear translocation of adeno-associated virus type 2"; Journal of Virology; vol. 76, No. 22, pp. 11505-11517 (Nov. 2002).
Xie, et al.; "The atomic structure of adeno-associated virus (AAV-2), a vector for human gene therapy"; PNAS; vol. 99, No. 16, pp. 10405-10410 (Aug. 6, 2002).
Yang, et al.; "A myocardium tropic adeno-associated virus (AAV) evolved by DNA shuffling and in vivo selection"; PNAS; vol. 106, No. 10, pp. 3946-3951 (Mar. 10, 2009).
Yang, et al.; "Directed Evolution of Adeno-Associated Virus (AAV) as Vector for Muscle Gene Therapy"; Methods in Molecular Biology; vol. 709, pp. 127-139 (2011).
Yu; "Current Approaches and Future Directions of Gene Therapy in Alzheimer's Disease"; Neurochemical Journal; vol. 5, No. 3, pp. 159-168 (2011).
Zabner, et al.; "Adeno-associated virus type 5 (AAV5) but not AAV2 binds to the apical surfaces of airway epithelia and facilitates gene transfer"; J Virol.; No. 74, No. 8, pp. 3852-3858 (Apr. 2000).
Zhao, et al.; "Molecular evolution by staggered extension process (StEP) in vitro recombination"; Nat Biotechnol; vol. 16, No. 3, pp. 258-261 (Mar. 1998).
Zincarelli, et al.; "Analysis of AAV Serotypes 1-9 Mediated Gene Expression and Tropism in Mice After Systemic Injection"; Molecular Therapy; vol. 16, No. 6, pp. 1073-1080 (Jun. 2008).
Zolotukhin, et al.; "Recombinant adeno-associated virus purification using novel methods improves infectious titer and yield"; Gene Therapy; vol. 6, pp. 973-985 (1999).

\* cited by examiner

```
                         1         10        20        30
Consensus                M A A D G Y L P D W L E D N L S E G I R E W W A L K P G A P
Identity 1. AAV1 translation      M A A D G Y L P D W L E D N L S E G I R E W W D L K P G A P
2. AAV2 translation      M A A D G Y L P D W L E D T L S E G I R Q W W K L K P G P P
3. AAV3 translation      M A A D G Y L P D W L E D N L S E G I R E W W A L K P G V P
4. AAV4 translation        M T D G Y L P D W L E D N L S E G V R E W W A L Q P G A P
5. AAV5 translation      M S F V D H P P D W L E E - V G E G L R E F L G L E A G P P
6. AAV6 translation      M A A D G Y L P D W L E D N L S E G I R E W W D L K P G A P
7. AAV7 translation      M A A D G Y L P D W L E D N L S E G I R E W W D L K P G A P
8. AAV8 translation      M A A D G Y L P D W L E D N L S E G I R E W W A L K P G A P
9. AAV9 translation      M A A D G Y L P D W L E D N L S E G I R E W W A L K P G A P
10. Shuffle 100.1 Translation  M A A D G Y L P D W L E D T L S E G I R Q W W K L K P G P P 40        50        60
Consensus                K P K A N Q Q H Q D D G R G L V L P G Y K Y L G P F N G L D
Identity 1. AAV1 translation      K P K A N Q Q K Q D D G R G L V L P G Y K Y L G P F N G L D
2. AAV2 translation      P P K P A E R H K D D S R G L V L P G Y K Y L G P F N G L D
3. AAV3 translation      Q P K A N Q Q H Q D N R R G L V L P G Y K Y L G P G N G L D
4. AAV4 translation      K P K A N Q Q H Q D N A R G L V L P G Y K Y L G P G N G L D
5. AAV5 translation      K P K P N Q Q H Q D Q A R G L V L P G Y N Y L G P G N G L D
6. AAV6 translation      K P K A N Q Q K Q D D G R G L V L P G Y K Y L G P F N G L D
7. AAV7 translation      K P K A N Q Q K Q D N G R G L V L P G Y K Y L G P F N G L D
8. AAV8 translation      K P K A N Q Q K Q D D G R G L V L P G Y K Y L G P F N G L D
9. AAV9 translation      Q P K A N Q Q H Q D N A R G L V L P G Y K Y L G P G N G L D
10. Shuffle 100.1 Translation  P P K P A E R H K D D S R G L V L P G Y K Y L G P F N G L D 70        80        90
Consensus                K G E P V N A A D A A A L E H D K A Y D Q Q L K A G D N P Y
Identity 1. AAV1 translation      K G E P V N A A D A A A L E H D K A Y D Q Q L K A G D N P Y
2. AAV2 translation      K G E P V N E A D A A A L E H D K A Y D R Q L D S G D N P Y
3. AAV3 translation      K G E P V N E A D A A A L E H D K A Y D Q Q L K A G D N P Y
4. AAV4 translation      K G E P V N A A D A A A L E H D K A Y D Q Q L K A G D N P Y
5. AAV5 translation      R G E P V N R A D E V A R E H D I S Y N E Q L E A G D N P Y
6. AAV6 translation      K G E P V N A A D A A A L E H D K A Y D Q Q L K A G D N P Y
7. AAV7 translation      K G E P V N A A D A A A L E H D K A Y D Q Q L K A G D N P Y
8. AAV8 translation      K G E P V N A A D A A A L E H D K A Y D Q Q L Q A G D N P Y
9. AAV9 translation      K G E P V N A A D A A A L E H D K A Y D Q Q L K A G D N P Y
10. Shuffle 100.1 Translation  K G E P V N E A D A A A L E H D K A Y D Q Q L K A G D N P Y
```

FIG. 8A

|  | 190 | 200 | 210 |
|---|---|---|---|

```
                                      190            200            210
Consensus                     E S V P D P Q P L G E P P A A P - S S V G X X T M A S G G G
Identity                      ████████████████████  ████████  ██ ██ ██  ████████████

1. AAV1 translation           E S V P D P Q P L G E P P A T P - A A V G P T T M A S G G G
2. AAV2 translation           D S V P D P Q P L G Q P P A A P - S G L G T N T M A T G S G
3. AAV3 translation           E S V P D P Q P L G E P P A A P - T S L G S N T M A S G G G
4. AAV4 translation           T G A G D G P P E G S T S G A - - M S D D S E M R A A A G G
5. AAV5 translation           E A G P S G S Q Q L Q I P A Q P A S S L G A D T M S A G G G
6. AAV6 translation           E S V P D P Q P L G E P P A T P - A A V G P T T M A S G G G
7. AAV7 translation           E S V P D P Q P L G E P P A A P - S S V G S G T V A A G G G
8. AAV8 translation           E S V P D P Q P L G E P P A A P - S G V G P N T M A A G G G
9. AAV9 translation           E S V P D P Q P I G E P P A A P - S G V G S L T M A S G G G
10. Shuffle 100.1 Translation E S V P D P Q P L G E P P A T P - A A V G P T T M A S G G G
                              ◄AAV1/6                                              A...►

220            230            240
Consensus                     A P M A D N N E G A D G V G N A S G N W H C D S T W L G D R
Identity                      ████████████████████████████████████████████████████████████

1. AAV1 translation           A P M A D N N E G A D G V G N A S G N W H C D S T W L G D R
2. AAV2 translation           A P M A D N N E G A D G V G N S S G N W H C D S T W M G D R
3. AAV3 translation           A P M A D N N E G A D G V G N S S G N W H C D S Q W L G D R
4. AAV4 translation           A A V - E G G Q G A D G V G N A S G D W H C D S T W S E G H
5. AAV5 translation           G P L G D N Q G A D G V G N A S G D W H C D S T W M G D R
6. AAV6 translation           A P M A D N N E G A D G V G N A S G N W H C D S T W L G D R
7. AAV7 translation           A P M A D N N E G A D G V G N A S G N W H C D S T W L G D R
8. AAV8 translation           A P M A D N N E G A D G V G S S S G N W H C D S T W L G D R
9. AAV9 translation           A P V A D N N E G A D G V G S S S G N W H C D S Q W L G D R
10. Shuffle 100.1 Translation A P M A D N N E G A D G V G N A S G N W H C D S T W L G D R
                              ◄A► ◄AAV1

250            260            270
Consensus                     V I T T S T R T W A L P T Y N N H L Y K Q I S S A S X - G A
Identity                      ████████████████████████████████████████████████  ██

1. AAV1 translation           V I T T S T R T W A L P T Y N N H L Y K Q I S S A S T - G A
2. AAV2 translation           V I T T S T R T W A L P T Y N N H L Y K Q I S S Q S - - G A
3. AAV3 translation           V I T T S T R T W A L P T Y N N H L Y K Q I S S Q S - - G A
4. AAV4 translation           V T T T S T R T W V L P T Y N N H L Y K R L G E S L - - - -
5. AAV5 translation           V V T K S T R T W V L P S Y N N H Q Y R E I K S G S V D G -
6. AAV6 translation           V I T T S T R T W A L P T Y N N H L Y K Q I S S A S T - G A
7. AAV7 translation           V I T T S T R T W A L P T Y N N H L Y K Q I S S E T A - G S
8. AAV8 translation           V I T T S T R T W A L P T Y N N H L Y K Q I S N G T S G G A
9. AAV9 translation           V I T T S T R T W A L P T Y N N H L Y K Q I S N S T S G G S
10. Shuffle 100.1 Translation V I T T S T R T W A L P T Y N N H L Y K Q I S S A S T - G A
                              ◄AAV1
```

FIG. 8C

```
                                           280               290               300
Consensus                        S N D N H Y F G Y S T P W G Y F D F N R F H C H F S P R D W
Identity 1. AAV1 translation              S N D N H Y F G Y S T P W G Y F D F N R F H C H F S P R D W
2. AAV2 translation              S N D N H Y F G Y S T P W G Y F D F N R F H C H F S P R D W
3. AAV3 translation              S N D N H Y F G Y S T P W G Y F D F N R F H C H F S P R D W
4. AAV4 translation              - Q S N T Y N G F S T P W G Y F D F N R F H C H F S P R D W
5. AAV5 translation              S N A N A Y F G Y S T P W G Y F D F N R F H S H W S P R D W
6. AAV6 translation              S N D N H Y F G Y S T P W G Y F D F N R F H C H F S P R D W
7. AAV7 translation              T N D N T Y F G Y S T P W G Y F D F N R F H C H F S P R D W
8. AAV8 translation              T N D N T Y F G Y S T P W G Y F D F N R F H C H F S P R D W
9. AAV9 translation              S N D N A Y F G Y S T P W G Y F D F N R F H C H F S P R D W
10. Shuffle 100.1 Translation    S N D N H Y F G Y S T P W G Y F D F N R F H C H F S P R D W
                                 AAV1

310               320               330
Consensus                        Q R L I N N N W G F R P K R L N F K L F N I Q V K E V T T N
Identity 1. AAV1 translation              Q R L I N N N W G F R P K R L N F K L F N I Q V K E V T T N
2. AAV2 translation              Q R L I N N N W G F R P K R L N F K L F N I Q V K E V T Q N
3. AAV3 translation              Q R L I N N N W G F R P K K L S F K L F N I Q V R G V T Q N
4. AAV4 translation              Q R L I N N N W G M R P K A M R V K I F N I Q V K E V T T S
5. AAV5 translation              Q R L I N N Y W G F R P R S L R V K I F N I Q V K E V T V Q
6. AAV6 translation              Q R L I N N N W G F R P K R L N F K L F N I Q V K E V T T N
7. AAV7 translation              Q R L I N N N W G F R P K K L R F K L F N I Q V K E V T T N
8. AAV8 translation              Q R L I N N N W G F R P K R L S F K L F N I Q V K E V T Q N
9. AAV9 translation              Q R L I N N N W G F R P K R L N F K L F N I Q V K E V T D N
10. Shuffle 100.1 Translation    Q R L I N N N W G F R P K R L N F K L F N I Q V K E V T T N
                                 AAV1

340               350               360
Consensus                        D G V T T I A N N L T S T V Q V F T D S E Y Q L P Y V L G S
Identity 1. AAV1 translation              D G V T T I A N N L T S T V Q V F S D S E Y Q L P Y V L G S
2. AAV2 translation              D G T T T I A N N L T S T V Q V F T D S E Y Q L P Y V L G S
3. AAV3 translation              D G T T T I A N N L T S T V Q V F T D S E Y Q L P Y V L G S
4. AAV4 translation              N G E T T V A N N L T S T V Q I F A D S S Y E L P Y V M D A
5. AAV5 translation              D S T T T I A N N L T S T V Q V F T D D D Y Q L P Y V V G N
6. AAV6 translation              D G V T T I A N N L T S T V Q V F S D S E Y Q L P Y V L G S
7. AAV7 translation              D G V T T I A N N L T S T I Q V F S D S E Y Q L P Y V L G S
8. AAV8 translation              E G T K T I A N N L T S T I Q V F T D S E Y Q L P Y V L G S
9. AAV9 translation              N G V K T I A N N L T S T V Q V F T D S D Y Q L P Y V L G S
10. Shuffle 100.1 Translation    D G V T T I A N N L T S T V Q V F S D S D Y Q L P Y V L G S
                                 AAV1                                 AAV9
```

FIG. 8D

|  | 370 | 380 | 390 |
|---|---|---|---|

```
                              370              380             390
Consensus                 A H Q G C L P P F P A D V F M I P Q Y G Y L T L N - - N G S
Identity                  ████████████████████▁████████████████▁▁██▁▁▁▁▁▁▁▁▁▁▁▁███

1. AAV1 translation       A H Q G C L P P F P A D V F M I P Q Y G Y L T L N - - N G S
2. AAV2 translation       A H Q G C L P P F P A D V F M V P Q Y G Y L T L N - - N G S
3. AAV3 translation       A H Q G C L P P F P A D V F M V P Q Y G Y L T L N - - N G S
4. AAV4 translation       G Q E G S L P P F P N D V F M V P Q Y G Y C G L V T G N T S
5. AAV5 translation       G T E G C L P A F P P Q V F T L P Q Y G Y A T L N R D N T E
6. AAV6 translation       A H Q G C L P P F P A D V F M I P Q Y G Y L T L N - - N G S
7. AAV7 translation       A H Q G C L P P F P A D V F M I P Q Y G Y L T L N - - N G S
8. AAV8 translation       A H Q G C L P P F P A D V F M I P Q Y G Y L T L N - - N G S
9. AAV9 translation       A H E G C L P P F P A D V F M I P Q Y G Y L T L N - - D G S
10. Shuffle 100.1 Translation  A H E G C L P P F P A D V F M V P Q Y G Y L T L N - - N G S
                          ◁AAV9       ◁AAV2

400              410             420
Consensus                 Q A - V G R S S F Y C L E Y F P S Q M L R T G N N F T F S Y
Identity                  ████▁███████████████████████████████████████████████▁▁███

1. AAV1 translation       Q A - V G R S S F Y C L E Y F P S Q M L R T G N N F T F S Y
2. AAV2 translation       Q A - V G R S S F Y C L E Y F P S Q M L R T G N N F T F S Y
3. AAV3 translation       Q A - V G R S S F Y C L E Y F P S Q M L R T G N N F Q F S Y
4. AAV4 translation       Q Q Q T D R N A F Y C L E Y F P S Q M L R T G N N F E I T Y
5. AAV5 translation       N P - T E R S S F P C L E Y F P S K M L R T G N N F E F T Y
6. AAV6 translation       Q A - V G R S S F Y C L E Y F P S Q M L R T G N N F T F S Y
7. AAV7 translation       Q S - V G R S S F Y C L E Y F P S Q M L R T G N N F E F S Y
8. AAV8 translation       Q A - V G R S S F Y C L E Y F P S Q M L R T G N N F Q F T Y
9. AAV9 translation       Q A - V G R S S F Y C L E Y F P S Q M L R T G N N F Q F S Y
10. Shuffle 100.1 Translation  Q A - V G R S S F Y C L E Y F P S Q M L R T G N N F T F S Y
                          ◁AAV2

430              440             450
Consensus                 T F E D V P F H S S Y A H S Q S L D R L M N P L I D Q Y L Y
Identity                  ████████████████████████████████████████████████████████

1. AAV1 translation       T F E E V P F H S S Y A H S Q S L D R L M N P L I D Q Y L Y
2. AAV2 translation       T F E D V P F H S S Y A H S Q S L D R L M N P L I D Q Y L Y
3. AAV3 translation       T F E D V P F H S S Y A H S Q S L D R L M N P L I D Q Y L Y
4. AAV4 translation       S F E K V P F H S M Y A H S Q S L D R L M N P L I D Q Y L W
5. AAV5 translation       N F E E V P F H S S F A P S Q N L F K L A N P L V D Q Y L Y
6. AAV6 translation       T F E D V P F H S S Y A H S Q S L D R L M N P L I D Q Y L Y
7. AAV7 translation       S F E D V P F H S S Y A H S Q S L D R L M N P L I D Q Y L Y
8. AAV8 translation       T F E D V P F H S S Y A H S Q S L D R L M N P L I D Q Y L Y
9. AAV9 translation       E F E N V P F H S S Y A H S Q S L D R L M N P L I D Q Y L Y
10. Shuffle 100.1 Translation  T F E D V P F H S S Y A H S Q S L D R L M N P L I D Q Y L Y
                          ◁AAV2
```

FIG. 8E

|  | 460 | 470 | 480 |
|---|---|---|---|

```
                          460              470              480
Consensus                 YLNRTQN-XSGTAXNKXLLFSQGGPXGMSV
Identity                  ▄▄▁▁▄▄▄▁▁▄▄▄▄▁▄▄▁▄▄▄▄▁▄▁▁▁▄▄▄▄

1. AAV1 translation       YLNRTQN-QSGSAQNKDLLFSRGSPAGMSV
2. AAV2 translation       YLSRTNT-PSGTTTQSRLQFSQAGASDIRD
3. AAV3 translation       YLNRTQGTTSGTTNQSRLLFSQAGPQSMSL
4. AAV4 translation       GLQSTTTGTTLNAGTATTNFTKLRPTNFSN
5. AAV5 translation       RFVSTNN-------TGGVQFNKNLAGRYAN
6. AAV6 translation       YLNRTQN-QSGSAQNKDLLFSRGSPAGMSV
7. AAV7 translation       YLARTQSNPGGTAGNRELQFYQGGPSTMAE
8. AAV8 translation       YLSRTQT-TGGTANTQTLGFSQGGPNTMAN
9. AAV9 translation       YLSKTIN--GSGQNQQTLKFSVAGPSNMAV
10. Shuffle 100.1 Translation  YLNRTQN-QSGSAQNKDLLFSRGSPAGMSV
                          [AAV1/6][AAV6              ][AAV1]

490              500              510
Consensus                 QXKNWLPGPCYRQQRVSKTKTDN-NNSNFA
Identity                  ▄▁▄▄▄▄▄▄▄▄▄▄▄▄▄▄▄▄▁▄▁▄▄▁▄▄▄▄▄▄

1. AAV1 translation       QPKNWLPGPCYRQQRVSKTKTDN-NNSNFT
2. AAV2 translation       QSRNWLPGPCYRQQRVSKTSADN-NNSEYS
3. AAV3 translation       QARNWLPGPCYRQQRLSKTANDN-NNSNFP
4. AAV4 translation       FKKNWLPGPSIKQQGFSKTANQNYKIPATG
5. AAV5 translation       TYKNWFPGMGRTQGWNLGSGVN-RASVSA
6. AAV6 translation       QPKNWLPGPCYRQQRVSKTKTDN-NNSNFT
7. AAV7 translation       QAKNWLPGPCFRQQRVSKTLDQN-NNSNFA
8. AAV8 translation       QAKNWLPGPCYRQQRVSTTTGQN-NNSNFA
9. AAV9 translation       QGRNYIPGPSYRQQRVSTTVTQN-NNSEFA
10. Shuffle 100.1 Translation  QPKNWLPGPCYRQQRVSKTKTDN-NNSNFT
                          [AAV1                             ]

520              530              540
Consensus                 WTGASKYH----LNGRXSLVNPGPAMASHK
Identity                  ▄▄▄▄▄▄▄▄▁▁▁▁▄▄▄▄▁▄▄▄▄▄▄▄▄▄▄▄▄▄

1. AAV1 translation       WTGASKYN----LNGRESIINPGTAMASHK
2. AAV2 translation       WTGATKYH----LNGRDSLVNPGPAMASHK
3. AAV3 translation       WTAASKYH----LNGRDSLVNPGPAMASHK
4. AAV4 translation       SDSLIKYETHSTLDGRWSALTPGPPMATAG
5. AAV5 translation       FATTNRME----LEGASYQVPPQPNGMTNN
6. AAV6 translation       WTGASKYN----LNGRESIINPGTAMASHK
7. AAV7 translation       WTGATKYH----LNGRNSLVNPGVAMATHK
8. AAV8 translation       WTAGTKYH----LNGRNSLANPGIAMATHK
9. AAV9 translation       WPGASSWA----LNGRNSLMNPGPAMASHK
10. Shuffle 100.1 Translation  WTGASKYN----LNGRESIINPGTAMASHK
                          [AAV6                             ]
```

FIG. 8F

```
                                        550              560              570
Consensus                       D D E D K F F P M S G V L I F G K Q G A G A S N T A L - - -
Identity 1. AAV1 translation             D D E D K F F P M S G V M I F G K E S A G A S N T A L - - -
2. AAV2 translation             D D E E K F F P Q S G V L I F G K Q G S E K T N V D I - - -
3. AAV3 translation             D D E E K F F P M H G N L I F G K E G T T A S N A E L - - -
4. AAV4 translation             P A D S K F S N Q L I F A G P K Q N G N T A T V P - - - - -
5. AAV5 translation             L Q G S N T Y A L E N T M I F N S Q P A N P G T T A T Y L E
6. AAV6 translation             D D K D K F F P M S G V M I F G K E S A G A S N T A L - - -
7. AAV7 translation             D D E D R F F P S S G V L I F G K T G A T N K T T L - - - -
8. AAV8 translation             D D E E R F F P S N G I L I F G K Q N A A R D N A D Y - - -
9. AAV9 translation             E G E D R F F P L S G S L I F G K Q G T G R D N V D A - - -
10. Shuffle 100.1 Translation   D D K D K F F P M S G V M I F G K E S A G A S N T A L - - -

580              590              600
Consensus                       D N V M I T D E E E I K X T N P V A T E R Y G T V A X N L Q
Identity 1. AAV1 translation             D N V M I T D E E E I K A T N P V A T E R F G T V A V N F Q
2. AAV2 translation             E K V M I T D E E E I R T T N P V A T E Q Y G S V S T N L Q
3. AAV3 translation             D N V M I T D E E E I R T T N P V A T E Q Y G T V A N N L Q
4. AAV4 translation             G T L I F T S E E E L A A T N A T D T D M W G N L P G G D Q
5. AAV5 translation             G N M L I T S E S E T Q P V N R V A Y N V G G Q M A T N N Q
6. AAV6 translation             D N V M I T D E E E I K A T N P V A T E R F G T V A V N L Q
7. AAV7 translation             E N V L M T N E E E I R P T N P V A T E E Y G I V S S N L Q
8. AAV8 translation             S D V M L T S E E E I K T T N P V A T E E Y G I V A D N L Q
9. AAV9 translation             D K V M I T N E E E I K T T N P V A T E S Y G Q V A T N H Q
10. Shuffle 100.1 Translation   D N V M I T D E E E I K A T N P V A T E R F G T V A V N L Q 610              620              630
Consensus                       S S X T A P A T G D V N X Q G A L P G M V W Q D R D V Y L Q
Identity 1. AAV1 translation             S S S T D P A T G D V H A M G A L P G M V W Q D R D V Y L Q
2. AAV2 translation             R G N R Q A A T A D V N T Q G V L P G M V W Q D R D V Y L Q
3. AAV3 translation             S S N T A P T T G T V N H Q G A L P G M V W Q D R D V Y L Q
4. AAV4 translation             S N S N L P T V D R L T A L G A V P G M V W Q N R D I Y Y Q
5. AAV5 translation             S S T T A P A T G T Y N L Q E I V P G S V W M E R D V Y L Q
6. AAV6 translation             S S S T D P A T G D V H V M G A L P G M V W Q D R D V Y L Q
7. AAV7 translation             A A N T A A Q T Q V V N N Q G A L P G M V W Q N R D V Y L Q
8. AAV8 translation             Q Q N T A P Q I G T V N S Q G A L P G M V W Q N R D V Y L Q
9. AAV9 translation             S A Q A Q A Q T G W V Q N Q G I L P G M V W Q D R D V Y L Q
10. Shuffle 100.1 Translation   S S S T D P A T G D V H V M G A L P G M V W Q D R D V Y L Q
```

FIG. 8G

```
                                     640               650              660
Consensus                   G P I W A K I P H T D G H F H P S P L M G G F G L K H P P P
Identity 1. AAV1 translation         G P I W A K I P H T D G H F H P S P L M G G F G L K N P P P
2. AAV2 translation         G P I W A K I P H T D G H F H P S P L M G G F G L K H P P P
3. AAV3 translation         G P I W A K I P H T D G H F H P S P L M G G F G L K H P P P
4. AAV4 translation         G P I W A K I P H T D G H F H P S P L I G G F G L K H P P P
5. AAV5 translation         G P I W A K I P E T G A H F H P S P A M G G F G L K H P P P
6. AAV6 translation         G P I W A K I P H T D G H F H P S P L M G G F G L K H P P P
7. AAV7 translation         G P I W A K I P H T D G N F H P S P L M G G F G L K H P P P
8. AAV8 translation         G P I W A K I P H T D G N F H P S P L M G G F G L K H P P P
9. AAV9 translation         G P I W A K I P H T D G N F H P S P L M G G F G M K H P P P
10. Shuffle 100.1 Translation G P I W A K I P H T D G H F H P S P L M G G F G L K N P P P
                            <AAV6          <AAV1

670               680              690
Consensus                   Q I L I K N T P V P A N P P T T F S A T K F A S F I T Q Y S
Identity 1. AAV1 translation         Q I L I K N T P V P A N P P A E F S A T K F A S F I T Q Y S
2. AAV2 translation         Q I L I K N T P V P A N P S T T F S A A K F A S F I T Q Y S
3. AAV3 translation         Q I M I K N T P V P A N P P T T F S P A K F A S F I T Q Y S
4. AAV4 translation         Q I F I K N T P V P A N P A T T F S S T P V N S F I T Q Y S
5. AAV5 translation         M M L I K N T P V P G N - I T S F S D V P V S S F I T Q Y S
6. AAV6 translation         Q I L I K N T P V P A N P P A E F S A T K F A S F I T Q Y S
7. AAV7 translation         Q I L I K N T P V P A N P P E V F T P A K F A S F I T Q Y S
8. AAV8 translation         Q I L I K N T P V P A D P P T T F N Q S K L N S F I T Q Y S
9. AAV9 translation         Q I L I K N T P V P A D P P T A F N K D K L N S F I T Q Y S
10. Shuffle 100.1 Translation Q I L I K N T P V P A N P P A E F S A T K F A S F I T Q Y S
                            <AAV1

700               710              720
Consensus                   T G Q V S V E I E W E L Q K E N S K R W N P E I Q Y T S N Y
Identity 1. AAV1 translation         T G Q V S V E I E W E L Q K E N S K R W N P E V Q Y T S N Y
2. AAV2 translation         T G Q V S V E I E W E L Q K E N S K R W N P E I Q Y T S N Y
3. AAV3 translation         T G Q V S V E I E W E L Q K E N S K R W N P E I Q Y T S N Y
4. AAV4 translation         T G Q V S V Q I D W E I Q K E R S K R W N P E V Q F T S N Y
5. AAV5 translation         T G Q V T V E M E W E L K K E N S K R W N P E I Q Y T N N Y
6. AAV6 translation         T G Q V S V E I E W E L Q K E N S K R W N P E V Q Y T S N Y
7. AAV7 translation         T G Q V S V E I E W E L Q K E N S K R W N P E I Q Y T S N F
8. AAV8 translation         T G Q V S V E I E W E L Q K E N S K R W N P E I Q Y T S N Y
9. AAV9 translation         T G Q V S V E I E W E L Q K E N S K R W N P E I Q Y T S N Y
10. Shuffle 100.1 Translation T G Q V S V E I E W E L Q K E N S K R W N P E V Q Y T S N Y
                            <AAV6
```

FIG. 8H

|  | 730 | 740 | 750 |
|---|---|---|---|
| Consensus | XKSANVDFXVDTNGVYSEPRPIGTRYLTRN | | |
| Identity | | | |
| 1. AAV1 translation | AKSANVDFTVDNNGLYTEPRPIGTRYLTRP | | |
| 2. AAV2 translation | NKSVNVDFTVDTNGVYSEPRPIGTRYLTRN | | |
| 3. AAV3 translation | NKSVNVDFTVDTNGVYSEPRPIGTRYLTRN | | |
| 4. AAV4 translation | GQQNSLLWAPDAAGKYTEPRAIGTRYLTHH | | |
| 5. AAV5 translation | NDPQFVDFAPDSTGEYRTTRPIGTRYLTRP | | |
| 6. AAV6 translation | AKSANVDFTVDNNGLYTEPRPIGTRYLTRP | | |
| 7. AAV7 translation | EKQTGVDFAVDSQGVYSEPRPIGTRYLTRN | | |
| 8. AAV8 translation | YKSTSVDFAVNTEGVYSEPRPIGTRYLTRN | | |
| 9. AAV9 translation | YKSNNVEFAVNTEGVYSEPRPIGTRYLTRN | | |
| 10. Shuffle 100.1 Translation | AKSANVDFTVDNNGLYTEPRPIGTRYLTRP | | |

|  | 752 |
|---|---|
| Consensus | L * |
| Identity | |
| 1. AAV1 translation | L * |
| 2. AAV2 translation | L * |
| 3. AAV3 translation | L * |
| 4. AAV4 translation | L * |
| 5. AAV5 translation | L * |
| 6. AAV6 translation | L * |
| 7. AAV7 translation | L * |
| 8. AAV8 translation | L * |
| 9. AAV9 translation | L * |
| 10. Shuffle 100.1 Translation | L * |

FIG. 8I

|  | 1 | 10 | 20 | 30 |
|---|---|---|---|---|

Consensus
MAADGYLPDWLEDNLSEGIREWWALKPGAP

Identity

1. AAV1 translation    MAADGYLPDWLEDNLSEGIREWWDLKPGAP
2. AAV2 translation    MAADGYLPDWLEDTLSEGIRQWWKLKPGPP
3. AAV3 translation    MAADGYLPDWLEDNLSEGIREWWALKPGVP
4. AAV4 translation     MTDGYLPDWLEDNLSEGVREWWALQPGAP
5. AAV5 translation    MSFVDHPPDWLEE-VGEGLREFLGLEAGPP
6. AAV6 translation    MAADGYLPDWLEDNLSEGIREWWDLKPGAP
7. AAV7 translation    MAADGYLPDWLEDNLSEGIREWWDLKPGAP
8. AAV8 translation    MAADGYLPDWLEDNLSEGIREWWALKPGAP
9. AAV9 translation    MAADGYLPDWLEDNLSEGIREWWALKPGAP
10. Shuffle 100-3 Translation  MAADGYLPDWLEDTLSEGIRQWWKLKPGPP

|  | 40 | 50 | 60 |
|---|---|---|---|

Consensus
KPKANQQHQDDGRGLVLPGYKYLGPFNGLD

Identity

1. AAV1 translation    KPKANQQKQDDGRGLVLPGYKYLGPFNGLD
2. AAV2 translation    PPKPAERHKDDSRGLVLPGYKYLGPFNGLD
3. AAV3 translation    QPKANQQHQDNRRGLVLPGYKYLGPGNGLD
4. AAV4 translation    KPKANQQHQDNARGLVLPGYKYLGPGNGLD
5. AAV5 translation    KPKPNQQHQDQARGLVLPGYNYLGPGNGLD
6. AAV6 translation    KPKANQQKQDDGRGLVLPGYKYLGPFNGLD
7. AAV7 translation    KPKANQQKQDNGRGLVLPGYKYLGPFNGLD
8. AAV8 translation    KPKANQQKQDDGRGLVLPGYKYLGPFNGLD
9. AAV9 translation    QPKANQQHQDNARGLVLPGYKYLGPGNGLD
10. Shuffle 100-3 Translation  PPKPAERHKDDSRGLVLPGYKYLGPFNGLD

|  | 70 | 80 | 90 |
|---|---|---|---|

Consensus
KGEPVNAADAAALEHDKAYDQQLKAGDNPY

Identity

1. AAV1 translation    KGEPVNAADAAALEHDKAYDQQLKAGDNPY
2. AAV2 translation    KGEPVNEADAAALEHDKAYDRQLDSGDNPY
3. AAV3 translation    KGEPVNEADAAALEHDKAYDQQLKAGDNPY
4. AAV4 translation    KGEPVNAADAAALEHDKAYDQQLKAGDNPY
5. AAV5 translation    RGEPVNRADEVAREHDISYNEQLEAGDNPY
6. AAV6 translation    KGEPVNAADAAALEHDKAYDQQLKAGDNPY
7. AAV7 translation    KGEPVNAADAAALEHDKAYDQQLKAGDNPY
8. AAV8 translation    KGEPVNAADAAALEHDKAYDQQLQAGDNPY
9. AAV9 translation    KGEPVNAADAAALEHDKAYDQQLKAGDNPY
10. Shuffle 100-3 Translation  KGEPVNEADAAALEHDKAYDQQLKAGDNPY

FIG. 9A

```
                                          100            110           120
Consensus                      LKYNHADAEFQERLQEDTSFGGNLGRAVFQ
Identity 1. AAV1 translation            LRYNHADAEFQERLQEDTSFGGNLGRAVFQ
2. AAV2 translation            LKYNHADAEFQERLKEDTSFGGNLGRAVFQ
3. AAV3 translation            LKYNHADAEFQERLQEDTSFGGNLGRAVFQ
4. AAV4 translation            LKYNHADAEFQQRLQGDTSFGGNLGRAVFQ
5. AAV5 translation            LKYNHADAEFQEKLADDTSFGGNLGKAVFQ
6. AAV6 translation            LRYNHADAEFQERLQEDTSFGGNLGRAVFQ
7. AAV7 translation            LRYNHADAEFQERLQEDTSFGGNLGRAVFQ
8. AAV8 translation            LRYNHADAEFQERLQEDTSFGGNLGRAVFQ
9. AAV9 translation            LKYNHADAEFQERLKEDTSFGGNLGRAVFQ
10. Shuffle 100-3 Translation  LKYNHADAEFQQRLQGDTSFGGNLGRAVFQ
                               [AAV4]

130            140           150
Consensus                      AKKRVLEPLGLVEEGAKTAPGKKRPVEQSP
Identity 1. AAV1 translation            AKKRVLEPLGLVEEGAKTAPGKKRPVEQSP
2. AAV2 translation            AKKRVLEPLGLVEEPVKTAPGKKRPVEHSP
3. AAV3 translation            AKKRILEPLGLVEEAAKTAPGKKGAVDQSP
4. AAV4 translation            AKKRVLEPLGLVEQAGETAPGKKRPLIESP
5. AAV5 translation            AKKRVLEPFGLVEEGAKTAPTGKRIDDHFP
6. AAV6 translation            AKKRVLEPFGLVEEGAKTAPGKKRPVEQSP
7. AAV7 translation            AKKRVLEPLGLVEEGAKTAPAKKRPVEPSP
8. AAV8 translation            AKKRVLEPLGLVEEGAKTAPGKKRPVEPSP
9. AAV9 translation            AKKRLLEPLGLVEEAAKTAPGKKRPVEQSP
10. Shuffle 100-3 Translation  AKKRVLEPLGLVEQAGETAPGKKRPLIESP
                               [AAV4]

160            170           180
Consensus                      QE-PDSSXGIGKKGQQPAKKRLNFGQTGDS
Identity 1. AAV1 translation            QE-PDSSSGIGKTGQQPAKKRLNFGQTGDS
2. AAV2 translation            VE-PDSSSGTGKAGQQPARKRLNFGQTGDA
3. AAV3 translation            QE-PDSSSGVGKSGKQPARKRLNFGQTGDS
4. AAV4 translation            QQ-PDSSTGIGKKGKQPAKKKVFE---DE
5. AAV5 translation            KR----KKARTEEDSKPST-------SSDA
6. AAV6 translation            QE-PDSSSGIGKTGQQPAKKRLNFGQTGDS
7. AAV7 translation            QRSPDSSTGIGKKGQQPARKRLNFGQTGDS
8. AAV8 translation            QRSPDSSTGIGKKGQQPARKRLNFGQTGDS
9. AAV9 translation            QE-PDSSAGIGKSGAQPAKKRLNFGQTGDT
10. Shuffle 100-3 Translation  QQ-PDSSTGIGKKGKQPAKKRLNFGQTGDS
                               [AAV4]                    [AAV1/6]
```

FIG. 9B

```
                              280         290         300
Consensus                SNDNHYFGYSTPWGYFDFNRFHCHFSPRDW
Identity 1. AAV1 translation      SNDNHYFGYSTPWGYFDFNRFHCHFSPRDW
2. AAV2 translation      SNDNHYFGYSTPWGYFDFNRFHCHFSPRDW
3. AAV3 translation      SNDNHYFGYSTPWGYFDFNRFHCHFSPRDW
4. AAV4 translation      -QSNTYNGFSTPWGYFDFNRFHCHFSPRDW
5. AAV5 translation      SNANAYFGYSTPWGYFDFNRFHSHWSPRDW
6. AAV6 translation      SNDNHYFGYSTPWGYFDFNRFHCHFSPRDW
7. AAV7 translation      TNDNTYFGYSTPWGYFDFNRFHCHFSPRDW
8. AAV8 translation      TNDNTYFGYSTPWGYFDFNRFHCHFSPRDW
9. AAV9 translation      SNDNAYFGYSTPWGYFDFNRFHCHFSPRDW
10. Shuffle 100-3 Translation SNDNHYFGYSTPWGYFDFNRFHCHFSPRDW
                         AAV1

310         320         330
Consensus                QRLINNNWGFRPKRLNFKLFNIQVKEVTTN
Identity 1. AAV1 translation      QRLINNNWGFRPKRLNFKLFNIQVKEVTTN
2. AAV2 translation      QRLINNNWGFRPKRLNFKLFNIQVKEVTQN
3. AAV3 translation      QRLINNNWGFRPKKLSFKLFNIQVRGVTQN
4. AAV4 translation      QRLINNNWGMRPKAMRVKIFNIQVKEVTTS
5. AAV5 translation      QRLINNYWGFRPRSLRVKIFNIQVKEVTVQ
6. AAV6 translation      QRLINNNWGFRPKRLNFKLFNIQVKEVTTN
7. AAV7 translation      QRLINNNWGFRPKKLRFKLFNIQVKEVTTN
8. AAV8 translation      QRLINNNWGFRPKRLSFKLFNIQVKEVTQN
9. AAV9 translation      QRLINNNWGFRPKRLNFKLFNIQVKEVTDN
10. Shuffle 100-3 Translation QRLINNNWGFRPKRLNFKLFNIQVKEVTTN
                         AAV1

340         350         360
Consensus                DGVTTIANNLTSTVQVFTDSEYQLPYVLGS
Identity 1. AAV1 translation      DGVTTIANNLTSTVQVFSDSEYQLPYVLGS
2. AAV2 translation      DGTTTIANNLTSTVQVFTDSEYQLPYVLGS
3. AAV3 translation      DGTTTIANNLTSTVQVFTDSEYQLPYVLGS
4. AAV4 translation      NGETTVANNLTSTVQIFADSSYELPYVMDA
5. AAV5 translation      DSTTTIANNLTSTVQVFTDDDYQLPYVVGN
6. AAV6 translation      DGVTTIANNLTSTVQVFSDSEYQLPYVLGS
7. AAV7 translation      DGVTTIANNLTSTIQVFSDSEYQLPYVLGS
8. AAV8 translation      EGTKTIANNLTSTIQVFTDSEYQLPYVLGS
9. AAV9 translation      NGVKTIANNLTSTVQVFTDSDYQLPYVLGS
10. Shuffle 100-3 Translation DGVTTIANNLTSTVQVFSDSDYQLPYVLGS
                         AAV1                     AAV9
```

FIG. 9D

|              | 370                  380                 390 |
|---|---|
| Consensus Identity | A H Q G C L P P F P A D V F M I P Q Y G Y L T L N - - N G S |
| 1. AAV1 translation | A H Q G C L P P F P A D V F M I P Q Y G Y L T L N - - N G S |
| 2. AAV2 translation | A H Q G C L P P F P A D V F M V P Q Y G Y L T L N - - N G S |
| 3. AAV3 translation | A H Q G C L P P F P A D V F M V P Q Y G Y L T L N - - N G S |
| 4. AAV4 translation | G Q E G S L P P F P N D V F M V P Q Y G Y C G L V T G N T S |
| 5. AAV5 translation | G T E G C L P A F P P Q V F T L P Q Y G Y A T L N R D N T E |
| 6. AAV6 translation | A H Q G C L P P F P A D V F M I P Q Y G Y L T L N - - N G S |
| 7. AAV7 translation | A H Q G C L P P F P A D V F M I P Q Y G Y L T L N - - N G S |
| 8. AAV8 translation | A H Q G C L P P F P A D V F M I P Q Y G Y L T L N - - N G S |
| 9. AAV9 translation | A H E G C L P P F P A D V F M I P Q Y G Y L T L N - - D G S |
| 10. Shuffle 100-3 Translation | A H E G C L P P F P A D V F M V P Q Y G Y L T L N - - N G S |

|              | 400                 410                 420 |
|---|---|
| Consensus Identity | Q A - V G R S S F Y C L E Y F P S Q M L R T G N N F T F S Y |
| 1. AAV1 translation | Q A - V G R S S F Y C L E Y F P S Q M L R T G N N F T F S Y |
| 2. AAV2 translation | Q A - V G R S S F Y C L E Y F P S Q M L R T G N N F T F S Y |
| 3. AAV3 translation | Q A - V G R S S F Y C L E Y F P S Q M L R T G N N F Q F S Y |
| 4. AAV4 translation | Q Q Q T D R N A F Y C L E Y F P S Q M L R T G N N F E I T Y |
| 5. AAV5 translation | N P - T E R S S F F C L E Y F P S K M L R T G N N F E F T Y |
| 6. AAV6 translation | Q A - V G R S S F Y C L E Y F P S Q M L R T G N N F T F S Y |
| 7. AAV7 translation | Q S - V G R S S F Y C L E Y F P S Q M L R T G N N F E F S Y |
| 8. AAV8 translation | Q A - V G R S S F Y C L E Y F P S Q M L R T G N N F Q F T Y |
| 9. AAV9 translation | Q A - V G R S S F Y C L E Y F P S Q M L R T G N N F Q F S Y |
| 10. Shuffle 100-3 Translation | Q A - V G R S S F Y C L E Y F P S Q M L R T G N N F T F S Y |

|              | 430                 440                 450 |
|---|---|
| Consensus Identity | T F E D V P F H S S Y A H S Q S L D R L M N P L I D Q Y L Y |
| 1. AAV1 translation | T F E E V P F H S S Y A H S Q S L D R L M N P L I D Q Y L Y |
| 2. AAV2 translation | T F E D V P F H S S Y A H S Q S L D R L M N P L I D Q Y L Y |
| 3. AAV3 translation | T F E D V P F H S S Y A H S Q S L D R L M N P L I D Q Y L Y |
| 4. AAV4 translation | S F E K V P F H S M Y A H S Q S L D R L M N P L I D Q Y L W |
| 5. AAV5 translation | N F E E V P F H S S F A P S Q N L F K L A N P L V D Q Y L Y |
| 6. AAV6 translation | T F E D V P F H S S Y A H S Q S L D R L M N P L I D Q Y L Y |
| 7. AAV7 translation | S F E D V P F H S S Y A H S Q S L D R L M N P L I D Q Y L Y |
| 8. AAV8 translation | T F E D V P F H S S Y A H S Q S L D R L M N P L I D Q Y L Y |
| 9. AAV9 translation | E F E N V P F H S S Y A H S Q S L D R L M N P L I D Q Y L Y |
| 10. Shuffle 100-3 Translation | T F E D V P F H S S Y A H S Q S L D R L M N P L I D Q Y L Y |

FIG. 9E

```
                                460              470              480
Consensus                       YLNRTQN-XSGTAXNKXLLFSQGGPSGMSV
Identity 1. AAV1 translation             YLNRTQN-QSGSAQNKDLLFSRGSPAGMSV
2. AAV2 translation             YLSRTNT-PSGTTTQSRLQFSQAGASDIRD
3. AAV3 translation             YLNRTQGTTSGTTNQSRLLFSQAGPQSMSL
4. AAV4 translation             GLQSTTTGTTLNAGTATTNFTKLRPTNFSN
5. AAV5 translation             RFVSTNN-------TGGVQFNKNLAGRYAN
6. AAV6 translation             YLNRTQN-QSGSAQNKDLLFSRGSPAGMSV
7. AAV7 translation             YLARTQSNPGGTAGNRELQFYQGGPSTMAE
8. AAV8 translation             YLSRTQT-TGGTANTQTLGFSQGGPNTMAN
9. AAV9 translation             YLSKTIN--GSGQNQQTLKFSVAGPSNMAV
10. Shuffle 100-3 Translation   YLNRTQN-QSGSAQNKDLLFSRGSPTGMSV
                                ▶AAV1/6◀▶AAV6◀━━━━━━━━━━━━━━▶▶AAV1◀

490              500              510
Consensus                       QXKNWLPGPCYRQQRVSKTKTDN-NNSNFA
Identity 1. AAV1 translation             QPKNWLPGPCYRQQRVSKTKTDN-NNSNFT
2. AAV2 translation             QSRNWLPGPCYRQQRVSKTSADN-NNSEYS
3. AAV3 translation             QARNWLPGPCYRQQRLSKTANDN-NNSNFP
4. AAV4 translation             FKKNWLPGPSIKQQGFSKTANQNYKIPATG
5. AAV5 translation             TYKNWFPGMGRTQGWNLGSGVN-RASVSA
6. AAV6 translation             QPKNWLPGPCYRQQRVSKTKTDN-NNSNFT
7. AAV7 translation             QAKNWLPGPCFRQQRVSKTLDQN-NNSNFA
8. AAV8 translation             QAKNWLPGPCYRQQRVSTTTGQN-NNSNFA
9. AAV9 translation             QGRNYIPGPSYRQQRVSTTVTQN-NNSEFA
10. Shuffle 100-3 Translation   QPKNWLPGPCYRQQRVSKTKTDN-NNSNFT
                                ▶AAV1◀━━━━━━━━━━━━━━━━━━━━━▶A◀

520              530              540
Consensus                       WTGASKYH----LNGRXSLVNPGPAMASHK
Identity 1. AAV1 translation             WTGASKYN----LNGRESIINPGTAMASHK
2. AAV2 translation             WTGATKYH----LNGRDSLVNPGPAMASHK
3. AAV3 translation             WTAASKYH----LNGRDSLVNPGPAMASHK
4. AAV4 translation             SDSLIKYETHSTLDGRWSALTPGPPMATAG
5. AAV5 translation             FATTNRME----LEGASYQVPPQPNGMTNN
6. AAV6 translation             WTGASKYN----LNGRESIINPGTAMASHK
7. AAV7 translation             WTGATKYH----LNGRNSLVNPGVAMATHK
8. AAV8 translation             WTAGTKYH----LNGRNSLANPGIAMATHK
9. AAV9 translation             WPGASSWA----LNGRNSLMNPGPAMASHK
10. Shuffle 100-3 Translation   WTGASKYN----LNGRESIINPGTAMASHK
                                ▶AAV6◀━━━━━━━━━━━━━━━━━━━━━━━━▶
```

FIG. 9F

|  | 550 | 560 | 570 |
|---|---|---|---|

Consensus: D D E D K F F P M S G V L I F G K Q G A G A S N T A L - - -

| # | Name | Sequence |
|---|---|---|
| 1 | AAV1 translation | D D E D K F F P M S G V M I F G K E S A G A S N T A L - - - |
| 2 | AAV2 translation | D D E E K F F P Q S G V L I F G K Q G S E K T N V D I - - - |
| 3 | AAV3 translation | D D E E K F F P M H G N L I F G K E G T T A S N A E L - - - |
| 4 | AAV4 translation | P A D S K F S N S Q L I F A G P K Q N G N T A T V P - - - - |
| 5 | AAV5 translation | L Q G S N T Y A L E N T M I F N S Q P A N P G T T A T Y L E |
| 6 | AAV6 translation | D D K D K F F P M S G V M I F G K E S A G A S N T A L - - - |
| 7 | AAV7 translation | D D E D R F F P S S G V L I F G K T G A T N K T T L - - - - |
| 8 | AAV8 translation | D D E E R F F P S N G I L I F G K Q N A A R D N A D Y - - - |
| 9 | AAV9 translation | E G E D R F F P L S G S L I F G K Q G T G R D N V D A - - - |
| 10 | Shuffle 100-3 Translation | D D K D K F F P M S G V M I F G K E S A G A S N T A L - - - |

⟨AAV6⟩

|  | 580 | 590 | 600 |
|---|---|---|---|

Consensus: D N V M I T D E E E I K X T N P V A T E R Y G T V A X N L Q

| # | Name | Sequence |
|---|---|---|
| 1 | AAV1 translation | D N V M I T D E E E I K A T N P V A T E R F G T V A V N F Q |
| 2 | AAV2 translation | E K V M I T D E E E I R T T N P V A T E Q Y G S V S T N L Q |
| 3 | AAV3 translation | D N V M I T D E E E I R T T N P V A T E Q Y G T V A N N L Q |
| 4 | AAV4 translation | G T L I F T S E E E L A A T N A T D T D M W G N L P G G D Q |
| 5 | AAV5 translation | G N M L I T S E S E T Q P V N R V A Y N V G G Q M A T N N Q |
| 6 | AAV6 translation | D N V M I T D E E E I K A T N P V A T E R F G T V A V N L Q |
| 7 | AAV7 translation | E N V L M T N E E E I R P T N P V A T E E Y G I V S S N L Q |
| 8 | AAV8 translation | S D V M L T S E E E I K T T N P V A T E E Y G I V A D N L Q |
| 9 | AAV9 translation | D K V M I T N E E E I K T T N P V A T E S Y G Q V A T N H Q |
| 10 | Shuffle 100-3 Translation | D N V M I T D E E E I K A T N P V A T E R F G T V A V N L Q |

⟨AAV6⟩ ⟨AAV1/6⟩ ⟨AAV6⟩

|  | 610 | 620 | 630 |
|---|---|---|---|

Consensus: S S X T A P A T G D V N A Q G A L P G M V W Q D R D V Y L Q

| # | Name | Sequence |
|---|---|---|
| 1 | AAV1 translation | S S S T D P A T G D V H A M G A L P G M V W Q D R D V Y L Q |
| 2 | AAV2 translation | R G N R Q A A T A D V N T Q G V L P G M V W Q D R D V Y L Q |
| 3 | AAV3 translation | S S N T A P T T G T V N H Q G A L P G M V W Q D R D V Y L Q |
| 4 | AAV4 translation | S N S N L P T V D R L T A L G A V P G M V W Q N R D I Y Y Q |
| 5 | AAV5 translation | S S T T A P A T G T Y N L Q E I V P G S V W M E R D V Y L Q |
| 6 | AAV6 translation | S S S T D P A T G D V H V M G A L P G M V W Q D R D V Y L Q |
| 7 | AAV7 translation | A A N T A A Q T Q V V N N Q G A L P G M V W Q N R D V Y L Q |
| 8 | AAV8 translation | Q Q N T A P Q I G T V N S Q G A L P G M V W Q N R D V Y L Q |
| 9 | AAV9 translation | S A Q A Q A Q T G W V Q N Q G I L P G M V W Q D R D V Y L Q |
| 10 | Shuffle 100-3 Translation | S S S T D P A T G D V H A M G A L P G M V W Q D R D V Y L Q |

⟨AAV6⟩ ⟨AAV1⟩ ⟨AAV6⟩

FIG. 9G

|  | 730 | 740 | 750 |
|---|---|---|---|

```
                         730                740               750
Consensus                X K S A N V D F X V D T N G V Y S E P R P I G T R Y L T R N
Identity 1. AAV1 translation      A K S A N V D F T V D N N G L Y T E P R P I G T R Y L T R P
2. AAV2 translation      N K S V N V D F T V D T N G V Y S E P R P I G T R Y L T R N
3. AAV3 translation      N K S V N V D F T V D T N G V Y S E P R P I G T R Y L T R N
4. AAV4 translation      G Q Q N S L L W A P D A A G K Y T E P R A I G T R Y L T H H
5. AAV5 translation      N D P Q F V D F A P D S T G E Y R T T R P I G T R Y L T R P
6. AAV6 translation      A K S A N V D F T V D N N G L Y T E P R P I G T R Y L T R P
7. AAV7 translation      E K Q T G V D F A V D S Q G V Y S E P R P I G T R Y L T R N
8. AAV8 translation      Y K S T S V D F A V N T E G V Y S E P R P I G T R Y L T R N
9. AAV9 translation      Y K S N N V E F A V N T E G V Y S E P R P I G T R Y L T R N
10. Shuffle 100-3 Translation  A K S A N V D F T V D N N G L Y T E P R P I G T R Y L T R P
                         AAV6

752
Consensus                L *
Identity

1. AAV1 translation      L *
2. AAV2 translation      L *
3. AAV3 translation      L *
4. AAV4 translation      L *
5. AAV5 translation      L *
6. AAV6 translation      L *
7. AAV7 translation      L *
8. AAV8 translation      L *
9. AAV9 translation      L *
10. Shuffle 100-3 Translation  L *
```

FIG. 9I

|                              | 1          10         20         30 |
|------------------------------|--------------------------------------|
| Consensus Identity           | M A A D G Y L P D W L E D N L S E G I R E W W A L K P G A P |
| 1. AAV1 translation          | M A A D G Y L P D W L E D N L S E G I R E W W D L K P G A P |
| 2. AAV2 translation          | M A A D G Y L P D W L E D T L S E G I R Q W W K L K P G P P |
| 3. AAV3 translation          | M A A D G Y L P D W L E D N L S E G I R E W W A L K P G V P |
| 4. AAV4 translation          |   M T D G Y L P D W L E D N L S E G V R E W W A L Q P G A P |
| 5. AAV5 translation          | M S F V D H P P D W L E E - V G E G L R E F L G L E A G P P |
| 6. AAV6 translation          | M A A D G Y L P D W L E D N L S E G I R E W W D L K P G A P |
| 7. AAV7 translation          | M A A D G Y L P D W L E D N L S E G I R E W W D L K P G A P |
| 8. AAV8 translation          | M A A D G Y L P D W L E D N L S E G I R E W W A L K P G A P |
| 9. AAV9 translation          | M A A D G Y L P D W L E D N L S E G I R E W W A L K P G A P |
| 10. Shuffle 100.7 Translation| M A A D G Y L P D W L E D N L S E G I R E W W A L K P G A P |

|                              | 40         50         60 |
|------------------------------|--------------------------|
| Consensus Identity           | K P K A N Q Q X Q D D G R G L V L P G Y K Y L G P F N G L D |
| 1. AAV1 translation          | K P K A N Q Q K Q D D G R G L V L P G Y K Y L G P F N G L D |
| 2. AAV2 translation          | P P K P A E R H K D D S R G L V L P G Y K Y L G P F N G L D |
| 3. AAV3 translation          | Q P K A N Q Q H Q D N R R G L V L P G Y K Y L G P G N G L D |
| 4. AAV4 translation          | K P K A N Q Q H Q D N A R G L V L P G Y K Y L G P G N G L D |
| 5. AAV5 translation          | K P K P N Q Q H Q D Q A R G L V L P G Y N Y L G P G N G L D |
| 6. AAV6 translation          | K P K A N Q Q K Q D D G R G L V L P G Y K Y L G P F N G L D |
| 7. AAV7 translation          | K P K A N Q Q K Q D N G R G L V L P G Y K Y L G P F N G L D |
| 8. AAV8 translation          | K P K A N Q Q K Q D D G R G L V L P G Y K Y L G P F N G L D |
| 9. AAV9 translation          | Q P K A N Q Q H Q D N A R G L V L P G Y K Y L G P G N G L D |
| 10. Shuffle 100.7 Translation| K P K A N Q Q K Q D D G R G L V L P G Y K Y L G P F N G L D |

|                              | 70         80         90 |
|------------------------------|--------------------------|
| Consensus Identity           | K G E P V N A A D A A A L E H D K A Y D Q Q L K A G D N P Y |
| 1. AAV1 translation          | K G E P V N A A D A A A L E H D K A Y D Q Q L K A G D N P Y |
| 2. AAV2 translation          | K G E P V N E A D A A A L E H D K A Y D R Q L D S G D N P Y |
| 3. AAV3 translation          | K G E P V N E A D A A A L E H D K A Y D Q Q L K A G D N P Y |
| 4. AAV4 translation          | K G E P V N A A D A A A L E H D K A Y D Q Q L K A G D N P Y |
| 5. AAV5 translation          | R G E P V N R A D E V A R E H D I S Y N E Q L E A G D N P Y |
| 6. AAV6 translation          | K G E P V N A A D A A A L E H D K A Y D Q Q L K A G D N P Y |
| 7. AAV7 translation          | K G E P V N A A D A A A L E H D K A Y D Q Q L K A G D N P Y |
| 8. AAV8 translation          | K G E P V N A A D A A A L E H D K A Y D Q Q L Q A G D N P Y |
| 9. AAV9 translation          | K G E P V N A A D A A A L E H D K A Y D Q Q L K A G D N P Y |
| 10. Shuffle 100.7 Translation| K G E P V N A A D A A A L E H D K A Y D Q Q L K A G D N P Y |

FIG. 10A

```
                                                100            110            120
Consensus                        L X Y N H A D A E F Q E R L Q E D T S F G G N L G R A V F Q
Identity 1. AAV1 translation              L R Y N H A D A E F Q E R L Q E D T S F G G N L G R A V F Q
2. AAV2 translation              L K Y N H A D A E F Q E R L K E D T S F G G N L G R A V F Q
3. AAV3 translation              L K Y N H A D A E F Q E R L Q E D T S F G G N L G R A V F Q
4. AAV4 translation              L K Y N H A D A E F Q Q R L Q G D T S F G G N L G R A V F Q
5. AAV5 translation              L K Y N H A D A E F Q E K L A D D T S F G G N L G K A V F Q
6. AAV6 translation              L R Y N H A D A E F Q E R L Q E D T S F G G N L G R A V F Q
7. AAV7 translation              L R Y N H A D A E F Q E R L Q E D T S F G G N L G R A V F Q
8. AAV8 translation              L R Y N H A D A E F Q E R L Q E D T S F G G N L G R A V F Q
9. AAV9 translation              L K Y N H A D A E F Q E R L K E D T S F G G N L G R A V F Q
10. Shuffle 100.7 Translation    L R Y N H A D A E F Q E R L Q E D T S F G G N L G R A V F Q 130            140            150
Consensus                        A K K R V L E P L G L V E E G A K T A P G K K R P V E Q S P
Identity 1. AAV1 translation              A K K R V L E P L G L V E E G A K T A P G K K R P V E Q S P
2. AAV2 translation              A K K R V L E P L G L V E E P V K T A P G K K R P V E H S P
3. AAV3 translation              A K K R I L E P L G L V E E A A K T A P G K K G A V D Q S P
4. AAV4 translation              A K K R V L E P L G L V E Q A G E T A P G K K R P L I E S P
5. AAV5 translation              A K K R V L E P F G L V E E G A K T A P T G K R I D D H F P
6. AAV6 translation              A K K R V L E P F G L V E E G A K T A P G K K R P V E Q S P
7. AAV7 translation              A K K R V L E P L G L V E E G A K T A P A K K R P V E P S P
8. AAV8 translation              A K K R V L E P L G L V E E G A K T A P G K K R P V E P S P
9. AAV9 translation              A K K R L L E P L G L V E E A A K T A P G K K R P V E Q S P
10. Shuffle 100.7 Translation    A K K R V L E P L G L V E E G A K T A P G K K R P V E Q S P 160            170            180
Consensus                        Q E - P D S S S G I G K X G Q Q P A K K R L N F G Q T G D S
Identity 1. AAV1 translation              Q E - P D S S S G I G K T G Q Q P A K K R L N F G Q T G D S
2. AAV2 translation              V E - P D S S S G T G K A G Q Q P A R K R L N F G Q T G D A
3. AAV3 translation              Q E - P D S S S G V G K S G K Q P A R K R L N F G Q T G D S
4. AAV4 translation              Q Q - P D S S T G I G K K G K Q P A K K K L V F - - - E D E
5. AAV5 translation              K R - - - - K K A R T E E D S K P S T - - - - - - - S S D A
6. AAV6 translation              Q E - P D S S S G I G K T G Q Q P A K K R L N F G Q T G D S
7. AAV7 translation              Q R S P D S S T G I G K K G Q Q P A R K R L N F G Q T G D S
8. AAV8 translation              Q R S P D S S T G I G K K G Q Q P A R K R L N F G Q T G D S
9. AAV9 translation              Q E - P D S A G I G K S G A Q P A K K R L N F G Q T G D T
10. Shuffle 100.7 Translation    Q E - P D S S S G I G K T G Q Q P A K K R L N F G Q T G D S
```

FIG. 10B

```
                                    190            200            210
Consensus                ESVPDPQPLGEPPAAP-SSVGXXTMASGGG
Identity 1. AAV1 translation      ESVPDPQPLGEPPATP-AAVGPTTMASGGG
2. AAV2 translation      DSVPDPQPLGQPPAAP-SGLGTNTMATGSG
3. AAV3 translation      ESVPDPQPLGEPPAAP-TSLGSNTMASGGG
4. AAV4 translation      TGAGDGPPEGSTSGA--MSDDSEMRAAAGG
5. AAV5 translation      EAGPSGSQQLQIPAQPASSLGADTMSAGGG
6. AAV6 translation      ESVPDPQPLGEPPATP-AAVGPTTMASGGG
7. AAV7 translation      ESVPDPQPLGEPPAAP-SSVGSGTVAAGGG
8. AAV8 translation      ESVPDPQPLGEPPAAP-SGVGPNTMAAGGG
9. AAV9 translation      ESVPDPQPIGEPPAAP-SGVGSLTMASGGG
10. Shuffle 100.7 Translation  ESVPDPQPLGEPPATP-AAVGPTTMASGGG 220            230            240
Consensus                APMADNNEGADGVGNASGNWHCDSTWLGDR
Identity 1. AAV1 translation      APMADNNEGADGVGNASGNWHCDSTWLGDR
2. AAV2 translation      APMADNNEGADGVGNSSGNWHCDSTWMGDR
3. AAV3 translation      APMADNNEGADGVGNSSGNWHCDSQWLGDR
4. AAV4 translation      AAV-EGGQGADGVGNASGDWHCDSTWSEGH
5. AAV5 translation      GPLGDNNQGADGVGNASGDWHCDSTWMGDR
6. AAV6 translation      APMADNNEGADGVGNASGNWHCDSTWLGDR
7. AAV7 translation      APMADNNEGADGVGNASGNWHCDSTWLGDR
8. AAV8 translation      APMADNNEGADGVGSSSGNWHCDSTWLGDR
9. AAV9 translation      APVADNNEGADGVGSSSGNWHCDSQWLGDR
10. Shuffle 100.7 Translation  APMADNNEGADGVGNASGNWHCDSTWLGDR 250            260            270
Consensus                VITTSTRTWALPTYNNHLYKQISSASX-GA
Identity 1. AAV1 translation      VITTSTRTWALPTYNNHLYKQISSAST-GA
2. AAV2 translation      VITTSTRTWALPTYNNHLYKQISSQS--GA
3. AAV3 translation      VITTSTRTWALPTYNNHLYKQISSQS--GA
4. AAV4 translation      VTTTSTRTWVLPTYNNHLYKRLGES-----
5. AAV5 translation      VVTKSTRTWVLPSYNNHQYREIKSGSVDG-
6. AAV6 translation      VITTSTRTWALPTYNNHLYKQISSAST-GA
7. AAV7 translation      VITTSTRTWALPTYNNHLYKQISSETA-GS
8. AAV8 translation      VITTSTRTWALPTYNNHLYKQISNGTSGGA
9. AAV9 translation      VITTSTRTWALPTYNNHLYKQISNSTSGGS
10. Shuffle 100.7 Translation  VITTSTRTWALPTYNNHLYKQISSAST-GA
```

FIG. 10C

```
                                                280            290           300
Consensus                       S N D N H Y F G Y S T P W G Y F D F N R F H C H F S P R D W
Identity 1. AAV1 translation             S N D N H Y F G Y S T P W G Y F D F N R F H C H F S P R D W
2. AAV2 translation             S N D N H Y F G Y S T P W G Y F D F N R F H C H F S P R D W
3. AAV3 translation             S N D N H Y F G Y S T P W G Y F D F N R F H C H F S P R D W
4. AAV4 translation             L Q S N T Y N G F S T P W G Y F D F N R F H C H F S P R D W
5. AAV5 translation             S N A N A Y F G Y S T P W G Y F D F N R F H S H W S P R D W
6. AAV6 translation             S N D N H Y F G Y S T P W G Y F D F N R F H C H F S P R D W
7. AAV7 translation             T N D N T Y F G Y S T P W G Y F D F N R F H C H F S P R D W
8. AAV8 translation             T N D N T Y F G Y S T P W G Y F D F N R F H C H F S P R D W
9. AAV9 translation             S N D N A Y F G Y S T P W G Y F D F N R F H C H F S P R D W
10. Shuffle 100.7 Translation   S N D N H Y F G Y S T P W G Y F D F N R F H C H F S P R D W
                                ◁AAV1                    ◁AAV8

310           320           330
Consensus                       Q R L I N N N W G F R P K R L N F K L F N I Q V K E V T T N
Identity 1. AAV1 translation             Q R L I N N N W G F R P K R L N F K L F N I Q V K E V T T N
2. AAV2 translation             Q R L I N N N W G F R P K R L N F K L F N I Q V K E V T Q N
3. AAV3 translation             Q R L I N N N W G F R P K K L S F K L F N I Q V R G V T Q N
4. AAV4 translation             Q R L I N N N W G M R P K A M R V K I F N I Q V K E V T T S
5. AAV5 translation             Q R L I N N Y W G F R P R S L R V K I F N I Q V K E V T V Q
6. AAV6 translation             Q R L I N N N W G F R P K R L N F K L F N I Q V K E V T T N
7. AAV7 translation             Q R L I N N N W G F R P K K L R F K L F N I Q V K E V T T N
8. AAV8 translation             Q R L I N N N W G F R P K R L S F K L F N I Q V K E V T Q N
9. AAV9 translation             Q R L I N N N W G F R P K R L N F K L F N I Q V K E V T D N
10. Shuffle 100.7 Translation   Q R L I N N N W G F R P K R L S F K L F N I Q V K E V T T N
                                ◁AAV8

340           350           360
Consensus                       D G V T T I A N N L T S T V Q V F T D S E Y Q L P Y V L G S
Identity 1. AAV1 translation             D G V T T I A N N L T S T V Q V F S D S E Y Q L P Y V L G S
2. AAV2 translation             D G T T T I A N N L T S T V Q V F T D S E Y Q L P Y V L G S
3. AAV3 translation             D G T T T I A N N L T S T V Q V F T D S E Y Q L P Y V L G S
4. AAV4 translation             N G E T T V A N N L T S T V Q I F A D S S Y E L P Y V M D A
5. AAV5 translation             D S T T T I A N N L T S T V Q V F T D D D Y Q L P Y V V G N
6. AAV6 translation             D G V T T I A N N L T S T V Q V F S D S E Y Q L P Y V L G S
7. AAV7 translation             D G V T T I A N N L T S T I Q V F S D S E Y Q L P Y V L G S
8. AAV8 translation             E G T K T I A N N L T S T I Q V F T D S E Y Q L P Y V L G S
9. AAV9 translation             N G V K T I A N N L T S T V Q V F T D S D Y Q L P Y V L G S
10. Shuffle 100.7 Translation   D G V T T I A N N L T S T V Q V F S D S E Y Q L P Y V L G S
                                ◁AAV1
```

FIG. 10D

```
                               370        380        390
Consensus                 A H Q G C L P P F P A D V F M I P Q Y G Y L T L N - - N G S
Identity 1. AAV1 translation       A H Q G C L P P F P A D V F M I P Q Y G Y L T L N - - N G S
2. AAV2 translation       A H Q G C L P P F P A D V F M V P Q Y G Y L T L N - - N G S
3. AAV3 translation       A H Q G C L P P F P A D V F M V P Q Y G Y L T L N - - N G S
4. AAV4 translation       G Q E G S L P P F P N D V F M V P Q Y G Y C G L V T G N T S
5. AAV5 translation       G T E G C L P A F P P Q V F T L P Q Y G Y A T L N R D N T E
6. AAV6 translation       A H Q G C L P P F P A D V F M I P Q Y G Y L T L N - - N G S
7. AAV7 translation       A H Q G C L P P F P A D V F M I P Q Y G Y L T L N - - N G S
8. AAV8 translation       A H Q G C L P P F P A D V F M I P Q Y G Y L T L N - - N G S
9. AAV9 translation       A H E G C L P P F P A D V F M I P Q Y G Y L T L N - - D G S
10. Shuffle 100.7 Translation  A H Q G C L P P F P A D V F M I P Q Y G Y L T L N - - N G S 400        410        420
Consensus                 - Q A V G R S S F Y C L E Y F P S Q M L R T G N N F T F S Y
Identity 1. AAV1 translation       - Q A V G R S S F Y C L E Y F P S Q M L R T G N N F T F S Y
2. AAV2 translation       - Q A V G R S S F Y C L E Y F P S Q M L R T G N N F T F S Y
3. AAV3 translation       - Q A V G R S S F Y C L E Y F P S Q M L R T G N N F Q F S Y
4. AAV4 translation       Q Q Q T D R N A F Y C L E Y F P S Q M L R T G N N F E I T Y
5. AAV5 translation       - N P T E R S S F P C L E Y F P S K M L R T G N N F E F T Y
6. AAV6 translation       - Q A V G R S S F Y C L E Y F P S Q M L R T G N N F T F S Y
7. AAV7 translation       - Q S V G R S S F Y C L E Y F P S Q M L R T G N N F E F S Y
8. AAV8 translation       - Q A V G R S S F Y C L E Y F P S Q M L R T G N N F Q F T Y
9. AAV9 translation       - Q A V G R S S F Y C L E Y F P S Q M L R T G N N F Q F S Y
10. Shuffle 100.7 Translation  - Q A V G R S S F Y C L E Y F P S Q M L R T G N N F T F S Y 430        440        450
Consensus                 T F E D V P F H S S Y A H S Q S L D R L M N P L I D Q Y L Y
Identity 1. AAV1 translation       T F E E V P F H S S Y A H S Q S L D R L M N P L I D Q Y L Y
2. AAV2 translation       T F E D V P F H S S Y A H S Q S L D R L M N P L I D Q Y L Y
3. AAV3 translation       T F E D V P F H S S Y A H S Q S L D R L M N P L I D Q Y L Y
4. AAV4 translation       S F E K V P F H S M Y A H S Q S L D R L M N P L I D Q Y L W
5. AAV5 translation       N F E E V P F H S S F A P S Q N L F K L A N P L V D Q Y L Y
6. AAV6 translation       T F E D V P F H S S Y A H S Q S L D R L M N P L I D Q Y L Y
7. AAV7 translation       S F E D V P F H S S Y A H S Q S L D R L M N P L I D Q Y L Y
8. AAV8 translation       T F E D V P F H S S Y A H S Q S L D R L M N P L I D Q Y L Y
9. AAV9 translation       E F E N V P F H S S Y A H S Q S L D R L M N P L I D Q Y L Y
10. Shuffle 100.7 Translation  T F E E V P F H S S Y A H S Q S L D R L M N P L I D Q Y L Y
```

FIG. 10E

```
                                       460              470              480
Consensus                     Y L N R T Q N - X S G T A X N K X L L F S Q G G P X G M S V
Identity 1. AAV1 translation           Y L N R T Q N - Q S G S A Q N K D L L F S R G S P A G M S V
2. AAV2 translation           Y L S R T N T - P S G T T T Q S R L Q F S Q A G A S D I R D
3. AAV3 translation           Y L N R T Q G T T S G T T N Q S R L L F S Q A G P Q S M S L
4. AAV4 translation           G L Q S T T T G T T L N A G T A T T N F T K L R P T N F S N
5. AAV5 translation           R F V S T N N - - - - - - - T G G V Q F N K N L A G R Y A N
6. AAV6 translation           Y L N R T Q N - Q S G S A Q N K D L L F S R G S P A G M S V
7. AAV7 translation           Y L A R T Q S N P G G T A G N R E L Q F Y Q G G P S T M A E
8. AAV8 translation           Y L S R T Q T - T G G T A N T Q T L G F S Q G G P N T M A N
9. AAV9 translation           Y L S K T I N - - G S G Q N Q Q T L K F S V A G P S N M A V
10. Shuffle 100.7 Translation Y L N R T Q N - Q S G S A Q N K D L L F S R G S P A G M S V
                              AAV1

490              500              510
Consensus                     Q X K N W L P G P C Y R Q Q R V S K T K T D N - - - - - N N
Identity 1. AAV1 translation           Q P K N W L P G P C Y R Q Q R V S K T K T D N - - - - - N N
2. AAV2 translation           Q S R N W L P G P C Y R Q Q R V S K T S A D N - - - - - N N
3. AAV3 translation           Q A R N W L P G P C Y R Q Q R L S K T A N D N - - - - - N N
4. AAV4 translation           F K K N W L P G P S I K Q Q G F S K T A N Q N Y K I P A T G
5. AAV5 translation           T Y K N W F P G P M G R T Q G W N L G S G V N - - - - - R A
6. AAV6 translation           Q P K N W L P G P C Y R Q Q R V S K T K T D N - - - - - N N
7. AAV7 translation           Q A K N W L P G P C F R Q Q R V S K T L D Q N - - - - - N N
8. AAV8 translation           Q A K N W L P G P C Y R Q Q R V S T T T G Q N - - - - - N N
9. AAV9 translation           Q G R N Y I P G P S Y R Q Q R V S T T V T Q N - - - - - N N
10. Shuffle 100.7 Translation Q P K N W L P G P C Y R Q Q R V S K T K T D N - - - - - N N
                              AAV1

520              530              540
Consensus                     S N F A W T G A S K Y H L N G R X S L V N P G P A M A S H K
Identity 1. AAV1 translation           S N F T W T G A S K Y N L N G R E S I I N P G T A M A S H K
2. AAV2 translation           S E Y S W T G A T K Y H L N G R D S L V N P G P A M A S H K
3. AAV3 translation           S N F P W T A A S K Y H L N G R D S L V N P G P A M A S H K
4. AAV4 translation           S D S L I K Y E T H S T L D G R W S A L T P G P P M A T A G
5. AAV5 translation           S V S A F A T T N R M E L E G A S Y Q V P P Q P N G M T N N
6. AAV6 translation           S N F T W T G A S K Y N L N G R E S I I N P G T A M A S H K
7. AAV7 translation           S N F A W T G A T K Y H L N G R N S L V N P G V A M A T H K
8. AAV8 translation           S N F A W T A G T K Y H L N G R N S L A N P G I A M A T H K
9. AAV9 translation           S E F A W P G A S S W A L N G R N S L M N P G P A M A S H K
10. Shuffle 100.7 Translation S N F T W T G A S K Y N L N G R E S I I N P G T A M A S H K
                              AAV1
```

FIG. 10F

```
                                    550              560              570
Consensus               D D E D K F F P M S G V L I F G K Q G A G A S N T A L - - -
Identity 1. AAV1 translation     D D E D K F F P M S G V M I F G K E S A G A S N T A L - - -
2. AAV2 translation     D D E E K F F P Q S G V L I F G K Q G S E K T N V D I - - -
3. AAV3 translation     D D E E K F F P M H G N L I F G K E G T T A S N A E L - - -
4. AAV4 translation     P A D S K F S N S Q L I F A G P K Q N G N T A T V P - - - -
5. AAV5 translation     L Q G S N T Y A L E N T M I F N S Q P A N P G T T A T Y L E
6. AAV6 translation     D D K D K F F P M S G V M I F G K E S A G A S N T A L - - -
7. AAV7 translation     D D E D R F F P S S G V L I F G K T G A T N K T T L - - - -
8. AAV8 translation     D D E E R F F P S N G I L I F G K Q N A A R D N A D Y - - -
9. AAV9 translation     E G E D R F F P L S G S L I F G K Q G T G R D N V D A - - -
10. Shuffle 100.7 Translation  D D E D K F F P M S G V M I F G K E S A G A S N T A L - - -

580              590              600
Consensus               D N V M I T D E E E I K X T N P V A T E R Y G T V A X N L Q
Identity 1. AAV1 translation     D N V M I T D E E E I K A T N P V A T E R F G T V A V N F Q
2. AAV2 translation     E K V M I T D E E E I R T T N P V A T E Q Y G S V S T N L Q
3. AAV3 translation     D N V M I T D E E E I R T T N P V A T E Q Y G T V A N N L Q
4. AAV4 translation     G T L I F T S E E E L A A T N A T D T D M W G N L P G G D Q
5. AAV5 translation     G N M L I T S E S E T Q P V N R V A Y N V G G Q M A T N N Q
6. AAV6 translation     D N V M I T D E E E I K A T N P V A T E R F G T V A V N L Q
7. AAV7 translation     E N V L M T N E E E I R P T N P V A T E E Y G I V S S N L Q
8. AAV8 translation     S D V M L T S E E E I K T T N P V A T E E Y G I V A D N L Q
9. AAV9 translation     D K V M I T N E E E I K T T N P V A T E S Y G Q V A T N H Q
10. Shuffle 100.7 Translation  D N V M I T D E E E I K A T N P V A T E R F G T V A V N F Q 610              620              630
Consensus               S S X T A P A T G D V N A Q G A L P G M V W Q D R D V Y L Q
Identity 1. AAV1 translation     S S S T D P A T G D V H A M G A L P G M V W Q D R D V Y L Q
2. AAV2 translation     R G N R Q A A T A D V N T Q G V L P G M V W Q D R D V Y L Q
3. AAV3 translation     S S N T A P T T G T V N H Q G A L P G M V W Q D R D V Y L Q
4. AAV4 translation     S N S N L P T V D R L T A L G A V P G M V W Q N R D I Y Y Q
5. AAV5 translation     S S T T A P A T G T Y N L Q E I V P G S V W M E R D V Y L Q
6. AAV6 translation     S S S T D P A T G D V H V M G A L P G M V W Q D R D V Y L Q
7. AAV7 translation     A A N T A A Q T Q V V N N Q G A L P G M V W Q N R D V Y L Q
8. AAV8 translation     Q Q N T A P Q I G T V N S Q G A L P G M V W Q N R D V Y L Q
9. AAV9 translation     S A Q A Q A T G W V Q N Q G I L P G M V W Q D R D V Y L Q
10. Shuffle 100.7 Translation  S S S T D P A T G D V H A M G A L P G M V W Q D R D V Y L Q
```

FIG. 10G

|  | 640 | 650 | 660 |
|---|---|---|---|
| Consensus | G P I W A K I P H T D G H F H P S P L M G G F G L K H P P P |  |  |
| Identity |  |  |  |
| 1. AAV1 translation | G P I W A K I P H T D G H F H P S P L M G G F G L K N P P P |  |  |
| 2. AAV2 translation | G P I W A K I P H T D G H F H P S P L M G G F G L K H P P P |  |  |
| 3. AAV3 translation | G P I W A K I P H T D G H F H P S P L M G G F G L K H P P P |  |  |
| 4. AAV4 translation | G P I W A K I P H T D G H F H P S P L I G G F G L K H P P P |  |  |
| 5. AAV5 translation | G P I W A K I P E T G A H F H P S P A M G G F G L K H P P P |  |  |
| 6. AAV6 translation | G P I W A K I P H T D G H F H P S P L M G G F G L K H P P P |  |  |
| 7. AAV7 translation | G P I W A K I P H T D G N F H P S P L M G G F G L K H P P P |  |  |
| 8. AAV8 translation | G P I W A K I P H T D G N F H P S P L M G G F G L K H P P P |  |  |
| 9. AAV9 translation | G P I W A K I P H T D G N F H P S P L M G G F G M K H P P P |  |  |
| 10. Shuffle 100.7 Translation | G P I W A K I P H T D G H F H P S P L M G G F G L K N P P P |  |  |

|  | 670 | 680 | 690 |
|---|---|---|---|
| Consensus | Q I L I K N T P V P A N P P T T F S A T K F A S F I T Q Y S |  |  |
| Identity |  |  |  |
| 1. AAV1 translation | Q I L I K N T P V P A N P P A E F S A T K F A S F I T Q Y S |  |  |
| 2. AAV2 translation | Q I L I K N T P V P A N P S T T F S A A K F A S F I T Q Y S |  |  |
| 3. AAV3 translation | Q I M I K N T P V P A N P P T T F S P A K F A S F I T Q Y S |  |  |
| 4. AAV4 translation | Q I F I K N T P V P A N P A T T F S S T P V N S F I T Q Y S |  |  |
| 5. AAV5 translation | M M L I K N T P V P G N - I T S F S D V P V S S F I T Q Y S |  |  |
| 6. AAV6 translation | Q I L I K N T P V P A N P P A E F S A T K F A S F I T Q Y S |  |  |
| 7. AAV7 translation | Q I L I K N T P V P A N P P E V F T P A K F A S F I T Q Y S |  |  |
| 8. AAV8 translation | Q I L I K N T P V P A D P P T T F N Q S K L N S F I T Q Y S |  |  |
| 9. AAV9 translation | Q I L I K N T P V P A D P P T A F N K D K L N S F I T Q Y S |  |  |
| 10. Shuffle 100.7 Translation | Q I L I K N T P V P A N P P A E F S A T K F A S F I T Q Y S |  |  |

|  | 700 | 710 | 720 |
|---|---|---|---|
| Consensus | T G Q V S V E I E W E L Q K E N S K R W N P E I Q Y T S N Y |  |  |
| Identity |  |  |  |
| 1. AAV1 translation | T G Q V S V E I E W E L Q K E N S K R W N P E V Q Y T S N Y |  |  |
| 2. AAV2 translation | T G Q V S V E I E W E L Q K E N S K R W N P E I Q Y T S N Y |  |  |
| 3. AAV3 translation | T G Q V S V E I E W E L Q K E N S K R W N P E I Q Y T S N Y |  |  |
| 4. AAV4 translation | T G Q V S V Q I D W E I Q K E R S K R W N P E V Q F T S N Y |  |  |
| 5. AAV5 translation | T G Q V T V E M E W E L K K E N S K R W N P E I Q Y T N N Y |  |  |
| 6. AAV6 translation | T G Q V S V E I E W E L Q K E N S K R W N P E V Q Y T S N Y |  |  |
| 7. AAV7 translation | T G Q V S V E I E W E L Q K E N S K R W N P E I Q Y T S N F |  |  |
| 8. AAV8 translation | T G Q V S V E I E W E L Q K E N S K R W N P E I Q Y T S N Y |  |  |
| 9. AAV9 translation | T G Q V S V E I E W E L Q K E N S K R W N P E I Q Y T S N Y |  |  |
| 10. Shuffle 100.7 Translation | T G Q V S V E I E W E L Q K E N S K R W N P E V Q Y T S N Y |  |  |

FIG. 10H

```
                                        730           740          750
Consensus                   X K S A N V D F X V D T N G V Y S E P R P I G T R Y L T R N
Identity                    ▬▬▬ ▄▄▄▄▄▄ ▄▄ ▄▄ ▄▄▄▄▄▄▄▄▄▄▄▄▄▄▄▄▄▄▄▄▄▄▄

1. AAV1 translation         A K S A N V D F T V D N N G L Y T E P R P I G T R Y L T R P
2. AAV2 translation         N K S V N V D F T V D T N G V Y S E P R P I G T R Y L T R N
3. AAV3 translation         N K S V N V D F T V D T N G V Y S E P R P I G T R Y L T R N
4. AAV4 translation         G Q Q N S L L W A P D A A G K Y T E P R A I G T R Y L T H H
5. AAV5 translation         N D P Q F V D F A P D S T G E Y R T T R P I G T R Y L T R P
6. AAV6 translation         A K S A N V D F T V D N N G L Y T E P R P I G T R Y L T R P
7. AAV7 translation         E K Q T G V D F A V D S Q G V Y S E P R P I G T R Y L T R N
8. AAV8 translation         Y K S T S V D F A V N T E G V Y S E P R P I G T R Y L T R N
9. AAV9 translation         Y K S N N V E F A V N T E G V Y S E P R P I G T R Y L T R N
10. Shuffle 100.7 Translation A K S A N I D F T V D N N G L Y T E P R P I G T R Y L T R P
                            ◀AAV6▶ ◀AAV6▶
```

```
                            752
Consensus                   L *
Identity                    ▬

1. AAV1 translation         L *
2. AAV2 translation         L *
3. AAV3 translation         L *
4. AAV4 translation         L *
5. AAV5 translation         L *
6. AAV6 translation         L *
7. AAV7 translation         L *
8. AAV8 translation         L *
9. AAV9 translation         L *
10. Shuffle 100.7 Translation Q *
```

FIG. 10I

| Serotype | Animal | Neutralizing Serum Dilution | | | | | |
|---|---|---|---|---|---|---|---|
| | | AAV1 | AAV2 | AAV8 | Shuffle 100-3 | Shuffle 100-7 | SM 10-2 |
| AAV1 | 1 | 1:1000 | none | 1:250 | 1:250 | 1:1000 | none |
| | 2 | 1:1000 | 1:25 | 1:250 | 1:250 | 1:1000 | none |
| | 3 | 1:1000 | none | 1:250 | 1:250 | 1:1000 | none |
| AAV2 | 1 | 1:50 | 1:500 | 1:100 | none | none | 1:250 |
| | 2 | 1:50 | 1:500 | 1:100 | none | 1:25 | 1:500 |
| | 3 | 1:1000 | 1:1000 | 1:100 | none | 1:100 | 1:500 |
| AAV8 | 1 | 1:100 | none | 1:250 | none | 1:100 | none |
| | 2 | 1:250 | none | 1:100 | none | 1:100 | none |
| | 3 | 1:250 | none | 1:250 | none | 1:250 | none |
| Shuffle 100-3 | 1 | 1:1000 | none | 1:500 | 1:100 | 1:1000 | none |
| | 2 | 1:1000 | none | 1:500 | 1:100 | 1:1000 | none |
| | 3 | 1:1000 | none | 1:100 | 1:250 | 1:1000 | none |
| Shuffle 100-7 | 1 | 1:1000 | none | 1:100 | 1:100 | 1:500 | none |
| | 2 | 1:1000 | none | 1:100 | 1:250 | 1:1000 | none |
| | 3 | 1:1000 | none | 1:50 | 1:100 | 1:1000 | none |

FIG. 11

                          SEQUENCE LISTING

<160> NUMBER OF SEQ ID NOS: 41

<210> SEQ ID NO 1
<211> LENGTH: 736
<212> TYPE: PRT
<213> ORGANISM: adeno-associated virus 1

<400> SEQUENCE: 1

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Thr Pro Ala Ala Val Gly Pro Thr Thr Met Ala Ser Gly Gly Gly
        195                 200                 205

Ala Pro Met Ala Asp Asn Asn Glu Gly Ala Asp Gly Val Gly Asn Ala
    210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Thr Gly Ala Ser Asn Asp Asn His
            260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
    290                 295                 300

Trp Gly Phe Arg Pro Lys Arg Leu Asn Phe Lys Leu Phe Asn Ile Gln
305                 310                 315                 320
```

```
Val Lys Glu Val Thr Thr Asn Asp Gly Val Thr Thr Ile Ala Asn Asn
                325                 330                 335

Leu Thr Ser Thr Val Gln Val Phe Ser Asp Ser Glu Tyr Gln Leu Pro
            340                 345                 350

Tyr Val Leu Gly Ser Ala His Gln Gly Cys Leu Pro Pro Phe Pro Ala
        355                 360                 365

Asp Val Phe Met Ile Pro Gln Tyr Gly Tyr Leu Thr Leu Asn Asn Gly
    370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
                405                 410                 415

Glu Glu Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Asn Arg
        435                 440                 445

Thr Gln Asn Gln Ser Gly Ser Ala Gln Asn Lys Asp Leu Leu Phe Ser
    450                 455                 460

Arg Gly Ser Pro Ala Gly Met Ser Val Gln Pro Lys Asn Trp Leu Pro
465                 470                 475                 480

Gly Pro Cys Tyr Arg Gln Gln Arg Val Ser Lys Thr Lys Thr Asp Asn
                485                 490                 495

Asn Asn Ser Asn Phe Thr Trp Thr Gly Ala Ser Lys Tyr Asn Leu Asn
            500                 505                 510

Gly Arg Glu Ser Ile Ile Asn Pro Gly Thr Ala Met Ala Ser His Lys
        515                 520                 525

Asp Asp Glu Asp Lys Phe Phe Pro Met Ser Gly Val Met Ile Phe Gly
    530                 535                 540

Lys Glu Ser Ala Gly Ala Ser Asn Thr Ala Leu Asp Asn Val Met Ile
545                 550                 555                 560

Thr Asp Glu Glu Glu Ile Lys Ala Thr Asn Pro Val Ala Thr Glu Arg
                565                 570                 575

Phe Gly Thr Val Ala Val Asn Phe Gln Ser Ser Ser Thr Asp Pro Ala
            580                 585                 590

Thr Gly Asp Val His Ala Met Gly Ala Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly His Phe His Pro Ser Pro Leu Met Gly Gly Phe Gly Leu
625                 630                 635                 640

Lys Asn Pro Pro Pro Gln Ile Leu Ile Lys Asn Thr Pro Val Pro Ala
                645                 650                 655

Asn Pro Pro Ala Glu Phe Ser Ala Thr Lys Phe Ala Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Val Gln Tyr Thr Ser Asn
    690                 695                 700

Tyr Ala Lys Ser Ala Asn Val Asp Phe Thr Val Asp Asn Asn Gly Leu
705                 710                 715                 720

Tyr Thr Glu Pro Arg Pro Ile Gly Thr Arg Tyr Leu Thr Arg Pro Leu
                725                 730                 735
```

```
<210> SEQ ID NO 2
<211> LENGTH: 735
<212> TYPE: PRT
<213> ORGANISM: adeno-associated virus 2

<400> SEQUENCE: 2

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
    130                 135                 140

Pro Val Glu His Ser Pro Val Glu Pro Asp Ser Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
    290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
        355                 360                 365

Val Phe Met Val Pro Gln Tyr Gly Tyr Leu Thr Leu Asn Asn Gly Ser
    370                 375                 380
```

```
Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
            405                 410                 415

Asp Val Pro Phe His Ser Ser Tyr Ala His Ser Gln Ser Leu Asp Arg
        420                 425                 430

Leu Met Asn Pro Leu Ile Asp Gln Tyr Leu Tyr Tyr Leu Ser Arg Thr
    435                 440                 445

Asn Thr Pro Ser Gly Thr Thr Thr Gln Ser Arg Leu Gln Phe Ser Gln
450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
            485                 490                 495

Asn Ser Glu Tyr Ser Trp Thr Gly Ala Thr Lys Tyr His Leu Asn Gly
        500                 505                 510

Arg Asp Ser Leu Val Asn Pro Gly Pro Ala Met Ala Ser His Lys Asp
    515                 520                 525

Asp Glu Glu Lys Phe Phe Pro Gln Ser Gly Val Leu Ile Phe Gly Lys
530                 535                 540

Gln Gly Ser Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
            565                 570                 575

Gly Ser Val Ser Thr Asn Leu Gln Arg Gly Asn Arg Gln Ala Ala Thr
        580                 585                 590

Ala Asp Val Asn Thr Gln Gly Val Leu Pro Gly Met Val Trp Gln Asp
    595                 600                 605

Arg Asp Val Tyr Leu Gln Gly Pro Ile Trp Ala Lys Ile Pro His Thr
610                 615                 620

Asp Gly His Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asn
            645                 650                 655

Pro Ser Thr Thr Phe Ser Ala Ala Lys Phe Ala Ser Phe Ile Thr Gln
        660                 665                 670

Tyr Ser Thr Gly Gln Val Ser Val Glu Ile Glu Trp Glu Leu Gln Lys
    675                 680                 685

Glu Asn Ser Lys Arg Trp Asn Pro Glu Ile Gln Tyr Thr Ser Asn Tyr
690                 695                 700

Asn Lys Ser Val Asn Val Asp Phe Thr Val Asp Thr Asn Gly Val Tyr
705                 710                 715                 720

Ser Glu Pro Arg Pro Ile Gly Thr Arg Tyr Leu Thr Arg Asn Leu
            725                 730                 735

<210> SEQ ID NO 3
<211> LENGTH: 736
<212> TYPE: PRT
<213> ORGANISM: adeno-associated virus 3

<400> SEQUENCE: 3

Met Ala Ala Asp Gly Tyr Leu Pro Asp Trp Leu Glu Asp Asn Leu Ser
1               5                   10                  15
```

```
Glu Gly Ile Arg Glu Trp Trp Ala Leu Lys Pro Gly Val Pro Gln Pro
         20                  25                  30

Lys Ala Asn Gln Gln His Gln Asp Asn Arg Arg Gly Leu Val Leu Pro
         35                  40                  45

Gly Tyr Lys Tyr Leu Gly Pro Gly Asn Gly Leu Asp Lys Gly Glu Pro
 50                  55                  60

Val Asn Glu Ala Asp Ala Ala Leu Glu His Asp Lys Ala Tyr Asp
 65                  70                  75                  80

Gln Gln Leu Lys Ala Gly Asp Asn Pro Tyr Leu Lys Tyr Asn His Ala
                 85                  90                  95

Asp Ala Glu Phe Gln Glu Arg Leu Gln Glu Asp Thr Ser Phe Gly Gly
             100                 105                 110

Asn Leu Gly Arg Ala Val Phe Gln Ala Lys Lys Arg Ile Leu Glu Pro
             115                 120                 125

Leu Gly Leu Val Glu Glu Ala Ala Lys Thr Ala Pro Gly Lys Lys Gly
         130                 135                 140

Ala Val Asp Gln Ser Pro Gln Glu Pro Asp Ser Ser Ser Gly Val Gly
145                 150                 155                 160

Lys Ser Gly Lys Gln Pro Ala Arg Lys Arg Leu Asn Phe Gly Gln Thr
                 165                 170                 175

Gly Asp Ser Glu Ser Val Pro Asp Pro Gln Pro Leu Gly Glu Pro Pro
             180                 185                 190

Ala Ala Pro Thr Ser Leu Gly Ser Asn Thr Met Ala Ser Gly Gly Gly
             195                 200                 205

Ala Pro Met Ala Asp Asn Asn Glu Gly Ala Asp Gly Val Gly Asn Ser
         210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                 245                 250                 255

Tyr Lys Gln Ile Ser Ser Gln Ser Gly Ala Ser Asn Asp Asn His Tyr
             260                 265                 270

Phe Gly Tyr Ser Thr Pro Trp Gly Tyr Phe Asp Phe Asn Arg Phe His
             275                 280                 285

Cys His Phe Ser Pro Arg Asp Trp Gln Arg Leu Ile Asn Asn Asn Trp
         290                 295                 300

Gly Phe Arg Pro Lys Lys Leu Ser Phe Lys Leu Phe Asn Ile Gln Val
305                 310                 315                 320

Arg Gly Val Thr Gln Asn Asp Gly Thr Thr Thr Ile Ala Asn Asn Leu
                 325                 330                 335

Thr Ser Thr Val Gln Val Phe Thr Asp Ser Glu Tyr Gln Leu Pro Tyr
             340                 345                 350

Val Leu Gly Ser Ala His Gln Gly Cys Leu Pro Pro Phe Pro Ala Asp
         355                 360                 365

Val Phe Met Val Pro Gln Tyr Gly Tyr Leu Thr Leu Asn Asn Gly Ser
 370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Gln Phe Ser Tyr Thr Phe Glu
             405                 410                 415

Asp Val Pro Phe His Ser Ser Tyr Ala His Ser Gln Ser Leu Asp Arg
             420                 425                 430
```

```
Leu Met Asn Pro Leu Ile Asp Gln Tyr Leu Tyr Tyr Leu Asn Arg Thr
        435                 440                 445

Gln Gly Thr Thr Ser Gly Thr Thr Asn Gln Ser Arg Leu Leu Phe Ser
    450                 455                 460

Gln Ala Gly Pro Gln Ser Met Ser Leu Gln Ala Arg Asn Trp Leu Pro
465                 470                 475                 480

Gly Pro Cys Tyr Arg Gln Gln Arg Leu Ser Lys Thr Ala Asn Asp Asn
            485                 490                 495

Asn Asn Ser Asn Phe Pro Trp Thr Ala Ala Ser Lys Tyr His Leu Asn
                500                 505                 510

Gly Arg Asp Ser Leu Val Asn Pro Gly Pro Ala Met Ala Ser His Lys
            515                 520                 525

Asp Asp Glu Glu Lys Phe Phe Pro Met His Gly Asn Leu Ile Phe Gly
        530                 535                 540

Lys Glu Gly Thr Thr Ala Ser Asn Ala Glu Leu Asp Asn Val Met Ile
545                 550                 555                 560

Thr Asp Glu Glu Glu Ile Arg Thr Thr Asn Pro Val Ala Thr Glu Gln
                565                 570                 575

Tyr Gly Thr Val Ala Asn Asn Leu Gln Ser Ser Asn Thr Ala Pro Thr
            580                 585                 590

Thr Gly Thr Val Asn His Gln Gly Ala Leu Pro Gly Met Val Trp Gln
            595                 600                 605

Asp Arg Asp Val Tyr Leu Gln Gly Pro Ile Trp Ala Lys Ile Pro His
        610                 615                 620

Thr Asp Gly His Phe His Pro Ser Pro Leu Met Gly Gly Phe Gly Leu
625                 630                 635                 640

Lys His Pro Pro Pro Gln Ile Met Ile Lys Asn Thr Pro Val Pro Ala
                645                 650                 655

Asn Pro Pro Thr Thr Phe Ser Pro Ala Lys Phe Ala Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
690                 695                 700

Tyr Asn Lys Ser Val Asn Val Asp Phe Thr Val Asp Thr Asn Gly Val
705                 710                 715                 720

Tyr Ser Glu Pro Arg Pro Ile Gly Thr Arg Tyr Leu Thr Arg Asn Leu
                725                 730                 735

<210> SEQ ID NO 4
<211> LENGTH: 734
<212> TYPE: PRT
<213> ORGANISM: adeno-associated virus 4

<400> SEQUENCE: 4

Met Thr Asp Gly Tyr Leu Pro Asp Trp Leu Glu Asp Asn Leu Ser Glu
1               5                   10                  15

Gly Val Arg Glu Trp Trp Ala Leu Gln Pro Gly Ala Pro Lys Pro Lys
            20                  25                  30

Ala Asn Gln Gln His Gln Asp Asn Ala Arg Gly Leu Val Leu Pro Gly
        35                  40                  45

Tyr Lys Tyr Leu Gly Pro Gly Asn Gly Leu Asp Lys Gly Glu Pro Val
    50                  55                  60

Asn Ala Ala Asp Ala Ala Ala Leu Glu His Asp Lys Ala Tyr Asp Gln
65                  70                  75                  80
```

```
Gln Leu Lys Ala Gly Asp Asn Pro Tyr Leu Lys Tyr Asn His Ala Asp
                85                  90                  95

Ala Glu Phe Gln Gln Arg Leu Gln Gly Asp Thr Ser Phe Gly Gly Asn
            100                 105                 110

Leu Gly Arg Ala Val Phe Gln Ala Lys Lys Arg Val Leu Glu Pro Leu
        115                 120                 125

Gly Leu Val Glu Gln Ala Gly Glu Thr Ala Pro Gly Lys Lys Arg Pro
    130                 135                 140

Leu Ile Glu Ser Pro Gln Pro Asp Ser Ser Thr Gly Ile Gly Lys
145                 150                 155                 160

Lys Gly Lys Gln Pro Ala Lys Lys Leu Val Phe Glu Asp Glu Thr
                165                 170                 175

Gly Ala Gly Asp Gly Pro Pro Glu Gly Ser Thr Ser Gly Ala Met Ser
                180                 185                 190

Asp Asp Ser Glu Met Arg Ala Ala Gly Ala Ala Val Glu Gly
            195                 200                 205

Gly Gln Gly Ala Asp Gly Val Gly Asn Ala Ser Gly Asp Trp His Cys
    210                 215                 220

Asp Ser Thr Trp Ser Glu Gly His Val Thr Thr Thr Ser Thr Arg Thr
225                 230                 235                 240

Trp Val Leu Pro Thr Tyr Asn Asn His Leu Tyr Lys Arg Leu Gly Glu
                245                 250                 255

Ser Leu Gln Ser Asn Thr Tyr Asn Gly Phe Ser Thr Pro Trp Gly Tyr
                260                 265                 270

Phe Asp Phe Asn Arg Phe His Cys His Phe Ser Pro Arg Asp Trp Gln
            275                 280                 285

Arg Leu Ile Asn Asn Asn Trp Gly Met Arg Pro Lys Ala Met Arg Val
    290                 295                 300

Lys Ile Phe Asn Ile Gln Val Lys Glu Val Thr Thr Ser Asn Gly Glu
305                 310                 315                 320

Thr Thr Val Ala Asn Asn Leu Thr Ser Thr Val Gln Ile Phe Ala Asp
                325                 330                 335

Ser Ser Tyr Glu Leu Pro Tyr Val Met Asp Ala Gly Gln Glu Gly Ser
            340                 345                 350

Leu Pro Pro Phe Pro Asn Asp Val Phe Met Val Pro Gln Tyr Gly Tyr
        355                 360                 365

Cys Gly Leu Val Thr Gly Asn Thr Ser Gln Gln Gln Thr Asp Arg Asn
370                 375                 380

Ala Phe Tyr Cys Leu Glu Tyr Phe Pro Ser Gln Met Leu Arg Thr Gly
385                 390                 395                 400

Asn Asn Phe Glu Ile Thr Tyr Ser Phe Glu Lys Val Pro Phe His Ser
                405                 410                 415

Met Tyr Ala His Ser Gln Ser Leu Asp Arg Leu Met Asn Pro Leu Ile
            420                 425                 430

Asp Gln Tyr Leu Trp Gly Leu Gln Ser Thr Thr Thr Gly Thr Thr Leu
        435                 440                 445

Asn Ala Gly Thr Ala Thr Thr Asn Phe Thr Lys Leu Arg Pro Thr Asn
    450                 455                 460

Phe Ser Asn Phe Lys Lys Asn Trp Leu Pro Gly Pro Ser Ile Lys Gln
465                 470                 475                 480

Gln Gly Phe Ser Lys Thr Ala Asn Gln Asn Tyr Lys Ile Pro Ala Thr
                485                 490                 495
```

```
Gly Ser Asp Ser Leu Ile Lys Tyr Glu Thr His Ser Thr Leu Asp Gly
                500                 505                 510

Arg Trp Ser Ala Leu Thr Pro Gly Pro Pro Met Ala Thr Ala Gly Pro
            515                 520                 525

Ala Asp Ser Lys Phe Ser Asn Ser Gln Leu Ile Phe Ala Gly Pro Lys
        530                 535                 540

Gln Asn Gly Asn Thr Ala Thr Val Pro Gly Thr Leu Ile Phe Thr Ser
545                 550                 555                 560

Glu Glu Glu Leu Ala Ala Thr Asn Ala Thr Asp Thr Asp Met Trp Gly
                565                 570                 575

Asn Leu Pro Gly Gly Asp Gln Ser Asn Ser Asn Leu Pro Thr Val Asp
            580                 585                 590

Arg Leu Thr Ala Leu Gly Ala Val Pro Gly Met Val Trp Gln Asn Arg
        595                 600                 605

Asp Ile Tyr Tyr Gln Gly Pro Ile Trp Ala Lys Ile Pro His Thr Asp
610                 615                 620

Gly His Phe His Pro Ser Pro Leu Ile Gly Gly Phe Gly Leu Lys His
625                 630                 635                 640

Pro Pro Pro Gln Ile Phe Ile Lys Asn Thr Pro Val Pro Ala Asn Pro
                645                 650                 655

Ala Thr Thr Phe Ser Ser Thr Pro Val Asn Ser Phe Ile Thr Gln Tyr
            660                 665                 670

Ser Thr Gly Gln Val Ser Val Gln Ile Asp Trp Glu Ile Gln Lys Glu
        675                 680                 685

Arg Ser Lys Arg Trp Asn Pro Glu Val Gln Phe Thr Ser Asn Tyr Gly
690                 695                 700

Gln Gln Asn Ser Leu Leu Trp Ala Pro Asp Ala Ala Gly Lys Tyr Thr
705                 710                 715                 720

Glu Pro Arg Ala Ile Gly Thr Arg Tyr Leu Thr His Leu
                725                 730

<210> SEQ ID NO 5
<211> LENGTH: 724
<212> TYPE: PRT
<213> ORGANISM: adeno-associated virus 5

<400> SEQUENCE: 5

Met Ser Phe Val Asp His Pro Pro Asp Trp Leu Glu Glu Val Gly Glu
1               5                   10                  15

Gly Leu Arg Glu Phe Leu Gly Leu Glu Ala Gly Pro Pro Lys Pro Lys
            20                  25                  30

Pro Asn Gln Gln His Gln Asp Gln Ala Arg Gly Leu Val Leu Pro Gly
        35                  40                  45

Tyr Asn Tyr Leu Gly Pro Gly Asn Gly Leu Asp Arg Gly Glu Pro Val
    50                  55                  60

Asn Arg Ala Asp Glu Val Ala Arg Glu His Asp Ile Ser Tyr Asn Glu
65                  70                  75                  80

Gln Leu Glu Ala Gly Asp Asn Pro Tyr Leu Lys Tyr Asn His Ala Asp
                85                  90                  95

Ala Glu Phe Gln Glu Lys Leu Ala Asp Asp Thr Ser Phe Gly Gly Asn
            100                 105                 110

Leu Gly Lys Ala Val Phe Gln Ala Lys Lys Arg Val Leu Glu Pro Phe
        115                 120                 125

Gly Leu Val Glu Glu Gly Ala Lys Thr Ala Pro Thr Gly Lys Arg Ile
    130                 135                 140
```

```
Asp Asp His Phe Pro Lys Arg Lys Ala Arg Thr Glu Glu Asp Ser
145                 150                 155                 160

Lys Pro Ser Thr Ser Ser Asp Ala Glu Ala Gly Pro Ser Gly Ser Gln
                165                 170                 175

Gln Leu Gln Ile Pro Ala Gln Pro Ala Ser Ser Leu Gly Ala Asp Thr
            180                 185                 190

Met Ser Ala Gly Gly Gly Pro Leu Gly Asp Asn Asn Gln Gly Ala
        195                 200                 205

Asp Gly Val Gly Asn Ala Ser Gly Asp Trp His Cys Asp Ser Thr Trp
    210                 215                 220

Met Gly Asp Arg Val Val Thr Lys Ser Thr Arg Thr Trp Val Leu Pro
225                 230                 235                 240

Ser Tyr Asn Asn His Gln Tyr Arg Glu Ile Lys Ser Gly Ser Val Asp
                245                 250                 255

Gly Ser Asn Ala Asn Ala Tyr Phe Gly Tyr Ser Thr Pro Trp Gly Tyr
            260                 265                 270

Phe Asp Phe Asn Arg Phe His Ser His Trp Ser Pro Arg Asp Trp Gln
        275                 280                 285

Arg Leu Ile Asn Asn Tyr Trp Gly Phe Arg Pro Arg Ser Leu Arg Val
    290                 295                 300

Lys Ile Phe Asn Ile Gln Val Lys Glu Val Thr Val Gln Asp Ser Thr
305                 310                 315                 320

Thr Thr Ile Ala Asn Asn Leu Thr Ser Thr Val Gln Val Phe Thr Asp
                325                 330                 335

Asp Asp Tyr Gln Leu Pro Tyr Val Val Gly Asn Gly Thr Glu Gly Cys
            340                 345                 350

Leu Pro Ala Phe Pro Pro Gln Val Phe Thr Leu Pro Gln Tyr Gly Tyr
        355                 360                 365

Ala Thr Leu Asn Arg Asp Asn Thr Glu Asn Pro Thr Glu Arg Ser Ser
    370                 375                 380

Phe Phe Cys Leu Glu Tyr Phe Pro Ser Lys Met Leu Arg Thr Gly Asn
385                 390                 395                 400

Asn Phe Glu Phe Thr Tyr Asn Phe Glu Glu Val Pro Phe His Ser Ser
                405                 410                 415

Phe Ala Pro Ser Gln Asn Leu Phe Lys Leu Ala Asn Pro Leu Val Asp
            420                 425                 430

Gln Tyr Leu Tyr Arg Phe Val Ser Thr Asn Asn Thr Gly Gly Val Gln
        435                 440                 445

Phe Asn Lys Asn Leu Ala Gly Arg Tyr Ala Asn Thr Tyr Lys Asn Trp
    450                 455                 460

Phe Pro Gly Pro Met Gly Arg Thr Gln Gly Trp Asn Leu Gly Ser Gly
465                 470                 475                 480

Val Asn Arg Ala Ser Val Ser Ala Phe Ala Thr Thr Asn Arg Met Glu
                485                 490                 495

Leu Glu Gly Ala Ser Tyr Gln Val Pro Pro Gln Pro Asn Gly Met Thr
            500                 505                 510

Asn Asn Leu Gln Gly Ser Asn Thr Tyr Ala Leu Glu Asn Thr Met Ile
        515                 520                 525

Phe Asn Ser Gln Pro Ala Asn Pro Gly Thr Thr Ala Thr Tyr Leu Glu
    530                 535                 540

Gly Asn Met Leu Ile Thr Ser Glu Ser Glu Thr Gln Pro Val Asn Arg
545                 550                 555                 560
```

Val Ala Tyr Asn Val Gly Gly Gln Met Ala Thr Asn Asn Gln Ser Ser
                565                 570                 575

Thr Thr Ala Pro Ala Thr Gly Tyr Asn Leu Gln Glu Ile Val Pro
            580                 585                 590

Gly Ser Val Trp Met Glu Arg Asp Val Tyr Leu Gln Gly Pro Ile Trp
        595                 600                 605

Ala Lys Ile Pro Glu Thr Gly Ala His Phe His Pro Ser Pro Ala Met
        610                 615                 620

Gly Gly Phe Gly Leu Lys His Pro Pro Pro Met Met Leu Ile Lys Asn
625                 630                 635                 640

Thr Pro Val Pro Gly Asn Ile Thr Ser Phe Ser Asp Val Pro Val Ser
            645                 650                 655

Ser Phe Ile Thr Gln Tyr Ser Thr Gly Gln Val Thr Val Glu Met Glu
            660                 665                 670

Trp Glu Leu Lys Lys Glu Asn Ser Lys Arg Trp Asn Pro Glu Ile Gln
        675                 680                 685

Tyr Thr Asn Asn Tyr Asn Asp Pro Gln Phe Val Asp Phe Ala Pro Asp
        690                 695                 700

Ser Thr Gly Glu Tyr Arg Thr Thr Arg Pro Ile Gly Thr Arg Tyr Leu
705                 710                 715                 720

Thr Arg Pro Leu

<210> SEQ ID NO 6
<211> LENGTH: 736
<212> TYPE: PRT
<213> ORGANISM: adeno-associated virus 6

<400> SEQUENCE: 6

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Phe Gly Leu Val Glu Glu Gly Ala Lys Thr Ala Pro Gly Lys Lys Arg
    130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Thr Pro Ala Ala Val Gly Pro Thr Thr Met Ala Ser Gly Gly Gly
        195                 200                 205

```
Ala Pro Met Ala Asp Asn Asn Glu Gly Ala Asp Gly Val Gly Asn Ala
    210                 215                 220
Ser Gly Asn Trp His Cys Asp Ser Thr Trp Leu Gly Asp Arg Val Ile
225                 230                 235                 240
Thr Thr Ser Thr Arg Thr Trp Ala Leu Pro Thr Tyr Asn Asn His Leu
            245                 250                 255
Tyr Lys Gln Ile Ser Ser Ala Ser Thr Gly Ala Ser Asn Asp Asn His
                260                 265                 270
Tyr Phe Gly Tyr Ser Thr Pro Trp Gly Tyr Phe Asp Phe Asn Arg Phe
            275                 280                 285
His Cys His Phe Ser Pro Arg Asp Trp Gln Arg Leu Ile Asn Asn Asn
    290                 295                 300
Trp Gly Phe Arg Pro Lys Arg Leu Asn Phe Lys Leu Phe Asn Ile Gln
305                 310                 315                 320
Val Lys Glu Val Thr Thr Asn Asp Gly Val Thr Ile Ala Asn Asn
                325                 330                 335
Leu Thr Ser Thr Val Gln Val Phe Ser Asp Ser Glu Tyr Gln Leu Pro
            340                 345                 350
Tyr Val Leu Gly Ser Ala His Gln Gly Cys Leu Pro Pro Phe Pro Ala
            355                 360                 365
Asp Val Phe Met Ile Pro Gln Tyr Gly Tyr Leu Thr Leu Asn Asn Gly
    370                 375                 380
Ser Gln Ala Val Gly Arg Ser Ser Phe Tyr Cys Leu Glu Tyr Phe Pro
385                 390                 395                 400
Ser Gln Met Leu Arg Thr Gly Asn Asn Phe Thr Phe Ser Tyr Thr Phe
            405                 410                 415
Glu Asp Val Pro Phe His Ser Ser Tyr Ala His Ser Gln Ser Leu Asp
            420                 425                 430
Arg Leu Met Asn Pro Leu Ile Asp Gln Tyr Leu Tyr Tyr Leu Asn Arg
    435                 440                 445
Thr Gln Asn Gln Ser Gly Ser Ala Gln Asn Lys Asp Leu Leu Phe Ser
    450                 455                 460
Arg Gly Ser Pro Ala Gly Met Ser Val Gln Pro Lys Asn Trp Leu Pro
465                 470                 475                 480
Gly Pro Cys Tyr Arg Gln Gln Arg Val Ser Lys Thr Lys Thr Asp Asn
            485                 490                 495
Asn Asn Ser Asn Phe Thr Trp Thr Gly Ala Ser Lys Tyr Asn Leu Asn
            500                 505                 510
Gly Arg Glu Ser Ile Ile Asn Pro Gly Thr Ala Met Ala Ser His Lys
    515                 520                 525
Asp Asp Lys Asp Lys Phe Phe Pro Met Ser Gly Val Met Ile Phe Gly
    530                 535                 540
Lys Glu Ser Ala Gly Ala Ser Asn Thr Ala Leu Asp Asn Val Met Ile
545                 550                 555                 560
Thr Asp Glu Glu Glu Ile Lys Ala Thr Asn Pro Val Ala Thr Glu Arg
            565                 570                 575
Phe Gly Thr Val Ala Val Asn Leu Gln Ser Ser Ser Thr Asp Pro Ala
            580                 585                 590
Thr Gly Asp Val His Val Met Gly Ala Leu Pro Gly Met Val Trp Gln
    595                 600                 605
Asp Arg Asp Val Tyr Leu Gln Gly Pro Ile Trp Ala Lys Ile Pro His
    610                 615                 620
```

```
Thr Asp Gly His Phe His Pro Ser Pro Leu Met Gly Gly Phe Gly Leu
625                 630                 635                 640

Lys His Pro Pro Gln Ile Leu Ile Lys Asn Thr Pro Val Pro Ala
        645                 650                 655

Asn Pro Pro Ala Glu Phe Ser Ala Thr Lys Phe Ala Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Val Gln Tyr Thr Ser Asn
690                 695                 700

Tyr Ala Lys Ser Ala Asn Val Asp Phe Thr Val Asp Asn Asn Gly Leu
705                 710                 715                 720

Tyr Thr Glu Pro Arg Pro Ile Gly Thr Arg Tyr Leu Thr Arg Pro Leu
            725                 730                 735
```

<210> SEQ ID NO 7
<211> LENGTH: 737
<212> TYPE: PRT
<213> ORGANISM: adeno-associated virus 7

<400> SEQUENCE: 7

```
Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asn Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Ala Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Ser Val Gly Ser Gly Thr Val Ala Ala Gly Gly
        195                 200                 205

Gly Ala Pro Met Ala Asp Asn Asn Glu Gly Ala Asp Gly Val Gly Asn
    210                 215                 220

Ala Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255
```

```
Leu Tyr Lys Gln Ile Ser Ser Glu Thr Ala Gly Ser Thr Asn Asp Asn
                260                 265                 270

Thr Tyr Phe Gly Tyr Ser Thr Pro Trp Gly Tyr Phe Asp Phe Asn Arg
            275                 280                 285

Phe His Cys His Phe Ser Pro Arg Asp Trp Gln Arg Leu Ile Asn Asn
        290                 295                 300

Asn Trp Gly Phe Arg Pro Lys Lys Leu Arg Phe Lys Leu Phe Asn Ile
305                 310                 315                 320

Gln Val Lys Glu Val Thr Thr Asn Asp Gly Val Thr Thr Ile Ala Asn
                325                 330                 335

Asn Leu Thr Ser Thr Ile Gln Val Phe Ser Asp Ser Glu Tyr Gln Leu
            340                 345                 350

Pro Tyr Val Leu Gly Ser Ala His Gln Gly Cys Leu Pro Pro Phe Pro
        355                 360                 365

Ala Asp Val Phe Met Ile Pro Gln Tyr Gly Tyr Leu Thr Leu Asn Asn
    370                 375                 380

Gly Ser Gln Ser Val Gly Arg Ser Ser Phe Tyr Cys Leu Glu Tyr Phe
385                 390                 395                 400

Pro Ser Gln Met Leu Arg Thr Gly Asn Asn Phe Glu Phe Ser Tyr Ser
                405                 410                 415

Phe Glu Asp Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ala
        435                 440                 445

Arg Thr Gln Ser Asn Pro Gly Gly Thr Ala Gly Asn Arg Glu Leu Gln
    450                 455                 460

Phe Tyr Gln Gly Gly Pro Ser Thr Met Ala Glu Gln Ala Lys Asn Trp
465                 470                 475                 480

Leu Pro Gly Pro Cys Phe Arg Gln Gln Arg Val Ser Lys Thr Leu Asp
                485                 490                 495

Gln Asn Asn Asn Ser Asn Phe Ala Trp Thr Gly Ala Thr Lys Tyr His
            500                 505                 510

Leu Asn Gly Arg Asn Ser Leu Val Asn Pro Gly Val Ala Met Ala Thr
        515                 520                 525

His Lys Asp Asp Glu Asp Arg Phe Phe Pro Ser Ser Gly Val Leu Ile
    530                 535                 540

Phe Gly Lys Thr Gly Ala Thr Asn Lys Thr Thr Leu Glu Asn Val Leu
545                 550                 555                 560

Met Thr Asn Glu Glu Glu Ile Arg Pro Thr Asn Pro Val Ala Thr Glu
                565                 570                 575

Glu Tyr Gly Ile Val Ser Ser Asn Leu Gln Ala Ala Asn Thr Ala Ala
            580                 585                 590

Gln Thr Gln Val Val Asn Asn Gln Gly Ala Leu Pro Gly Met Val Trp
        595                 600                 605

Gln Asn Arg Asp Val Tyr Leu Gln Gly Pro Ile Trp Ala Lys Ile Pro
    610                 615                 620

His Thr Asp Gly Asn Phe His Pro Ser Pro Leu Met Gly Gly Phe Gly
625                 630                 635                 640

Leu Lys His Pro Pro Pro Gln Ile Leu Ile Lys Asn Thr Pro Val Pro
                645                 650                 655

Ala Asn Pro Pro Glu Val Phe Thr Pro Ala Lys Phe Ala Ser Phe Ile
            660                 665                 670
```

```
Thr Gln Tyr Ser Thr Gly Gln Val Ser Val Glu Ile Glu Trp Glu Leu
            675                 680                 685

Gln Lys Glu Asn Ser Lys Arg Trp Asn Pro Glu Ile Gln Tyr Thr Ser
    690                 695                 700

Asn Phe Glu Lys Gln Thr Gly Val Asp Phe Ala Val Asp Ser Gln Gly
705                 710                 715                 720

Val Tyr Ser Glu Pro Arg Pro Ile Gly Thr Arg Tyr Leu Thr Arg Asn
                725                 730                 735

Leu

<210> SEQ ID NO 8
<211> LENGTH: 738
<212> TYPE: PRT
<213> ORGANISM: adeno-associated virus 8

<400> SEQUENCE: 8

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp Gln
65                  70                  75                  80

Gln Leu Gln Ala Gly Asp Asn Pro Tyr Leu Arg Tyr Asn His Ala Asp
                85                  90                  95

Ala Glu Phe Gln Glu Arg Leu Gln Glu Asp Thr Ser Phe Gly Gly Asn
            100                 105                 110

Leu Gly Arg Ala Val Phe Gln Ala Lys Lys Arg Val Leu Glu Pro Leu
        115                 120                 125

Gly Leu Val Glu Glu Gly Ala Lys Thr Ala Pro Gly Lys Lys Arg Pro
    130                 135                 140

Val Glu Pro Ser Pro Gln Arg Ser Pro Asp Ser Ser Thr Gly Ile Gly
145                 150                 155                 160

Lys Lys Gly Gln Gln Pro Ala Arg Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Ala Pro Ser Gly Val Gly Pro Asn Thr Met Ala Ala Gly Gly Gly
        195                 200                 205

Ala Pro Met Ala Asp Asn Asn Glu Gly Ala Asp Gly Val Gly Ser Ser
    210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Gly Thr Ser Gly Gly Ala Thr Asn Asp Asn
            260                 265                 270

Thr Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn
    290                 295                 300
```

-continued

```
Asn Asn Trp Gly Phe Arg Pro Lys Arg Leu Ser Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
                340                 345                 350

Leu Pro Tyr Val Leu Gly Ser Ala His Gln Gly Cys Leu Pro Pro Phe
                355                 360                 365

Pro Ala Asp Val Phe Met Ile Pro Gln Tyr Gly Tyr Leu Thr Leu Asn
370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Gln Phe Thr Tyr
                405                 410                 415

Thr Phe Glu Asp Val Pro Phe His Ser Ser Tyr Ala His Ser Gln Ser
                420                 425                 430

Leu Asp Arg Leu Met Asn Pro Leu Ile Asp Gln Tyr Leu Tyr Tyr Leu
                435                 440                 445

Ser Arg Thr Gln Thr Thr Gly Gly Thr Ala Asn Thr Gln Thr Leu Gly
450                 455                 460

Phe Ser Gln Gly Gly Pro Asn Thr Met Ala Asn Gln Ala Lys Asn Trp
465                 470                 475                 480

Leu Pro Gly Pro Cys Tyr Arg Gln Gln Arg Val Ser Thr Thr Thr Gly
                485                 490                 495

Gln Asn Asn Asn Ser Asn Phe Ala Trp Thr Ala Gly Thr Lys Tyr His
                500                 505                 510

Leu Asn Gly Arg Asn Ser Leu Ala Asn Pro Gly Ile Ala Met Ala Thr
                515                 520                 525

His Lys Asp Asp Glu Glu Arg Phe Phe Pro Ser Asn Gly Ile Leu Ile
                530                 535                 540

Phe Gly Lys Gln Asn Ala Ala Arg Asp Asn Ala Asp Tyr Ser Asp Val
545                 550                 555                 560

Met Leu Thr Ser Glu Glu Glu Ile Lys Thr Thr Asn Pro Val Ala Thr
                565                 570                 575

Glu Glu Tyr Gly Ile Val Ala Asp Asn Leu Gln Gln Gln Asn Thr Ala
                580                 585                 590

Pro Gln Ile Gly Thr Val Asn Ser Gln Gly Ala Leu Pro Gly Met Val
                595                 600                 605

Trp Gln Asn Arg Asp Val Tyr Leu Gln Gly Pro Ile Trp Ala Lys Ile
610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Ile Lys Asn Thr Pro Val
                645                 650                 655

Pro Ala Asp Pro Pro Thr Thr Phe Asn Gln Ser Lys Leu Asn Ser Phe
                660                 665                 670

Ile Thr Gln Tyr Ser Thr Gly Gln Val Ser Val Glu Ile Glu Trp Glu
                675                 680                 685

Leu Gln Lys Glu Asn Ser Lys Arg Trp Asn Pro Glu Ile Gln Tyr Thr
                690                 695                 700

Ser Asn Tyr Tyr Lys Ser Thr Ser Val Asp Phe Ala Val Asn Thr Glu
705                 710                 715                 720
```

```
Gly Val Tyr Ser Glu Pro Arg Pro Ile Gly Thr Arg Tyr Leu Thr Arg
                    725                 730                 735

Asn Leu

<210> SEQ ID NO 9
<211> LENGTH: 736
<212> TYPE: PRT
<213> ORGANISM: adeno-associated virus 9

<400> SEQUENCE: 9

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350
```

```
Pro Tyr Val Leu Gly Ser Ala His Glu Gly Cys Leu Pro Phe Pro
            355                 360                 365

Ala Asp Val Phe Met Ile Pro Gln Tyr Gly Tyr Leu Thr Leu Asn Asp
370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
                420                 425                 430

Asp Arg Leu Met Asn Pro Leu Ile Asp Gln Tyr Leu Tyr Tyr Leu Ser
            435                 440                 445

Lys Thr Ile Asn Gly Ser Gly Gln Asn Gln Gln Thr Leu Lys Phe Ser
        450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
    530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735

<210> SEQ ID NO 10
<211> LENGTH: 735
<212> TYPE: PRT
<213> ORGANISM: Artificial sequence
<220> FEATURE:
```

<223> OTHER INFORMATION: Synthetic amino acid sequence

<400> SEQUENCE: 10

```
Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
            85                  90                  95

Asp Ala Glu Phe Gln Glu Arg Leu Lys Glu Asp Thr Ser Phe Gly Gly
        100                 105                 110

Asn Leu Gly Arg Ala Val Phe Gln Ala Lys Lys Arg Val Leu Glu Pro
    115                 120                 125

Leu Gly Leu Val Glu Glu Pro Val Lys Thr Ala Pro Gly Lys Lys Arg
130                 135                 140

Pro Val Glu His Ser Pro Val Glu Pro Asp Ser Ser Ser Gly Thr Gly
145                 150                 155                 160

Lys Ala Gly Gln Gln Pro Ala Arg Lys Arg Leu Asn Phe Gly Gln Thr
            165                 170                 175

Gly Asp Ala Asp Ser Val Pro Asp Pro Gln Pro Leu Gly Gln Pro Pro
        180                 185                 190

Ala Ala Pro Ser Gly Leu Gly Thr Asn Thr Met Ala Thr Gly Ser Gly
    195                 200                 205

Ala Pro Met Ala Asp Asn Asn Glu Gly Ala Asp Gly Val Gly Asn Ser
210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
            245                 250                 255

Tyr Lys Gln Ile Ser Ser Gln Ser Gly Ala Ser Asn Asp Asn His Tyr
        260                 265                 270

Phe Gly Tyr Ser Thr Pro Trp Gly Tyr Phe Asp Phe Asn Arg Phe His
    275                 280                 285

Cys His Phe Ser Pro Arg Asp Trp Gln Arg Leu Ile Asn Asn Asn Trp
290                 295                 300

Gly Phe Arg Pro Lys Arg Leu Lys Phe Lys Leu Phe Asn Ile Gln Val
305                 310                 315                 320

Lys Glu Val Thr Gln Asn Asp Gly Thr Thr Ile Ala Asn Asn Leu
            325                 330                 335

Thr Ser Thr Val Gln Val Phe Thr Asp Ser Glu Tyr Gln Leu Pro Tyr
        340                 345                 350

Val Leu Gly Ser Ala His Gln Gly Cys Leu Pro Pro Phe Pro Ala Asp
    355                 360                 365

Val Phe Met Val Pro Gln Tyr Gly Tyr Leu Thr Leu Asn Asn Gly Ser
370                 375                 380

Gln Ala Val Gly Arg Ser Ser Phe Tyr Cys Leu Glu Tyr Phe Pro Ser
385                 390                 395                 400
```

Gln Met Leu Arg Thr Gly Asn Asn Phe Thr Phe Ser Tyr Thr Phe Glu
                405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Ser Arg Thr
        435                 440                 445

Asp Thr Pro Ser Gly Thr Thr Thr Gln Ser Arg Leu Gln Phe Ser Gln
    450                 455                 460

Ala Gly Ala Ser Asp Ile Arg Asn Gln Ser Arg Asn Trp Leu Pro Gly
465                 470                 475                 480

Pro Cys Tyr Arg Gln Gln Arg Val Ser Lys Thr Ser Ala Asp Asn Asn
                485                 490                 495

Asn Ser Glu Tyr Ser Trp Thr Gly Ala Thr Lys Tyr His Leu Asn Gly
            500                 505                 510

Arg Asp Ser Leu Val Asn Pro Gly Pro Ala Met Ala Ser His Lys Asp
        515                 520                 525

Asp Glu Glu Lys Phe Phe Pro Gln Ser Gly Val Leu Ile Phe Gly Lys
    530                 535                 540

Gln Gly Ser Glu Lys Thr Ser Val Asp Ile Glu Lys Val Met Ile Thr
545                 550                 555                 560

Asp Glu Glu Glu Ile Arg Thr Thr Asn Pro Val Ala Thr Glu Gln Tyr
                565                 570                 575

Gly Ser Val Ser Thr Asn Leu Gln Arg Gly Asn Arg Gln Ala Ala Thr
            580                 585                 590

Ala Asp Val Asn Thr Gln Gly Val Leu Pro Gly Met Val Trp Gln Asp
        595                 600                 605

Arg Asp Val Tyr Leu Gln Gly Pro Ile Trp Ala Lys Ile Pro His Thr
    610                 615                 620

Asp Gly His Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asn
                645                 650                 655

Pro Ser Thr Thr Phe Ser Ala Ala Lys Phe Ala Ser Phe Ile Thr Gln
            660                 665                 670

Tyr Ser Thr Gly Gln Val Ser Val Glu Ile Glu Trp Glu Leu Gln Lys
        675                 680                 685

Glu Asn Ser Lys Arg Trp Asn Pro Glu Val Gln Tyr Thr Ser Asn Tyr
    690                 695                 700

Asn Lys Ser Val Asn Val Asp Phe Thr Val Asp Thr Asn Gly Val Tyr
705                 710                 715                 720

Ser Glu Pro Arg Pro Ile Gly Thr Arg Tyr Leu Thr Arg Asn Gln
                725                 730                 735

<210> SEQ ID NO 11
<211> LENGTH: 736
<212> TYPE: PRT
<213> ORGANISM: Artificial sequence
<220> FEATURE:
<223> OTHER INFORMATION: Synthetic amino acid sequence

<400> SEQUENCE: 11

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro
                20                  25                  30

-continued

```
Lys Pro Ala Glu Arg His Lys Asp Asp Ser Arg Gly Leu Val Leu Pro
             35                  40                  45

Gly Tyr Lys Tyr Leu Gly Pro Phe Asn Gly Leu Asp Lys Gly Glu Pro
 50                  55                  60

Val Asn Glu Ala Asp Ala Ala Leu Glu His Asp Lys Ala Tyr Asp
 65                  70                  75                  80

Gln Gln Leu Lys Ala Gly Asp Asn Pro Tyr Leu Lys Tyr Asn His Ala
                 85                  90                  95

Asp Ala Glu Phe Gln Gln Arg Leu Gln Gly Asp Thr Ser Phe Gly Gly
            100                 105                 110

Asn Leu Gly Arg Ala Val Phe Gln Ala Lys Lys Arg Val Leu Glu Pro
            115                 120                 125

Leu Gly Leu Val Glu Gln Ala Gly Glu Thr Ala Pro Gly Lys Lys Arg
        130                 135                 140

Pro Leu Ile Glu Ser Pro Gln Gln Pro Asp Ser Ser Thr Gly Ile Gly
145                 150                 155                 160

Lys Lys Gly Lys Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Thr Pro Ala Ala Val Gly Pro Thr Thr Met Ala Ser Gly Gly Gly
        195                 200                 205

Ala Pro Met Ala Asp Asn Asn Glu Gly Ala Asp Gly Val Gly Asn Ala
    210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Thr Gly Ala Ser Asn Asp Asn His
            260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
    290                 295                 300

Trp Gly Phe Arg Pro Lys Arg Leu Asn Phe Lys Leu Phe Asn Ile Gln
305                 310                 315                 320

Val Lys Glu Val Thr Thr Asn Asp Gly Val Thr Thr Ile Ala Asn Asn
                325                 330                 335

Leu Thr Ser Thr Val Gln Val Phe Ser Asp Ser Asp Tyr Gln Leu Pro
            340                 345                 350

Tyr Val Leu Gly Ser Ala His Glu Gly Cys Leu Pro Pro Phe Pro Ala
        355                 360                 365

Asp Val Phe Met Val Pro Gln Tyr Gly Tyr Leu Thr Leu Asn Asn Gly
    370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
                405                 410                 415

Glu Asp Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Asn Arg
        435                 440                 445
```

Thr Gln Asn Gln Ser Gly Ser Ala Gln Asn Lys Asp Leu Leu Phe Ser
    450                 455                 460

Arg Gly Ser Pro Ala Gly Met Ser Val Gln Pro Lys Asn Trp Leu Pro
465                 470                 475                 480

Gly Pro Cys Tyr Arg Gln Gln Arg Val Ser Lys Thr Lys Thr Asp Asn
                485                 490                 495

Asn Asn Ser Asn Phe Thr Trp Thr Gly Ala Ser Lys Tyr Asn Leu Asn
                500                 505                 510

Gly Arg Glu Ser Ile Ile Asn Pro Gly Thr Ala Met Ala Ser His Lys
            515                 520                 525

Asp Asp Lys Asp Lys Phe Phe Pro Met Ser Gly Val Met Ile Phe Gly
    530                 535                 540

Lys Glu Ser Ala Gly Ala Ser Asn Thr Ala Leu Asp Asn Val Met Ile
545                 550                 555                 560

Thr Asp Glu Glu Glu Ile Lys Ala Thr Asn Pro Val Ala Thr Glu Arg
                565                 570                 575

Phe Gly Thr Val Ala Val Asn Leu Gln Ser Ser Ser Thr Asp Pro Ala
                580                 585                 590

Thr Gly Asp Val His Val Met Gly Ala Leu Pro Gly Met Val Trp Gln
    595                 600                 605

Asp Arg Asp Val Tyr Leu Gln Gly Pro Ile Trp Ala Lys Ile Pro His
    610                 615                 620

Thr Asp Gly His Phe His Pro Ser Pro Leu Met Gly Gly Phe Gly Leu
625                 630                 635                 640

Lys Asn Pro Pro Pro Gln Ile Leu Ile Lys Asn Thr Pro Val Pro Ala
                645                 650                 655

Asn Pro Pro Ala Glu Phe Ser Ala Thr Lys Phe Ala Ser Phe Ile Thr
                660                 665                 670

Gln Tyr Ser Thr Gly Gln Val Ser Val Glu Ile Glu Trp Glu Leu Gln
            675                 680                 685

Lys Glu Asn Ser Lys Arg Trp Asn Pro Glu Val Gln Tyr Thr Ser Asn
    690                 695                 700

Tyr Ala Lys Ser Ala Asn Val Asp Phe Thr Val Asp Asn Asn Gly Leu
705                 710                 715                 720

Tyr Thr Glu Pro Arg Pro Ile Gly Thr Arg Tyr Leu Thr Arg Pro Leu
                725                 730                 735

<210> SEQ ID NO 12
<211> LENGTH: 736
<212> TYPE: PRT
<213> ORGANISM: Artificial sequence
<220> FEATURE:
<223> OTHER INFORMATION: Synthetic amino acid sequence

<400> SEQUENCE: 12

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

```
Gln Gln Leu Lys Ala Gly Asp Asn Pro Tyr Leu Lys Tyr Asn His Ala
                85                  90                  95

Asp Ala Glu Phe Gln Gln Arg Leu Gln Gly Asp Thr Ser Phe Gly Gly
            100                 105                 110

Asn Leu Gly Arg Ala Val Phe Gln Ala Lys Lys Arg Val Leu Glu Pro
            115                 120                 125

Leu Gly Leu Val Glu Gln Ala Gly Glu Thr Ala Pro Gly Lys Lys Arg
    130                 135                 140

Pro Leu Ile Glu Ser Pro Gln Gln Pro Asp Ser Ser Thr Gly Ile Gly
145                 150                 155                 160

Lys Lys Gly Lys Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Thr Pro Ala Ala Val Gly Pro Thr Thr Met Ala Ser Gly Gly Gly
            195                 200                 205

Ala Pro Met Ala Asp Asn Asn Glu Gly Ala Asp Gly Val Gly Asn Ala
            210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Thr Gly Ala Ser Asn Asp Asn His
                260                 265                 270

Tyr Phe Gly Tyr Ser Thr Pro Trp Gly Tyr Phe Asp Phe Asn Arg Phe
            275                 280                 285

His Cys His Phe Ser Pro Arg Asp Trp Gln Arg Leu Ile Asn Asn Asn
            290                 295                 300

Trp Gly Phe Arg Pro Lys Arg Leu Asn Phe Lys Leu Phe Asn Ile Gln
305                 310                 315                 320

Val Lys Glu Val Thr Thr Asn Asp Gly Val Thr Thr Ile Ala Asn Asn
                325                 330                 335

Leu Thr Ser Thr Val Gln Val Phe Ser Asp Ser Asp Tyr Gln Leu Pro
            340                 345                 350

Tyr Val Leu Gly Ser Ala His Glu Gly Cys Leu Pro Pro Phe Pro Ala
            355                 360                 365

Asp Val Phe Met Val Pro Gln Tyr Gly Tyr Leu Thr Leu Asn Asn Gly
    370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
                405                 410                 415

Glu Asp Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Asn Arg
            435                 440                 445

Thr Gln Asn Gln Ser Gly Ser Ala Gln Asn Lys Asp Leu Leu Phe Ser
    450                 455                 460

Arg Gly Ser Pro Thr Gly Met Ser Val Gln Pro Lys Asn Trp Leu Pro
465                 470                 475                 480

Gly Pro Cys Tyr Arg Gln Gln Arg Val Ser Lys Thr Lys Thr Asp Asn
                485                 490                 495
```

```
Asn Asn Ser Asn Phe Thr Trp Thr Gly Ala Ser Lys Tyr Asn Leu Asn
            500                 505                 510

Gly Arg Glu Ser Ile Ile Asn Pro Gly Thr Ala Met Ala Ser His Lys
        515                 520                 525

Asp Asp Lys Asp Lys Phe Phe Pro Met Ser Gly Val Met Ile Phe Gly
    530                 535                 540

Lys Glu Ser Ala Gly Ala Ser Asn Thr Ala Leu Asp Asn Val Met Ile
545                 550                 555                 560

Thr Asp Glu Glu Ile Lys Ala Thr Asn Pro Val Ala Thr Glu Arg
                565                 570                 575

Phe Gly Thr Val Ala Val Asn Leu Gln Ser Ser Thr Asp Pro Ala
            580                 585                 590

Thr Gly Asp Val His Ala Met Gly Ala Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly His Phe His Pro Ser Pro Leu Met Gly Gly Phe Gly Leu
625                 630                 635                 640

Lys Asn Pro Pro Pro Gln Ile Leu Ile Lys Asn Thr Pro Val Pro Ala
                645                 650                 655

Asn Pro Pro Ala Glu Phe Ser Ala Thr Lys Phe Ala Ser Phe Ile Thr
        660                 665                 670

Gln Tyr Ser Thr Gly Gln Val Ser Val Glu Ile Glu Trp Glu Leu Gln
    675                 680                 685

Lys Glu Asn Ser Lys Arg Trp Asn Pro Glu Val Gln Tyr Thr Ser Asn
690                 695                 700

Tyr Ala Lys Ser Ala Asn Val Asp Phe Thr Val Asp Asn Asn Gly Leu
705                 710                 715                 720

Tyr Thr Glu Pro Arg Pro Ile Gly Thr Arg Tyr Leu Thr Arg Pro Leu
                725                 730                 735

<210> SEQ ID NO 13
<211> LENGTH: 736
<212> TYPE: PRT
<213> ORGANISM: Artificial sequence
<220> FEATURE:
<223> OTHER INFORMATION: Synthetic amino acid sequence

<400> SEQUENCE: 13

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125
```

```
Leu Gly Leu Val Glu Glu Gly Ala Lys Thr Ala Pro Gly Lys Lys Arg
        130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Thr Pro Ala Ala Val Gly Pro Thr Thr Met Ala Ser Gly Gly Gly
        195                 200                 205

Ala Pro Met Ala Asp Asn Asn Glu Gly Ala Asp Gly Val Gly Asn Ala
210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Thr Gly Ala Ser Asn Asp Asn His
            260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
290                 295                 300

Trp Gly Phe Arg Pro Lys Arg Leu Ser Phe Lys Leu Phe Asn Ile Gln
305                 310                 315                 320

Val Lys Glu Val Thr Thr Asn Asp Gly Val Thr Thr Ile Ala Asn Asn
                325                 330                 335

Leu Thr Ser Thr Val Gln Val Phe Ser Asp Ser Glu Tyr Gln Leu Pro
            340                 345                 350

Tyr Val Leu Gly Ser Ala His Gln Gly Cys Leu Pro Pro Phe Pro Ala
        355                 360                 365

Asp Val Phe Met Ile Pro Gln Tyr Gly Tyr Leu Thr Leu Asn Asn Gly
370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
                405                 410                 415

Glu Glu Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Asn Arg
        435                 440                 445

Thr Gln Asn Gln Ser Gly Ser Ala Gln Asn Lys Asp Leu Leu Phe Ser
450                 455                 460

Arg Gly Ser Pro Ala Gly Met Ser Val Gln Pro Lys Asn Trp Leu Pro
465                 470                 475                 480

Gly Pro Cys Tyr Arg Gln Gln Arg Val Ser Lys Thr Lys Thr Asp Asn
                485                 490                 495

Asn Asn Ser Asn Phe Thr Trp Thr Gly Ala Ser Lys Tyr Asn Leu Asn
            500                 505                 510

Gly Arg Glu Ser Ile Ile Asn Pro Gly Thr Ala Met Ala Ser His Lys
        515                 520                 525

Asp Asp Glu Asp Lys Phe Phe Pro Met Ser Gly Val Met Ile Phe Gly
530                 535                 540
```

Lys Glu Ser Ala Gly Ala Ser Asn Thr Ala Leu Asp Asn Val Met Ile
545                 550                 555                 560

Thr Asp Glu Glu Ile Lys Ala Thr Asn Pro Val Ala Thr Glu Arg
            565                 570                 575

Phe Gly Thr Val Ala Val Asn Phe Gln Ser Ser Ser Thr Asp Pro Ala
                580                 585                 590

Thr Gly Asp Val His Ala Met Gly Ala Leu Pro Gly Met Val Trp Gln
            595                 600                 605

Asp Arg Asp Val Tyr Leu Gln Gly Pro Ile Trp Ala Lys Ile Pro His
            610                 615                 620

Thr Asp Gly His Phe His Pro Ser Pro Leu Met Gly Gly Phe Gly Leu
625                 630                 635                 640

Lys Asn Pro Pro Pro Gln Ile Leu Ile Lys Asn Thr Pro Val Pro Ala
                645                 650                 655

Asn Pro Pro Ala Glu Phe Ser Ala Thr Lys Phe Ala Ser Phe Ile Thr
            660                 665                 670

Gln Tyr Ser Thr Gly Gln Val Ser Val Glu Ile Glu Trp Glu Leu Gln
            675                 680                 685

Lys Glu Asn Ser Lys Arg Trp Asn Pro Glu Val Gln Tyr Thr Ser Asn
690                 695                 700

Tyr Ala Lys Ser Ala Asn Ile Asp Phe Thr Val Asp Asn Asn Gly Leu
705                 710                 715                 720

Tyr Thr Glu Pro Arg Pro Ile Gly Thr Arg Tyr Leu Thr Arg Pro Gln
                725                 730                 735

<210> SEQ ID NO 14
<211> LENGTH: 23
<212> TYPE: DNA
<213> ORGANISM: Artificial sequence
<220> FEATURE:
<223> OTHER INFORMATION: Synthetic nucleic acid sequence

<400> SEQUENCE: 14
gcggaagctt cgatcaacta cgc                                              23

<210> SEQ ID NO 15
<211> LENGTH: 41
<212> TYPE: DNA
<213> ORGANISM: Artificial sequence
<220> FEATURE:
<223> OTHER INFORMATION: Synthetic nucleic acid sequence

<400> SEQUENCE: 15
ggggcggccg caattacaga ttacgagtca ggtatctggt g                          41

<210> SEQ ID NO 16
<211> LENGTH: 25
<212> TYPE: DNA
<213> ORGANISM: Artificial sequence
<220> FEATURE:
<223> OTHER INFORMATION: Synthetic nucleic acid sequence
<220> FEATURE:
<221> NAME/KEY: misc_feature
<222> LOCATION: (5)..(6)
<223> OTHER INFORMATION: n is a, c, g, or t

<400> SEQUENCE: 16
cattnnkgac cagtctagga actgg                                            25

<210> SEQ ID NO 17

```
<211> LENGTH: 90
<212> TYPE: DNA
<213> ORGANISM: Artificial sequence
<220> FEATURE:
<223> OTHER INFORMATION: Synthetic nucleic acid sequence
<220> FEATURE:
<221> NAME/KEY: misc_feature
<222> LOCATION: (21)..(22)
<223> OTHER INFORMATION: n is a, c, g, or t
<220> FEATURE:
<221> NAME/KEY: misc_feature
<222> LOCATION: (69)..(70)
<223> OTHER INFORMATION: n is a, c, g, or t

<400> SEQUENCE: 17
gccacaagga cgatgaagaa nnkttttttc ctcagagcgg ggttctcatc tttgggaagc    60
aaggctcann kaaaacaagt gtggacattg                                    90

<210> SEQ ID NO 18
<211> LENGTH: 35
<212> TYPE: DNA
<213> ORGANISM: Artificial sequence
<220> FEATURE:
<223> OTHER INFORMATION: Synthetic nucleic acid sequence
<220> FEATURE:
<221> NAME/KEY: misc_feature
<222> LOCATION: (18)..(19)
<223> OTHER INFORMATION: n is a, c, g, or t

<400> SEQUENCE: 18
ccaacctcca gagaggcnnk agacaagcag ctacc                              35

<210> SEQ ID NO 19
<211> LENGTH: 57
<212> TYPE: DNA
<213> ORGANISM: Artificial sequence
<220> FEATURE:
<223> OTHER INFORMATION: Synthetic nucleic acid sequence
<220> FEATURE:
<221> NAME/KEY: misc_feature
<222> LOCATION: (18)..(19)
<223> OTHER INFORMATION: n is a, c, g, or t
<220> FEATURE:
<221> NAME/KEY: misc_feature
<222> LOCATION: (42)..(43)
<223> OTHER INFORMATION: n is a, c, g, or t

<400> SEQUENCE: 19
ccaactacaa caagtctnnk aatgtggact ttactgtgga cnnkaatggc gtgtatt      57

<210> SEQ ID NO 20
<211> LENGTH: 20
<212> TYPE: DNA
<213> ORGANISM: Artificial sequence
<220> FEATURE:
<223> OTHER INFORMATION: Synthetic nucleic acid sequence

<400> SEQUENCE: 20
catgggaaag gtgccagacg                                               20

<210> SEQ ID NO 21
<211> LENGTH: 20
<212> TYPE: DNA
<213> ORGANISM: Artificial sequence
<220> FEATURE:
<223> OTHER INFORMATION: Synthetic nucleic acid sequence

<400> SEQUENCE: 21
accatcggca gccatacctg                                               20
```

<210> SEQ ID NO 22
<211> LENGTH: 2208
<212> TYPE: DNA
<213> ORGANISM: Artificial sequence
<220> FEATURE:
<223> OTHER INFORMATION: Synthetic nucleic acid sequence

<400> SEQUENCE: 22

```
atggctgccg atggttatct tccagattgg ctcgaggaca ctctctctga aggaataaga      60
cagtggtgga agctcaaacc tggcccacca ccaccaaagc ccgcagagcg cataaggac      120
gacagcaggg gtcttgtgct tcctgggtac aagtacctcg acccttcaa cggactcgac      180
aagggagagc cggtcaacga ggcagacgcc gcggccctcg agcacgacaa agcctatgac      240
cggcagctcg acagcggaga caacccgtac ctcaagtaca ccacgccga cgcggagttt      300
caggaacgcc ttaaagaaga tacgtctttt gggggcaacc tcggacgagc agtcttccag      360
gcgaaaaaga gggttcttga acctctgggc ctggttgagg aacctgttaa gacggctccg      420
ggaaaaaaga ggccggtaga gcactctcct gtggagccag actcctcctc gggaaccgga      480
aaggcgggcc agcagcctgc aagaaaaaga ttgaattttg gtcagactgg agacgcagac      540
tcagtacctg accccagcc tctcggacag ccaccagcag ccccctctgg tctgggaact      600
aatacgatgg ctacaggcag tggcgcacca atggcagaca taacgagggg cgccgacgga      660
gtgggtaatt cctcgggaaa ttggcattgc gattccacat ggatgggcga cagagtcatc      720
accaccagca cccgaacctg ggcccctgccc acctacaaca accacctcta caaacaaatt      780
tccagccaat caggagcctc gaacgacaat cactactttg gctacagcac cccttggggg      840
tattttgact tcaacagatt ccactgccac ttttcaccac gtgactggca agactcatc      900
aacaacaact ggggattccg acccaagaga ctcaagttca gctctttaa cattcaagtc      960
aaagaggtca cgcagaatga cggtacgacg acgattgcca ataaccttac cagcacggtt     1020
caggtgtta ctgactcgga gtaccagctc ccgtacgtcc tcggctcggc gcatcaagga     1080
tgcctcccgc cgttccagc agacgtcttc atggtgccac agtatggata cctcacctg      1140
aacaacggga gtcaggcagt aggacgctct tcatttact gcctggagta cttttccttct     1200
cagatgctgc gtaccggtaa caactttacc ttcagctaca cttttgagga cgttcctttc     1260
cacagcagct acgctcacag ccagagtctg gaccgtctca tgaatcctct catcgaccag     1320
tacctgtatt acttgagcag aacagacact ccaagtggaa ccaccacgca gtcaaggctt     1380
cagttttctc aggccggagc gagtgacatt cggaaccagt ctaggaactg gcttcctgga     1440
ccctgttacc gccagcagcg agtatcaaag acatctgcgg ataacaacaa cagtgaatac     1500
tcgtggactg gagctaccaa gtaccacctc aatggcagag actctctggt gaatccgggc     1560
ccggccatgg caagccacaa ggacgatgaa gaaaagtttt ttcctcagag cggggttctc     1620
atctttggga agcaaggctc agagaaaaca agtgtggaca ttgaaaaggt catgattaca     1680
gacgaagagg aaatcaggac aaccaatccc gtggctacgg agcagtatgg ttctgtatct     1740
accaacctcc agagaggcaa cagacaagca gctaccgcag atgtcaacac acaaggcgtt     1800
cttccaggca tggtctggca ggacagagat gtgtaccttc aggggcccat ctgggcaaag     1860
attccacaca cggacggaca ttttcaccc tctcccctca tgggtggatt cggacttaaa     1920
cacccctcctc cacagattct catcaagaac acccccgtac ctgcgaatcc ttcgaccacc     1980
ttcagtgcgg caaagttgc ttccttcatc acacagtact ccacgggaca ggtcagcgtg     2040
```

```
gagatcgagt gggagctgca gaaggaaaac agcaaacgct ggaatcccga agttcagtac    2100
acttccaact acaacaagtc tgttaatgtg gactttactg tggacactaa tggcgtgtat    2160
tcagagcctc gccccattgg caccagatac ctgactcgta atcagtaa                 2208

<210> SEQ ID NO 23
<211> LENGTH: 2211
<212> TYPE: DNA
<213> ORGANISM: Artificial sequence
<220> FEATURE:
<223> OTHER INFORMATION: Synthetic nucleic acid sequence

<400> SEQUENCE: 23
atggctgctg atggttatct tccagattgg ctcgaggaca ctctctctga aggaataaga      60
cagtggtgga agctcaaacc tggcccacca ccaccaaagc ccgcagagcg gcataaggac     120
gacagcaggg gtcttgtgct tcctgggtac aagtacctcg acccttcaa cggactcgac     180 aagggagagc cggtcaacga ggcagacgca gcggccctcg agcacgacaa ggcctacgac    240
cagcagctca aggccggtga caaccccytac ctcaagtaca ccacgccga cgcggagttc    300 cagcagcggc ttcagggcga cacatcgttt gggggcaacc tcggcagagc agtcttccag    360
gccaaaaaga gggttcttga acctcttggt ctggttgagc aagcgggtga cggctcct      420 ggaaagaaga gaccgttgat tgaatccccc cagcagcccg actcctccac gggtatcggc    480
aaaaaaggca agcagccggc taaaaagaga ctcaattttg gtcagactgg cgactcagag    540
tcagtccccg acccacaacc tctcggagaa cctccagcaa cccccgctgc tgtgggacct    600
actacaatgg cttcaggtgg tggcgcacca atggcagaca taacgaagg cgccgacgga    660 gtgggtaatg cctcaggaaa ttggcattgc gattccacat ggctgggcga cagagtcatc    720
accaccagca cccgcacctg gccttgccc acctacaata accacctcta caagcaaatc    780
tccagtgctt caacgggggc cagcaacgac aaccactact cggctacag cacccctgg    840 gggtattttg acttcaacag attccactgc cactttttcac cacgtgactg gcagcgactc    900
atcaacaaca ttggggatt ccggcccaag agactcaact tcaaactctt caacatccaa    960
gtcaaggagg tcacgacgaa tgatggcgtc acaaccatcg ctaataacct taccagcacg    1020
gttcaagtct ctcggactc agactatcag ctcccgtacg tgctcgggtc ggctcacgag    1080
ggctgcctcc cgccgttccc agcagacgtc ttcatggtgc acagtatgg ataccytcacc    1140 ctgaacaacg ggagtcaggc agtaggacgc tcttcatttt actgcctgga gtactttcct    1200
tctcagatgc tgcgtaccgg aaacaacttt accttcagct acactttga ggacgttcct    1260 ttccacagca gctacgctca cagccagagt ctggaccgtc tcatgaatcc tctcatcgac    1320
cagtacctgt attacctgaa cagaactcag aatcagtccg gaagtgccca aaacaaggac    1380 ttgctgtttta gccgggggtc tccagctggc atgtctgttc agcccaaaaa ctggctacct    1440
ggaccctgtt atcggcagca gcgcgtttct aaaacaaaaa cagacaacaa caacagcaac    1500
tttacctgga ctggtgcttc aaaatataac cttaatgggc gtgaatctat aatcaaccct    1560
ggcactgcta tggcctcaca caagacgac aaagacaagt ctttccat gagcggtgtc    1620 atgattttg aaaggagag cgccggagct tcaaacactg cattggacaa tgtcatgatc    1680
acagacgaag aggaaatcaa agccactaac cccgtggcca ccgaaagatt tgggactgtg    1740
gcagtcaatc tccagagcag cagcacagac cctgcgaccg gagatgtgca tgttatggga    1800
gccttacctg gaatggtgtg gcaagacaga gacgtatacc tgcagggtcc catttgggcc    1860
aaaattcctc acacagatgg acactttcac ccgtctcctc ttatgggcgg ctttggactc    1920
```

```
aagaacccgc ctcctcagat cctcatcaaa acacgcctg ttcctgcgaa tcctccggcg    1980
gagttttcag ctacaaagtt tgcttcattc atcacccaat actccacagg acaagtgagt    2040
gtggaaattg aatgggagct gcagaaagaa acagcaagc gctggaatcc cgaagtgcag    2100
tacacatcca attatgcaaa atctgccaac gttgatttta ctgtggacaa caatggactt    2160
tatactgagc ctcgccccat tggcacccgt tacctcaccc gtcccctgta a            2211

<210> SEQ ID NO 24
<211> LENGTH: 2211
<212> TYPE: DNA
<213> ORGANISM: Artificial sequence
<220> FEATURE:
<223> OTHER INFORMATION: Synthetic nucleic acid sequence

<400> SEQUENCE: 24
atggctgctg atggttatct tccagattgg ctcgaggaca ctctctctga aggaataaga     60
cagtggtgga agctcaaacc tggcccacca ccaccaaagc ccgcagagcg gcataaggac    120
gacagcaggg gtcttgtgct tcctgggtac aagtacctcg gacccttcaa cggactcgac    180
aagggagagc cggtcaacga ggcagacgca gcggccctcg agcacgacaa ggcctacgac    240
cagcagctca aggccggtga caacccctac ctcaagtaca ccacgccga cgcggagttc    300 cagcagcggt tcagggcga cacatcgttt ggggcaacc tcggcagagc agtcttccag    360
gccaaaaaga gggttcttga acctcttggt ctggttgagc aagcgggtga acggctcct    420 ggaaagaaga accgttgat tgaatccccc cagcagcccg actcctccac gggtatcggc    480 aaaaaggca agcagccggc taaaagaga ctcaattttg gtcagactgg cgactcagag    540
tcagtccccg acccacaacc tctcggagaa cctccagcaa ccccgctgc tgtgggacct    600 actacaatgg cttcaggtgg tggcgcacca atggcagaca ataacgaagg cgccgacgga    660
gtgggtaatg cctcaggaaa ttggcattgc gattccacat ggctgggcga cagagtcatc    720
accaccagca cccgcacctg gcccttgccc acctacaata accacctcta caagcaaatc    780
tccagtgctt caacgggggc cagcaacgac aaccactact cggctacag cacccctgg    840 gggtattttg acttcaacag attccactgc cacttttcac cacgtgactg gcagcgactc    900
atcaacaaca attggggatt ccggcccaag agactcaact tcaaactctt caacatccaa    960
gtcaaggagg tcacgacgaa tgatggcgtc acaaccatcg ctaataacct taccagcacg   1020
gttcaagtct ctcggactc agactatcag ctcccgtacg tgctcgggtc ggctcacgag   1080
ggctgcctcc cgccgttccc agcagacgtc ttcatggtgc acagtatgg atacctcacc   1140 ctgaacaacg ggagtcaggc agtaggacgc tcttcatttt actgcctgga gtactttcct   1200
tctcagatgc tgcgtaccgg aaacaacttt accttcagct acacttttga ggacgttcct   1260
ttccacagca gctacgctca gccagagt ctggaccgtc tcatgaatcc tctcatcgac   1320
cagtacctgt attactgaa cagaactcag aatcagtccg aagtgccca aaacaaggac   1380 ttgctgttta gccgggggtc tccaactggc atgtctgttc agcccaaaaa ctggctacct   1440 ggacccctgtt atcggcagca gcgcgttct aaaacaaaaa cagacaacaa caacagcaac   1500
tttacctgga ctggtgcttc aaaatataac cttaatgggc gtgaatctat aatcaaccct   1560
ggcactgcta tggcctcaca caagacgac aaagacaagt ctttccccat gagcggtgtc   1620
atgatttttg gaaggagag cgccggagct tcaaacactg cattgacaa tgtcatgatc   1680 acagacgaag aggaaatcaa agccactaac cccgtggcca ctgaaagatt tgggactgtg   1740
```

| gcagtcaatc tccagagcag cagcacagac cctgcgaccg agatgtgca tgccatggga | 1800 |
| gccttacctg gaatggtgtg gcaagacaga gacgtatacc tgcagggtcc tatttgggcc | 1860 |
| aaaattcctc acacggatgg acactttcac ccgtctcctc tcatgggcgg ctttggactc | 1920 |
| aagaacccgc ctcctcagat cctcatcaaa aacacgcctg ttcctgcgaa tcctccggcg | 1980 |
| gagttttcag ctacaaagtt tgcttcattc atcacccagt attccacagg acaagtgagc | 2040 |
| gtggagattg aatgggagct gcagaaagaa aacagcaaac gctggaatcc gaagtgcag | 2100 |
| tatacatcta actatgcaaa atctgccaac gttgatttca ctgtggacaa caatggactt | 2160 |
| tatactgagc tcgccccat tggcacccgt tacctcaccc gtcccctgta a | 2211 |

<210> SEQ ID NO 25
<211> LENGTH: 2211
<212> TYPE: DNA
<213> ORGANISM: Artificial sequence
<220> FEATURE:
<223> OTHER INFORMATION: Synthetic nucleic acid sequence

<400> SEQUENCE: 25

| atggctgccg atggttatct tccagattgg ctcgaggaca acctctctga gggcattcgc | 60 |
| gagtggtggg cgctgaaacc tggagccccg aagcccaaag ccaaccagca aaagcaggac | 120 |
| gacggccggg gtctggtgct tcctggctac aagtacctcg gacccttcaa cggactcgac | 180 |
| aaggggggagc ccgtcaacgc ggcggatgca gcggccctcg agcacgacaa ggcctacgac | 240 |
| cagcagctca aagcgggtga caatccgtac ctgcggtata ccacgccga cgccgagttt | 300 |
| caggagcgtc tgcaagaaga tacgtctttt ggggggcaacc tcgggcgagc agtcttccag | 360 |
| gccaagaagc gggttctcga acctctcggt ctggttgagg aaggcgctaa gacggctcct | 420 |
| ggaaagaaac gtccggtaga gcaatcgcca aagagccag actcctcctc gggcatcggc | 480 |
| aagacaggcc agcagcccgc taaaaagaga ctcaattttg gtcagactgg cgactcagag | 540 |
| tcagtccccg acccacaacc tctcggagaa cctccagcaa cccccgctgc tgtgggacct | 600 |
| actacaatgg cttcaggcgg tggcgcacca atggcagaca taacgaagg cgccgacgga | 660 |
| gtgggtaatg cctcaggaaa ttggcattgc gattccacat ggctgggcga cagagtcatc | 720 |
| accaccagca cccgaacatg ggccttgccc acctataaca accacctcta caagcaaatc | 780 |
| tccagtgctt cgacggggc cagcaacgac aaccactact tcggctacag cacccctgg | 840 |
| gggtattttg acttttaacag attccactgc cacttttcac cacgtgactg gcagcgactc | 900 |
| atcaacaaca actggggatt ccggcccaag agactcagct tcaagctctt caacatccag | 960 |
| gtcaaggagg tcacgacgaa tgatggcgtc acaaccatcg ctaataacct taccagcacg | 1020 |
| gttcaagtct tctcggactc ggagtaccag cttccgtacg tcctcggctc tgcgcaccag | 1080 |
| ggctgcctcc ctccgttccc ggcggacgtg ttcatgattc cgcaatacgg ctacctgacg | 1140 |
| ctcaacaatg gcagccaagc cgtgggacgt tcatccttt actgcctgga atatttccct | 1200 |
| tctcagatgc tgagaacggg caacaacttt accttcagct acaccttga ggaagtgcct | 1260 |
| ttccacagca gctacgcgca cagccagagc ctggaccggc tgatgaatcc tctcatcgat | 1320 |
| caataccgt attacctgaa cagaactcaa aatcagtccg gaagtgccca aaacaaggac | 1380 |
| ttgctgttta gccgtgggtc tccagctggc atgtctgttc agcccaaaaa ctggctacct | 1440 |
| ggaccctgtt atcggcagca gcgcgttct aaaacaaaaa cagacaacaa caacagcaat | 1500 |
| tttacctgga ctggtgcttc aaaatataac ctcaatgggc gtgaatccat catcaaccct | 1560 |
| ggcactgcta tggcctcaca taaagacgac gaagacaagt tcttcccat gagcggtgtc | 1620 |

-continued

```
atgattttg gaaagagag cgccggagct tcaaacactg cattggacaa tgtcatgatt    1680
acagacgaag aggaaattaa agccactaac cctgtggcca ccgaaagatt tgggaccgtg    1740
gcagtcaatt tccagagcag cagcacagac cctgcgaccg gagatgtgca tgctatggga    1800
gcattacctg gcatggtgtg gcaagataga gacgtgtacc tgcagggtcc catttgggcc    1860
aaaattcctc acacagatgg acactttcac ccgtctcctc ttatgggcgg ctttggactc    1920
aagaacccgc ctcctcagat cctcatcaaa aacacgcctg ttcctgcgaa tcctccggcg    1980
gagttttcag ctacaaagtt tgcttcattc atcacccaat actccacagg acaagtgagc    2040
gtggagattg aatgggagct gcagaaagaa acagcaaac gctggaatcc cgaagtgcag    2100
tatacatcta actatgcaaa atctgccaac attgatttca ctgtggacaa caatggactt    2160
tatactgagc ctcgccccat tggcacccgt tacctcaccc gtccccagta a             2211
```

<210> SEQ ID NO 26
<211> LENGTH: 736
<212> TYPE: PRT
<213> ORGANISM: Artificial sequence
<220> FEATURE:
<223> OTHER INFORMATION: Synthetic amino acid sequence

<400> SEQUENCE: 26

```
Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Ala Pro Ser Gly Val Gly Ser Leu Thr Met Ala Ser Gly Gly Gly
        195                 200                 205

Ala Pro Met Ala Asp Asn Asn Glu Gly Ala Asp Gly Val Gly Asn Ala
    210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255
```

```
Tyr Lys Gln Ile Ser Ser Ala Ser Thr Gly Ala Ser Asn Asp Asn His
            260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
    290                 295                 300

Trp Gly Phe Arg Pro Lys Arg Leu Asn Phe Lys Leu Phe Asn Ile Gln
305                 310                 315                 320

Val Lys Glu Val Thr Thr Asn Asp Gly Val Thr Thr Ile Ala Asn Asn
                325                 330                 335

Leu Thr Ser Thr Val Gln Val Phe Ser Asp Ser Glu Tyr Gln Leu Pro
            340                 345                 350

Tyr Val Leu Gly Ser Ala His Gln Gly Cys Leu Pro Pro Phe Pro Ala
        355                 360                 365

Asp Val Phe Met Ile Pro Gln Tyr Gly Tyr Leu Thr Leu Asn Asn Gly
    370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
                405                 410                 415

Glu Glu Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Asn Arg
        435                 440                 445

Thr Gln Asn Gln Ser Gly Ser Ala Gln Asn Lys Asp Leu Leu Phe Ser
    450                 455                 460

Arg Gly Ser Pro Ala Gly Met Ser Val Gln Pro Lys Asn Trp Leu Pro
465                 470                 475                 480

Gly Pro Cys Tyr Arg Gln Gln Cys Val Ser Lys Thr Lys Thr Asp Asn
                485                 490                 495

Asn Asn Ser Asn Phe Thr Trp Thr Gly Ala Ser Lys Tyr Asn Leu Asn
            500                 505                 510

Gly Arg Glu Ser Ile Ile Asn Pro Gly Thr Ala Met Ala Ser His Lys
        515                 520                 525

Asp Asp Lys Asp Lys Phe Phe Pro Met Ser Gly Val Met Ile Phe Gly
    530                 535                 540

Lys Glu Ser Ala Gly Ala Ser Asn Thr Ala Leu Asp Asn Val Met Ile
545                 550                 555                 560

Thr Asp Glu Glu Glu Ile Lys Ala Thr Asn Pro Val Ala Thr Glu Arg
                565                 570                 575

Phe Gly Thr Val Ala Val Asn Leu Gln Ser Ser Ser Thr Asp Pro Ala
            580                 585                 590

Thr Gly Asp Val His Val Met Gly Ala Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly His Phe His Pro Ser Pro Leu Met Gly Gly Phe Gly Leu
625                 630                 635                 640

Lys Asn Pro Pro Pro Gln Ile Leu Ile Lys Asn Thr Pro Val Pro Ala
                645                 650                 655

Asn Pro Pro Ala Glu Phe Ser Ala Thr Lys Phe Ala Ser Phe Ile Thr
            660                 665                 670
```

```
Gln Tyr Ser Thr Gly Gln Val Ser Val Glu Ile Glu Trp Glu Leu Gln
            675                 680                 685

Lys Glu Asn Ser Lys Arg Trp Asn Pro Glu Val Gln Tyr Thr Ser Asn
        690                 695                 700

Tyr Ala Lys Ser Ala Asn Val Asp Phe Thr Val Asp Asn Asn Gly Leu
705                 710                 715                 720

Tyr Thr Glu Pro Arg Pro Ile Gly Thr Arg Tyr Leu Thr Arg Pro Leu
                725                 730                 735

<210> SEQ ID NO 27
<211> LENGTH: 736
<212> TYPE: PRT
<213> ORGANISM: Artificial sequence
<220> FEATURE:
<223> OTHER INFORMATION: Synthetic amino acid sequence

<400> SEQUENCE: 27

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Val Asn Gln Gln Lys Gln Asp Asn Ala Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Phe Gly Leu Val Glu Glu Gly Ala Lys Thr Ala Pro Gly Lys Lys Arg
    130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Thr Pro Ala Ala Val Gly Pro Thr Thr Met Ala Ser Gly Gly Gly
        195                 200                 205

Ala Pro Met Ala Asp Asn Asn Glu Gly Ala Asp Gly Val Gly Asn Ala
    210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Thr Gly Ala Ser Asn Asp Asn His
            260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
    290                 295                 300
```

```
Trp Gly Phe Arg Pro Lys Arg Leu Asn Phe Lys Leu Phe Asn Ile Gln
305                 310                 315                 320

Val Lys Glu Val Thr Thr Asn Asp Gly Val Thr Thr Ile Ala Asn Asn
            325                 330                 335

Leu Thr Ser Thr Val Gln Val Phe Ser Asp Ser Glu Tyr Gln Leu Pro
            340                 345                 350

Tyr Val Leu Gly Ser Ala His Gln Gly Cys Leu Pro Pro Phe Pro Ala
            355                 360                 365

Asp Val Phe Met Ile Pro Gln Tyr Gly Tyr Leu Thr Leu Asn Asn Gly
            370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
            405                 410                 415

Glu Asp Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Asn Arg
            435                 440                 445

Thr Gln Asn Gln Ser Gly Ser Ala Gln Asn Lys Asp Leu Leu Phe Ser
            450                 455                 460

Arg Gly Ser Pro Thr Gly Met Ser Val Gln Pro Lys Asn Trp Leu Pro
465                 470                 475                 480

Gly Pro Cys Tyr Arg Gln Gln Arg Val Ser Lys Thr Lys Thr Asp Asn
            485                 490                 495

Asn Asn Ser Asn Phe Thr Trp Thr Gly Ala Ser Lys Tyr Asn Leu Asn
            500                 505                 510

Gly Arg Glu Ser Ile Ile Asn Pro Gly Thr Ala Met Ala Ser His Lys
            515                 520                 525

Asp Asp Glu Asp Lys Phe Phe Pro Met Ser Gly Val Met Ile Phe Gly
            530                 535                 540

Lys Glu Ser Ala Gly Ala Ser Asn Thr Ala Leu Asp Asn Val Met Ile
545                 550                 555                 560

Thr Asp Glu Glu Glu Ile Lys Ala Thr Asn Pro Val Ala Thr Glu Arg
                565                 570                 575

Phe Gly Thr Val Ala Val Asn Leu Gln Ser Ser Ser Thr Asp Pro Ala
            580                 585                 590

Thr Gly Asp Val His Ala Met Gly Ala Leu Pro Gly Met Val Trp Gln
            595                 600                 605

Asp Arg Asp Val Tyr Leu Gln Gly Pro Ile Trp Ala Lys Ile Pro His
            610                 615                 620

Thr Asp Gly His Phe His Pro Ser Pro Leu Met Gly Gly Phe Gly Leu
625                 630                 635                 640

Lys His Pro Pro Pro Gln Ile Leu Ile Lys Asn Thr Pro Val Pro Ala
            645                 650                 655

Asn Pro Pro Ala Glu Phe Ser Ala Thr Lys Phe Ala Ser Phe Ile Thr
            660                 665                 670

Gln Tyr Ser Thr Gly Gln Val Ser Val Glu Ile Glu Trp Glu Leu Gln
            675                 680                 685

Lys Glu Asn Ser Lys Arg Trp Asn Pro Glu Val Gln Tyr Thr Ser Asn
            690                 695                 700

Tyr Ala Lys Ser Ala Asn Val Asp Phe Thr Val Asp Asn Asn Gly Leu
705                 710                 715                 720
```

-continued

Tyr Thr Glu Pro Arg Pro Ile Gly Thr Arg Tyr Leu Thr Arg Pro Leu
                725                 730                 735

<210> SEQ ID NO 28
<211> LENGTH: 723
<212> TYPE: PRT
<213> ORGANISM: Artificial sequence
<220> FEATURE:
<223> OTHER INFORMATION: Synthetic amino acid sequence

<400> SEQUENCE: 28

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Val Asn Gln Gln Lys Gln Asp Asn Ala Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Phe Gly Leu Val Glu Glu Gly Ala Lys Thr Ala Pro Gly Lys Lys Arg
    130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Thr Pro Ala Ala Val Gly Pro Thr Thr Met Ala Ser Gly Gly Gly
        195                 200                 205

Ala Pro Met Ala Asp Asn Asn Glu Gly Ala Asp Gly Val Gly Asn Ala
    210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Thr Gly Ala Ser Asn Asp Asn His
            260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
    290                 295                 300

Trp Gly Phe Arg Pro Lys Arg Leu Asn Phe Lys Leu Phe Asn Gln Val
305                 310                 315                 320

Lys Glu Thr Thr Asp Val Thr Ile Ala Asn Asn Leu Thr Ser Thr
                325                 330                 335

Val Gln Val Phe Ser Asp Ser Glu Tyr Gln Leu Pro Tyr Val Leu Gly
            340                 345                 350

```
Ser Ala His Gln Gly Cys Leu Pro Pro Phe Pro Ala Asp Val Phe Met
            355                 360                 365

Ile Pro Gln Tyr Gly Tyr Leu Thr Leu Asn Asn Gly Ser Gln Ala Val
370                 375                 380

Gly Arg Ser Ser Phe Tyr Cys Leu Glu Tyr Phe Pro Ser Gln Met Leu
385                 390                 395                 400

Arg Thr Gly Asn Asn Phe Thr Ser Tyr Thr Phe Glu Asp Val Pro Phe
                405                 410                 415

His Ser Ser Tyr Ala His Ser Gln Ser Leu Asp Arg Leu Met Asn Pro
            420                 425                 430

Leu Ile Asp Gln Tyr Leu Tyr Tyr Leu Asn Arg Thr Gln Asn Gln Ser
        435                 440                 445

Gly Ser Ala Gln Asn Lys Asp Leu Leu Phe Ser Arg Gly Ser Pro Thr
450                 455                 460

Gly Met Ser Val Gln Pro Lys Asn Trp Leu Pro Gly Pro Cys Tyr Arg
465                 470                 475                 480

Gln Gln Arg Val Ser Lys Thr Lys Thr Asp Asn Asn Asn Ser Asn Phe
                485                 490                 495

Thr Trp Thr Gly Ala Ser Lys Tyr Asn Leu Asn Gly Arg Glu Ser Ile
            500                 505                 510

Ile Asn Pro Gly Thr Ala Met Ala Ser His Lys Asp Asp Glu Asp Lys
        515                 520                 525

Phe Phe Pro Met Ser Gly Val Met Ile Phe Gly Lys Glu Ser Ala Gly
        530                 535                 540

Ala Ser Asn Thr Ala Leu Asp Asn Val Met Ile Thr Asp Glu Glu Ala
545                 550                 555                 560

Thr Asn Pro Val Ala Thr Glu Arg Phe Gly Thr Val Ala Val Asn Leu
                565                 570                 575

Gln Ser Ser Pro Ala Thr Asp Val His Ala Met Gly Ala Leu Pro Gly
            580                 585                 590

Met Val Trp Gln Asp Arg Asp Val Tyr Leu Gln Gly Pro Ile Trp Ala
        595                 600                 605

Lys Ile Pro His Thr Asp Gly His Phe His Pro Ser Pro Leu Met Gly
610                 615                 620

Gly Phe Gly Leu Lys His Pro Pro Gln Ile Leu Ile Lys Asn Thr
625                 630                 635                 640

Pro Val Pro Ala Asn Pro Ala Glu Phe Ser Ala Thr Lys Phe Ala
                645                 650                 655

Ser Phe Ile Thr Gln Tyr Ser Thr Gly Gln Val Ser Val Glu Ile Glu
            660                 665                 670

Trp Glu Leu Gln Lys Glu Asn Ser Lys Arg Trp Asn Pro Glu Val Gln
        675                 680                 685

Tyr Thr Ser Asn Tyr Ala Lys Ser Ala Asn Val Asp Phe Thr Val Asp
690                 695                 700

Asn Asn Gly Leu Tyr Thr Glu Pro Arg Pro Ile Gly Thr Arg Tyr Leu
705                 710                 715                 720

Thr Arg Pro

<210> SEQ ID NO 29
<211> LENGTH: 736
<212> TYPE: PRT
<213> ORGANISM: Artificial sequence
<220> FEATURE:
<223> OTHER INFORMATION: Synthetic amino acid sequence
```

```
<400> SEQUENCE: 29

Met Ala Ser Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Arg Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Phe Gly Leu Val Glu Glu Gly Ala Lys Thr Ala Pro Gly Lys Lys Arg
    130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Thr Pro Ala Ala Val Gly Pro Thr Thr Met Ala Ser Gly Gly Gly
        195                 200                 205

Ala Pro Met Ala Asp Asn Asn Glu Gly Ala Asp Gly Val Gly Asn Ala
    210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Thr Gly Ala Ser Asn Asp Asn His
            260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
    290                 295                 300

Trp Gly Phe Arg Pro Lys Arg Leu Asn Phe Lys Leu Phe Asn Ile Gln
305                 310                 315                 320

Val Lys Glu Val Thr Thr Asn Asp Gly Val Thr Thr Ile Ala Asn Asn
                325                 330                 335

Leu Thr Ser Thr Val Gln Val Phe Ser Asp Ser Glu Tyr Gln Leu Pro
            340                 345                 350

Tyr Val Leu Gly Ser Ala His Gln Gly Cys Leu Pro Pro Phe Pro Ala
        355                 360                 365

Asp Val Phe Met Ile Pro Gln Tyr Gly Tyr Leu Thr Leu Asn Asn Gly
    370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
                405                 410                 415
```

```
Glu Asp Val Pro Phe His Ser Ser Tyr Ala His Ser Gln Ser Leu Asp
                420                 425                 430

Arg Leu Met Asn Pro Leu Ile Asp Gln Tyr Leu Tyr Tyr Leu Asn Arg
            435                 440                 445

Thr Gln Asn Gln Ser Gly Ser Ala Gln Asn Lys Asp Leu Leu Phe Ser
        450                 455                 460

Arg Gly Ser Pro Ala Gly Met Ser Val Gln Pro Lys Asn Trp Leu Pro
465                 470                 475                 480

Gly Pro Cys Tyr Arg Gln Gln Arg Val Ser Lys Thr Lys Thr Asp Asn
                485                 490                 495

Asn Asn Ser Asn Phe Thr Trp Thr Gly Ala Ser Lys Tyr Asn Leu Asn
                500                 505                 510

Gly Arg Glu Ser Ile Ile Asn Pro Gly Thr Ala Met Ala Ser His Lys
            515                 520                 525

Asp Asp Lys Asp Lys Phe Phe Pro Met Ser Gly Val Met Ile Phe Gly
        530                 535                 540

Lys Glu Ser Ala Gly Ala Ser Asn Thr Ala Leu Asp Asn Val Met Ile
545                 550                 555                 560

Thr Asp Glu Glu Glu Ile Lys Ala Thr Asn Pro Val Ala Thr Glu Arg
                565                 570                 575

Phe Gly Thr Val Ala Val Asn Leu Gln Ser Ser Thr Asp Pro Ala
                580                 585                 590

Thr Gly Asp Val His Val Met Gly Ala Leu Pro Gly Met Val Trp Gln
            595                 600                 605

Asp Arg Asp Val Tyr Leu Gln Gly Pro Ile Trp Ala Lys Ile Pro His
        610                 615                 620

Thr Asp Gly His Phe His Pro Ser Pro Leu Met Gly Gly Phe Gly Leu
625                 630                 635                 640

Lys His Pro Pro Gln Ile Leu Ile Lys Asn Thr Pro Val Pro Ala
                645                 650                 655

Asn Pro Pro Ala Glu Phe Ser Ala Thr Lys Phe Ala Ser Phe Ile Thr
                660                 665                 670

Gln Tyr Ser Thr Gly Gln Val Ser Val Glu Ile Glu Trp Glu Leu Gln
            675                 680                 685

Lys Glu Asn Ser Lys Arg Trp Asn Pro Glu Val Gln Tyr Thr Ser Asn
        690                 695                 700

Tyr Ala Lys Ser Ala Asn Val Asp Phe Thr Val Asp Asn Asn Gly Leu
705                 710                 715                 720

Tyr Thr Glu Pro Arg Pro Ile Gly Thr Arg Tyr Leu Thr Arg Pro Leu
                725                 730                 735

<210> SEQ ID NO 30
<211> LENGTH: 736
<212> TYPE: PRT
<213> ORGANISM: Artificial sequence
<220> FEATURE:
<223> OTHER INFORMATION: Synthetic amino acid sequence

<400> SEQUENCE: 30

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro
            20                  25                  30

Lys Pro Ala Glu Arg His Lys Asp Asp Ser Arg Gly Leu Val Leu Pro
        35                  40                  45
```

```
Gly Tyr Lys Tyr Leu Gly Pro Phe Asn Gly Leu Asp Lys Gly Glu Pro
     50                  55                  60

Val Asn Glu Ala Asp Ala Ala Leu Glu His Asp Lys Ala Tyr Asp
 65              70                  75                  80

Gln Gln Leu Lys Ala Gly Asp Pro Tyr Leu Arg Tyr Asn His Ala
             85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
            115                 120                 125

Leu Gly Leu Val Glu Glu Gly Ala Lys Thr Ala Pro Gly Lys Lys Arg
            130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
                180                 185                 190

Ala Thr Pro Ala Ala Val Gly Pro Thr Thr Met Ala Ser Gly Gly Gly
            195                 200                 205

Ala Pro Met Ala Asp Asn Asn Glu Gly Ala Asp Gly Val Gly Asn Ala
210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Thr Gly Ala Ser Asn Asp Asn His
                260                 265                 270

Tyr Phe Gly Tyr Ser Thr Pro Trp Gly Tyr Phe Asp Phe Asn Arg Phe
            275                 280                 285

His Cys His Phe Ser Pro Arg Asp Trp Gln Arg Leu Ile Asn Asn Asn
290                 295                 300

Trp Gly Phe Arg Pro Lys Arg Leu Ser Phe Lys Leu Phe Asn Ile Gln
305                 310                 315                 320

Val Lys Glu Val Thr Thr Asn Asp Gly Val Thr Thr Ile Ala Asn Asn
                325                 330                 335

Leu Thr Ser Thr Val Gln Val Phe Ser Asp Ser Glu Tyr Gln Leu Pro
            340                 345                 350

Tyr Val Leu Gly Ser Ala His Gln Gly Cys Leu Pro Pro Phe Pro Ala
            355                 360                 365

Asp Val Phe Met Ile Pro Gln Tyr Gly Tyr Leu Thr Leu Asn Asn Gly
370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
                405                 410                 415

Glu Glu Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Asn Arg
            435                 440                 445

Thr Gln Asn Gln Ser Gly Ser Ala Gln Asn Lys Asp Leu Leu Phe Ser
450                 455                 460
```

-continued

Arg Gly Ser Pro Ala Gly Met Ser Val Gln Pro Lys Asn Trp Leu Pro
465                 470                 475                 480

Gly Pro Cys Tyr Arg Gln Gln Arg Val Ser Lys Thr Lys Thr Asp Asn
            485                 490                 495

Asn Asn Ser Asn Phe Thr Trp Thr Gly Ala Ser Lys Tyr Asn Leu Asn
        500                 505                 510

Gly Arg Glu Ser Ile Ile Asn Pro Gly Thr Ala Met Ala Ser His Lys
    515                 520                 525

Asp Asp Glu Asp Lys Phe Phe Pro Met Ser Gly Val Met Ile Phe Gly
530                 535                 540

Lys Glu Ser Ala Gly Ala Ser Asn Thr Ala Leu Asp Asn Val Met Ile
545                 550                 555                 560

Thr Asp Glu Glu Glu Ile Lys Ala Thr Asn Pro Val Ala Thr Glu Arg
                565                 570                 575

Phe Gly Thr Val Ala Val Asn Phe Gln Ser Ser Ser Thr Asp Pro Ala
                580                 585                 590

Thr Gly Asp Val His Ala Met Gly Ala Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly His Phe His Pro Ser Pro Leu Met Gly Gly Phe Gly Leu
625                 630                 635                 640

Lys Asn Pro Pro Pro Gln Ile Leu Ile Lys Asn Thr Pro Val Pro Ala
                645                 650                 655

Asn Pro Pro Ala Glu Phe Ser Ala Thr Lys Phe Ala Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Val Gln Tyr Thr Ser Asn
690                 695                 700

Tyr Ala Lys Ser Ala Asn Val Asp Phe Thr Val Asp Asn Asn Gly Leu
705                 710                 715                 720

Tyr Thr Glu Pro Arg Pro Ile Gly Thr Arg Tyr Leu Thr Arg Pro Leu
                725                 730                 735

<210> SEQ ID NO 31
<211> LENGTH: 735
<212> TYPE: PRT
<213> ORGANISM: Artificial sequence
<220> FEATURE:
<223> OTHER INFORMATION: Synthetic amino acid sequence

<400> SEQUENCE: 31

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro
                20                  25                  30

Lys Pro Ala Glu Arg His Lys Asp Asp Ser Arg Gly Leu Val Leu Pro
            35                  40                  45

Gly Tyr Lys Tyr Leu Gly Pro Phe Asn Gly Leu Asp Lys Gly Glu Pro
        50                  55                  60

Val Asn Glu Ala Asp Ala Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

```
Asp Ala Glu Phe Gln Glu Arg Leu Lys Glu Asp Thr Ser Phe Gly Gly
                100                 105                 110

Asn Leu Gly Arg Ala Val Phe Gln Ala Lys Lys Arg Val Leu Glu Pro
            115                 120                 125

Leu Gly Leu Val Glu Glu Pro Val Lys Thr Ala Pro Gly Lys Lys Arg
130                 135                 140

Pro Val Glu His Ser Pro Val Glu Pro Asp Ser Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
            195                 200                 205

Ala Pro Met Ala Asp Asn Asn Glu Gly Ala Asp Gly Val Gly Asn Ser
        210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
            275                 280                 285

Cys His Phe Ser Pro Arg Asp Trp Gln Arg Leu Ile Asn Asn Asn Trp
        290                 295                 300

Gly Phe Arg Pro Lys Arg Leu Lys Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
            355                 360                 365

Val Phe Met Val Pro Gln Tyr Gly Tyr Leu Thr Leu Asn Asn Gly Ser
        370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Ser Arg Thr
            435                 440                 445

Asp Thr Pro Ser Gly Thr Thr Thr Gln Ser Arg Leu Gln Phe Ser Gln
        450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
                485                 490                 495

Asn Ser Glu Tyr Ser Trp Thr Gly Ala Thr Lys Tyr His Leu Asn Gly
            500                 505                 510
```

Arg Asp Ser Leu Val Asn Pro Gly Pro Ala Met Ala Ser His Lys Asp
                515                 520                 525

Asp Glu Glu Lys Phe Phe Pro Gln Ser Gly Val Leu Ile Phe Gly Lys
            530                 535                 540

Gln Gly Ser Glu Lys Thr Ser Val Asp Ile Glu Lys Val Met Ile Thr
545                 550                 555                 560

Asp Glu Glu Ile Arg Thr Thr Asn Pro Val Ala Thr Glu Gln Tyr
                565                 570                 575

Gly Ser Val Ser Thr Asn Leu Gln Arg Gly Asn Arg Gln Ala Ala Thr
            580                 585                 590

Ala Asp Val Asn Thr Gln Gly Val Leu Pro Gly Met Val Trp Gln Asp
                595                 600                 605

Arg Asp Val Tyr Leu Gln Gly Pro Ile Trp Ala Lys Ile Pro His Thr
            610                 615                 620

Asp Gly His Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asn
                645                 650                 655

Pro Ser Thr Thr Phe Ser Ala Ala Lys Phe Ala Ser Phe Ile Thr Gln
            660                 665                 670

Tyr Ser Thr Gly Gln Val Ser Val Glu Ile Glu Trp Glu Leu Gln Lys
            675                 680                 685

Glu Asn Ser Lys Arg Trp Asn Pro Glu Val Gln Tyr Thr Ser Asn Tyr
690                 695                 700

Asn Lys Ser Val Asn Val Asp Phe Thr Val Asp Thr Asn Gly Val Tyr
705                 710                 715                 720

Ser Glu Pro Arg Pro Ile Gly Thr Arg Tyr Leu Thr Arg Asn Leu
                725                 730                 735

<210> SEQ ID NO 32
<211> LENGTH: 735
<212> TYPE: PRT
<213> ORGANISM: Artificial sequence
<220> FEATURE:
<223> OTHER INFORMATION: Synthetic amino acid sequence

<400> SEQUENCE: 32

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro
            20                  25                  30

Lys Pro Ala Glu Arg His Lys Asp Asp Ser Arg Gly Leu Val Leu Pro
                35                  40                  45

Gly Tyr Lys Tyr Leu Gly Pro Phe Asn Gly Leu Asp Lys Gly Glu Pro
        50                  55                  60

Val Asn Glu Ala Asp Ala Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
130                 135                 140

```
Pro Val Glu His Ser Pro Val Glu Pro Asp Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asn Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
        195                 200                 205

Ala Pro Met Ala Asp Asn Asn Glu Gly Ala Asp Gly Val Gly Asn Ser
210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
290                 295                 300

Gly Phe Arg Pro Lys Arg Leu Lys Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
        355                 360                 365

Val Phe Met Val Pro Gln Tyr Gly Tyr Leu Thr Leu Asn Asn Gly Ser
370                 375                 380

Arg Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Ser Arg Thr
        435                 440                 445

Asp Thr Pro Ser Gly Thr Thr Thr Gln Ser Arg Leu Gln Phe Ser Gln
450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
                485                 490                 495

Asn Ser Glu Tyr Ser Trp Thr Gly Ala Thr Lys Tyr His Leu Asn Gly
            500                 505                 510

Arg Asp Ser Leu Val Asn Pro Gly Pro Ala Met Ala Ser His Lys Asp
        515                 520                 525

Asp Glu Glu Lys Phe Phe Pro Gln Ser Gly Val Leu Ile Phe Gly Lys
530                 535                 540

Gln Gly Ser Glu Lys Thr Ser Val Asp Ile Glu Lys Val Met Ile Thr
545                 550                 555                 560
```

Asp Glu Glu Glu Ile Arg Thr Thr Asn Pro Val Ala Thr Glu Gln Tyr
                565                 570                 575

Gly Ser Val Ser Thr Asn Leu Gln Arg Gly Asn Arg Gln Ala Ala Thr
            580                 585                 590

Ala Asp Val Asn Thr Gln Gly Val Leu Pro Gly Met Val Trp Gln Asp
        595                 600                 605

Arg Asp Val Tyr Leu Gln Gly Pro Ile Trp Ala Lys Ile Pro His Thr
    610                 615                 620

Asp Gly His Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asn
                645                 650                 655

Pro Ser Thr Thr Phe Ser Ala Ala Lys Phe Ala Ser Phe Ile Thr Gln
            660                 665                 670

Tyr Ser Thr Gly Gln Val Ser Val Glu Ile Glu Trp Glu Leu Gln Lys
        675                 680                 685

Glu Asn Ser Lys Arg Trp Asn Pro Glu Val Gln Tyr Thr Ser Asn Tyr
    690                 695                 700

Asn Lys Ser Val Asn Val Asp Phe Thr Val Asp Thr Asn Gly Val Tyr
705                 710                 715                 720

Thr Glu Pro Arg Pro Ile Gly Thr Arg Tyr Leu Thr Arg Asn Leu
                725                 730                 735

<210> SEQ ID NO 33
<211> LENGTH: 735
<212> TYPE: PRT
<213> ORGANISM: Artificial sequence
<220> FEATURE:
<223> OTHER INFORMATION: Synthetic amino acid sequence

<400> SEQUENCE: 33

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
    130                 135                 140

Pro Val Glu His Ser Pro Val Glu Pro Asp Ser Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

-continued

```
Ala Ala Pro Ser Gly Leu Gly Thr Asn Thr Met Ala Thr Gly Ser Gly
        195                 200                 205
Ala Pro Met Ala Asp Asn Asn Glu Gly Ala Asp Gly Val Gly Asn Ser
210                 215                 220
Ser Gly Asn Trp His Cys Asp Ser Thr Trp Met Gly Asp Arg Val Ile
225                 230                 235                 240
Thr Thr Ser Thr Arg Thr Trp Ala Leu Pro Thr Tyr Asn Asn His Leu
                245                 250                 255
Tyr Lys Gln Ile Ser Ser Gln Ser Gly Ala Ser Asn Asp Asn His Tyr
                260                 265                 270
Phe Gly Tyr Ser Thr Pro Trp Gly Tyr Phe Asp Phe Asn Arg Phe His
                275                 280                 285
Cys His Phe Ser Pro Arg Asp Trp Gln Arg Leu Ile Asn Asn Asn Trp
        290                 295                 300
Gly Phe Arg Pro Lys Arg Leu Lys Phe Lys Leu Phe Asn Ile Gln Val
305                 310                 315                 320
Lys Glu Val Thr Gln Asn Asp Gly Thr Thr Thr Ile Ala Asn Asn Leu
                325                 330                 335
Thr Ser Thr Val Gln Val Phe Thr Asp Ser Glu Tyr Gln Leu Pro Tyr
                340                 345                 350
Val Leu Gly Ser Ala His Gln Gly Cys Leu Pro Pro Phe Pro Ala Asp
        355                 360                 365
Val Phe Met Val Pro Gln Tyr Gly Tyr Leu Thr Leu Asn Asn Gly Ser
        370                 375                 380
Gln Ala Val Gly Arg Ser Ser Phe Tyr Cys Leu Glu Tyr Phe Pro Ser
385                 390                 395                 400
Gln Met Leu Arg Thr Gly Asn Asn Phe Thr Phe Ser Tyr Thr Phe Glu
                405                 410                 415
Asp Val Pro Phe His Ser Ser Tyr Ala His Ser Gln Ser Leu Asp Arg
                420                 425                 430
Leu Met Asn Pro Leu Ile Asp Gln Tyr Leu Tyr Tyr Leu Ser Arg Thr
        435                 440                 445
Asp Ala Pro Ser Gly Thr Thr Thr Gln Ser Arg Leu Gln Phe Ser Gln
        450                 455                 460
Ala Gly Ala Ser Asp Ile Arg Asp Gln Ser Arg Asn Trp Leu Pro Gly
465                 470                 475                 480
Pro Cys Tyr Arg Gln Gln Arg Val Ser Lys Thr Ser Ala Asp Asn Asn
                485                 490                 495
Asn Ser Glu Tyr Ser Trp Thr Gly Ala Thr Lys Tyr His Leu Asn Gly
                500                 505                 510
Arg Asp Ser Leu Val Asn Pro Gly Pro Ala Met Ala Ser His Lys Asp
        515                 520                 525
Asp Glu Glu Lys Phe Phe Pro Gln Ser Gly Val Leu Ile Phe Gly Lys
        530                 535                 540
Gln Gly Ser Glu Lys Thr Ser Val Asp Ile Glu Lys Val Met Ile Thr
545                 550                 555                 560
Asp Glu Glu Glu Ile Arg Thr Thr Asn Pro Val Ala Thr Glu Gln Tyr
                565                 570                 575
Gly Ser Val Ser Thr Asn Leu Gln Arg Gly Asn Arg Gln Ala Ala Thr
                580                 585                 590
Ala Asp Val Asn Thr Gln Gly Val Leu Pro Gly Met Val Trp Gln Asp
        595                 600                 605
```

| | | | | | | | | | | | |
|---|---|---|---|---|---|---|---|---|---|---|---|
|Arg|Asp|Val|Tyr|Leu|Gln|Gly|Pro|Ile|Trp|Ala|Lys|Ile|Pro|His|Thr|
| |610| | | |615| | | |620| | | | | | |

Arg Asp Val Tyr Leu Gln Gly Pro Ile Trp Ala Lys Ile Pro His Thr
    610             615             620

Asp Gly His Phe His Pro Ser Pro Leu Met Gly Phe Gly Leu Lys
625             630             635             640

His Pro Pro Gln Ile Leu Ile Lys Asn Thr Pro Val Pro Ala Asn
            645             650             655

Pro Ser Thr Thr Phe Ser Ala Ala Lys Phe Ala Ser Phe Ile Thr Gln
            660             665             670

Tyr Ser Thr Gly Gln Val Ser Val Glu Ile Glu Trp Glu Leu Gln Lys
        675             680             685

Glu Asn Ser Lys Arg Trp Asn Pro Glu Val Gln Tyr Thr Ser Asn Tyr
    690             695             700

Asn Lys Ser Val Asn Val Asp Phe Thr Val Asp Thr Asn Gly Val Tyr
705             710             715             720

Ser Glu Pro Arg Pro Ile Gly Thr Arg Tyr Leu Thr Arg Asn Leu
            725             730             735

<210> SEQ ID NO 34
<211> LENGTH: 2211
<212> TYPE: DNA
<213> ORGANISM: Artificial sequence
<220> FEATURE:
<223> OTHER INFORMATION: Synthetic nucleic acid sequence

<400> SEQUENCE: 34

```
atggctgccg atggttatct tccagattgg ctcgaggaca acctctctga gggcattcgc    60
gagtggtggg acttgaaacc tggagccccg aaacccaaag ccaaccagca aaagcaggac   120
gacggccggg tctggtgct tcctggctac aagtacctcg acccttcaa cggactcgac    180
aaggggagc ccgtcaacgc ggcggatgca gcggccctcg agcacgacaa ggcctacgac   240
cagcagctca aagcgggtga caatccgtac cttcggtata ccacgccga cgccgagttt   300
caggagcgtc tgcaagaaga tacgtctttt gggggcaacc tcgggcgagc agtcttccag   360
gccaaaaaga gggttctcga acctctcggt ctggttgagg aagcggctaa gacggctcct   420
ggaaagaaac gtccggtaga gcagtcgcca aagagccag actcctcctc gggcattggc    480
aagacaggcc agcagcccgc taaaaagaga ctcaattttg gtcagactgg cgactcagag   540
tcagtccccg acccacaacc tctcggagaa cctcccgcag ccccctcagg tgtgggatct   600
cttacaatgg cttcaggtgg tggcgcacca atggcagaca taacgaagg cgccgacgga   660
gtgggtaatg cctcaggaaa ttggcattgc gattccacat ggctgggcga cagagtcatc   720
accaccagca cccgcacctg gccttgccc acctacaata accacctcta caagcaaatc   780
tccagtgctt caacggggc cagcaacgac aaccactact cggctacag cacccctgg    840
gggtattttg acttcaacag attccactgc cacttttcac cacgtgactg caaagactc    900
atcaacaaca attgggat ccggcccaag agactcaact tcaagctctt caacatccaa    960
gtcaaggagg tcacgacgaa tgatggcgtc acgaccatcg ctaataacct taccagcacg   1020
gttcaagtct ctctcggactc ggagtaccag ttgccgtacg tcctcggctc tgcgcaccag   1080
ggctgcctcc ctccgttccc ggcggacgtg ttcatgattc cgcagtacgg ctacctaacg   1140
ctcaacaatg gcagccaggc agtgggacgg tcatcctttt actgcctgga atatttccca   1200
tcgcagatgc tgagaacggg caacaacttt acctccagct acacctttga ggaagtgcct   1260
ttccacagca gctacgcgca cagccagagc ctggaccggc tgatgaatcc tctcatcgac   1320
```

| | | |
|---|---|---|
| cagtacctgt attacctgaa cagaactcaa aatcagtccg gaagtgccca aaacaaggac | 1380 | |
| ttgctgttta gccgtgggtc tccagctggc atgtctgttc agcccaaaaa ctggctacct | 1440 | |
| ggaccctgtt accggcagca gtgcgtttct aaaacaaaaa cagacaacaa caacagcaac | 1500 | |
| tttacctgga ctggtgcttc aaaatataac cttaatgggc gtgaatctat aatcaaccct | 1560 | |
| ggcactgcta tggcctcaca caaagacgac aaagacaagt tctttcccat gagcggtgtc | 1620 | |
| atgattttg gaaaggagag cgccggagct tcaaacactg cattggacaa tgtcatgatc | 1680 | |
| acagacgaag aggaaatcaa agccactaac cccgtggcca ccgaaagatt tgggactgtg | 1740 | |
| gcagtcaatc tccagagcag cagcacagac cctgcgaccg gagatgtgca tgttatggga | 1800 | |
| gccttacctg gaatggtgtg gcaagacaga gacgtatacc tgcagggtcc tatttgggcc | 1860 | |
| aaaattcctc acacagatgg acactttcac ccgtctcctc ttatgggcgg ctttggactc | 1920 | |
| aagaacccgc tcctcagat cctcatcaaa aacacgcctg ttcctgcgaa tcctccggcg | 1980 | |
| gagttttcag ctacaaagtt tgcttcattc atcacccaat actccacagg acaagtgagc | 2040 | |
| gtggagattg aatgggagct gcagaaagaa acagcaagc gctggaatcc cgaagtgcag | 2100 | |
| tacacatcca attatgcaaa atctgccaac gttgatttca ctgtggacaa caatggactt | 2160 | |
| tatactgagc ctcgccccat ggcacccgt tacctcaccc gtccctgta a | 2211 | |

<210> SEQ ID NO 35
<211> LENGTH: 2211
<212> TYPE: DNA
<213> ORGANISM: Artificial sequence
<220> FEATURE:
<223> OTHER INFORMATION: Synthetic nucleic acid sequence

<400> SEQUENCE: 35

| | | |
|---|---|---|
| atggctgccg atggttatct tccagattgg ctcgaggaca acctctctga gggcattcgc | 60 | |
| gaatggtggg acttgaaacc tggagccccg aaacccaaag tcaaccagca aaagcaggac | 120 | |
| aacgctcggg gtcttgtgct tccgggttac aaatacctcg dacccttcaa cggactcgac | 180 | |
| aaggggagc ccgtcaacgc ggcggacgca gcggccctcg agcacgacaa ggcctacgac | 240 | |
| cagcagctca aagcgggtga caatccgtac cttcggtata ccacgccga cgccgagttt | 300 | |
| caggagcgtc tgcaagaaga tacgtctttt gggggcaacc ttggacgagc agtcttccag | 360 | |
| gccaagaaga gggttctcga accttttggt ctggttgagg aaggtgctaa gacggctcct | 420 | |
| ggaaagaaac gtccggtaga gcagtcgcca caagagccag actcctcctc gggcattggc | 480 | |
| aagacaggcc agcagcccgc taaaaagaga ctcaattttg gtcagactgg cgactcagag | 540 | |
| tcagtccccg acccacaacc tctcggagaa cctccagcaa ccccgctgc tgtgggacct | 600 | |
| actacaatgg cttcaggcgg tggcgcacca atggcagaca taacgaagg cgccgacgga | 660 | |
| gtgggtaatg cctcaggaaa ttggcattgc gattccacat ggctgggcga cagagtcatc | 720 | |
| accaccagca cccgcacctg gccttgccc acctacaata accacctcta caagcaaatc | 780 | |
| tccagtgctt caacgggggc cagcaacgac aaccactact cggctacag cacccctgg | 840 | |
| gggtatttg acttcaacag attccactgc cacttttcac cacgtgactg gcaaagactc | 900 | |
| atcaacaaca ttggggatt ccggcccaag agactcaact tcaagctctt caacatccaa | 960 | |
| gtcaaggagg tcacgacgaa tgatggcgtc acgaccatcg ctaataacct taccagcacg | 1020 | |
| gttcaagtct tctcggactc ggagtaccag ttgccgtacg tctcggctc tgcgcaccag | 1080 | |
| ggctgcctcc ctccgttccc ggcggacgtg ttcatgattc gcaatacgg ctacctgacg | 1140 | |
| ctcaacaatg gcagccaggc agtgggacgg tcatcctttt actgcctgga atatttccca | 1200 | |

```
tcgcagatgc tgagaacggg caataacttt accttcagct acactttga ggacgttcct    1260 ttccacagca gctacgctca cagccagagc ctggaccggc tgatgaatcc tctcatcgac    1320
cagtacctgt attacctgaa cagaactcag aatcagtccg gaagtgccca aaacaaggac    1380
ttgctgttta gccgtgggtc tccaactggc atgtctgttc agcccaaaaa ctggctacct    1440
ggaccctgtt atcggcagca gcgcgtttct aaaacaaaaa cagacaacaa caacagcaac    1500
tttacctgga ctggtgcttc aaaatataac cttaatgggc gtgaatctat aatcaaccct    1560
ggcactgcta tggcctcaca caaagacgac gaagacaagt tctttcccat gagcggtgtc    1620 atgattttg gaaaggagag cgccggagct tcaaacactg cattggacaa tgtcatgatc    1680
acagacgaag aggaaatcaa agccactaac cccgtggcca ctgaaagatt tgggactgtg    1740
gcagtcaatc tccagagcag cagcacagac cctgcgaccg gagatgtgca tgccatggga    1800
gccttacctg gaatggtgtg gcaagacaga gacgtatacc tgcagggtcc tatttgggcc    1860
aaaattcctc acacggatgg acactttcac ccgtctcctc tcatgggcgg ctttggactt    1920
aagcacccgc tcctcagat cctcatcaaa aacacgcctg ttcctgcgaa tcctccggca    1980
gagttttcgg ctacaaagtt tgcttcattc atcacccagt attccacagg acaagtgagc    2040
gtggagattg aatgggagct gcagaaagaa aacagcaaac gctggaatcc cgaagtgcag    2100
tatacatcta actatgcaaa atctgccaac gttgatttca ctgtggacaa caatggactt    2160
tatactgagc ctcgccccat tggcacccgt tacctcaccc gtcccctgta a             2211
```

<210> SEQ ID NO 36
<211> LENGTH: 2208
<212> TYPE: DNA
<213> ORGANISM: Artificial sequence
<220> FEATURE:
<223> OTHER INFORMATION: Synthetic nucleic acid sequence
<220> FEATURE:
<221> NAME/KEY: misc_feature
<222> LOCATION: (955)..(955)
<223> OTHER INFORMATION: n is a, c, g, or t
<220> FEATURE:
<221> NAME/KEY: misc_feature
<222> LOCATION: (971)..(972)
<223> OTHER INFORMATION: n is a, c, g, or t
<220> FEATURE:
<221> NAME/KEY: misc_feature
<222> LOCATION: (981)..(981)
<223> OTHER INFORMATION: n is a, c, g, or t
<220> FEATURE:
<221> NAME/KEY: misc_feature
<222> LOCATION: (986)..(986)
<223> OTHER INFORMATION: n is a, c, g, or t
<220> FEATURE:
<221> NAME/KEY: misc_feature
<222> LOCATION: (1235)..(1235)
<223> OTHER INFORMATION: n is a, c, g, or t
<220> FEATURE:
<221> NAME/KEY: misc_feature
<222> LOCATION: (1694)..(1696)
<223> OTHER INFORMATION: n is a, c, g, or t
<220> FEATURE:
<221> NAME/KEY: misc_feature
<222> LOCATION: (1698)..(1698)
<223> OTHER INFORMATION: n is a, c, g, or t
<220> FEATURE:
<221> NAME/KEY: misc_feature
<222> LOCATION: (1763)..(1765)
<223> OTHER INFORMATION: n is a, c, g, or t
<220> FEATURE:
<221> NAME/KEY: misc_feature
<222> LOCATION: (1778)..(1778)
<223> OTHER INFORMATION: n is a, c, g, or t
<220> FEATURE:

<221> NAME/KEY: misc_feature
<222> LOCATION: (2204)..(2204)
<223> OTHER INFORMATION: n is a, c, g, or t

<400> SEQUENCE: 36

```
atggctgccg atggttatct tccagattgg ctcgaggaca acctctctga gggcattcgc      60
gaatggtggg acttgaaacc tggagccccg aaacccaaag tcaaccagca aaagcaggac     120
aacgctcggg gtcttgtgct tccgggttac aaatacctcg gacccttcaa cggactcgac     180
aagggggagc ccgtcaacgc ggcggacgca gcggccctcg agcacgacaa ggcctacgac     240
cagcagctca aagcgggtga caatccgtac cttcggtata accacgccga cgccgagttt     300
caggagcgtc tgcaagaaga tacgtctttt gggggcaacc ttggacgagc agtcttccag     360
gccaagaaga gggttctcga accttttggt ctggttgagg aaggtgctaa gacggctcct     420
ggaaagaaac gtccggtaga gcagtcgcca aagagccag actcctcctc gggcattggc     480
aagacaggcc agcagcccgc taaaaagaga ctcaattttg gtcagactgg cgactcagag     540
tcagtccccg acccacaacc tctcggagaa cctccagcaa cccccgctgc tgtgggacct     600
actacaatgg cttcaggcgg tggcgcacca atggcagaca ataacgaagg cgccgacgga     660
gtgggtaatg cctcaggaaa ttggcattgc gattccacat ggctgggcga cagagtcatc     720
accaccagca cccgaacatg ggccttgccc acctataaca accacctcta caagcaaatc     780
tccagtgctt caacggggc cagcaacgac aaccactact cggctacag cacccccctgg    840
gggtattttg atttcaacag attccactgc cacttttcac cacgtgactg gcagcgactc     900
atcaataaca attgggggatt ccggcccaag agactcaact tcaaaactctt caacntccaa    960
gtcaaggagg nnacgacgaa ngatgncgtc acaaccatcg ctaataacct taccagcacg    1020
gttcaagtct tctcggactc ggagtaccag cttccgtacg tcctcggctc tgcgcaccag    1080
ggctgcctcc ctccgttccc ggcggacgtg ttcatgattc cgcaatacgg ctacctgacg    1140
ctcaacaatg gcagccaggc agtgggacgg tcatcctttt actgcctgga atatttccca    1200
tcgcagatgc tgagaacggg caataacttt acctncagct cacttttga ggacgttcct    1260
ttccacagca gctacgctca cagccagagc ctggaccggc tgatgaatcc tctcatcgac    1320
cagtacctgt attacctgaa cagaactcag aatcagtccg gaagtgccca aaacaaggac    1380
ttgctgttta gccgtgggtc tccaactggc atgtctgttc agcccaaaaa ctggctacct    1440
ggaccctgtt atcggcagca gcgcgtttct aaaacaaaaa cagacaacaa caacagcaac    1500
tttacctgga ctggtgcttc aaaatataac cttaatgggc gtgaatctat aatcaaccct    1560
ggcactgcta tggcctcaca caaagacgac gaagacaagt tctttcccat gagcggtgtc    1620
atgattttttg gaaggagag cgccggagct tcaaacactg cattggacaa tgtcatgatc    1680
acagacgaag agannncnaa gccactaacc ccgtggccac tgaaagattt gggactgtgg    1740
cagtcaatct ccaagcagca cannnaccct gcgaccgnag atgtgcatgc catgggagcc    1800
ttacctggaa tggtgtggca agacagagac gtatacctgc agggtcctat ttgggccaaa    1860
attcctcaca cggatggaca ctttcacccg tctcctctca tgggcggctt tggacttaag    1920
cacccgcctc ctcagatcct catcaaaaac acgcctgttc ctgcgaatcc tccggcagag    1980
ttttcggcta caaagtttgc ttcattcatc acccagtatt ccacaggaca agtgagcgtg    2040
gagattgaat gggagctgca gaaagaaaac agcaaacgct ggaatcccga agtgcagtat    2100
acatctaact atgcaaaatc tgccaacgtt gatttcactg tggacaacaa tggactttat    2160
actgagcctc gccccattgg cacccgttac ctcacccgtc cccngtaa               2208
```

<210> SEQ ID NO 37
<211> LENGTH: 2211
<212> TYPE: DNA
<213> ORGANISM: Artificial sequence
<220> FEATURE:
<223> OTHER INFORMATION: Synthetic nucleic acid sequence

<400> SEQUENCE: 37

| | | | | |
|---|---|---|---|---|
| atggcttccg | atggttatct | tccagattgg | ctcgaggaca | acctctctga | gggcatccgc | 60 |
| gagtggtggg | acttgaaacc | tggagccccg | aaacccaaag | ccaaccagca | aaagcaggac | 120 |
| gacggccggg | gtctggtgct | tcctggctac | aagtacctcg | acccttcaa | cggactcgac | 180 |
| aaggggagc | ccgtcaacgc | ggcggatgca | gcggccctcg | agcacgacaa | ggcctacgac | 240 |
| cagcagctca | gagcgggtga | caatccgtac | ctgcggtata | accacgccga | cgccgagttt | 300 |
| caggagcgtc | tgcaagaaga | tacgtctttt | gggggcaacc | tcgggcgagc | agtcttccag | 360 |
| gccaagaaga | gggttctcga | accttttggt | ctggttgagg | aaggtgctaa | gacggctcct | 420 |
| ggaaagaaac | gtccggtaga | gcagtcgcca | caagagccag | actcctcctc | gggcattggc | 480 |
| aagacaggcc | agcagcccgc | taaaaagaga | ctcaattttg | gtcagactgg | cgactcagag | 540 |
| tcagtccccg | acccacaacc | tctcggagaa | cctccagcaa | ccccgctgc | tgtgggacct | 600 |
| actacaatgg | cttcaggcgg | tggcgcacca | atggcagaca | taacgaagg | cgccgacgga | 660 |
| gtgggtaatg | cctcaggaaa | ttggcattgc | gattccacat | ggctgggcga | cagagtcatc | 720 |
| accaccagca | cccgaacatg | ggccttgccc | acctataaca | accacctcta | caagcaaatc | 780 |
| tccagtgctt | caacggggc | cagcaacgac | aaccactact | tcggctacag | cacccctgg | 840 |
| gggtattttg | atttcaacag | attccactgc | catttctcac | cacgtgactg | gcagcgactc | 900 |
| atcaacaaca | attggggatt | ccggcccaag | agactcaact | tcaaactctt | caacatccaa | 960 |
| gtcaaggagg | tcacgacgaa | tgatggcgtc | acaaccatcg | ctaataacct | taccagcacg | 1020 |
| gttcaagtct | ctcggactc | ggagtaccag | cttccgtacg | tcctcggctc | tgcgcaccag | 1080 |
| ggctgcctcc | ctccgttccc | ggcggacgtg | ttcatgattc | cgcagtacgg | ctacctaacg | 1140 |
| ctcaacaatg | gcagccaggc | agtgggacgg | tcatcctttt | actgcctgga | atatttccca | 1200 |
| tcgcagatgc | tgagaacggg | caataacttt | accttcagct | acaccttcga | ggacgtgcct | 1260 |
| ttccacagca | gctacgcgca | cagccagagc | ctggaccggc | tgatgaatcc | tctcatcgac | 1320 |
| cagtacctgt | attacctgaa | cagaactcag | aatcagtccg | aagtgcccca | aaacaaggac | 1380 |
| ttgctgttta | gccggggtc | tccagctggc | atgtctgttc | agcccaaaaa | ctggctacct | 1440 |
| ggaccctgtt | accggcagca | gcgcgtttct | aaaacaaaaa | cagacaacaa | caacagcaac | 1500 |
| tttacctgga | ctggtgcttc | aaaatataac | cttaatgggc | gtgaatctat | aatcaaccct | 1560 |
| ggcactgcta | tggcctcaca | caagacgac | aaagacaagt | tctttcccat | gagcggtgtc | 1620 |
| atgatttttg | gaaaggagag | cgccggagct | tcaaacactg | cattggacaa | tgtcatgatc | 1680 |
| acagacgaag | aggaaatcaa | agccactaac | cccgtggcca | ccgaaagatt | tgggactgtg | 1740 |
| gcagtcaatc | tccagagcag | cagcacagac | cctgcgaccg | gagatgtgca | tgttatggga | 1800 |
| gccttacctg | gaatggtgtg | gcaagacaga | gacgtatacc | tgcagggtcc | catttgggcc | 1860 |
| aaaattcctc | acacagatgg | acactttcac | ccgtctcctc | ttatgggcgg | ctttggactt | 1920 |
| aagcacccgc | ctcctcagat | cctcatcaaa | aacacgcctg | ttcctgcgaa | tcctccggca | 1980 |
| gagttttcgg | ctacaaagtt | tgcttcattc | atcacccagt | attctactgg | ccaagtcagc | 2040 |

| | |
|---|---:|
| gtggagattg aatgggagct gcagaaagaa aacagcaaac gctggaatcc cgaagtgcag | 2100 |
| tatacatcta actatgcaaa atctgccaac gttgatttca ctgtggacaa caatggactt | 2160 |
| tatactgagc ctcgtcccat tggcacccgt tacctcaccc gtccctgta a | 2211 |

<210> SEQ ID NO 38
<211> LENGTH: 2211
<212> TYPE: DNA
<213> ORGANISM: Artificial sequence
<220> FEATURE:
<223> OTHER INFORMATION: Synthetic nucleic acid sequence

<400> SEQUENCE: 38

| | |
|---|---:|
| atggctgccg atggttatct tccagattgg ctcgaggaca ctctctctga aggaataaga | 60 |
| cagtggtgga agctcaaacc tggcccacca ccaccaaagc ccgcagagcg gcataaggac | 120 |
| gacagcaggg gtcttgtgct tcctgggtac aagtacctcg gacccttcaa cggactcgac | 180 |
| aagggagagc cggtcaacga ggcagacgcc gcggccctcg agcacgacaa ggcctacgac | 240 |
| cagcagctca aagcgggtga caatccgtac ctgcggtata accacgccga cgccgagttt | 300 |
| caggagcgtc tgcaagaaga tacgtctttt gggggcaacc tcgggcgagc agtcttccag | 360 |
| gccaagaagc gggttctcga acctctcggt ctggttgagg aaggcgctaa gacggctcct | 420 |
| ggaaagaaac gtccggtaga gcagtcgcca caagagccag actcctcctc gggcatcggc | 480 |
| aagacaggcc agcagcccgc taaaaagaga ctcaattttg gtcagactgg cgactcagag | 540 |
| tcagtccccg acccacaacc tctcggagaa cctccagcaa cccccgctgc tgtgggacct | 600 |
| actacaatgg cttcaggcgg tggcgcacca atggcagaca taacgaaggc gccgacgga | 660 |
| gtgggtaatg cctcaggaaa ttggcattgc gattccacat ggctgggcga cagagtcatc | 720 |
| accaccagca cccgaacatg ggccttgccc acctataaca accacctcta caagcaaatc | 780 |
| tccagtgctt cgacggggc cagcaacgac aaccactact cggctacag cacccctgg | 840 |
| gggtattttg actttaacag attccactgc cactttcac cacgtgactg gcagcgactc | 900 |
| atcaacaata actgggggatt ccggcccaag agactcagct tcaagctctt caacatccag | 960 |
| gtcaaggagg tcacgacgaa tgatggcgtc acaaccatcg ctaataacct taccagcacg | 1020 |
| gttcaagtct tctcggactc ggagtaccag cttccgtacg tcctcggctc tgcgcaccag | 1080 |
| ggctgcctcc ctccgttccc ggcggacgtg ttcatgattc cgcaatacgg ctacctgacg | 1140 |
| ctcaacaatg gcagccaagc cgtgggacgt tcatcctttt actgcctgga atatttccct | 1200 |
| tctcagatgc tgagaacggg caacaacttt accttcagct acaccttga ggaagtgcct | 1260 |
| ttccacagca gctacgcgca gccagagc ctggaccggc tgatgaatcc tctcatcgat | 1320 |
| caataccctgt attacctgaa cagaactcaa aatcagtccg gaagtgccca aaacaaggac | 1380 |
| ttgctgtttta gccgtgggtc tccagctggc atgtctgttc agcccaaaaa ctggctacct | 1440 |
| ggaccctgtt atcggcagca gcgcgtttct aaaacaaaaa cagacaacaa caacagcaat | 1500 |
| tttacctgga ctggtgcttc aaaatataac ctcaatgggc gtgaatccat catcaaccct | 1560 |
| ggcactgcta tggcctcaca caaagacgac gaagacaagt tctttcccat gagcggtgtc | 1620 |
| atgattttttg gaaagagag cgccggagct tcaaacactg cattggacaa tgtcatgatt | 1680 |
| acggacgaag aggaaattaa agccactaac cctgtggcca ccgaaagatt tgggaccgtg | 1740 |
| gcagtcaatt tccagagcag cagcacagac cctgcgaccg gagatgtgca tgctatggga | 1800 |
| gcattacctg gcatggtgtg gcaagataga gacgtgtacc tgcagggtcc catttgggcc | 1860 |
| aaaattcctc acacagatgg acactttcac ccgtctcctc ttatgggcgg ctttggactc | 1920 |

| | |
|---|---|
| aagaacccgc ctcctcagat cctcatcaaa aacacgcctg ttcctgcgaa tcctccggcg | 1980 |
| gagttttcag ctacaaagtt tgcttcattc atcactcaat actccacagg acaagtgagc | 2040 |
| gtggaaattg aatgggagct gcagaaagaa aacagcaaac gctggaatcc cgaagtgcag | 2100 |
| tatacatcta actatgcaaa atctgccaac gttgatttca ctgtggacaa caatggactt | 2160 |
| tatactgagc ctcgccccat tggcacccgt tacctcaccc gtcccctgta a | 2211 |

<210> SEQ ID NO 39
<211> LENGTH: 2208
<212> TYPE: DNA
<213> ORGANISM: Artificial sequence
<220> FEATURE:
<223> OTHER INFORMATION: Synthetic nucleic acid sequence

<400> SEQUENCE: 39

| | |
|---|---|
| atggctgccg atggttatct tccagattgg ctcgaggaca ctctctctga aggaataaga | 60 |
| cagtggtgga agctcaaacc tggcccacca ccaccaaagc ccgcagagcg gcataaggac | 120 |
| gacagcaggg gtcttgtgct tcctgggtac aagtacctcg gacccttcaa cggactcgac | 180 |
| aagggagagc cggtcaacga ggcagacgcc gcggccctcg agcacgacaa agcctatgac | 240 |
| cggcagctcg acagcggaga caacccgtac ctcaagtaca ccacgccga cgcggagttt | 300 |
| caggagcgcc ttaaagaaga tacgtctttt ggggggcaacc tcggacgagc agtcttccag | 360 |
| gcgaaaaaga gggttcttga acctctgggc ctggttgagg aacctgttaa gacggctccg | 420 |
| ggaaaaaaga ggccggtaga gcactctcct gtggagccag actcctcctc gggaaccgga | 480 |
| aaggcgggcc agcagcctgc aagaaaaaga ttgaattttg gtcagactgg agacgcagac | 540 |
| tcagtacctg atccccagcc ctcggacag ccaccagcag ccccctctgg tctgggaact | 600 |
| aatacgatgg ctacaggcag tggcgcacca atggcagaca ataacgaggg cgccgacgga | 660 |
| gtgggtaatt cctcgggaaa ttggcattgc gattccacat ggatgggcga cagagtcatc | 720 |
| accaccagca cccgaacctg ggccctgccc acctacaaca accacctcta caaacaaatt | 780 |
| tccagccaat caggagcctc gaacgacaat cactactttg ctacagcac cccttggggg | 840 |
| tattttgact tcaacagatt ccactgccac ttttcaccac gtgactggca agactcatc | 900 |
| aacaacaact ggggattccg acccaagaga ctcaagttca gctctttaa cattcaagtc | 960 |
| aaagaggtca cgcagaatga cggtacgacg acgattgcca ataaccttac cagcacggtt | 1020 |
| caggtgttta ctgactcgga gtaccagctc ccgtatgtcc tcggctcggc gcatcaagga | 1080 |
| tgcctcccgc cgttcccagc agacgtcttc atggtgccac agtatggata cctcaccctg | 1140 |
| aacaacggga gtcaggcagt aggacgctct tcatttact gcctggagta ctttcctcct | 1200 |
| cagatgctgc gtaccggtaa caactttacc ttcagctaca cttttgagga cgttcctttc | 1260 |
| cacagcagct acgctcacag ccagagtctg gaccgtctca tgaatcctct catcgaccag | 1320 |
| tacctgtatt acttgagcag aacagacact ccaagtggaa ccaccacgca gtcaaggctt | 1380 |
| cagttttctc aggccggagc gagtgacatt cgggaccagt ctaggaactg gcttcctgga | 1440 |
| ccctgttacc gccagcagcg agtatcaaag acatctgcgg ataacaacaa cagtgaatac | 1500 |
| tcgtggactg gagctaccaa gtaccacctc aatggcagag actctctggt gaatccgggc | 1560 |
| ccggccatgg caagccacaa ggacgatgaa gaaaagtttt tccctcagag cggggttctc | 1620 |
| atctttggga agcaaggctc agagaaaaca agtgtggaca ttgaaaaggt catgattaca | 1680 |
| gacgaagagg aaatcaggac aaccaatccc gtggctacgg agcagtatgg ttctgtatct | 1740 |

| | |
|---|---|
| accaacctcc agagaggcaa cagacaagca gctaccgcag atgtcaacac acaaggcgtt | 1800 |
| cttccaggca tggtctggca ggacagagat gtgtaccttc aggggcccat ctgggcaaag | 1860 |
| attccacaca cggacggaca ttttcacccc tctcccctca tgggtggatt cggacttaaa | 1920 |
| caccctcctc cacagattct catcaagaac accccggtac ctgcgaatcc ttcgaccacc | 1980 |
| ttcagtgcgg caaagtttgc ttccttcatc acacagtact ccacgggaca ggtcagcgtg | 2040 |
| gagatcgagt gggagctgca gaaggaaaac agcaaacgct ggaatcccga agttcagtac | 2100 |
| acttccaact acaacaagtc tgttaatgtg gactttactg tggacactaa tggcgtgtat | 2160 |
| tcagagcctc gccccattgg caccagatac ctgactcgta atctgtaa | 2208 |

<210> SEQ ID NO 40
<211> LENGTH: 2208
<212> TYPE: DNA
<213> ORGANISM: Artificial sequence
<220> FEATURE:
<223> OTHER INFORMATION: Synthetic nucleic acid sequence

<400> SEQUENCE: 40

| | |
|---|---|
| atggctgccg atggttatct tccagattgg ctcgaggaca ctctctctga aggaataaga | 60 |
| cagtggtgga agctcaaacc tggcccacca ccaccaaagc ccgcagagcg gcataaggac | 120 |
| gacagcaggg gtcttgtgct tcctgggtac aagtacctcg acccttcaa cggactcgac | 180 |
| aagggagagc cggtcaacga ggcagacgcc gcggccctcg agcacgacaa agcctatgac | 240 |
| cggcagctcg acagcggaga caacccgtac ctcaagtaca accacgccga cgcggagttt | 300 |
| caggagcgcc ttaaagaaga tacgtctttt ggggggcaacc tcggacgagc agtcttccag | 360 |
| gcgaaaaaga gggttcttga acctctgggc ctggttgagg aacctgttaa gacggctccg | 420 |
| ggaaaaaaga ggccggtaga gcactctcct gtggagccag actcctcctc gggaaccgga | 480 |
| aaggcgggcc agcagcctgc aagaaaaaga ttgaattttg gtcagactgg agacgcaaac | 540 |
| tcagtacctg accccagcc tctcggacag ccaccagcag cccctctgg tctgggaact | 600 |
| aatacgatgg ctacaggcag tggcgcacca atggcagaca taacgagg cgccgacgga | 660 |
| gtgggtaatt cctcgggaaa ttggcattgc gattccacat ggatgggcga cagagtcatc | 720 |
| accaccagca cccgaacctg ggccctgccc acctacaaca accacctcta caaacaaatt | 780 |
| tccagccaat caggagcctc gaacgacaat cactactttg gctacagcac cccttggggg | 840 |
| tattttgact tcaacagatt ccactgccac ttttcaccac gtgactggca agactcatc | 900 |
| aacaacaact ggggattccg acccaagaga ctcaagttca gctctttaa cattcaagtc | 960 |
| aaagaggtca cgcagaatga cggtacgacg acgattgcca ataaccttac cagcacggtt | 1020 |
| caggtgttta ctgactcgga gtaccagctc ccgtacgtcc tcggctcggc gcatcaagga | 1080 |
| tgcctcccgc cgttcccagc agacgtcttc atggtgccac agtatggata cctcaccctg | 1140 |
| aacaacggga tcgggcagt aggacgctct tcattttact gcctggagta cttccctcct | 1200 |
| cagatgctgc gtaccggtaa caacttacc ttcagctaca cttttgagga cgttcctttc | 1260 |
| cacagcagct acgctcacag ccagagtctg gaccgtctca tgaatcctct catcgaccag | 1320 |
| tacctgtatt acttgagcag aacagacact ccaagtggaa ccaccacgca gtcaaggctt | 1380 |
| cagttttctc aggccggagc gagtgacatt cggaccagt ctaggaactg gcttcctgga | 1440 |
| ccctgttacc gccagcagcg agtatcaaag acatctgcgg ataacaacaa cagtgaatac | 1500 |
| tcgtggactg gagctaccaa gtaccacctc aatggcagag actctctggt gaatccgggc | 1560 |
| ccggccatgg caagccacaa ggacgatgaa gaaaagtttt ttcctcagag cggggttctc | 1620 |

```
atctttggga agcaaggctc agagaaaaca agtgtggaca ttgaaaaggt catgattaca      1680
gacgaagagg aaatcaggac gaccaatccc gtggctacgg agcagtatgg ttctgtatct      1740
accaacctcc agagaggcaa cagacaagca gctaccgcag atgtcaacac acaaggcgtt      1800
cttccaggca tggtctggca ggacagagat gtgtaccttc aggggcccat ctgggcaaag      1860
attccacaca cggacggaca ttttcacccc tctcccctca tgggtggatt cggacttaaa      1920
caccctcctc cacagattct catcaagaac accccgtac  ctgcgaatcc ttcgaccacc      1980
ttcagtgcgg caaagtttgc ttccttcatc acacagtact ccacgggaca ggtcagcgtg      2040
gagatcgagt gggagctgca aaggaaaac  agcaaacgct ggaatcccga agttcagtac      2100
acttccaact acaacaagtc tgttaatgtg gactttactg tggacactaa tggcgtgtat      2160
acagagcctc gccccattgg caccagatac ctgactcgta atctgtaa                  2208
```

<210> SEQ ID NO 41
<211> LENGTH: 2208
<212> TYPE: DNA
<213> ORGANISM: Artificial sequence
<220> FEATURE:
<223> OTHER INFORMATION: Synthetic nucleic acid sequence

<400> SEQUENCE: 41

```
atggctgccg atggttatct tccagattgg ctcgaggaca ctctctctga aggaataaga        60
cagtggtgga agctcaaacc tggcccacca ccaccaaagc ccgcagagcg gcataaggac       120
gacagcaggg gtcttgtgct tcctgggtac aagtacctcg gacccttcaa cggactcgac       180
aagggagagc cggtcaacga ggcagacgcc gcggccctcg agcacgacaa agcctatgac       240
cggcagctcg acagcggaga caacccgtac ctcaagtaca accacgccga cgcggagttt       300
caggagcgcc ttaaagaaga tacgtctttt ggggggcaacc tcggacgagc agtcttccag       360
gcgaaaaaga gggttcttga acctctgggc ctggttgagg aacctgttaa  acggctccg       420 ggaaaaaaga ggccggtaga gcactctcct gtggagccag actcctcctc gggaaccgga       480
aaggcgggtc agcagcctgc aagaaaaaga ttgaattttg gtcagactgg agacgcagac       540
tcagtacctg acccccagcc tctcggacag ccaccagcag cccctctgg  tctgggaact      600 aatacgatgg ctacaggcag tggcgcacca atggcagaca ataacgaggg cgccgacgga       660
gtgggtaatt cctcgggaaa ttggcattgc gattccacat ggatgggcga cagagtcatc       720
accaccagca cccgaacctg gccctgccc  acctacaaca accacctcta caaacaaatt       780
tccagccaat caggagcctc gaacgacaat cactactttg gctacagcac cccttggggg       840
tattttgact tcaacagatt ccactgccac tttcaccac  gtgactggca aagactcatc       900
aacaacaact ggggattccg acccaagaga ctcaagttca gctctttaa  cattcaagtc       960 aaagaggtca cgcagaatga cggtacgacg acgattgcca ataaccttac cagcacggtt      1020
caggtgttta ctgactcgga gtaccagctc ccgtacgtcc tcggctcggc gcatcaagga      1080
tgcctcccgc cgttcccagc agacgtcttc atggtgccac agtatggata cctcaccctg      1140
aacaacggga tcaggcagt  aggacgctct tcatttact  gcctggagta cttcccttct      1200
cagatgctgc gtaccggtaa caactttacc ttcagctaca cttttgagga cgttcctttc      1260
cacagcagct acgctcacag ccagagtctg gaccgtctca tgaatcctct catcgaccag      1320
tacctgtatt acttgagcag aacagacgct ccaagtggaa ccaccacgca gtcaaggctt      1380 cagtttttctc aggccggagc gagtgacatt cggaccagt  ctaggaactg gcttcctgga      1440
```

```
ccctgttacc gccagcagcg agtatcaaag acatctgcgg ataacaacaa cagtgaatac    1500
tcgtggactg gagctaccaa gtaccacctc aatggcagag actctctggt gaatccgggc    1560
ccggccatgg caagccacaa ggacgatgaa gaaaagtttt ttcctcagag cggggttctc    1620
atctttggga agcaaggctc agagaaaaca agtgtggaca ttgaaaaggt catgattaca    1680
gacgaagagg aaatcaggac aaccaatccc gtggctacgg agcagtatgg ttctgtatct    1740
accaacctcc agagaggcaa cagacaagca gctaccgcag atgtcaacac acaaggcgtt    1800
cttccaggca tggtctggca ggacagagat gtgtaccttc aggggcccat ctgggcaaag    1860
attccacaca cggacggaca ttttcacccc tctcccctca tgggtggatt cggacttaaa    1920
caccctcctc cacagattct catcaagaac accccggtac ctgcgaatcc ttcgaccacc    1980
ttcagtgcgg caaagtttgc ttccttcatc acacagtact ccacgggaca ggtcagcgtg    2040
gagatcgagt gggagctgca gaaggaaaac agcaaacgct ggaatcccga agttcagtac    2100
acttccaact acaacaagtc tgttaatgtg gactttactg tggacactaa tggcgtgtat    2160
tcagagcctc gccccattgg caccagatac ctgactcgta atctgtaa                 2208
```

COMPOSITIONS AND METHODS OF TREATMENT

CROSS REFERENCE TO RELATED APPLICATIONS

This application is a continuation of U.S. patent application Ser. No. 17/468,290 filed on Sep. 7, 2021, which is a continuation of U.S. patent application Ser. No. 14/774,972 filed on Sep. 11, 2015, issued as U.S. Pat. No. 11,136,557 on Oct. 5, 2021, which application is a 371 filing of International Application No. US2014/040083 filed on May 29, 2014, which claims the benefit of U.S. Provisional Application No. 61/829,735 filed on May 31, 2013, which applications are incorporated herein by reference in their entirety.

STATEMENT REGARDING FEDERALLY SPONSORED RESEARCH

This invention was made with government support under Grant No. HL081527 awarded by the National Institutes of Health. The government has certain rights in the invention.

INCORPORATION BY REFERENCE OF SEQUENCE LISTING PROVIDED AS A TEXT FILE

A Sequence Listing is provided herewith as a text file, "BERK-216CON2_ST25.txt" created on Apr. 20, 2022 and having a size of 172,848 bytes. The contents of the text file are incorporated by reference herein in their entirety.

INTRODUCTION

Gene delivery vectors based on adeno-associated viruses (AAV) have demonstrated promise in both preclinical disease models and recently in human clinical trials for several disease targets. Vectors based on AAV are extremely safe because wild-type AAV is nonpathogenic and has no etiologic association with any known diseases. In addition, AAV offers the capability for highly efficient gene delivery and sustained transgene expression in numerous tissues, including liver, muscle, lung, retina, and brain.

AAV is a single stranded DNA virus that contains two open reading frames, rep and cap. The first gene encodes four proteins necessary for genome replication (Rep78, Rep68, Rep52, and Rep40), and the second expresses three structural proteins (VP1-3) that assemble to form the viral capsid. As its name implies, AAV is dependent upon the presence of a helper virus, such as an adenovirus or herpesvirus, for active replication. In the absence of a helper it establishes a latent state in which its genome is maintained episomally or integrated into the host chromosome. Multiple homologous primate AAV serotypes and numerous nonhuman primate types have been identified. AAV2 is the best characterized as a gene delivery vehicle.

As of 2010, there were 75 ongoing clinical trials that used AAV as the gene delivery vehicle. However, the high prevalence of anti-capsid neutralizing antibodies, due to widespread exposure to numerous AAV variants and serotypes within the human population, decrease the efficacy of AAV gene therapy. This pre-existing immunity, as well as the subsequent development of immunity due to vector administration, can impede the broader implementation of AAV gene therapy. For example, to date, AAV has been most successful in clinical studies involving delivery to immune privileged regions.

Recent analysis indicated that the prevalence of anti-AAV IgG antibodies in humans was highest for AAV2 (72%) and AAV1 (67%), but AAV9 (47%), AAV6 (46%), AAV5 (40%), and AAV8 (38%) antibodies were also present in a large portion of the population studied. Several studies found that humoral immunity to the AAV capsid during gene therapy could be prevented by lowering the amount of rAAV particles delivered. Unfortunately, administration of low vector doses leads to low transduction and thus low therapeutic gene expression.

There is a need in the art for the development of novel AAV variants that are resistant to neutralization by anti-AAV antibodies.

LITERATURE

Asuri et al., Mol Ther. 2012 February; 20(2):329-38; Bainbridge et al., N Engl J Med. 2008 May 22; 358(21): 2231-9; Excoffon et al., Proc Natl Acad Sci USA. 2009 Mar. 10; 106(10):3865-70; Grimm et al., J Virol. 2008 June; 82(12):5887-911; Jang et al., Mol Ther. 2011 April; 19(4): 667-75; Klimczak et al., PLoS One. 2009 Oct. 14; 4(10): e7467; Koerber et al.; Mol Ther. 2008 October; 16(10): 1703-9; Koerber et al.; Mol Ther. 2009 December; 17(12): 2088-95; Maguire et al., N Engl J Med. 2008 May 22; 358(21):2240-8; Maguire et al., Lancet. 2009 Nov. 7; 374 (9701):1597-605; Maheshri et al., Nat Biotechnol. 2006 February; 24(2):198-204; Perabo et al., J Gene Med. 2006 February; 8(2):155-62; Yang et al., Proc Natl Acad Sci USA. 2009 Mar. 10; 106(10):3946-51; WO2012145601; U.S. Patent Publication No. US20050053922

SUMMARY

The present disclosure provides infectious recombinant adeno-associated virus (rAAV) virions that comprise a variant capsid protein and a heterologous nucleic acid. The present disclosure further provides the variant adeno-associated virus (AAV) capsid proteins (and/or a nucleic acid encoding the variant AAV capsid proteins), which confer to an infectious rAAV virion an increased resistance to human AAV neutralizing antibodies. The present disclosure further provides host cells comprising an infectious rAAV virion and/or a nucleic acid encoding a subject variant AAV capsid protein. The present disclosure further provides libraries of the above virions, capsid proteins, nucleic acids, and/or host cells; where the variant AAV capsid protein of at least one member of the library comprises an amino acid sequence having at least one amino acid substitution relative to the amino acid sequence set forth in one of SEQ ID NOs: 10-13 and 26-33.

The present disclosure further provides methods of delivering a heterologous nucleic acid to a target cell where the target cell is contacted with a subject infectious rAAV virion. The present disclosure further provides methods of delivering a gene product to an individual, the methods generally involving administering an effective amount of a subject rAAV virion to an individual in need thereof. Also provided herein are compositions and kits for practicing the subject methods.

FEATURES

Features of the present disclosure include an infectious recombinant adeno-associated virus (rAAV) virion comprising (a) a variant adeno-associated virus (AAV) capsid protein comprising an amino acid sequence having at least about 90% amino acid sequence identity to the amino acid sequence set forth in one of SEQ ID NOs: 11-13 and 26-33; and (b) a heterologous nucleic acid. In some cases, the variant AAV capsid protein comprises an amino acid sequence having at least about 95% amino acid sequence identity to the amino acid sequence set forth in one of SEQ ID NOs: 11-13 and 26-33. In some cases, the variant AAV capsid protein comprises the amino acid sequence set forth in one of SEQ ID NOs: 11-13 and 26-33.

Features of the present disclosure include an infectious recombinant adeno-associated virus (rAAV) virion comprising (a) a variant adeno-associated virus (AAV) capsid protein that comprises an amino acid sequence having at least about 95% amino acid sequence identity to the amino acid sequence set forth in SEQ ID NO: 10, and includes the amino acid substitutions N312K, N449D, D472N, N551S, I698V, and L735Q relative to SEQ ID NO: 2; and (b) a heterologous nucleic acid. In some cases, the variant AAV capsid protein comprises the amino acid sequence set forth in SEQ ID NO: 10. In some cases, the rAAV exhibits increased resistance to human AAV neutralizing antibodies compared to the resistance exhibited by AAV2 (wild type AAV serotype 2). In some cases, the rAAV exhibits at least about 1.5-fold (e.g., at least about 3-fold, at least about 5-fold, at least about 10-fold, at least about 30-fold, etc.) greater resistance to human AAV neutralizing antibodies than the resistance exhibited by AAV2. In some cases, the rAAV exhibits increased transduction of mammalian cells in the presence of human AAV neutralizing antibodies compared to the transduction of mammalian cells exhibited by wild type AAV serotype 2 (AAV2). In some cases, the mammalian cells are liver cells, pancreatic cells, skeletal muscle cells, heart muscle cells, fibroblasts, retinal cells, synovial joint cells, lung cells, T cells, neurons, glial cells, stem cells (e.g., hematopoietic stem cells, hematopoietic progenitor cells, neural stem cells, neural progenitor cells, neural crest stem cells, embryonic stem cells, induced pluripotent stem cells (iPS cells), mesenchymal stem cells, mesodermal stem cells, liver stem cells, pancreatic stem cells, pancreatic progenitor cells, muscle stem cells, retinal stem cells, and the like), endothelial cells, or cancer cells. In some cases, the heterologous nucleic acid comprises an RNA interfering agent. In some cases, the heterologous nucleic acid comprises a nucleotide sequence encoding a polypeptide.

Features of the present disclosure include an isolated nucleic acid comprising a nucleotide sequence that encodes a variant adeno-associated virus (AAV) capsid protein comprising an amino acid sequence having at least about 90% amino acid sequence identity to the amino acid sequence set forth in one of SEQ ID NOs: 11-13 and 26-33. In some cases, the encoded variant AAV capsid protein comprises an amino acid sequence having at least about 95% amino acid sequence identity to the amino acid sequence set forth in one of SEQ ID NOs: 11-13 and 26-33. In some cases, the encoded variant AAV capsid protein comprises the amino acid sequence set forth in one of SEQ ID NOs: 11-13 and 26-33.

Features of the present disclosure include an isolated nucleic acid comprising a nucleotide sequence that encodes a variant adeno-associated virus (AAV) capsid protein that comprises an amino acid sequence having at least about 95% amino acid sequence identity to the amino acid sequence set forth in SEQ ID NO: 10, and includes the amino acid substitutions N312K, N449D, D472N, N551S, I698V, and L735Q relative to SEQ ID NO: 2.

In some cases, the encoded variant AAV capsid protein (encoded by an isolated nucleic acid) confers to an infectious recombinant adeno-associated virus (rAAV) virion an increased resistance to human AAV neutralizing antibodies compared to the resistance exhibited by AAV2 (wild type AAV serotype 2). In some cases, increased resistance is at least about 1.5-fold (e.g., at least about 3-fold, at least about 5-fold, at least about 10-fold, at least about 30-fold, etc.) greater than the resistance exhibited by AAV2. In some cases, the encoded variant AAV capsid protein (encoded by an isolated nucleic acid) confers to an infectious recombinant adeno-associated virus (rAAV) virion an increased transduction of mammalian cells in the presence of human AAV neutralizing antibodies compared to the transduction exhibited by AAV2.

Features of the present disclosure include an isolated host cell comprising a subject nucleic acid as described above. In some cases, the host cell is stably transfected with the nucleic acid. In some cases, the host cell further comprises a nucleic acid comprising a nucleotide sequence encoding an AAV rep protein. In some cases, the host cell further comprises a recombinant AAV vector.

Features of the present disclosure include a method of delivering a heterologous nucleic acid to a target cell, comprising contacting the target cell with a subject virion (described above). In some cases, the target cell is a liver cell, a pancreatic cell, a skeletal muscle cell, a heart muscle cell, a fibroblast, a retinal cell, a synovial joint cell, a lung cell, a T cell, a neuron, a glial cell, a stem cell (e.g., a hematopoietic stem cell, a hematopoietic progenitor cell, a neural stem cell, a neural progenitor cell, a neural crest stem cell, an embryonic stem cell, an induced pluripotent stem cell (iPS cell), a mesenchymal stem cell, a mesodermal stem cell, a liver stem cell, a pancreatic stem cell, a pancreatic progenitor cell, a muscle stem cell, or a retinal stem cell, and the like), an endothelial cell, or a cancer cell. In some cases, the target cell is in vitro. In some cases, the target cell is in vivo.

Features of the present disclosure include a method of delivering a gene product to an individual in need thereof, the method comprising administering to the individual an effective amount of a subject infectious recombinant adeno-associated virus (rAAV) virion (described above). In some cases, the heterologous nucleic acid of the rAAV virion comprises an RNA interfering agent. In some cases, the heterologous nucleic acid of the rAAV virion comprises a nucleotide sequence encoding a polypeptide. In some cases, the administering step comprises the indirect delivery of the infectious rAAV virion. In some cases, the administering step comprises the direct delivery of the infectious rAAV virion.

Features of the present disclosure include a variant adeno-associated virus (AAV) capsid protein comprising an amino acid sequence having at least about 90% amino acid sequence identity to the amino acid sequence set forth in one of SEQ ID NOs: 11-13 and 26-33. In some cases, the AAV capsid protein comprises an amino acid sequence having at least about 95% amino acid sequence identity to the amino acid sequence set forth in one of SEQ ID NOs: 11-13 and 26-33. In some cases, the AAV capsid protein comprises the amino acid sequence set forth in one of SEQ ID NOs: 11-13 and 26-33.

Features of the present disclosure include a variant adeno-associated virus (AAV) capsid protein that comprises an amino acid sequence having at least about 95% amino acid sequence identity to the amino acid sequence set forth in SEQ ID NO: 10, and includes the amino acid substitutions N312K, N449D, D472N, N551S, I698V, and L735Q relative to SEQ ID NO: 2. In some cases, the variant AAV capsid protein comprises the amino acid sequence set forth in SEQ ID NO: 10. In some cases, the variant AAV capsid protein confers to an infectious recombinant adeno-associated virus (rAAV) virion an increased resistance to human AAV neutralizing antibodies compared to the resistance exhibited by AAV2. In some cases, the increased resistance is at least about 1.5-fold (e.g., at least about 3-fold, at least about 5-fold, at least about 10-fold, at least about 30-fold, etc.) greater than the resistance exhibited by AAV2. In some cases, the variant AAVcapsid protein confers to an infectious recombinant adeno-associated virus (rAAV) virion an increased transduction of mammalian cells in the presence of human AAV neutralizing antibodies compared to the transduction exhibited by AAV2.

Features of the present disclosure include a library comprising at least one of: (i) two or more infectious rAAV virions, each comprising a variant adeno-associated virus (AAV) capsid protein and a heterologous nucleic acid; (ii) two or more isolated nucleic acids, each comprising a nucleotide sequence that encodes a variant AAV capsid protein; (iii) two or more host cells, each comprising a nucleic acid that comprises a nucleotide sequence that encodes a variant AAV capsid protein; and (iv) two or more variant AAV capsid proteins; wherein the variant AAV capsid protein of at least one member of the library comprises an amino acid sequence having at least one amino acid substitution relative to the amino acid sequence set forth in one of SEQ ID NOs: 10-13 and 26-33.

Features of the present disclosure include a method of generating and identifying a modified infectious rAAV virion that exhibits an altered property of infection relative to a starter (parent) virion comprising a starter capsid protein, the method comprising: (a) generating variant adeno-associated virus (AAV) capsid proteins from the starter capsid protein, wherein the starter capsid protein comprises the amino acid sequence set forth in one of SEQ ID NOs: 10-13 and 26-33, and wherein each variant AAV capsid protein comprises at least one amino acid substitution relative to the starter capsid protein; (b) generating variant AAV virions, each comprising a variant capsid AAV protein generated in step (a); and (c) assaying variant AAV virions generated in step (b) for the altered property of infection to identify the modified infectious rAAV virion. In some cases, the generation of the library of variant AAV capsid proteins comprises a method of mutagenesis selected from the group consisting of: polymerase chain reaction mutagenesis, oligonucleotide-directed mutagenesis, saturation mutagenesis, loop-swapping mutagenesis, fragment shuffling mutagenesis, and a combination thereof. In some cases, the altered property of infection is an increased resistance to human neutralizing AAV antibodies compared to the resistance exhibited by the starter virion. In some cases, the altered property of infection is an increased transduction of mammalian cells in the presence of human AAV neutralizing antibodies compared to the transduction exhibited by the starter virion. In some cases, the modified infectious rAAV virion comprises a modified AAV capsid protein comprising an amino acid sequence having at least about 90% amino acid sequence identity to the starter capsid protein.

Features of the present disclosure include a method of generating a variant AAV capsid protein from a starter capsid protein, the method comprising: subjecting a nucleic acid that comprises a nucleotide sequence encoding the starter capsid protein to a type of mutagenesis selected from the group consisting of: polymerase chain reaction mutagenesis, oligonucleotide-directed mutagenesis, saturation mutagenesis, loop-swapping mutagenesis, fragment shuffling mutagenesis, and a combination thereof; wherein the starter capsid protein comprises the amino acid sequence set forth in one of SEQ ID NOs: 10-13 and 26-33.

BRIEF DESCRIPTION OF THE DRAWINGS

FIGS. 2A-B depict the neutralization profiles of antibody evading variants using human IVIG.

FIGS. 3A-C depict the neutralization profiles of antibody evading variants using human sera acquired from individuals that were excluded from hemophilia B clinical trials due to the presence of high neutralizing antibody titers against AAV.

FIGS. 4A-B depict the amino acid sequences of loop-swap/shuffle and saturation mutagenesis clones.

FIG. 5 demonstrates the in vitro tropism of AAV variants.

FIGS. 6A-B show in vivo localization and neutralization of novel AAV variants.

FIGS. 7A-D demonstrate the generation of human antibody evaders.

FIGS. 8A-I depict the capsid protein sequence of Shuffle 100-1 (SEQ ID NO: 11) aligned with the wild type capsid protein sequences of AAV1-9 (SEQ ID NOs: 1-9).

FIGS. 9A-I depict the capsid protein sequence of Shuffle 100-3 (SEQ ID NO: 12) aligned with the wild type capsid protein sequences of AAV1-9 (SEQ ID NOs: 1-9).

FIGS. 10A-I depict the capsid protein sequence of Shuffle 100-7 (SEQ ID NO: 13) aligned with the wild type capsid protein sequences of AAV1-9 (SEQ ID NOs: 1-9).

FIG. 11 shows the neutralizing antibody titers of library clones and parent serotypes in immunized mouse sera.

DEFINITIONS

Adeno-associated virus is a nonpathogenic parvovirus composed of a 4.7 kb single-stranded DNA genome within a non-enveloped, icosahedral capsid. "AAV" is an abbreviation for adeno-associated virus, and may be used to refer to the virus itself or derivatives thereof. The genome contains three open reading frames (ORF) flanked by inverted terminal repeats (ITR) that function as the viral origin of replication and packaging signal. The rep ORF encodes four nonstructural proteins that play roles in viral replication, transcriptional regulation, site-specific integration, and virion assembly. The cap ORF encodes three structural proteins (VP1-3) that assemble to form a 60-mer viral capsid. Finally, an ORF present as an alternate reading frame within the cap gene produces the assembly-activating protein (AAP), a viral protein that localizes AAV capsid proteins to the nucleolus and functions in the capsid assembly process.

There are several naturally occurring serotypes and over 100 variants of AAV, each of which differs in amino acid sequence, particularly within the hypervariable regions of the capsid proteins, and thus in their gene delivery properties. No AAV has been associated with any human disease, making recombinant AAV attractive for clinical applications.

The term "AAV" as used herein covers all subtypes and both naturally occurring and recombinant forms, except where required otherwise. The term "AAV" includes AAV type 1 (AAV-1 or AAV1), AAV type 2 (AAV-2 or AAV2), AAV type 3 (AAV-3 or AAV3), AAV type 4 (AAV-4 or AAV4), AAV type 5 (AAV-5 or AAV5), AAV type 6 (AAV-6 or AAV6), AAV type 7 (AAV-7 or AAV7), AAV type 8 (AAV-8 or AAV8), AAV type 9 (AAV-9 or AAV9), avian AAV, bovine AAV, canine AAV, equine AAV, primate AAV, non-primate AAV, and ovine AAV. "Primate AAV" refers to AAV that infect primates, "non-primate AAV" refers to AAV that infect non-primate mammals, "bovine AAV" refers to AAV that infect bovine mammals, etc.

Figure 1A:
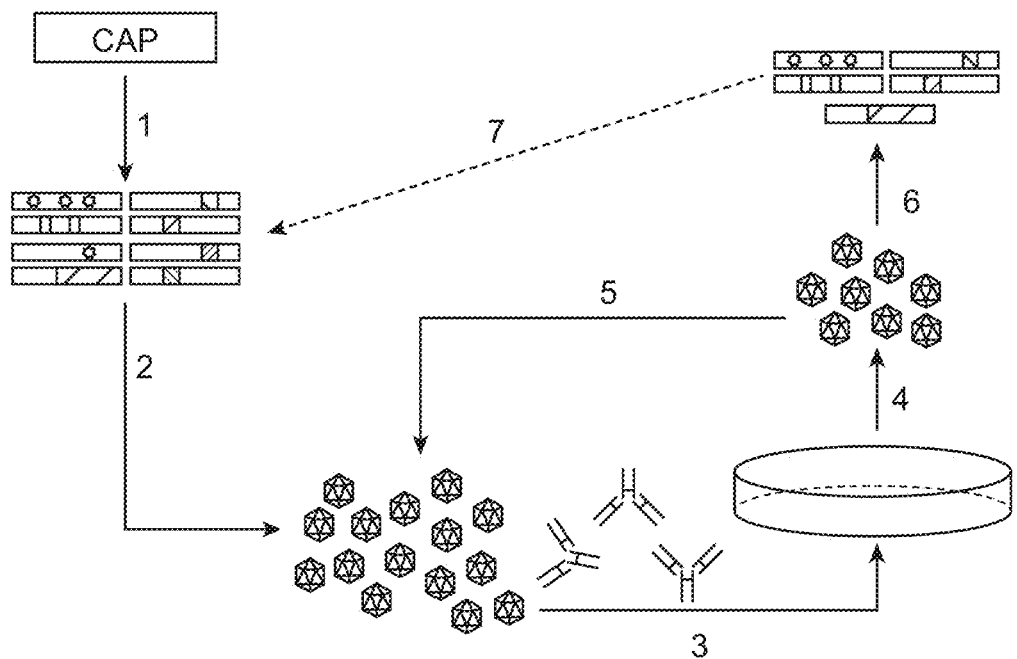
FIGS. 1A-B depict directed Evolution of AAV for Enhanced Antibody Evasion.

The genomic sequences of various serotypes of AAV, as well as the sequences of the native terminal repeats (TRs), Rep proteins, and capsid subunits are known in the art. Such sequences may be found in the literature or in public databases such as GenBank. See, e.g., GenBank Accession Numbers NC_002077.1 (AAV-1), AF063497.1 (AAV-1), NC_001401.2 (AAV-2), AF043303.1 (AAV-2), J01901.1 (AAV-2), U48704.1 (AAV-3), NC_001729.1 (AAV-3), NC_001829.1 (AAV-4), U89790.1 (AAV-4), NC_006152.1 (AAV-5), AF085716.1 (AAV-5), AF028704.1 (AAV-6), NC_006260.1 (AAV-7), AF513851.1 (AAV-7), AF513852.1 (AAV-8) NC_006261.1 (AAV-8), and AY530579.1 (AAV-9); the disclosures of which are incorporated by reference herein for teaching AAV nucleic acid and amino acid sequences. See also, e.g., Srivistava et al. (1983) *J. Virology* 45:555; Chiorini et al. (1998) *J. Virology* 71:6823; Chiorini et al. (1999) *J. Virology* 73:1309; Bantel-Schaal et al. (1999) *J. Virology* 73:939; Xiao et al. (1999) *J. Virology* 73:3994; Muramatsu et al. (1996) *Virology* 221:208; Shade et al., (1986) *J. Virol.* 58:921; Gao et al. (2002) *Proc. Nat. Acad. Sci. USA* 99:11854; Moris et al. (2004) *Virology* 33:375-383; international patent publications WO 00/28061, WO 99/61601, WO 98/11244; and U.S. Pat. No. 6,156,303.

The sequences of naturally existing cap (capsid) proteins associated with AAV serotypes are known in the art and include: AAV1 (SEQ ID NO: 1), AAV2 (SEQ ID NO: 2), AAV3 (SEQ ID NO: 3), AAV4 (SEQ ID NO: 4), AAV5 (SEQ ID NO: 5), AAV6 (SEQ ID NO: 6), AAV7 (SEQ ID NO: 7), AAV8 (SEQ ID NO: 8), and AAV9 (SEQ ID NO: 9). The term "variant AAV capsid protein" is a an AAV capsid protein comprising an amino acid sequence that includes at least one substitution (including deletion, insertion, etc.) relative to one of the naturally existing AAV capsid protein sequences set forth in SEQ ID NOs:1-9.

An "AAV virion" or "AAV viral particle" refers to a viral particle composed of at least one AAV capsid protein and an encapsidated AAV polynucleotide.

"Recombinant," as applied to a polynucleotide means that the polynucleotide is the product of various combinations of cloning, restriction or ligation steps, and other procedures that result in a construct that is distinct from a polynucleotide found in nature. A recombinant virus is a viral particle comprising a recombinant polynucleotide. The terms respectively include replicates of the original polynucleotide construct and progeny of the original virus construct.

If an AAV virion comprises a heterologous polynucleotide (i.e. a polynucleotide other than a wild-type AAV genome, e.g., a transgene to be delivered to a target cell, an RNAi agent or CRISPR agent to be delivered to a target cell, etc.), it is typically referred to as a "recombinant AAV (rAAV) virion" or an "rAAV viral particle." In general, the heterologous polynucleotide is flanked by at least one, and generally by two, AAV inverted terminal repeat sequences (ITRs).

The term "rAAV vector" encompasses rAAV virions (i.e., rAAV viral particles) (e.g., an infectious rAAV virion), which by definition include an rAAV polynucleotide; and also encompasses polynucleotides encoding rAAV (e.g., a single stranded polynucleotide encoding rAAV (ss-rAAV); a double stranded polynucleotide encoding rAAV (ds-rAAV), e.g., plasmids encoding rAAV; and the like).

"Packaging" refers to a series of intracellular events that result in the assembly and encapsidation of an AAV particle.

AAV "rep" and "cap" genes refer to polynucleotide sequences encoding replication and encapsidation proteins of adeno-associated virus. AAV rep and cap are referred to herein as AAV "packaging genes."

A "helper virus" for AAV refers to a virus that allows AAV (e.g. wild-type AAV) to be replicated and packaged by a mammalian cell. A variety of such helper viruses for AAV are known in the art, including adenoviruses, herpesviruses and poxviruses such as vaccinia. The adenoviruses encompass a number of different subgroups, although Adenovirus type 5 of subgroup C is most commonly used. Numerous adenoviruses of human, non-human mammalian and avian origin are known and available from depositories such as the ATCC. Viruses of the herpes family include, for example, herpes simplex viruses (HSV) and Epstein-Barr viruses (EBV), as well as cytomegaloviruses (CMV) and pseudorabies viruses (PRV); which are also available from depositories such as ATCC.

"Helper virus function(s)" refers to function(s) encoded in a helper virus genome which allow AAV replication and packaging (in conjunction with other requirements for replication and packaging described herein). As described herein, "helper virus function" may be provided in a number of ways, including by providing helper virus or providing, for example, polynucleotide sequences encoding the requisite function(s) to a producer cell in trans. For example, a plasmid or other expression vector comprising nucleotide sequences encoding one or more adenoviral proteins is transfected into a producer cell along with an rAAV vector.

An "infectious" virus or viral particle is one that comprises a competently assembled viral capsid and is capable of delivering a polynucleotide component into a cell for which the viral species is tropic. The term does not necessarily imply any replication capacity of the virus. Assays for counting infectious viral particles are described elsewhere in this disclosure and in the art. Viral infectivity can be expressed as the ratio of infectious viral particles to total viral particles. Methods of determining the ratio of infectious viral particle to total viral particle are known in the art. See, e.g., Grainger et al. (2005) *Mol. Ther.* 11:S337 (describing a TCID50 infectious titer assay); and Zolotukhin et al. (1999) *Gene Ther.* 6:973. See also the Examples.

The term "tropism" as used herein refers to the preferential targeting of specific host species or specific cell types within a host species by a virus (e.g., an AAV). For example, a virus that can infect cells of the heart, lung, liver, and muscle has a broader (i.e., increased) tropism relative to a virus that can infect only lung and muscle cells. Tropism can also include the dependence of a virus on particular types of cell surface molecules of the host. For example, some viruses can infect only cells with surface glycosaminoglycans, while other viruses can infect only cells with sialic acid (such dependencies can be tested using various cells lines deficient in particular classes of molecules as potential host cells for viral infection). In some cases, the tropism of a virus describes the virus's relative preferences. For example, a first virus may be able to infect all cell types but is much more successful in infecting those cells with surface glycosaminoglycans. A second virus can be considered to have a similar (or identical) tropism as the first virus if the second virus also prefers the same characteristics (e.g., the second virus is also more successful in infecting those cells with surface glycosaminoglycans), even if the absolute transduction efficiencies are not similar. For example, the second virus might be more efficient than the first virus at infecting every given cell type tested, but if the relative preferences are similar (or identical), the second virus can still be considered to have a similar (or identical) tropism as the first virus. In some embodiments, the tropism of a virion comprising a subject variant AAV capsid protein is not altered relative to a naturally occurring virion. In some embodiments, the tropism of a virion comprising a subject variant AAV capsid protein is expanded (i.e., broadened) relative to a naturally occurring virion. In some embodiments, the tropism of a virion comprising a subject variant AAV capsid protein is reduced relative to a naturally occurring virion.

A "replication-competent" virus (e.g. a replication-competent AAV) refers to a phenotypically wild-type virus that is infectious, and is also capable of being replicated in an infected cell (i.e. in the presence of a helper virus or helper virus functions). In the case of AAV, replication competence generally requires the presence of functional AAV packaging genes. In general, rAAV vectors as described herein are replication-incompetent in mammalian cells (especially in human cells) by virtue of the lack of one or more AAV packaging genes. Typically, such rAAV vectors lack any AAV packaging gene sequences in order to minimize the possibility that replication competent AAV are generated by recombination between AAV packaging genes and an incoming rAAV vector. In many embodiments, rAAV vector preparations as described herein are those which contain few if any replication competent AAV (rcAAV, also referred to as RCA) (e.g., less than about 1 rcAAV per $10^2$ rAAV particles, less than about 1 rcAAV per $10^4$ rAAV particles, less than about 1 rcAAV per $10^8$ rAAV particles, less than about 1 rcAAV per $10^{12}$ rAAV particles, or no rcAAV).

The term "polynucleotide" refers to a polymeric form of nucleotides of any length, including deoxyribonucleotides or ribonucleotides, or analogs thereof. A polynucleotide may comprise modified nucleotides, such as methylated nucleotides and nucleotide analogs, and may be interrupted by non-nucleotide components. If present, modifications to the nucleotide structure may be imparted before or after assembly of the polymer. The term polynucleotide, as used herein, refers interchangeably to double- and single-stranded molecules. Unless otherwise specified or required, any embodiment herein that comprises a polynucleotide encompasses both the double-stranded form and each of two complementary single-stranded forms known or predicted to make up the double-stranded form.

A polynucleotide or polypeptide has a certain percent "sequence identity" to another polynucleotide or polypeptide, meaning that, when aligned, that percentage of bases or amino acids are the same when comparing the two sequences. Sequence similarity can be determined in a number of different manners. To determine sequence identity, sequences can be aligned using the methods and computer programs, including BLAST, available over the world wide web at ncbi.nlm.nih.gov/BLAST/. Another alignment algorithm is FASTA, available in the Genetics Computing Group (GCG) package, from Madison, Wis., USA, a wholly owned subsidiary of Oxford Molecular Group, Inc. Other techniques for alignment are described in Methods in Enzymology, vol. 266: Computer Methods for Macromolecular Sequence Analysis (1996), ed. Doolittle, Academic Press, Inc., a division of Harcourt Brace & Co., San Diego, Calif., USA. Of particular interest are alignment programs that permit gaps in the sequence. The Smith-Waterman is one type of algorithm that permits gaps in sequence alignments. See *Meth. Mol. Biol.* 70: 173-187 (1997). Also, the GAP program using the Needleman and Wunsch alignment method can be utilized to align sequences. See *J. Mol. Biol.* 48: 443-453 (1970)

A "gene" refers to a polynucleotide that performs a function of some kind in the cell. For example, a gene can contain an open reading frame that is capable of encoding a particular protein after being transcribed and translated. On the other hand a gene can encode a functional RNA product that is not translated (e.g., an aptamer, an interfering RNA, a ribosomal RNA (rRNA), a transfer RNA (tRNA), etc.).

A "gene expression product" or "gene product" is a molecule resulting from expression of a particular gene, as defined above. Gene expression products include, e.g., a polypeptide, an aptamer, an interfering RNA, a messenger RNA (mRNA), an rRNA, a tRNA, a non-coding RNA (ncRNA), and the like.

An "RNA interfering agent" or "RNAi agent" encompasses any agent (or a polynucleotide encoding such an agent) that can be used to change the expression of a gene (as defined above). Examples of RNAi agents known to one of ordinary skill in the art include, but are not limited to, (i) siRNA agents; (ii) antisense RNA; (iii) CRISPR agents; (iv) Zinc finger nuclease agents, and (v) Transcription activator-like effector nuclease (TALEN) agents.

(i) an siRNA agent ("small interfering" or "short interfering RNA" (or siRNA)) is an RNA duplex of nucleotides that is targeted to a gene interest (a "target gene"). An "RNA duplex" refers to the structure formed by the complementary pairing between two regions of a RNA molecule, forming a region of double stranded RNA (dsRNA). siRNA is "targeted" to a gene in that the nucleotide sequence of the duplex portion of the siRNA is complementary to a nucleotide sequence of the targeted gene. In some embodiments, the length of the duplex of siRNAs is less than 30 nucleotides. In some embodiments, the duplex can be 29, 28, 27, 26, 25, 24, 23, 22, 21, 20, 19, 18, 17, 16, 15, 14, 13, 12, 11 or 10 nucleotides in length. In some embodiments, the length of the duplex is 19-25 nucleotides in length. The RNA duplex portion of the siRNA can be part of a hairpin structure. siRNA agents that contain a hairpin can also be referred to as "shRNA (short hairpin RNA) agents." In addition to the duplex portion, the hairpin structure may contain a loop portion positioned between the two sequences that form the duplex. The loop can vary in length. In some embodiments the loop is 5, 6, 7, 8, 9, 10, 11, 12 or 13 nucleotides in length. The hairpin structure can also contain 3' or 5' overhang portions. In some embodiments, the overhang is a 3' or a 5' overhang 0, 1, 2, 3, 4 or 5 nucleotides in length. In general, the level of expression product (e.g., mRNA, polypeptide, etc.) of a target gene is reduced by an siRNA agent (e.g., an siRNA, an shRNA, etc.) that contains specific double stranded nucleotide sequences that are complementary to at least a 19-25 nucleotide long segment (e.g., a 20-21 nucleotide sequence) of the target gene transcript, including the 5' untranslated (UT) region, the ORF, or the 3' UT region. In some embodiments, short interfering RNAs are about 19-25 nt in length. See, e.g., PCT applications WO0/44895, WO99/32619, WO01/75164, WO01/92513, WO01/29058, WO01/89304, WO02/16620, and WO02/29858; and U.S. Patent Publication No. 20040023390 for descriptions of siRNA technology. The siRNA and/or shRNA can be encoded by a nucleic acid sequence, and the nucleic acid sequence can also include a promoter. The nucleic acid sequence can also include a polyadenylation signal. In some embodiments, the polyadenylation signal is a synthetic minimal polyadenylation signal.

(ii) antisense RNA is RNA that is complementary to a gene expression product. For example, an antisense RNA targeted to a specific mRNA is an RNA-based agent (or can be a modified RNA) that is complementary to the mRNA, where hybridization of the antisense RNA to the mRNA alters the expression of the mRNA (e.g., via altering the stability of the RNA, altering the translation of the RNA, etc.). Also included in "antisense RNA" are nucleic acids encoding an antisense RNA.

(iii) CRISPR agents. CRISPR (Clustered regularly interspaced short palindromic repeats)/CRISPR-associated (Cas) systems provide bacteria and archaea with adaptive immunity against viruses and plasmids by using CRISPR RNAs (crRNAs) to guide the silencing of invading nucleic acids. The Cas 9 protein (or functional equivalent and/or variant thereof, i.e., Cas9-like protein) naturally contains DNA endonuclease activity that depends on association of the protein with two naturally occurring or synthetic RNA molecules called crRNA and tracrRNA (also called guide RNAs). In some cases, the two molecules are covalently linked to form a single molecule (also called a single guide RNA ("sgRNA")). Thus, the Cas9 or Cas9-like protein associates with a DNA-targeting RNA (which term encompasses both the two-molecule guide RNA configuration and the single-molecule guide RNA configuration), which activates the Cas9 or Cas9-like protein and guides the protein to a target nucleic acid sequence. If the Cas9 or Cas9-like protein retains its natural enzymatic function, it will cleave target DNA to create a double-strand break, which can lead to genome alteration (i.e., editing: deletion, insertion (when a donor polynucleotide is present), replacement, etc.), thereby altering gene expression. Some variants of Cas9 (which variants are encompassed by the term Cas9-like) have been altered such that they have a decreased DNA cleaving activity (in some cases, they cleave a single strand instead of both strands of the target DNA, while in other cases, they have severely reduced to no DNA cleavage activity). Cas9-like proteins with decreased DNA-cleavage activity (even no DNA-cleaving activity) can still be guided to a target DNA and can block RNA polymerase activity. Thus enzymatically inactive Cas9-like proteins can be targeted to a specific location in a target DNA by a DNA-targeting RNA in order to block transcription of the target DNA. Detailed information regarding CRISPR agents can be found, for example in (a) Jinek et. al., Science. 2012 Aug. 17; 337(6096):816-21: "A programmable dual-RNA-guided DNA endonuclease in adaptive bacterial immunity"; (b) Qi et al., Cell. 2013 Feb. 28; 152(5):1173-83: "Repurposing CRISPR as an RNA-guided platform for sequence-specific control of gene expression", and (c) U.S. patent application Ser. No. 13/842,859 and PCT application number PCT/US13/32589; all of which are hereby incorporated by reference in their entirety. Thus, the term "CRISPR agent" as used herein encompasses any agent (or nucleic acid encoding such an agent), comprising naturally occurring and/or synthetic sequences, that can be used in the Cas9-based system (e.g., a Cas9 or Cas9-like protein; any component of a DNA-targeting RNA, e.g., a crRNA-like RNA, a tracrRNA-like RNA, a single guide RNA, etc.; a donor polynucleotide; and the like).

(iv) Zinc finger nuclease (ZFN) agents. Zinc-finger nucleases (ZFNs) are artificial DNA endonucleases generated by fusing a zinc finger DNA binding domain to a DNA cleavage domain. ZFNs can be engineered to target desired DNA sequences and this enables zinc-finger nucleases to cleave unique target sequences. When introduced into a cell, ZFNs can be used to edit target DNA in the cell (e.g., the cell's genome) by inducing double strand breaks. For more information on the use of ZFNs, see, for example: Asuri et al., Mol Ther. 2012 February; 20(2):329-38; Bibikova et al. Science. 2003 May 2; 300(5620):764; Wood et al. Science. 2011 Jul. 15; 333(6040):307; Ochiai et al. Genes Cells. 2010 August; 15(8):875-85; Takasu et. al., Insect Biochem Mol Biol. 2010 October; 40(10):759-65; Ekker et al, Zebrafish 2008 Summer; 5(2):121-3; Young et al, Proc Natl Acad Sci USA. 2011 Apr. 26; 108(17):7052-7; Goldberg et al, Cell. 2010 Mar. 5; 140(5):678-91; Geurts et al, Science. 2009 Jul. 24; 325(5939):433; Flisikowska et al, PLoS One. 2011; 6(6):e21045. doi: 10.1371/journal.pone.0021045. Epub 2011 Jun. 13; Hauschild et al, Proc Natl Acad Sci USA. 2011 Jul. 19; 108(29):12013-7; and Yu et al, Cell Res. 2011 November; 21(11):1638-40; all of which are herein incorporated by reference for their teachings related to ZFNs. The term "ZFN agent" encompasses a zinc finger nuclease and/or a polynucleotide comprising a nucleotide sequence encoding a zinc finger nuclease.

(v) Transcription activator-like effector nuclease (TALEN) agents. Transcription activator-like effector nucleases (TALENs) are artificial DNA endonucleases generated by fusing a TAL (Transcription activator-like) effector DNA binding domain to a DNA cleavage domain. TALENS can be quickly engineered to bind practically any desired DNA sequence and when introduced into a cell, TALENs can be used to edit target DNA in the cell (e.g., the cell's genome) by inducing double strand breaks. For more information on the use of TALENs, see, for example: Hockemeyer et al. Nat Biotechnol. 2011 Jul. 7; 29(8):731-4; Wood et al. Science. 2011 Jul. 15; 333(6040):307; Tesson et al. Nat Biotechnol. 2011 Aug. 5; 29(8):695-6; and Huang et. al., Nat Biotechnol. 2011 Aug. 5; 29(8):699-700; all of which are herein incorporated by reference for their teachings related to TALENs. The term "TALEN agent" encompasses a TALEN and/or a polynucleotide comprising a nucleotide sequence encoding a TALEN.

A "control element" or "control sequence" is a nucleotide sequence involved in an interaction of molecules that contributes to the functional regulation of a polynucleotide, including replication, duplication, transcription, splicing, translation, or degradation of the polynucleotide. The regulation may affect the frequency, speed, or specificity of the process, and may be enhancing or inhibitory in nature. Control elements known in the art include, for example, transcriptional regulatory sequences such as promoters and enhancers. A promoter is a DNA region capable under certain conditions of binding RNA polymerase and initiating transcription of a coding region usually located downstream (in the 3' direction) from the promoter.

"Operatively linked" or "operably linked" refers to a juxtaposition of genetic elements, wherein the elements are in a relationship permitting them to operate in the expected manner. For instance, a promoter is operatively linked to a coding region if the promoter helps initiate transcription of the coding sequence. There may be intervening residues between the promoter and coding region so long as this functional relationship is maintained.

An "expression vector" is a vector comprising a region which encodes a polypeptide of interest, and is used for effecting the expression of the protein in an intended target cell. An expression vector also comprises control elements operatively linked to the encoding region to facilitate expression of the protein in the target. The combination of control elements and a gene or genes to which they are operably linked for expression is sometimes referred to as an "expression cassette," a large number of which are known and available in the art or can be readily constructed from components that are available in the art.

"Heterologous" means derived from a genotypically distinct entity from that of the rest of the entity to which it is being compared. For example, a polynucleotide introduced by genetic engineering techniques into a plasmid or vector derived from a different species is a heterologous polynucleotide. A promoter removed from its native coding sequence and operatively linked to a coding sequence with which it is not naturally found linked is a heterologous promoter. Thus, for example, an rAAV that includes a heterologous nucleic acid encoding a heterologous gene product is an rAAV that includes a nucleic acid not normally included in a naturally-occurring, wild-type AAV, and the encoded heterologous gene product is a gene product not normally encoded by a naturally-occurring, wild-type AAV.

The terms "genetic alteration" and "genetic modification" (and grammatical variants thereof), are used interchangeably herein to refer to a process wherein a genetic element (e.g., a polynucleotide) is introduced into a cell other than by mitosis or meiosis. The element may be heterologous to the cell, or it may be an additional copy or improved version of an element already present in the cell. Genetic alteration may be effected, for example, by transfecting a cell with a recombinant plasmid or other polynucleotide through any process known in the art, such as electroporation, calcium phosphate precipitation, or contacting with a polynucleotide-liposome complex. Genetic alteration may also be effected, for example, by transduction or infection with a DNA or RNA virus or viral vector. Generally, the genetic element is introduced into a chromosome or mini-chromosome in the cell; but any alteration that changes the phenotype and/or genotype of the cell and its progeny is included in this term.

A cell has been "genetically modified" or "transformed" or "transfected" by exogenous DNA (e.g. via a recombinant virus), when such DNA has been introduced inside the cell. The presence of the exogenous DNA results in permanent or transient genetic change. The transforming DNA may or may not be integrated (covalently linked) into the genome of the cell. A "clone" is a population of cells derived from a single cell or common ancestor by mitosis. A "cell line" is a clone of a primary cell that is capable of stable growth in vitro for many generations.

A cell is said to be "stably" altered, transduced, genetically modified, or transformed with a genetic sequence if the sequence is available to perform its function during extended culture of the cell in vitro and/or for an extended period of time in vivo. Generally, such a cell is "heritably" altered (genetically modified) in that a genetic alteration is introduced which is also inheritable by progeny of the altered cell.

The terms "polypeptide," "peptide," and "protein" are used interchangeably herein to refer to polymers of amino acids of any length. The terms also encompass an amino acid polymer that has been modified; for example, disulfide bond formation, glycosylation, lipidation, phosphorylation, or conjugation with a labeling component. Polypeptides such as anti-angiogenic polypeptides, neuroprotective polypeptides, and the like, when discussed in the context of delivering a gene product to a mammalian subject, and compositions therefor, refer to the respective intact polypeptide, or any fragment or genetically engineered derivative thereof, which retains the desired biochemical function of the intact protein. Similarly, references to nucleic acids encoding anti-angiogenic polypeptides, nucleic acids encoding neuroprotective polypeptides, and other such nucleic acids for use in delivery of a gene product to a mammalian subject (which may be referred to as "transgenes" to be delivered to a recipient cell), include polynucleotides encoding the intact polypeptide or any fragment or genetically engineered derivative possessing the desired biochemical function.

An "isolated" plasmid, nucleic acid, vector, virus, virion, host cell, protein, or other substance refers to a preparation of the substance devoid of at least some of the other components that may also be present where the substance or a similar substance naturally occurs or is initially prepared from. Thus, for example, an isolated substance may be prepared by using a purification technique to enrich it from a source mixture. Enrichment can be measured on an absolute basis, such as weight per volume of solution, or it can be measured in relation to a second, potentially interfering substance present in the source mixture. Increasing enrichments of the embodiments of this disclosure are increasingly more isolated. An isolated plasmid, nucleic acid, vector, virus, host cell, or other substance is in some embodiments purified, e.g., from about 80% to about 90% pure, at least about 90% pure, at least about 95% pure, at least about 98% pure, or at least about 99%, or more, pure.

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment," as used herein, covers any treatment of a disease in a mammal, particularly in a human, and includes: (a) preventing the disease (and/or symptoms caused by the disease) from occurring in a subject which may be predisposed to the disease or at risk of acquiring the disease but has not yet been diagnosed as having it; (b) inhibiting the disease (and/or symptoms caused by the disease), i.e., arresting its development; and (c) relieving the disease (and/or symptoms caused by the disease), i.e., causing regression of the disease (and/or symptoms caused by the disease).

The terms "individual," "host," "subject," and "patient" are used interchangeably herein, and refer to a mammal, including, but not limited to, humans; non-human primates, including simians; mammalian sport animals (e.g., horses); mammalian farm animals (e.g., sheep, goats, etc.); mammalian pets (dogs, cats, etc.); and rodents (e.g., mice, rats, etc.).

In some embodiments, the individual is a human who has previously been naturally exposed to AAV and as a result harbors anti-AAV antibodies (i.e., AAV neutralizing antibodies). In some embodiments, the individual is a human who has previously been administered an AAV vector (and as a result may harbor anti-AAV antibodies) and needs re-administration of vector for treatment of a different condition or for further treatment of the same condition. Based on positive results in clinical trials involving AAV gene delivery to, for example, liver, muscle, and retina—all tissues affected by neutralizing antibodies against this vehicle—there are many such therapeutic applications/disease targets.

The term "effective amount" as used herein is an amount sufficient to effect beneficial or desired clinical results. An effective amount can be administered in one or more administrations. For purposes of this disclosure, an effective amount of a compound (e.g., an infectious rAAV virion) is an amount that is sufficient to palliate, ameliorate, stabilize, reverse, prevent, slow or delay the progression of (and/or symptoms associated with) a particular disease state (e.g., cancer). Accordingly, an effective amount of an infectious rAAV virion is an amount of the infectious rAAV virion that is able to evade the neutralizing activity of an individual's anti-AAV antibodies, thus effectively delivering the heterologous nucleic acid to a target cell (or target cells) of the individual.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "an infectious recombinant adeno-associated virus (rAAV) virion" includes a plurality of such virions and reference to "the infectious recombinant adeno-associated virus (rAAV) virion" includes reference to one or more such virions and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides infectious recombinant adeno-associated virus (rAAV) virions that comprise a variant capsid protein and a heterologous nucleic acid. The present disclosure further provides the variant adeno-associated virus (AAV) capsid proteins (and/or a nucleic acid encoding the variant AAV capsid proteins), which confer to an infectious rAAV virion an increased resistance to human AAV neutralizing antibodies. The present disclosure further provides host cells comprising an infectious rAAV virion and/or a nucleic acid encoding a subject variant AAV capsid protein. The present disclosure further provides libraries of the above virions, capsid proteins, nucleic acids, and/or host cells; where the variant AAV capsid protein of at least one member of the library comprises an amino acid sequence having at least one amino acid substitution relative to the amino acid sequence set forth in one of SEQ ID NOs:10-13 and 26-33.

The present disclosure further provides methods of delivering a heterologous nucleic acid to a target cell where the target cell is contacted with a subject infectious rAAV virion. The present disclosure further provides methods of delivering a gene product to an individual, the methods generally involving administering an effective amount of a subject rAAV virion to an individual in need thereof. Also provided herein are compositions and kits for practicing the subject methods. In many embodiments, a subject infectious rAAV virion, a subject nucleic acid, a subject variant AAV capsid protein, a subject host cell, etc., is isolated.

Variant AAV Capsid Polypeptides

A subject variant AAV capsid polypeptide (or the variant AAV capsid protein encoded by a subject nucleic acid) confers to an infectious rAAV virion comprising the variant AAV capsid polypeptide an increased resistance to human AAV neutralizing antibodies compared to the resistance exhibited by a wild type AAV (e.g., AAV2 (wild type AAV serotype 2)) or an AAV comprising a wild-type capsid protein. In some embodiments, the increased resistance is at least about 1.5-fold (e.g., at least about 1.5-fold, at least about 2-fold, at least about 3-fold, at least about 4-fold, at least about 5-fold, at least about 7.5-fold, at least about 10-fold, at least about 12-fold, at least about 15-fold, at least about 17-fold, at least about 20-fold, at least about 25-fold, at least about 30-fold, at least about 40-fold, at least about 50-fold, at least about 75-fold, at least about 100-fold, at least about 150-fold, at least about 200-fold, at least about 250-fold, at least about 300-fold, etc.) greater than the resistance exhibited by a wild type AAV (e.g., AAV2 (wild type AAV serotype 2)) or an AAV comprising a wild-type capsid protein.

A subject variant AAV capsid protein (or the variant AAV capsid protein encoded by a subject nucleic acid) can be said to confer to an infectious rAAV virion an increased transduction of mammalian cells in the presence of human AAV neutralizing antibodies compared to the transduction exhibited by a wild type AAV (e.g., AAV2 (wild type AAV serotype 2)) or an AAV comprising a wild-type capsid protein. In some embodiments, the increased transduction is at least about 1.5-fold (e.g., at least about 1.5-fold, at least about 2-fold, at least about 3-fold, at least about 4-fold, at least about 5-fold, at least about 7.5-fold, at least about 10-fold, at least about 12-fold, at least about 15-fold, at least about 17-fold, at least about 20-fold, at least about 25-fold, at least about 30-fold, at least about 40-fold, at least about 50-fold, at least about 75-fold, at least about 100-fold, at least about 150-fold, at least about 200-fold, at least about 250-fold, at least about 300-fold, etc.) greater than the transduction exhibited by a wild type AAV (e.g., AAV2 (wild type AAV serotype 2)) or an AAV comprising a wild-type capsid protein.

In some embodiments, a subject variant AAV capsid protein (or the variant AAV capsid protein encoded by a subject nucleic acid) exhibits decreased binding to a neutralizing antibody that binds a wild-type AAV capsid protein. For example, a subject variant AAV capsid protein can exhibit at least about 1.5-fold (e.g., at least about 1.5-fold, at least about 2-fold, at least about 3-fold, at least about 4-fold, at least about 5-fold, at least about 7.5-fold, at least about 10-fold, at least about 12-fold, at least about 15-fold, at least about 17-fold, at least about 20-fold, at least about 25-fold, at least about 30-fold, at least about 40-fold, at least about 50-fold, at least about 75-fold, at least about 100-fold, at least about 150-fold, at least about 200-fold, at least about 250-fold, at least about 300-fold, etc.) reduced binding (e.g., reduced affinity) to a neutralizing antibody that binds a wild-type capsid AAV protein, compared to the binding affinity of the antibody to wild-type AAV capsid protein.

In some embodiments, an anti-AAV neutralizing antibody binds to a subject variant AAV capsid protein (or the variant AAV capsid protein encoded by a subject nucleic acid) with an affinity of less than about $10^{-7}$ M, less than about $5 \times 10^{-6}$ M, less than about $10^{-6}$ M, less than about $5 \times 10^{-5}$ M, less than about $10^{-5}$ M, less than about $10^{-4}$ M, or lower.

The term "variant capsid protein" does not encompass wild type AAV capsid proteins. A "variant AAV capsid protein" does not comprise an amino acid sequence present in a naturally occurring AAV capsid protein. For example, a subject variant capsid protein does not comprise an amino acid sequence having 100% sequence identity to any of the sequences set forth in SEQ ID NOs:1-9. In other words, a subject variant capsid protein does not comprise an amino acid sequence as set forth in any of SEQ ID NOs:1-9. A variant capsid protein can differ in amino acid sequence from a "starter" or "parental" AAV capsid protein, which parental AAV capsid protein may be a wild-type AAV capsid protein or non-wild-type AAV capsid protein.

In some embodiments a subject variant AAV capsid protein (or the variant AAV capsid protein encoded by a subject nucleic acid) comprises an amino acid sequence having at least about 90% (e.g., at least about 92%, at least about 95%, at least about 96%, at least about 97%, at least about 98%, at least about 99%, at least about 99.5%, or 100%) amino acid sequence identity to amino acids 203-736 of the amino acid sequence set forth in one of SEQ ID NOs:10-13 and 26-33.

In some embodiments a subject variant AAV capsid protein (or the variant AAV capsid protein encoded by a subject nucleic acid) comprises an amino acid sequence having at least about 90% (e.g., at least about 92%, at least about 95%, at least about 96%, at least about 97%, at least about 98%, at least about 99%, at least about 99.5%, or 100%) amino acid sequence identity to the amino acid sequence set forth in one of SEQ ID NOs:10-13 and 26-33.

In some embodiments a subject variant AAV capsid protein (or the variant AAV capsid protein encoded by a subject nucleic acid) comprises an amino acid sequence having at least about 95% (e.g., at least about 96%, at least about 97%, at least about 98%, at least about 99%, at least about 99.5%, or 100%) amino acid sequence identity to amino acids 203-736 of the amino acid sequence set forth in SEQ ID NO:10, and includes the amino acid substitutions N312K, N449D, D472N, N551S, I698V, and L735Q relative to the AAV capsid protein of AAV2 (e.g., SEQ ID NO: 2), or the corresponding positions in another AAV parental serotype.

In some embodiments a subject variant AAV capsid protein (or the variant AAV capsid protein encoded by a subject nucleic acid) comprises an amino acid sequence having at least about 95% (e.g., at least about 96%, at least about 97%, at least about 98%, at least about 99%, at least about 99.5%, or 100%) amino acid sequence identity to the amino acid sequence set forth in SEQ ID NO:10, and includes the amino acid substitutions N312K, N449D, D472N, N551S, I698V, and L735Q relative to the AAV capsid protein of AAV2 (e.g., SEQ ID NO: 2), or the corresponding positions in another AAV parental serotype.

In some embodiments a subject variant AAV capsid protein (or the variant AAV capsid protein encoded by a subject nucleic acid) comprises an amino acid sequence having at least about 95% (e.g., at least about 96%, at least about 97%, at least about 98%, at least about 99%, at least about 99.5%, or 100%) amino acid sequence identity to amino acids 203-736 of the amino acid sequence set forth in SEQ ID NO:31, and includes the amino acid substitutions N312K, N449D, N551S, and I698V relative to the AAV capsid protein of AAV2 (e.g., SEQ ID NO:2), or the corresponding positions in another AAV parental serotype.

In some embodiments a subject variant AAV capsid protein (or the variant AAV capsid protein encoded by a subject nucleic acid) comprises an amino acid sequence having at least about 95% (e.g., at least about 96%, at least about 97%, at least about 98%, at least about 99%, at least about 99.5%, or 100%) amino acid sequence identity to the amino acid sequence set forth in SEQ ID NO:31, and includes the amino acid substitutions N312K, N449D, N551S, and I698V relative to the AAV capsid protein of AAV2 (e.g., SEQ ID NO:2), or the corresponding positions in another AAV parental serotype.

In some embodiments a subject variant AAV capsid protein (or the variant AAV capsid protein encoded by a subject nucleic acid) comprises an amino acid sequence having at least about 95% (e.g., at least about 96%, at least about 97%, at least about 98%, at least about 99%, at least about 99.5%, or 100%) amino acid sequence identity to amino acids 203-736 of the amino acid sequence set forth in SEQ ID NO:32, and includes the amino acid substitutions D180N, N312K, Q385R, N449D, N551S, I698V, and S721T relative to the AAV capsid protein of AAV2 (e.g., SEQ ID NO:2), or the corresponding positions in another AAV parental serotype.

In some embodiments a subject variant AAV capsid protein (or the variant AAV capsid protein encoded by a subject nucleic acid) comprises an amino acid sequence having at least about 95% (e.g., at least about 96%, at least about 97%, at least about 98%, at least about 99%, at least about 99.5%, or 100%) amino acid sequence identity to the amino acid sequence set forth in SEQ ID NO:32, and includes the amino acid substitutions D180N, N312K, Q385R, N449D, N551S, I698V, and S721T relative to the AAV capsid protein of AAV2 (e.g., SEQ ID NO:2), or the corresponding positions in another AAV parental serotype.

In some embodiments a subject variant AAV capsid protein (or the variant AAV capsid protein encoded by a subject nucleic acid) comprises an amino acid sequence having at least about 95% (e.g., at least about 96%, at least about 97%, at least about 98%, at least about 99%, at least about 99.5%, or 100%) amino acid sequence identity to amino acids 203-736 of the amino acid sequence set forth in SEQ ID NO:33, and includes the amino acid substitutions N312K, N449D, T450A, N551S, and I698V relative to the AAV capsid protein of AAV2 (e.g., SEQ ID NO:2), or the corresponding positions in another AAV parental serotype.

In some embodiments a subject variant AAV capsid protein (or the variant AAV capsid protein encoded by a subject nucleic acid) comprises an amino acid sequence having at least about 95% (e.g., at least about 96%, at least about 97%, at least about 98%, at least about 99%, at least about 99.5%, or 100%) amino acid sequence identity to the amino acid sequence set forth in SEQ ID NO:33, and includes the amino acid substitutions N312K, N449D, T450A, N551S, and I698V relative to the AAV capsid protein of AAV2 (e.g., SEQ ID NO:2), or the corresponding positions in another AAV parental serotype.

Figure 8B:
Figure 9C:
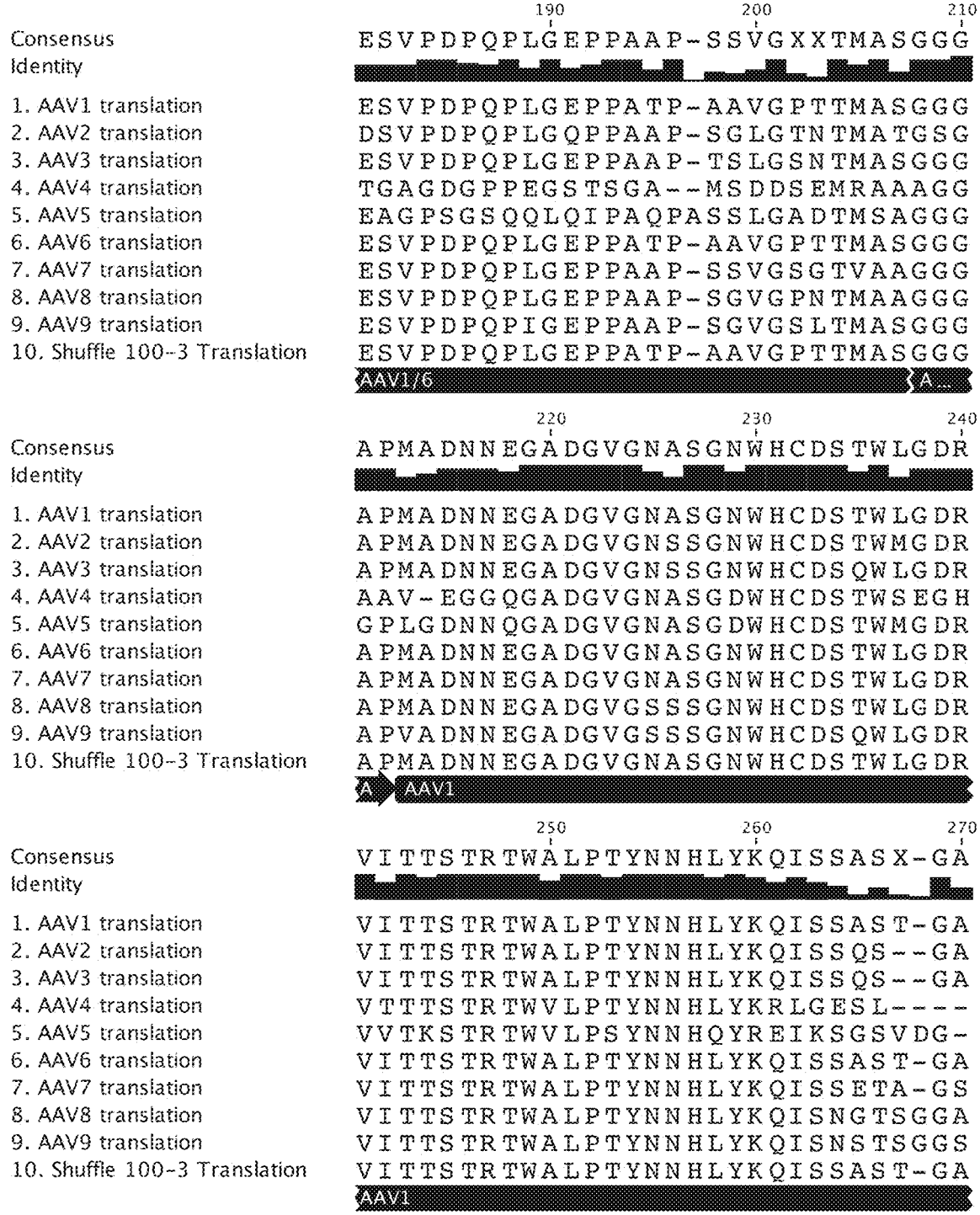
Figure 9H:

Exemplary variant AAV capsid proteins include, but are not limited to (see FIGS. 8-10 for selected exemplary sequence alignments):

```
SM 10-2 (amino acid sequence) (SEQ ID NO: 10):
MAADGYLPDWLEDTLSEGIRQWWKLKPGPPPPKPAERHKDDSRGLVLPGYKYL

GPFNGLDKGEPVNEADAAALEHDKAYDRQLDSGDNPYLKYNHADAEFQERLK

EDTSFGGNLGRAVFQAKKRVLEPLGLVEEPVKTAPGKKRPVEHSPVEPDSSSGT

GKAGQQPARKRLNFGQTGDADSVPDPQPLGQPPAAPSGLGTNTMATGSGAPM

ADNNEGADGVGNSSGNWHCDSTWMGDRVITTSTRTWALPTYNNHLYKQISSQ

SGASNDNHYFGYSTPWGYFDFNRFHCHFSPRDWQRLINNNWGFRPKRLKFKLF

NIQVKEVTQNDGTTTIANNLTSTVQVFTDSEYQLPYVLGSAHQGCLPPFPADVF

MVPQYGYLTLNNGSQAVGRSSFYCLEYFPSQMLRTGNNFTFSYTFEDVPFHSSY

AHSQSLDRLMNPLIDQYLYYLSRTDTPSGTTTQSRLQFSQAGASDIRNQSRNWL

PGPCYRQQRVSKTSADNNNSEYSWTGATKYHLNGRDSLVNPGPAMASHKDDE

EKFFPQSGVLIFGKQGSEKTSVDIEKVMITDEEEIRTTNPVATEQYGSVSTNLQRG

NRQAATADVNTQGVLPGMVWQDRDVYLQGPIWAKIPHTDGHFHPSPLMGGFG

LKHPPPQILIKNTPVPANPSTTFSAAKFASFITQYSTGQVSVEIEWELQKENSKRW

NPEVQYTSNYNKSVNVDFTVDTNGVYSEPRPIGTRYLTRNQ;

SM10-2 (nucleotide sequence) (SEQ ID NO: 22):
atggctgccgatggttatcttccagattggctcgaggacactctctctgaaggaataagacagtggtggaagctcaa acctggcccaccaccaccaaagcccgcagagcggcataaggacgacagcaggggtcttgtgcttcctgggtacaagtacctc ggacccttcaacggactcgacaagggagagccggtcaacgaggcagacgccgcggccctcgagcacgacaaagcctatg accggcagctcgacagcggagacaacccgtacctcaagtacaaccacgccgacgcggagtttcaggaacgccttaaagaag atacgtcttttgggggcaacctcggacgagcagtcttccaggcgaaaaagagggttcttgaacctctgggcctggttgaggaac ctgttaagacggctccgggaaaaagaggccggtagagcactctcctgtggagccagactcctcctcgggaaccggaaagg cgggccagcagcctgcaagaaaaagattgaattttggtcagactggagacgcagactcagtacctgaccccagcctctcgg acagccaccagcagcccctctggtctgggaactaatacgatggctacaggcagtggcgcaccaatggcagacaataacga gggcgccgacggagtgggtaattcctcgggaaattggcattgcgattccacatggatgggcgacagagtcatcaccaccagc acccgaacctgggccctgcccacctacaacaaccacctctacaaacaaatttccagccaatcaggagcctcgaacgacaatca ctactttggctacagcacccttggggtattttgacttcaacagattccactgccacttttcaccacgtgactggcaaagactcat caacaacaactggggattccgacccaagagactcaagttcagctcttaacattcaagtcaaagaggtcacgcagaatgacg gtacgacgacgattgccaataaccttaccagcacggttcaggtgtttactgactcggagtaccagctcccgtacgtcctcggctc ggcgcatcaaggatgcctcccgccgttccagcagacgtcttcatggtgccacagtatggatacctcaccctgaacaacggga gtcaggcagtaggacgctcttcattttactgcctggagtacttccttctcagatgctgcgtaccggtaacaactttaccttcagcta cacttttgaggacgttcctttccacagcagctacgctcacagccagagtctggaccgtctcatgaatcctctcatcgaccagtacc tgtattacttgagcagaacagacactccaagtggaaccaccacgcagtcaaggcttcagttttctcaggccggagcgagtgaca ttcggaaccagtctaggaactggcttcctggaccctgttaccgccagcagcgagtatcaaagacatctgcggataacaacaaca gtgaatactcgtggactggagctaccaagtaccacctcaatggcagagactctctggtgaatccgggcccggccatggcaagc
```

-continued

```
cacaaggacgatgaagaaaagtttttcctcagagcggggttctcatctttgggaagcaaggctcagagaaaacaagtgtggac attgaaaaggtcatgattacagacgaagaggaaatcaggacaaccaatcccgtggctacggagcagtatggttctgtatctacc aacctccagagaggcaacagacaagcagctaccgcagatgtcaacacacaaggcgttcttccaggcatggtctggcaggac agagatgtgtaccttcaggggcccatctgggcaaagattccacacacggacggacattttcaccccctctccctcatgggtgga ttcggacttaaacaccctcctccacagattctcatcaagaacaccccggtacctgcgaatccttcgaccaccttcagtgcggcaa agtttgcttccttcatcacacagtactccacgggacaggtcagcgtggagatcgagtgggagctgcagaaggaaaacagcaaa cgctggaatcccgaagttcagtacacttccaactacaacaagtctgttaatgtggactttactgtggacactaatggcgtgtattca gagcctcgcccattggcaccagatacctgactcgtaatcagtaa
```

Shuffle 100-1 (amino acid sequence) (SEQ ID NO: 11):
```
MAADGYLPDWLEDTLSEGIRQWWKLKPGPPPPKPAERHKDDSRGLVLP

GYKYLGPFNGLDKGEPVNEADAAALEHDKAYDQQLKAGDNPYLKYNHADAE

FQQRLQGDTSFGGNLGRAVFQAKKRVLEPLGLVEQAGETAPGKKRPLIESPQQP

DSSTGIGKKGKQPAKKRLNFGQTGDSESVPDPQPLGEPPATPAAVGPTTMASGG

GAPMADNNEGADGVGNASGNWHCDSTWLGDRVITTSTRTWALPTYNNHLYK

QISSASTGASNDNHYFGYSTPWGYFDFNRFHCHFSPRDWQRLINNNWGFRPKRL

NFKLFNIQVKEVTTNDGVTTIANNLTSTVQVFSDSDYQLPYVLGSAHEGCLPPFP

ADVFMVPQYGYLTLNNGSQAVGRSSFYCLEYFPSQMLRTGNNFTFSYTFEDVPF

HSSYAHSQSLDRLMNPLIDQYLYYLNRTQNQSGSAQNKDLLFSRGSPAGMSVQ

PKNWLPGPCYRQQRVSKTKTDNNNSNFTWTGASKYNLNGRESIINPGTAMASH

KDDKDKFFPMSGVMIFGKESAGASNTALDNVMITDEEEIKATNPVATERFGTVA

VNLQSSSTDPATGDVHVMGALPGMVWQDRDVYLQGPIWAKIPHTDGHFHPSPL

MGGFGLKNPPPQILIKNTPVPANPPAEFSATKFASFITQYSTGQVSVEIEWELQKE

NSKRWNPEVQYTSNYAKSANVDFTVDNNGLYTEPRPIGTRYLTRPL;
```

Shuffle 100-1 (nucleotide sequence) (SEQ ID NO: 23):
```
atggctgctgatggttatcttccagattggctcgaggacactctctctgaaggaataagacagtggtggaagctcaaa cctggcccaccaccaccaaagcccgcagagcggcataaggacgacagcagggtcttgtgcttcctgggtacaagtacctcg gacccttcaacggactcgacaagggagagccggtcaacgaggcagacgcagcggccctcgagcacgacaaggcctacga ccagcagctcaaggccggtgacaaccccctacctcaagtacaaccacgccgacgcggagttccagcagcggcttcagggcga cacatcgtttgggggcaacctcggcagagcagtcttccaggccaaaaagagggttcttgaacctcttggtctggttgagcaagc gggtgagacggctcctggaaagaagagaccgttgattgaatcccccagcagcccgactcctccacgggtatcggcaaaaaa ggcaagcagccggctaaaaagagactcaattttggtcagactggcgactcagagtcagtccccgacccacaacctctcggag aacctccagcaaccccgctgctgtgggacctactacaatggcttcaggtggtggcgcaccaatggcagacaataacgaagg cgccgacggagtgggtaatgcctcaggaaattggcattgcgattccacatggctgggcgacagagtcatcaccaccagcacc cgcacctgggccttgcccacctacaataaccacctctacaagcaaatctccagtgcttcaacgggggccagcaacgacaacca ctacttcggctacagcacccctggggtattttgacttcaacagattccactgccacttttcaccacgtgactggcagcgactca tcaacaacaattggggattccggcccaagagactcaacttcaaactcttcaacatccaagtcaaggaggtcacgacgaatgatg gcgtcacaaccatcgctaataaccttaccagcacggttcaagtcttctcggactcagactatcagctcccgtacgtgctcgggtc ggctcacgagggctgcctcccgccgttcccagcagacgtcttcatggtgccacagtatggatacctcaccctgaacaacggga gtcaggcagtaggacgctcttcattttactgcctggagtactttccttctcagatgctgcgtaccggaaacaactttaccttcagcta cacttttgaggacgttcctttccacagcagctacgctcacagccagagtctggaccgtctcatgaatcctctcatcgaccagtacc tgtattacctgaacagaactcagaatcagtccggaagtgcccaaaacaaggacttgctgtttagccgggggtctccagctggca
```

-continued tgtctgttcagcccaaaaactggctacctggaccctgttatcggcagcagcgcgtttctaaaacaaaaacagacaacaacaaca gcaactttacctggactggtgcttcaaaatataaccttaatgggcgtgaatctataatcaaccctggcactgctatggcctcacaca aagacgacaaagacaagttctttcccatgagcggtgtcatgattttttggaaaggagagcgccggagcttcaaacactgcattgg acaatgtcatgatcacagacgaagaggaaatcaaagccactaaccccgtggccaccgaaagatttgggactgtggcagtcaat ctccagagcagcagcacagaccctgcgaccggagatgtgcatgttatgggagccttacctggaatggtgtggcaagacagag acgtatacctgcagggtcccatttgggccaaaattcctcacacagatggacactttcacccgtctcctcttatgggcggctttgga ctcaagaacccgcctcctcagatcctcatcaaaaacacgcctgttcctgcgaatcctccggcggagttttcagctacaaagtttgc ttcattcatcacccaatactccacaggacaagtgagtgtggaaattgaatgggagctgcagaaagaaaacagcaagcgctgga atcccgaagtgcagtacacatccaattatgcaaaatctgccaacgttgattttactgtggacaacaatggactttatactgagcctc gccccattggcacccgttacctcacccgtccctgtaa;

Shuffle 100-3 (amino acid sequence) (SEQ ID NO: 12):
MAADGYLPDWLEDTLSEGIRQWWKLKPGPPPPKPAERHKDDSRGLVLP

GYKYLGPFNGLDKGEPVNEADAAALEHDKAYDQQLKAGDNPYLKYNHADAE

FQQRLQGDTSFGGNLGRAVFQAKKRVLEPLGLVEQAGETAPGKKRPLIESPQQP

DSSTGIGKKGKQPAKKRLNFGQTGDSESVPDPQPLGEPPATPAAVGPTTMASGG

GAPMADNNEGADGVGNASGNWHCDSTWLGDRVITTSTRTWALPTYNNHLYK

QISSASTGASNDNHYFGYSTPWGYFDFNRFHCHFSPRDWQRLINNNWGFRPKRL

NFKLFNIQVKEVTTNDGVTTIANNLTSTVQVFSDSDYQLPYVLGSAHEGCLPPFP

ADVFMVPQYGYLTLNNGSQAVGRSSFYCLEYFPSQMLRTGNNFTFSYTFEDVPF

HSSYAHSQSLDRLMNPLIDQYLYYLNRTQNQSGSAQNKDLLFSRGSPTGMSVQP

KNWLPGPCYRQQRVSKTKTDNNNSNFTWTGASKYNLNGRESIINPGTAMASHK

DDKDKFFPMSGVMIFGKESAGASNTALDNVMITDEEEIKATNPVATERFGTVAV

NLQSSSTDPATGDVHAMGALPGMVWQDRDVYLQGPIWAKIPHTDGHFHPSPL

MGGFGLKNPPPQILIKNTPVPANPPAEFSATKFASFITQYSTGQVSVEIEWELQKE

NSKRWNPEVQYTSNYAKSANVDFTVDNNGLYTEPRPIGTRYLTRPL;

Shuffle 100-3 (nucleotide sequence) (SEQ ID NO: 24):
atggctgctgatggttatcttccagattggctcgaggacactctctctgaaggaataagacagtggtggaagctcaaa cctggcccaccaccaccaaagcccgcagagcggcataaggacgacagcagggtcttgtgcttcctgggtacaagtacctcg gacccttcaacggactcgacaagggagagccggtcaacgaggcagacgcagcggcctcgagcacgacaaggcctacga ccagcagctcaaggccggtgacaaccccctacctcaagtacaaccacgccgacgcggagttccagcagcggcttcagggcga cacatcgtttgggggcaacctcggcagagcagtcttccaggccaaaaagagggttcttgaacctcttggtctggttgagcaagc gggtgagacggctcctggaaagaagagaccgttgattgaatccccccagcagcccgactcctcacgggtatcggcaaaaaa ggcaagcagccggctaaaaagagactcaattttggtcagactggcgactcagagtcagtcccgacccacaacctctcggag aacctccagcaaccccgctgctgtgggacctactacaatggcttcaggtggtggcgcaccaatggcagacaataacgaagg cgccgacggagtgggtaatgcctcaggaaattggcattgcgattccacatggctgggcgacagagtcatcaccaccagcacc cgcacctgggccttgcccacctacaataaccacctctacaagcaaatctccagtgcttcaacgggggccagcaacgacaacca ctacttcggctacagcacccctgggggtattttgacttcaacagattccactgccacttttcaccacgtgactggcagcgactca tcaacaacaattggggattccggcccaagagactcaacttcaaactcttcaacatccaagtcaaggaggtcacgacgaatgatg gcgtcacaaccatcgctaataaccttaccagcacggttcaagtcttctcggactcagactatcagctcccgtacgtgctcgggtc ggctcacgagggctgcctcccgccgttcccagcagacgtcttcatggtgccacagtatggatacctcaccctgaacaacggga gtcaggcagtaggacgctcttcattttactgcctggagtactttcctttctcagatgctgcgtaccggaaacaactttaccttcagcta cacttttgaggacgttcctttccacagcagctacgctcacagccagagtctggaccgtctcatgaatcctctcatcgaccagtacc -continued

```
tgtattacctgaacagaactcagaatcagtccggaagtgcccaaaacaaggacttgctgtttagccgggggtctccaactggca tgtctgttcagcccaaaaactggctacctggaccctgttatcggcagcagcgcgtttctaaaacaaaaacagacaacaacaaca gcaactttacctggactggtgcttcaaaatataaccttaatgggcgtgaatctataatcaaccctggcactgctatggcctcacaca aagacgacaaagacaagttctttcccatgagcggtgtcatgattttttggaaaggagagcgccggagcttcaaacactgcattgg acaatgtcatgatcacagacgaagaggaaatcaaagccactaaccccgtggccactgaaagatttgggactgtggcagtcaat ctccagagcagcagcacagaccctgcgaccggagatgtgcatgccatgggagccttacctggaatggtgtggcaagacaga gacgtatacctgcagggtcctatttgggccaaaattcctcacacggatggacactttcacccgtctcctctcatgggcggctttgg actcaagaacccgcctcctcagatcctcatcaaaaacacgcctgttcctgcgaatcctccggcggagttttcagctacaaagtttg cttcattcatcacccagtattccacaggacaagtgagcgtggagattgaatgggagctgcagaaagaaaacagcaaacgctgg aatcccgaagtgcagtatacatctaactatgcaaaatctgccaacgttgatttcactgtggacaacaatggactttatactgagcct cgccccattggcacccgttacctcacccgtccctgtaa;
Shuffle 100-7 (amino acid sequence) (SEQ ID NO: 13):
MAADGYLPDWLEDNLSEGIREWWALKPGAPKPKANQQKQDDGRGLVL

PGYKYLGPFNGLDKGEPVNAADAAALEHDKAYDQQLKAGDNPYLRYNHADA

EFQERLQEDTSFGGNLGRAVFQAKKRVLEPLGLVEEGAKTAPGKKRPVEQSPQE

PDSSSGIGKTGQQPAKKRLNFGQTGDSESVPDPQPLGEPPATPAAVGPTTMASG

GGAPMADNNEGADGVGNASGNWHCDSTWLGDRVITTSTRTWALPTYNNHLY

KQISSASTGASNDNHYFGYSTPWGYFDFNRFHCHFSPRDWQRLINNNWGFRPK

RLSFKLFNIQVKEVTTNDGVTTIANNLTSTVQVFSDSEYQLPYVLGSAHQGCLPP

FPADVFMIPQYGYLTLNNGSQAVGRSSFYCLEYFPSQMLRTGNNFTFSYTFEEVP

FHSSYAHSQSLDRLMNPLIDQYLYYLNRTQNQSGSAQNKDLLFSRGSPAGMSV

QPKNWLPGPCYRQQRVSKTKTDNNNSNFTWTGASKYNLNGRESIINPGTAMAS

HKDDEDKFFPMSGVMIFGKESAGASNTALDNVMITDEEEIKATNPVATERFGTV

AVNFQSSSTDPATGDVHAMGALPGMVWQDRDVYLQGPIWAKIPHTDGHFHPSP

LMGGFGLKNPPPQILIKNTPVPANPPAEFSATKFASFITQYSTGQVSVEIEWELQK

ENSKRWNPEVQYTSNYAKSANIDFTVDNNGLYTEPRPIGTRYLTRPQ;
Shuffle 100-7 (nucleotide sequence) (SEQ ID NO: 25):
atggctgccgatggttatcttccagattggctcgaggacaacctctctgagggcattcgcgagtggtgggcgctgaa acctggagccccgaagcccaaagccaaccagcaaaagcaggacgacggccggggtctggtgcttcctggctacaagtacct cggacccttcaacggactcgacaaggggggagcccgtcaacgcggcggatgcagcggccctcgagcacgacaaggcctac gaccagcagctcaaagcgggtgacaatccgtacctgcggtataaccacgccgacgccgagtttcaggagcgtctgcaagaa gatacgtcttttgggggcaaccctcgggcgagcagtcttccaggccaagaagcgggttctcgaacctctcggtctggttgagga aggcgctaagacggctcctggaaagaaacgtccggtagagcaatcgccacaagagccagactcctcctcgggcatcggcaa gacaggccagcagcccgctaaaaagagactcaattttggtcagactggcgactcagagtcagtcccgacccacaacctctc ggagaacctccagcaaccccgctgctgtgggacctactacaatggcttcaggcggtggcgcaccaatggcagacaataacg aaggcgccgacggagtgggtaatgcctcaggaaattggcattgcgattccacatggctgggcgacagagtcatcaccaccag cacccgaacatgggccttgccccactataacaaccacctctacaagcaaatctccagtgcttcgacggggccagcaacgac aaccactacttcggctacagcacccccctgggggtattttgactttaacagattccactgccacttttccaccacgtgactggcagcg actcatcaacaacaactggggattccggcccaagagactcagcttcaagctcttcaacatccaggtcaaggaggtcacgacga atgatggcgtcacaaccatcgctaataaccttaccagcacggttcaagtcttctcggactcggagtaccagcttccgtacgtcctc ggctctgcgcaccagggctgcctccctccgttcccggcggacgtgttcatgattccgcaatacggctacctgacgctcaacaat
```

-continued

```
ggcagccaagccgtgggacgttcatccttttactgcctggaatatttcccttctcagatgctgagaacgggcaacaactttaccttc agctacacctttgaggaagtgcctttccacagcagctacgcgcacagccagagcctggaccggctgatgaatcctctcatcgat caatacctgtattacctgaacagaactcaaaatcagtccggaagtgcccaaaacaaggacttgctgtttagccgtgggtctccag ctggcatgtctgttcagcccaaaaactggctacctggaccctgttatcggcagcagcgcgtttctaaaacaaaaacagacaaca acaacagcaattttacctggactggtgcttcaaaatataacctcaatgggcgtgaatccatcatcaaccctggcactgctatggcc tcacataaagacgacgaagacaagttcttcccatgagcggtgtcatgattttggaaaagagagcgccggagcttcaaacact gcattggacaatgtcatgattacagacgaagaggaaattaaagccactaaccctgtggccaccgaaagatttgggaccgtggc agtcaatttccagagcagcagcacagaccctgcgaccggagatgtgcatgctatgggagcattacctggcatggtgtggcaag atagagacgtgtacctgcagggtcccatttgggccaaaattcctcacacagatggacactttcacccgtctcctcttatgggcgg ctttggactcaagaacccgcctcctcagatcctcatcaaaaacacgcctgttcctgcgaatcctccggcggagttttcagctacaa agtttgcttcattcatcacccaatactccacaggacaagtgagcgtggagattaatgggagctgcagaaagaaaacagcaaa cgctggaatcccgaagtgcagtatacatctaactatgcaaaatctgccaacattgatttcactgtggacaacaatggactttatact gagcctcgcccattggcacccgttacctcacccgtccccagtaa;
```

Shuffle 10-2 (amino acid sequence) (SEQ ID NO: 26):
MAADGYLPDWLEDNLSEGIREWWDLKPGAPKPKANQQKQDDGRGLVL

PGYKYLGPFNGLDKGEPVNAADAAALEHDKAYDQQLKAGDNPYLRYNHADA

EFQERLQEDTSFGGNLGRAVFQAKKRVLEPLGLVEEAAKTAPGKKRPVEQSPQE

PDSSSGIGKTGQQPAKKRLNFGQTGDSESVPDPQPLGEPPAAPSGVGSLTMASG

GGAPMADNNEGADGVGNASGNWHCDSTWLGDRVITTSTRTWALPTYNNHLY

KQISSASTGASNDNHYFGYSTPWGYFDFNRFHCHFSPRDWQRLINNNWGFRPK

RLNFKLFNIQVKEVTTNDGVTTIANNLTSTVQVFSDSEYQLPYVLGSAHQGCLPP

FPADVFMIPQYGYLTLNNGSQAVGRSSFYCLEYFPSQMLRTGNNFTFSYTFEEVP

FHSSYAHSQSLDRLMNPLIDQYLYYLNRTQNQSGSAQNKDLLFSRGSPAGMSV

QPKNWLPGPCYRQQCVSKTKTDNNNSNFTWTGASKYNLNGRESIINPGTAMAS

HKDDKDKFFPMSGVMIFGKESAGASNTALDNVMITDEEEIKATNPVATERFGTV

AVNLQSSSTDPATGDVHVMGALPGMVWQDRDVYLQGPIWAKIPHTDGHFHPS

PLMGGFGLKNPPPQILIKNTPVPANPPAEFSATKFASFITQYSTGQVSVEIEWELQ

KENSKRWNPEVQYTSNYAKSANVDFTVDNNGLYTEPRPIGTRYLTRPL;

Shuffle 10-2 (nucleotide sequence) (SEQ ID NO: 34):
```
atggctgccgatggttatcttccagattggctcgaggacaacctctctgagggcattcgcgagtggtgggacttgaa acctggagccccgaaacccaaagccaaccagcaaaagcaggacgacggccggggtctggtgcttcctggctacaagtacct cggacccttcaacggactcgacaaggggggagcccgtcaacgcggcggatgcagcggccctcgagcacgacaaggcctac gaccagcagctcaaagcgggtgacaatccgtaccttcggtataaccacgccgacgccgagtttcaggagcgtctgcaagaag atacgtcttttgggggcaacctcgggcgagcagtcttccaggccaaaaagagggttctcgaacctctcggtctggttgaggaag cggctaagacggctcctggaaagaaacgtccggtagagcagtcgccacaagagccagactcctcctcgggcattggcaaga caggccagcagcccgctaaaaagagactcaattttggtcagactggcgactcagagtcagtccccgacccacaacctctcgg agaacctcccgcagcccctcaggtgtgggatctcttacaatggcttcaggtggtggcgcaccaatggcagacaataacgaag gcgccgacggagtgggtaatgcctcaggaaattggcattgcgattccacatggctgggcgacagagtcatcaccaccagcac ccgcacctgggccttgcccacctacaataaccacctctacaagcaaatctccagtgcttcaacggggccagcaacgacaacc actacttcggctacagcacccctgggggtattttgacttcaacagattccactgccacttttcaccacgtgactggcaaagactc atcaacaacaattgggattccggcccaagagactcaacttcaagctcttcaacatccaagtcaaggaggtcacgacgaatgat ggcgtcacgaccatcgctaataaccttaccagcacggttcaagtcttctcggactcggagtaccagttgccgtacgtcctcggct -continued

```
ctgcgcaccagggctgcctccctccgttcccggcggacgtgttcatgattccgcagtacggctacctaacgctcaacaatggca gccaggcagtgggacggtcatccttttactgcctggaatatttcccatcgcagatgctgagaacgggcaacaactttaccttcag ctacacctttgaggaagtgcctttccacagcagctacgcgcacagccagagcctggaccggctgatgaatcctctcatcgacca gtacctgtattacctgaacagaactcaaaatcagtccggaagtgcccaaaacaaggacttgctgtttagccgtgggtctccagct ggcatgtctgttcagcccaaaaactggctacctggaccctgttaccggcagcagtgcgtttctaaaacaaaaacagacaacaac aacagcaactttacctggactggtgcttcaaaatataaccttaatgggcgtgaatctataatcaaccctggcactgctatggcctca cacaaagacgacaaagacaagttcttccccatgagcggtgtcatgatttttggaaaggagagcgccggagcttcaaacactgca ttggacaatgtcatgatcacagacgaagaggaaatcaaagccactaaccccgtggccaccgaaagatttgggactgtggcagt caatctccagagcagcagcacagaccctgcgaccggagatgtgcatgttatgggagccttacctggaatggtgtggcaagac agagacgtatacctgcagggtcctatttgggccaaaattcctcacacagatggacactttcacccgtctcctcttatgggcggcttt ggactcaagaacccgcctcctcagatcctcatcaaaaacacgcctgttcctgcgaatcctccggcggagttttcagctacaaagt ttgcttcattcatcacccaatactccacaggacaagtgagcgtggagattgaatgggagctgcagaaagaaaacagcaagcgc tggaatcccgaagtgcagtacacatccaattatgcaaaatctgccaacgttgatttcactgtggacaacaatggactttatactga gcctcgccccattggcacccgttacctcacccgtccctgtaa;

Shuffle 10-6 (amino acid sequence) (SEQ ID NO: 27):
MAADGYLPDWLEDNLSEGIREWWDLKPGAPKPKVNQQKQDNARGLVL

PGYKYLGPFNGLDKGEPVNAADAAALEHDKAYDQQLKAGDNPYLRYNHADA

EFQERLQEDTSFGGNLGRAVFQAKKRVLEPFGLVEEGAKTAPGKKRPVEQSPQE

PDSSSGIGKTGQQPAKKRLNFGQTGDSESVPDPQPLGEPPATPAAVGPTTMASG

GGAPMADNNEGADGVGNASGNWHCDSTWLGDRVITTSTRTWALPTYNNHLY

KQISSASTGASNDNHYFGYSTPWGYFDFNRFHCHFSPRDWQRLINNNWGFRPK

RLNFKLFNIQVKEVTTNDGVTTIANNLTSTVQVFSDSEYQLPYVLGSAHQGCLPP

FPADVFMIPQYGYLTLNNGSQAVGRSSFYCLEYFPSQMLRTGNNFTFSYTFEDV

PFHSSYAHSQSLDRLMNPLIDQYLYYLNRTQNQSGSAQNKDLLFSRGSPTGMSV

QPKNWLPGPCYRQQRVSKTKTDNNNSNFTWTGASKYNLNGRESIINPGTAMAS

HKDDEDKFFPMSGVMIFGKESAGASNTALDNVMITDEEEIKATNPVATERFGTV

AVNLQSSSTDPATGDVHAMGALPGMVWQDRDVYLQGPIWAKIPHTDGHFHPS

PLMGGFGLKHPPPQILIKNTPVPANPPAEFSATKFASFITQYSTGQVSVEIEWELQ

KENSKRWNPEVQYTSNYAKSANVDFTVDNNGLYTEPRPIGTRYLTRPL;

Shuffle 10-6 (nucleotide sequence) (SEQ ID NO: 35):
atggctgccgatggttatcttccagattggctcgaggacaacctctctgagggcattcgcgaatggtgggacttgaaa cctggagcccccgaaacccaaagtcaaccagcaaaagcaggacaacgctcgggtcttgtgcttccgggttacaaatacctcg gacccttcaacggactcgacaagggggagcccgtcaacgcggcggacgcagcggccctcgagcacgacaaggcctacga ccagcagctcaaagcgggtgacaatccgtaccttcggtataaccacgccgacgccgagtttcaggagcgtctgcaagaagat acgtcttttgggggcaaccttggacgagcagtcttccaggccaagaagagggttctcgaaccttttggtctggttgaggaaggt gctaagacggctcctggaaagaaacgtccggtagagcagtcgccacaagagccagactcctcctcgggcattggcaagaca ggccagcagcccgctaaaaagagactcaattttggtcagactggcgactcagagtcagtccccgacccacaacctctcggag aacctccagcaaccccgctgctgtgggacctactacaatggcttcaggcggtggcgccaccaatggcagacaataacgaagg cgccgacggagtgggtaatgcctcaggaaattggcattgcgattccacatggctgggcgacagagtcatcaccaccagcacc cgcacctgggccttgcccacctacaataaccacctctacaagcaaatctccagtgcttcaacgggggccagcaacgacaacca ctacttcggctacagcacccccctgggggtattttgacttcaacagattccactgccacttttcaccacgtgactggcaaagactcat
```

-continued

```
caacaacaattggggattccggcccaagagactcaacttcaagctcttcaacatccaagtcaaggaggtcacgacgaatgatg gcgtcacgaccatcgctaataaccttaccagcacggttcaagtcttctcggactcggagtaccagttgccgtacgtcctcggctc tgcgcaccagggctgcctcctccgttcccggcggacgtgttcatgattccgcaatacggctacctgacgctcaacaatggcag ccaggcagtgggacggtcatccttttactgcctggaatatttcccatcgcagatgctgagaacgggcaataactttaccttcagct acacttttgaggacgttcctttccacagcagctacgctcacagccagagcctggaccggctgatgaatcctctcatcgaccagta cctgtattacctgaacagaactcagaatcagtccggaagtgcccaaaacaaggacttgctgtttagccgtgggtctccaactggc atgtctgttcagcccaaaaactggctacctggaccctgttatcggcagcagcgcgtttctaaaacaaaaacagacaacaacaac agcaacttacctggactggtgcttcaaaatataaccttaatgggcgtgaatctataatcaaccctggcactgctatggcctcacac aaagacgacgaagacaagttctttcccatgagcggtgtcatgattttttggaaaggagagcgccggagcttcaaacactgcattg gacaatgtcatgatcacagacgaagaggaaatcaaagccactaacccccgtggccactgaaagatttgggactgtggcagtcaa tctccagagcagcagcacagaccctgcgaccggagatgtgcatgccatgggagccttacctggaatggtgtggcaagacaga gacgtatacctgcagggtcctatttgggccaaaattcctcacacggatggacactttcacccgtctcctctcatgggcggctttgg acttaagcacccgcctcctcagatcctcatcaaaaacacgcctgttcctgcgaatcctccggcagagttttcggctacaaagtttg cttcattcatcacccagtattccacaggacaagtgagcgtggagattgaatgggagctgcagaaagaaaacagcaaacgctgg aatcccgaagtgcagtatacatctaactatgcaaaatctgccaacgttgatttcactgtggacaacaatggactttatactgagcct cgccccattggcacccgttacctcacccgtcccctgtaa;

Shuffle 10-8 (amino acid sequence) (SEQ ID NO: 28):
MAADGYLPDWLEDNLSEGIREWWDLKPGAPKPKVNQQKQDNARGLVL

PGYKYLGPFNGLDKGEPVNAADAAALEHDKAYDQQLKAGDNPYLRYNHADA

EFQERLQEDTSFGGNLGRAVFQAKKRVLEPFGLVEEGAKTAPGKKRPVEQSPQE

PDSSSGIGKTGQQPAKKRLNFGQTGDSESVPDPQPLGEPPATPAAVGPTTMASG

GGAPMADNNEGADGVGNASGNWHCDSTWLGDRVITTSTRTWALPTYNNHLY

KQISSASTGASNDNHYFGYSTPWGYFDFNRFHCHFSPRDWQRLINNNWGFRPK

RLNFKLFNQVKETTDVTTIANNLTSTVQVFSDSEYQLPYVLGSAHQGCLPPFPAD

VFMIPQYGYLTLNNGSQAVGRSSFYCLEYFPSQMLRTGNNFTSYTFEDVPFHSS

YAHSQSLDRLMNPLIDQYLYYLNRTQNQSGSAQNKDLLFSRGSPTGMSVQPKN

WLPGPCYRQQRVSKTKTDNNNSNFTWTGASKYNLNGRESIINPGTAMASHKDD

EDKFFPMSGVMIFGKESAGASNTALDNVMITDEEATNPVATERFGTVAVNLQSS

PATDVHAMGALPGMVWQDRDVYLQGPIWAKIPHTDGHFHPSPLMGGFGLKHP

PPQILIKNTPVPANPPAEFSATKFASFITQYSTGQVSVEIEWELQKENSKRWNPEV

QYTSNYAKSANVDFTVDNNGLYTEPRPIGTRYLTRP;

Shuffle 10-8 (nucleotide sequence) (SEQ ID NO: 36):
atggctgccgatggttatcttccagattggctcgaggacaacctctctgagggcattcgcgaatggtgggacttgaaa cctggagccccgaaacccaaagtcaaccagcaaaagcaggacaacgctcggggtcttgtgcttccgggttacaaatacctcg gacccttcaacggactcgacaaggggagcccgtcaacgcggcggacgcagcggccctcgagcacgacaaggcctacga ccagcagctcaaagcgggtgacaatccgtaccttcggtataaccacgccgacgccgagtttcaggagcgtctgcaagaagat acgtcttttgggggcaaccttggacgagcagtcttccaggccaagaagagggttctcgaaccttttggtctggttgaggaaggt gctaagacggctcctggaaagaaacgtccggtagagcagtcgccacaagagccagactcctcctcgggcattggcaagaca ggccagcagcccgctaaaaagagactcaattttggtcagactggcgactcagagtcagtcccgacccacaacctctcggag aacctccagcaacccccgctgctgtgggacctactacaatggcttcaggcggtggcgcaccaatggcagacaataacgaagg cgccgacggagtgggtaatgcctcaggaaattggcattgcgattccacatggctgggcgacagagtcatcaccaccagcacc cgaacatgggccttgcccacctataacaaccacctctacaagcaaatctccagtgcttcaacgggggccagcaacgacaacca
```

-continued

```
ctacttcggctacagcaccccctgggggtattttgattttcaacagattccactgccacttttccaccacgtgactggcagcgactcat caataacaattggggattccggcccaagagactcaacttcaaactcttcaacntccaagtcaaggaggnnacgacgaangatg ncgtcacaaccatcgctaataaccttaccagcacggttcaagtcttctcggactcggagtaccagcttccgtacgtcctcggctct gcgcaccagggctgcctccctccgttcccggcggacgtgttcatgattccgcaatacggctacctgacgctcaacaatggcag ccaggcagtgggacggtcatccttttactgcctggaatatttcccatcgcagatgctgagaacgggcaataactttacctncagct acacttttgaggacgttccttccacagcagctacgctcacagccagagcctggaccggctgatgaatcctctcatcgaccagta cctgtattacctgaacagaactcagaatcagtccggaagtgcccaaaacaaggacttgctgtttagccgtgggtctccaactggc atgtctgttcagcccaaaaactggctacctggaccctgttatcggcagcagcgcgtttctaaaacaaaaacagacaacaacaac agcaactttacctggactggtgcttcaaaatataaccttaatgggcgtgaatctataatcaaccctggcactgctatggcctcacac aaagacgacgaagacaagttctttcccatgagcggtgtcatgattttttggaaaggagagcgccggagcttcaaacactgcattg gacaatgtcatgatcacagacgaagagannncnaagccactaaccccgtggccactgaaagatttgggactgtggcagtcaa tctccaagcagcacannnaccctgcgaccgnagatgtgcatgccatgggagccttacctggaatggtgtggcaagacagag acgtatacctgcagggtcctatttgggccaaaattcctcacacggatggacactttcacccgtctcctctcatgggcggctttgga cttaagcacccgcctcctcagatcctcatcaaaaacacgcctgttcctgcgaatcctccggcagagttttcggctacaaagtttgc ttcattcatcacccagtattccacaggacaagtgagcgtggagattgaatgggagctgcagaaagaaaacagcaaacgctgga atcccgaagtgcagtatacatctaactatgcaaaatctgccaacgttgatttcactgtggacaacaatggactttatactgagcctc gccccattggcacccgttacctcacccgtccccngtaa;

Shuffle 100-2 (amino acid sequence) (SEQ ID NO: 29):
MASDGYLPDWLEDNLSEGIREWWDLKPGAPKPKANQQKQDDGRGLVL

PGYKYLGPFNGLDKGEPVNAADAAALEHDKAYDQQLRAGDNPYLRYNHADA

EFQERLQEDTSFGGNLGRAVFQAKKRVLEPFGLVEEGAKTAPGKKRPVEQSPQE

PDSSSGIGKTGQQPAKKRLNFGQTGDSESVPDPQPLGEPPATPAAVGPTTMASG

GGAPMADNNEGADGVGNASGNWHCDSTWLGDRVITTSTRTWALPTYNNHLY

KQISSASTGASNDNHYFGYSTPWGYFDFNRFHCHFSPRDWQRLINNNWGFRPK

RLNFKLFNIQVKEVTTNDGVTTIANNLTSTVQVFSDSEYQLPYVLGSAHQGCLPP

FPADVFMIPQYGYLTLNNGSQAVGRSSFYCLEYFPSQMLRTGNNFTFSYTFEDV

PFHSSYAHSQSLDRLMNPLIDQYLYYLNRTQNQSGSAQNKDLLFSRGSPAGMSV

QPKNWLPGPCYRQQRVSKTKTDNNNSNFTWTGASKYNLNGRESIINPGTAMAS

HKDDKDKFFPMSGVMIFGKESAGASNTALDNVMITDEEEIKATNPVATERFGTV

AVNLQSSSTDPATGDVHVMGALPGMVWQDRDVYLQGPIWAKIPHTDGHFHPS

PLMGGFGLKHPPPQILIKNTPVPANPPAEFSATKFASFITQYSTGQVSVEIEWELQ

KENSKRWNPEVQYTSNYAKSANVDFTVDNNGLYTEPRPIGTRYLTRPL;

Shuffle 100-2 (nucleotide sequence) (SEQ ID NO: 37):
atggcttccgatggttatcttccagattggctcgaggacaacctctctgagggcatccgcgagtggtgggacttgaaa cctggagccccgaaacccaaagccaaccagcaaaagcaggacgacggccggggtctggtgcttcctggctacaagtacctc ggacccttcaacggactcgacaaggggagccccgtcaacgcggcggatgcagcggccctcgagcacgacaaggcctacg accagcagctcagagcgggtgacaatccgtacctgcggtataaccacgccgacgccgagtttcaggagcgtctgcaagaag atacgtcttttgggggcaacctcgggcgagcagtcttccaggccaagaagagggttctcgaaccttttggtctggttgaggaag gtgctaagacggctcctggaaagaaacgtccggtagagcagtcgccacaagagccagactcctcctcgggcattggcaaga caggccagcagcccgctaaaaagagactcaattttggtcagactggcgactcagagtcagtcccgacccacaacctctcgg agaacctccagcaaccccgctgctgtgggacctactacaatggcttcaggcggtggcgcaccaatggcagacaataacgaa
```

-continued

```
ggcgccgacggagtgggtaatgcctcaggaaattggcattgcgattccacatggctgggcgacagagtcatcaccaccagca cccgaacatgggccttgcccacctataacaaccacctctacaagcaaatctccagtgcttcaacgggggccagcaacgacaac cactacttcggctacagcacccccctgggggtattttgatttcaacagattccactgccatttctcaccacgtgactggcagcgact catcaacaacaattggggattccggcccaagagactcaacttcaaactcttcaacatccaagtcaaggaggtcacgacgaatga tggcgtcacaaccatcgctaataaccttaccagcacggttcaagtcttctcggactcggagtaccagcttccgtacgtcctcggct ctgcgcaccagggctgcctccctccgttcccggcggacgtgttcatgattccgcagtacggctacctaacgctcaacaatggca gccaggcagtgggacggtcatccttttactgcctggaatatttcccatcgcagatgctgagaacgggcaataactttaccttcagc tacaccttcgaggacgtgcctttccacagcagctacgcgcacagccagagcctggaccggctgatgaatcctctcatcgacca gtacctgtattacctgaacagaactcagaatcagtccggaagtgcccaaaacaaggacttgctgtttagccgggggtctccagc tggcatgtctgttcagcccaaaaactggctacctggaccctgttaccggcagcagcgcgtttctaaaacaaaaacagacaacaa caacagcaactttacctggactggtgcttcaaaatataaccttaatgggcgtgaatctataatcaaccctggcactgctatggcctc acacaaagacgacaaagacaagttctttcccatgagcggtgtcatgattttttggaaaggagagcgccggagcttcaaacactgc attggacaatgtcatgatcacagacgaagaggaaatcaaagccactaaccccgtggccaccgaaagatttgggactgtggca gtcaatctccagagcagcagcacagaccctgcgaccggagatgtgcatgttatgggagccttacctggaatggtgtggcaaga cagagacgtatacctgcagggtcccatttgggccaaaattcctcacacagatggacacttttcacccgtctcctcttatgggcggc tttggacttaagcacccgcctcctcagatcctcatcaaaaacacgcctgttcctgcgaatcctccggcagagttttcggctacaaa gtttgcttcattcatcacccagtattctactggccaagtcagcgtggagattgaatgggagctgcagaaagaaaacagcaaacg ctggaatcccgaagtgcagtatacatctaactatgcaaaatctgccaacgttgatttcactgtggacaacaatggactttatactga gcctcgtcccattggcacccgttacctcacccgtcccctgtaa;
```

SM 10-1 (amino acid sequence) (SEQ ID NO: 30):
MAADGYLPDWLEDTLSEGIRQWWKLKPGPPPPKPAERHKDDSRGLVLP

GYKYLGPFNGLDKGEPVNEADAAALEHDKAYDQQLKAGDNPYLRYNHADAEF

QERLQEDTSFGGNLGRAVFQAKKRVLEPLGLVEEGAKTAPGKKRPVEQSPQEP

DSSSGIGKTGQQPAKKRLNFGQTGDSESVPDPQPLGEPPATPAAVGPTTMASGG

GAPMADNNEGADGVGNASGNWHCDSTWLGDRVITTSTRTWALPTYNNHLYK

QISSASTGASNDNHYFGYSTPWGYFDFNRFHCHFSPRDWQRLINNNWGFRPKRL

SFKLFNIQVKEVTTNDGVTTIANNLTSTVQVFSDSEYQLPYVLGSAHQGCLPPFP

ADVFMIPQYGYLTLNNGSQAVGRSSFYCLEYFPSQMLRTGNNFTFSYTFEEVPF

HSSYAHSQSLDRLMNPLIDQYLYYLNRTQNQSGSAQNKDLLFSRGSPAGMSVQ

PKNWLPGPCYRQQRVSKTKTDNNNSNFTWTGASKYNLNGRESIINPGTAMASH

KDDEDKFFPMSGVMIFGKESAGASNTALDNVMITDEEEIKATNPVATERFGTVA

VNFQSSSTDPATGDVHAMGALPGMVWQDRDVYLQGPIWAKIPHTDGHFHPSPL

MGGFGLKNPPPQILIKNTPVPANPPAEFSATKFASFITQYSTGQVSVEIEWELQKE

NSKRWNPEVQYTSNYAKSANVDFTVDNNGLYTEPRPIGTRYLTRPL;

SM 10-1 (nucleotide sequence) (SEQ ID NO: 38):
```
atggctgccgatggttatcttccagattggctcgaggacactctctctgaaggaataagacagtggtggaagctcaa acctggcccaccaccaccaaagcccgcagagcggcataaggacgacagcaggggtcttgtgcttcctgggtacaagtacctc ggacccttcaacggactcgacaagggagagccggtcaacgaggcagacgccgcggccctcgagcacgacaaggcctacg accagcagctcaaagcgggtgacaatccgtacctgcggtataaccacgccgacgccgagtttcaggagcgtctgcaagaaga tacgtcttttggggcaacctcggcgagcagtcttccaggccaagaagcgggttctcgaacctctcggtctggttgaggaag gcgctaagacggctcctggaaagaaacgtccggtagagcagtcgccacaagagccagactcctcctcgggcatcggcaaga caggccagcagcccgctaaaaagagactcaattttggtcagactggcgactcagagtcagtccccgacccacaacctctcgg
```

-continued

```
agaacctccagcaaccccgctgctgtgggacctactacaatggcttcaggcggtggcgcaccaatggcagacaataacgaa ggcgccgacggagtgggtaatgcctcaggaaattggcattgcgattccacatggctgggcgacagagtcatcaccaccagca cccgaacatgggccttgcccacctataacaaccacctctacaagcaaatctccagtgcttcgacggggccagcaacgacaa ccactacttcggctacagcacccctgggggtattttgactttaacagattccactgccacttttcaccacgtgactggcagcgac tcatcaacaataactggggattccggcccaagagactcagcttcaagctcttcaacatccaggtcaaggaggtcacgacgaatg atggcgtcacaaccatcgctaataaccttaccagcacggttcaagtcttctcggactcggagtaccagcttccgtacgtcctcgg ctctgcgcaccagggctgcctccctccgttcccggcggacgtgttcatgattccgcaatacggctacctgacgctcaacaatgg cagccaagccgtgggacgttcatccttttactgcctggaatatttcccttctcagatgctgagaacgggcaacaactttaccttcag ctacacctttgaggaagtgcctttccacagcagctacgcgcacagccagagcctggaccggctgatgaatcctctcatcgatca atacctgtattacctgaacagaactcaaaatcagtccggaagtgcccaaaacaaggacttgctgtttagccgtgggtctccagct ggcatgtctgttcagcccaaaaactggctacctggaccctgttatcggcagcagcgcgtttctaaaacaaaaacagacaacaac aacagcaattttacctggactggtgcttcaaaatataacctcaatgggcgtgaatccatcatcaaccctggcactgctatggcctc acacaaagacgacgaagacaagttctttcccatgagcggtgtcatgatttttggaaaagagagcgccggagcttcaaacactgc attggacaatgtcatgattacggacgaagaggaaattaaagccactaaccctgtggccaccgaaagatttgggaccgtggcag tcaatttccagagcagcagcacagaccctgcgaccggagatgtgcatgctatgggagcattacctggcatggtgtggcaagat agagacgtgtacctgcagggtcccatttgggccaaaattcctcacacagatggcactttcacccgtctcctcttatgggcggctt tggactcaagaacccgcctcctcagatcctcatcaaaaacacgcctgttcctgcgaatcctccggcggagttttcagctacaaag tttgcttcattcatcactcaatactccacaggacaagtgagcgtggaaattgaatgggagctgcagaaagaaaacagcaaacgc tggaatcccgaagtgcagtatacatctaactatgcaaaatctgccaacgttgatttcactgtggacaacaatggactttatactgag cctcgcccattggcacccgttacctcacccgtcccctgtaa;
```

SM 10-8 (amino acid sequence) (SEQ ID NO: 31):
MAADGYLPDWLEDTLSEGIRQWWKLKPGPPPPKPAERHKDDSRGLVLP

GYKYLGPFNGLDKGEPVNEADAAALEHDKAYDRQLDSGDNPYLKYNHADAEF

QERLKEDTSFGGNLGRAVFQAKKRVLEPLGLVEEPVKTAPGKKRPVEHSPVEPD

SSSGTGKAGQQPARKRLNFGQTGDADSVPDPQPLGQPPAAPSGLGTNTMATGS

GAPMADNNEGADGVGNSSGNWHCDSTWMGDRVITTSTRTWALPTYNNHLYK

QISSQSGASNDNHYFGYSTPWGYFDFNRFHCHFSPRDWQRLINNNWGFRPKRL

KFKLFNIQVKEVTQNDGTTTIANNLTSTVQVFTDSEYQLPYVLGSAHQGCLPPFP

ADVFMVPQYGYLTLNNGSQAVGRSSFYCLEYFPSQMLRTGNNFTFSYTFEDVPF

HSSYAHSQSLDRLMNPLIDQYLYYLSRTDTPSGTTTQSRLQFSQAGASDIRDQSR

NWLPGPCYRQQRVSKTSADNNNSEYSWTGATKYHLNGRDSLVNPGPAMASHK

DDEEKFFPQSGVLIFGKQGSEKTSVDIEKVMITDEEEIRTTNPVATEQYGSVSTNL

QRGNRQAATADVNTQGVLPGMVWQDRDVYLQGPIWAKIPHTDGHFHPSPLMG

GFGLKHPPPQILIKNTPVPANPSTTFSAAKFASFITQYSTGQVSVEIEWELQKENS

KRWNPEVQYTSNYNKSVNVDFTVDTNGVYSEPRPIGTRYLTRNL;

SM 10-8 (nucleotide sequence) (SEQ ID NO: 39):
```
atggctgccgatggttatcttccagattggctcgaggacactctctctgaaggaataagacagtggtggaagctcaa acctggcccaccaccaccaaagcccgcagagcggcataaggacgacagcaggggtcttgtgcttcctgggtacaagtacctc ggacccttcaacggactcgacaagggagagccggtcaacgaggcagacgccgcggccctcgagcacgacaaagcctatg accggcagctcgacagcggagacaacccgtacctcaagtacaaccacgccgacgcggagtttcaggagcgccttaaagaag atacgtcttttgggggcaacctcggacgagcagtcttccaggcgaaaaagagggttcttgaacctctgggcctggttgaggaac
```

-continued

```
ctgttaagacggctccgggaaaaagaggccggtagagcactctcctgtggagccagactcctcctcgggaaccggaaagg cgggccagcagcctgcaagaaaaagattgaattttggtcagactggagacgcagactcagtacctgatcccagcctctcgga cagccaccagcagcccctctggtctgggaactaatacgatggctacaggcagtggcgcaccaatggcagacaataacgag ggcgccgacggagtgggtaattcctcgggaaattggcattgcgattccacatggatgggcgacagagtcatcaccaccagca cccgaacctgggccctgcccacctacaacaaccacctctacaaacaaatttccagccaatcaggagcctcgaacgacaatcac tactttggctacagcacccttgggggtattttgacttcaacagattccactgccacttttcaccacgtgactggcaaagactcatc aacaacaactggggattccgacccaagagactcaagttcaagctctttaacattcaagtcaaagaggtcacgcagaatgacggt acgacgacgattgccaataaccttaccagcacggttcaggtgtttactgactcggagtaccagctcccgtatgtcctcggctcgg cgcatcaaggatgcctcccgccgttcccagcagacgtcttcatggtgccacagtatggatacctcaccctgaacaacgggagt caggcagtaggacgctcttcattttactgcctggagtactttccttctcagatgctgcgtaccggtaacaactttaccttcagctaca cttttgaggacgttcctttccacagcagctacgctcacagccagagtctggaccgtctcatgaatcctctcatcgaccagtacctg tattacttgagcagaacagacactccaagtggaaccaccacgcagtcaaggcttcagttttctcaggccggagcgagtgacatt cgggaccagtctaggaactggcttcctggaccctgttaccgccagcagcgagtatcaaagacatctgcggataacaacaacag tgaatactcgtggactggagctaccaagtaccacctcaatggcagagactctctggtgaatccgggcccggccatggcaagcc acaaggacgatgaagaaaagttttttcctcagagcggggttctcatctttgggaagcaaggctcagagaaaacaagtgtggaca ttgaaaaggtcatgattacagacgaagaggaaatcaggacaaccaatcccgtggctacggagcagtatggttctgtatctacca acctccagagaggcaacagacaagcagctaccgcagatgtcaacacacaaggcgttcttccaggcatggtctggcaggaca gagatgtgtaccttcaggggcccatctgggcaaagattccacacacggacggacattttcacccctctccctcatgggtggatt cggacttaaacaccctcctccacagattctcatcaagaacacccccgtacctgcgaatccttcgaccaccttcagtgcggcaaa gtttgcttccttcatcacacagtactccacgggacaggtcagcgtggagatcgagtgggagctgcagaaggaaaacagcaaac gctggaatcccgaagttcagtacacttccaactacaacaagtctgttaatgtggactttactgtggacactaatggcgtgtattcag agcctcgccccattggcaccagatacctgactcgtaatctgtaa;
```

SM 100-3 (amino acid sequence) (SEQ ID NO: 32):
MAADGYLPDWLEDTLSEGIRQWWKLKPGPPPPKPAERHKDDSRGLVLP

GYKYLGPFNGLDKGEPVNEADAAALEHDKAYDRQLDSGDNPYLKYNHADAEF

QERLKEDTSFGGNLGRAVFQAKKRVLEPLGLVEEPVKTAPGKKRPVEHSPVEPD

SSSGTGKAGQQPARKRLNFGQTGDANSVPDPQPLGQPPAAPSGLGTNTMATGS

GAPMADNNEGADGVGNSSGNWHCDSTWMGDRVITTSTRTWALPTYNNHLYK

QISSQSGASNDNHYFGYSTPWGYFDFNRFHCHFSPRDWQRLINNNWGFRPKRL

KFKLFNIQVKEVTQNDGTTTIANNLTSTVQVFTDSEYQLPYVLGSAHQGCLPPFP

ADVFMVPQYGYLTLNNGSRAVGRSSFYCLEYFPSQMLRTGNNFTFSYTFEDVPF

HSSYAHSQSLDRLMNPLIDQYLYYLSRTDTPSGTTTQSRLQFSQAGASDIRDQSR

NWLPGPCYRQQRVSKTSADNNNSEYSWTGATKYHLNGRDSLVNPGPAMASHK

DDEEKFFPQSGVLIFGKQGSEKTSVDIEKVMITDEEEIRTTNPVATEQYGSVSTNL

QRGNRQAATADVNTQGVLPGMVWQDRDVYLQGPIWAKIPHTDGHFHPSPLMG

GFGLKHPPPQILIKNTPVPANPSTTFSAAKFASFITQYSTGQVSVEIEWELQKENS

KRWNPEVQYTSNYNKSVNVDFTVDTNGVYTEPRPIGTRYLTRNL;

SM 100-3 (nucleotide sequence) (SEQ ID NO: 40):
```
atggctgccgatggttatcttccagattggctcgaggacactctctctgaaggaataagacagtggtggaagctcaa acctggcccaccaccaccaaagcccgcagagcggcataaggacgacagcaggggtcttgtgcttcctgggtacaagtacctc ggacccttcaacggactcgacaagggagagccggtcaacgaggcagacgccgcggccctcgagcacgacaaagcctatg accggcagctcgacagcggagacaacccgtacctcaagtacaaccacgccgacgcggagtttcaggagcgccttaaagaag
```

```
atacgtcttttgggggcaacctcggacgagcagtcttccaggcgaaaaagagggttcttgaacctctgggcctggttgaggaac ctgttaagacggctccgggaaaaagaggccggtagagcactctcctgtggagcagactcctcctcgggaaccggaaagg cgggccagcagcctgcaagaaaaagattgaattttggtcagactggagacgcaaactcagtacctgaccccagcctctcgga cagccaccagcagcccctctggtctgggaactaatacgatggctacaggcagtggcgcaccaatggcagacaataacgag ggcgccgacggagtgggtaattcctcgggaaattggcattgcgattccacatggatgggcgacagagtcatcaccaccagca cccgaacctgggccctgccacctacaacaaccacctctacaaacaaatttccagccaatcaggagcctcgaacgacaatcac tactttggctacagcacccttggggtattttgacttcaacagattccactgccacttttcaccacgtgactggcaaagactcatc aacaacaactggggattccgacccaagagactcaagttcaagctctttaacattcaagtcaaagaggtcacgcagaatgacggt acgacgacgattgccaataaccttaccagcacggttcaggtgtttactgactcggagtaccagctcccgtacgtcctcggctcg gcgcatcaaggatgcctcccgccgttcccagcagacgtcttcatggtgccacagtatggatacctcaccctgaacaacgggag tcgggcagtaggacgctcttcattttactgcctggagtactttccttctcagatgctgcgtaccggtaacaactttaccttcagctac acttttgaggacgttcctttccacagcagctacgctcacagccagagtctggaccgtctcatgaatcctctcatcgaccagtacct gtattacttgagcagaacagacactccaagtggaaccaccacgcagtcaaggcttcagttttctcaggccggagcgagtgacat tcggaccagtctaggaactggcttcctggaccctgttaccgccagcagcgagtatcaaagacatctgcggataacaacaaca gtgaatactcgtggactggagctaccaagtaccacctcaatggcagagactctctggtgaatccgggcccggccatggcaagc cacaaggacgatgaagaaaagtttttttcctcagagcggggttctcatctttgggaagcaaggctcagagaaaacaagtgtggac attgaaaaggtcatgattacagacgaagaggaaatcaggacgaccaatcccgtggctacggagcagtatggttctgtatctacc aacctccagagaggcaacagacaagcagctaccgcagatgtcaacacacaaggcgttcttccaggcatggtctggcaggac agagatgtgtaccttcaggggcccatctgggcaaagattccacacacggacggacattttcacccctctcccctcatgggtgga ttcggacttaaacaccctcctccacagattctcatcaagaacaccccggtacctgcgaatccttcgaccaccttcagtgcggcaa agtttgcttccttcatcacacagtactccacgggacaggtcagcgtggagatcgagtgggagctgcagaaggaaaacagcaaa cgctggaatcccgaagttcagtacacttccaactacaacaagtctgttaatgtggactttactgtggacactaatggcgtgtataca gagcctcgccccattggcaccagatacctgactcgtaatctgtaa;
SM 100-10 (amino acid sequence) (SEQ ID NO: 33):
MAADGYLPDWLEDTLSEGIRQWWKLKPGPPPPKPAERHKDDSRGLVLP

GYKYLGPFNGLDKGEPVNEADAAALEHDKAYDRQLDSGDNPYLKYNHADAEF

QERLKEDTSFGGNLGRAVFQAKKRVLEPLGLVEEPVKTAPGKKRPVEHSPVEPD

SSSGTKGAGQQPARKRLNFGQTGDADSVPDPQPLGQPPAAPSGLGTNTMATGS

GAPMADNNEGADGVGNSSGNWHCDSTWMGDRVITTSTRTWALPTYNNHLYK

QISSQSGASNDNHYFGYSTPWGYFDFNRFHCHFSPRDWQRLINNNWGFRPKRL

KFKLFNIQVKEVTQNDGTTTIANNLTSTVQVFTDSEYQLPYVLGSAHQGCLPPFP

ADVFMVPQYGYLTLNNGSQAVGRSSFYCLEYFPSQMLRTGNNFTFSYTFEDVPF

HSSYAHSQSLDRLMNPLIDQYLYYLSRTDAPSGTTTQSRLQFSQAGASDIRDQSR

NWLPGPCYRQQRVSKTSADNNNSEYSWTGATKYHLNGRDSLVNPGPAMASHK

DDEEKFFPQSGVLIFGKQGSEKTSVDIEKVMITDEEEIRTTNPVATEQYGSVSTNL

QRGNRQAATADVNTQGVLPGMVWQDRDVYLQGPIWAKIPHTDGHFHPSPLMG

GFGLKHPPPQILIKNTPVPANPSTTFSAAKFASFITQYSTGQVSVEIEWELQKENS

KRWNPEVQYTSNYNKSVNVDFTVDTNGVYSEPRPIGTRYLTRNL;

SM 100-10 (nucleotide sequence) (SEQ ID NO: 41):
atggctgccgatggttatcttccagattggctcgaggacactctctctgaaggaataagacagtggtggaagctcaa acctggcccaccaccaccaaagcccgcagagcggcataaggacgacagcaggggtcttgtgcttcctgggtacaagtacctc
```

-continued

```
ggacccttcaacggactcgacaagggagagccggtcaacgaggcagacgccgcggccctcgagcacgacaaagcctatg accggcagctcgacagcggagacaacccgtacctcaagtacaaccacgccgacgcggagtttcaggagcgccttaaagaag atacgtcttttgggggcaacctcggacgagcagtcttccaggcgaaaaagagggttcttgaacctctgggcctggttgaggaac ctgttaagacggctccgggaaaaagaggccggtagagcactctcctgtggagccagactcctcctcgggaaccggaaagg cgggtcagcagcctgcaagaaaaagattgaattttggtcagactggagacgcagactcagtacctgaccccagcctctcgga cagccaccagcagcccctctggtctgggaactaatacgatggctacaggcagtggcgcaccaatggcagacaataacgag ggcgccgacggagtgggtaattcctcgggaaattggcattgcgattccacatggatgggcgacagagtcatcaccaccagca cccgaacctgggccctgcccacctacaacaaccacctctacaaacaaatttccagccaatcaggagcctcgaacgacaatcac tactttggctacagcaccccttgggggtattttgacttcaacagattccactgccacttttcaccacgtgactggcaaagactcatc aacaacaactggggattccgacccaagagactcaagttcaagctcttaacattcaagtcaaagaggtcacgcagaatgacggt acgacgacgattgccaataaccttaccagcacggttcaggtgtttactgactcggagtaccagctcccgtacgtcctcggctcg gcgcatcaaggatgcctcccgccgttcccagcagacgtcttcatggtgccacagtatggatacctcaccctgaacaacgggag tcaggcagtaggacgctcttcatttactgcctggagtacttcccttctcagatgctgcgtaccggtaacaactttaccttcagctac acttttgaggacgttcctttccacagcagctacgctcacagccagagtctggaccgtctcatgaatcctctcatcgaccagtacct gtattacttgagcagaacagacgctccaagtggaaccaccacgcagtcaaggcttcagttttctcaggccggagcgagtgacat tcgggaccagtctaggaactggcttcctggaccctgttaccgccagcagcgagtatcaaagacatctgcggataacaacaaca gtgaatactcgtggactggagctaccaagtaccacctcaatggcagagactctctggtgaatccgggccggccatggcaagc cacaaggacgatgaagaaaagttttttcctcagagcggggttctcatctttgggaagcaaggctcagagaaaacaagtgtggac attgaaaaggtcatgattacagacgaagaggaaatcaggacaaccaatcccgtggctacggagcagtatggttctgtatctacc aacctccagagaggcaacagacaagcagctaccgcagatgtcaacacacaaggcgttcttccaggcatggtctggcaggac agagatgtgtaccttcaggggcccatctgggcaaagattccacacacggacggacattttcacccctctccctcatgggtgga ttcggacttaaacaccctcctccacagattctcatcaagaacaccccggtacctgcgaatccttcgaccaccttcagtgcggcaa agtttgcttccttcatcacacagtactccacgggacaggtcagcgtggagatcgagtgggagctgcagaaggaaaacagcaaa cgctggaatcccgaagttcagtacacttccaactacaacaagtctgttaatgtggactttactgtggacactaatggcgtgtattca gagcctcgccccattggcaccagatacctgactcgtaatctgtaa.
```

Nucleic Acids and Host Cells

The present disclosure provides nucleic acids comprising nucleotide sequences encoding a variant AAV capsid protein (as described above), as well as host cells comprising a subject nucleic acid. The nucleic acids and host cells are useful for generating rAAV virions (as described below).

The present disclosure provides host cells, e.g., isolated host cells, comprising a subject nucleic acid. A subject host cell can be referred to as a "genetically modified host cell" and is typically an isolated cell, e.g., a cell in in vitro culture. A subject host cell is useful for producing a subject rAAV virion, as described below. Where a subject host cell is used to produce a subject rAAV virion, it is referred to as a "packaging cell." In some embodiments, a subject host cell is stably genetically modified (i.e., stably transfected) with a subject nucleic acid. In other embodiments, a subject host cell is transiently genetically modified (i.e., transiently transfected) with a subject nucleic acid.

A subject nucleic acid is introduced stably or transiently into a host cell, using established techniques, including, but not limited to, electroporation, calcium phosphate precipitation, liposome-mediated transfection, and the like. For stable transformation, a subject nucleic acid will generally further include a selectable marker, e.g., any of several well-known selectable markers such as neomycin resistance, and the like.

A subject host cell is generated by introducing a subject nucleic acid into any of a variety of cells, e.g., mammalian cells, including, e.g., murine cells, and primate cells (e.g., human cells). Suitable mammalian cells include, but are not limited to, primary cells and cell lines, where suitable cell lines include, but are not limited to, 293 cells, COS cells, HeLa cells, Vero cells, 3T3 mouse fibroblasts, C3H10T1/2 fibroblasts, CHO cells, and the like.

In some embodiments, a subject host cell includes, in addition to a nucleic acid comprising a nucleotide sequence encoding a mutant capsid protein, a nucleic acid that comprises a nucleotide sequence encoding one or more AAV rep proteins. In other embodiments, a subject host cell further comprises an rAAV vector, as described below. As described in more detail below, an rAAV virion is generated using a subject host cell.

Infectious rAAV Virions

A subject infectious rAAV virion comprises a variant AAV capsid protein and a heterologous nucleic acid (described in greater detail below), and exhibits an increased resistance to human AAV neutralizing antibodies compared to the resistance exhibited by a wild type AAV (e.g., AAV2 (wild type AAV serotype 2)) or an AAV comprising a wild-type capsid protein. By "increased resistance" it is meant that a subject infectious rAAV virion exhibits an increased infectivity in the presence of human anti-AAV antibodies. As described above, viral infectivity can be expressed as the ratio of infectious viral particles to total viral particles. Thus in increased infectivity means an increased ratio of infectious viral particles to total viral particles. To determine resistance of an AAV to human anti-AAV antibodies, infectivity of the AAV is measured in the presence of various concentrations of human anti-AAV antibodies in order to obtain the antibody concentration (e.g., serum concentration, IVIG concentration, etc.) (mg/mL) required to reduce gene delivery efficiency (i.e., infectivity) to 50% of that in the absence of human anti-AAV antibodies. A virus that requires a higher antibody concentration to reduce gene delivery efficiency to 50% of that in the absence of human anti-AAV antibodies is said to have increased resistance to antibody neutralization. Thus, a two-fold increase in resistance means a two-fold increase in the antibody concentration required to reduce gene delivery efficiency to 50% of that in the absence of human anti-AAV antibodies. In some embodiments, a subject infectious rAAV virion exhibits at least about 1.5-fold (e.g., at least about 1.5-fold, at least about 2-fold, at least about 3-fold, at least about 4-fold, at least about 5-fold, at least about 7.5-fold, at least about 10-fold, at least about 12-fold, at least about 15-fold, at least about 17-fold, at least about 20-fold, at least about 25-fold, at least about 30-fold, at least about 40-fold, at least about 50-fold, at least about 75-fold, at least about 100-fold, at least about 150-fold, at least about 200-fold, at least about 250-fold, at least about 300-fold, etc.) greater resistance to human AAV neutralizing antibodies than the resistance exhibited by a wild type AAV (e.g., AAV2 (wild type AAV serotype 2)) or an AAV comprising a wild-type capsid protein.

A subject infectious rAAV virion can be said to exhibit increased transduction of mammalian cells in the presence of human AAV neutralizing antibodies. In some embodiments, a subject infectious rAAV virion exhibits at least about 1.5-fold (e.g., at least about 1.5-fold, at least about 2-fold, at least about 3-fold, at least about 4-fold, at least about 5-fold, at least about 7.5-fold, at least about 10-fold, at least about 12-fold, at least about 15-fold, at least about 17-fold, at least about 20-fold, at least about 25-fold, at least about 30-fold, at least about 40-fold, at least about 50-fold, at least about 75-fold, at least about 100-fold, at least about 150-fold, at least about 200-fold, at least about 250-fold, at least about 300-fold, etc.) greater transduction of mammalian cells in the presence of human AAV neutralizing antibodies than the transduction exhibited by a wild type AAV (e.g., AAV2 (wild type AAV serotype 2)) or an AAV comprising a wild-type capsid protein.

In some embodiments, a subject infectious rAAV virion exhibits decreased binding to a neutralizing antibody that binds a wild-type AAV capsid protein. For example, a subject infectious rAAV virion can exhibit at least about 1.5-fold (e.g., at least about 1.5-fold, at least about 2-fold, at least about 3-fold, at least about 4-fold, at least about 5-fold, at least about 7.5-fold, at least about 10-fold, at least about 12-fold, at least about 15-fold, at least about 17-fold, at least about 20-fold, at least about 25-fold, at least about 30-fold, at least about 40-fold, at least about 50-fold, at least about 75-fold, at least about 100-fold, at least about 150-fold, at least about 200-fold, at least about 250-fold, at least about 300-fold, etc.) reduced binding (e.g., reduced affinity) to a neutralizing antibody that binds a wild-type capsid AAV protein, compared to the binding affinity of the antibody to wild-type AAV capsid protein.

In some embodiments, an anti-AAV neutralizing antibody binds to a subject infectious rAAV virion with an affinity of less than about $10^{-7}$ M, less than about $5 \times 10^{-6}$ M, less than about $10^{-6}$ M, less than about $5 \times 10^{-5}$ M, less than about $10^{-5}$ M, less than about $10^{-4}$ M, or lower.

In some embodiments, a subject infectious rAAV virion exhibits increased in vivo residence time compared to a wild-type AAV. For example, a subject infectious rAAV virion exhibits a residence time that is at least about 10%, at least about 25%, at least about 50%, at least about 100%, at least about 3-fold, at least about 5-fold, at least about 10-fold, at least about 25-fold, at least about 50-fold, at least about 100-fold, or more, longer than the residence time of a wild-type AAV.

Whether a given subject infectious rAAV virion exhibits reduced binding to a neutralizing antibody and/or increased resistance to neutralizing antibody can be determined using any convenient assay known to one of ordinary skill in the art.

In some embodiments, a subject infectious rAAV virion comprises wild-type Rep78, Rep68, Rep52, and Rep40 proteins. In other embodiments, a subject infectious rAAV virion comprises, in addition to one or more variant capsid proteins, one or more mutations in one or more of Rep78, Rep68, Rep52, and Rep40 proteins.

Heterologous Nucleic Acids

A suitable heterologous DNA molecule (also referred to herein as a "heterologous nucleic acid") for use in a subject rAAV vector (e.g., a subject infectious rAAV virion) can be any heterologous nucleic acid. In some embodiments, the heterologous nucleic acid comprises a nucleotide sequence encoding a polypeptide (e.g., a protein that imparts some desired characteristic to the target cell, e.g., a fluorescent protein that allows for cell tracking, an enzyme that provides an activity missing or altered in the target cell, etc.). In some embodiments, the heterologous nucleic acid comprises an RNA interfering agent (as defined above).

A subject heterologous nucleic acid will generally be less than about 5 kilobases (kb) in size and will include, for example, a gene (a nucleotide sequence) that encodes a protein that is defective or missing from a recipient individual or target cell; a gene that encodes a protein having a desired biological or therapeutic effect (e.g., an antibacterial, antiviral or antitumor/anti-cancer function); a nucleotide sequence that encodes an RNA that inhibits or reduces production of a deleterious or otherwise undesired protein (e.g., a nucleotide sequence that encodes an RNA interfering agent, as defined above); and/or a nucleotide sequence that encodes an antigenic protein.

Suitable heterologous nucleic acids include, but are not limited to, those encoding proteins used for the treatment of endocrine, metabolic, hematologic, cardiovascular, neurologic, musculoskeletal, urologic, pulmonary and immune disorders, including such disorders as inflammatory diseases, autoimmune, chronic and infectious diseases, such as acquired immunodeficiency syndrome (AIDS), cancer, hypercholestemia, lysosomal storage diseases such as Activator Deficiency/GM2 Gangliosidosis, Alpha-mannosidosis, Aspartylglucosaminuria, Cholesteryl ester storage disease, Chronic Hexosaminidase A Deficiency, Cystinosis, Danon disease, Fabry disease, Farber disease, Fucosidosis, Galactosialidosis, Gaucher Disease, GM1 gangliosidosis, I-Cell disease/Mucolipidosis II, Infantile Free Sialic Acid Storage Disease/ISSD, Juvenile Hexosaminidase A Deficiency, Krabbe disease, Lysosomal acid lipase deficiency, Metachromatic Leukodystrophy, Mucopolysaccharidoses disorders (including Pseudo-Hurler polydystrophy/Mucolipidosis IIIA, MPSI Hurler Syndrome, MPSI Scheie Syndrome, MPS I Hurler-Scheie Syndrome, MPS II Hunter syndrome, Sanfilippo syndrome Type A/MPS III A, Sanfilippo syndrome Type B/MPS III B, Sanfilippo syndrome Type C/MPS III C, Sanfilippo syndrome Type D/MPS III D, Morquio Type A/MPS IVA, Morquio Type B/MPS IVB, MPS IX Hyaluronidase Deficiency, MPS VI Maroteaux-Lamy, MPS VII Sly Syndrome, Mucolipidosis I/Sialidosis, Mucolipidosis IIIC, and Mucolipidosis type IV), Multiple sulfatase deficiency, Niemann-Pick Disease, Neuronal Ceroid Lipofuscinoses, Pompe disease/Glycogen storage disease type II, Pycnodysostosis, Sandhoff disease/Adult Onset/GM2 Gangliosidosis, Sandhoff disease/GM2 gangliosidosis—Infantile, Sandhoff disease/GM2 gangliosidosis—Juvenile, Schindler disease, Salla disease/Sialic Acid Storage Disease, Tay-Sachs/GM2 gangliosidosis, and Wolman disease, insulin disorders such as diabetes, growth disorders, various blood disorders including various anemias, thalassemias and hemophilia; genetic defects such as cystic fibrosis, Gaucher's Disease, Hurler's Disease, adenosine deaminase (ADA) deficiency, emphysema, or the like.

Suitable heterologous nucleic acids include, but are not limited to, those encoding any of a variety of proteins, including, but not limited to: an interferon (e.g., IFN-γ, IFN-α, IFN-β, IFN-ω; IFN-τ); an insulin (e.g., Novolin, Humulin, Humalog, Lantus, Ultralente, etc.); an erythropoietin ("EPO"; e.g., Procrit®, Eprex®, or Epogen® (epoetin-α); Aranesp® (darbepoietin-α); NeoRecormon®, Epogin® (epoetin-β); and the like); an antibody (e.g., a monoclonal antibody) (e.g., Rituxan® (rituximab); Remicade® (infliximab); Herceptin® (trastuzumab); Humira™ (adalimumab); Xolair® (omalizumab); Bexxar® (tositumomab); Raptiva™ (efalizumab); Erbitux™ (cetuximab); Avastin® (bevacizumab); and the like), including an antigen-binding fragment of a monoclonal antibody (e.g., Lucentis® (ranibizumab)); a blood factor (e.g., Activase® (alteplase) tissue plasminogen activator; NovoSeven® (recombinant human factor VIIa); Factor VIIa; Factor VIII (e.g., Kogenate®); Factor IX; β-globin; hemoglobin; and the like); a colony stimulating factor (e.g., Neupogen® (filgrastim; G-CSF); Neulasta (pegfilgrastim); granulocyte colony stimulating factor (G-CSF), granulocyte-monocyte colony stimulating factor, macrophage colony stimulating factor, megakaryocyte colony stimulating factor; and the like); a growth hormone (e.g., a somatotropin, e.g., Genotropin®, Nutropin®, Norditropin®, Saizen®, Serostim®, Humatrope®, etc.; a human growth hormone; and the like); an interleukin (e.g., IL-1; IL-2, including, e.g., Proleukin®; IL-3, IL-4, IL-5, IL-6, IL-7, IL-8, IL-9; etc.); a growth factor (e.g., Regranex® (beclapermin; PDGF); Fiblast® (trafermin; bFGF); Stemgen® (ancestim; stem cell factor); keratinocyte growth factor; an acidic fibroblast growth factor, a stem cell factor, a basic fibroblast growth factor, a hepatocyte growth factor; and the like); a soluble receptor (e.g., a TNF-α-binding soluble receptor such as Enbrel® (etanercept); a soluble VEGF receptor; a soluble interleukin receptor; a soluble γ/δ T cell receptor; and the like); an enzyme (e.g., α-glucosidase; Cerazyme® (imiglucarase; β-glucocerebrosidase, Ceredase® (alglucerase;); an enzyme activator (e.g., tissue plasminogen activator); a chemokine (e.g., IP-10; Mig; Groα/IL-8, RANTES; MIP-1α; MIP-1β; MCP-1; PF-4; and the like); an angiogenic agent (e.g., vascular endothelial growth factor (VEGF)); an anti-angiogenic agent (e.g., a soluble VEGF receptor); a protein vaccine; a neuroactive peptide such as bradykinin, cholecystokinin, gastin, secretin, oxytocin, gonadotropin-releasing hormone, beta-endorphin, enkephalin, substance P, somatostatin, prolactin, galanin, growth hormone-releasing hormone, bombesin, dynorphin, neurotensin, motilin, thyrotropin, neuropeptide Y, luteinizing hormone, calcitonin, insulin, glucagon, vasopres sin, angiotensin II, thyrotropin-releasing hormone, vasoactive intestinal peptide, a sleep peptide, etc.; other proteins such as a thrombolytic agent, an atrial natriuretic peptide, bone morphogenic protein, thrombopoietin, relaxin, glial fibrillary acidic protein, follicle stimulating hormone, a human alpha-1 antitrypsin, a leukemia inhibitory factor, a transforming growth factor, an insulin-like growth factor, a luteinizing hormone, a macrophage activating factor, tumor necrosis factor, a neutrophil chemotactic factor, a nerve growth factor a tissue inhibitor of metalloproteinases; a vasoactive intestinal peptide, angiogenin, angiotropin, fibrin; hirudin; a leukemia inhibitory factor; an IL-1 receptor antagonist (e.g., Kineret® (anakinra)); an ion channel, e.g., cystic fibrosis transmembrane conductance regulator (CFTR); dystrophin; utrophin, a tumor suppressor; lysosomal enzyme acid α-glucosidase (GAA); and the like. Suitable nucleic acids also include those that encode a functional fragment of any of the aforementioned proteins; and nucleic acids that encode functional variants of any of the aforementioned proteins.

Suitable heterologous nucleic acids also include those that encode antigenic proteins. A subject rAAV vector that comprises a heterologous nucleic acid that encodes an antigenic protein is suitable for stimulating an immune response to the antigenic protein in a mammalian host. The antigenic protein is derived from an autoantigen, an allergen, a tumor/cancer-associated antigen, a pathogenic virus, a pathogenic bacterium, a pathogenic protozoan, a pathogenic helminth, or any other pathogenic organism that infects a mammalian host. As used herein, the term "a nucleic acid encoding an antigenic protein derived from" includes nucleic acids encoding wild-type antigenic proteins, e.g., a nucleic acid isolated from a pathogenic virus that encodes a viral protein; synthetic nucleic acids generated in the laboratory that encode antigenic proteins that are identical in amino acid sequence to a naturally-occurring antigenic protein; synthetic nucleic acids generated in the laboratory that encode antigenic proteins that differ in amino acid sequence (e.g., by from one amino acid to about 15 amino acids) from a naturally-occurring antigenic protein, but that nonetheless induce an immune response to the corresponding naturally-occurring antigenic protein; synthetic nucleic acids generated in the laboratory that encode fragments of antigenic proteins (e.g., fragments of from about 5 amino acids to about 50 amino acids, which fragments comprises one or more antigenic epitopes), which fragments induce an immune response to the corresponding naturally-occurring antigenic protein; etc.

Similarly, an antigenic protein "derived from" an autoantigen, an allergen, a tumor/cancer-associated antigen, a pathogenic virus, a pathogenic bacterium, a pathogenic protozoan, a pathogenic helminth, or any other pathogenic organism that infects a mammalian host, includes proteins that are identical in amino acid sequence to a naturally-occurring antigenic protein, and proteins that differ in amino acid sequence (e.g., by from one amino acid to about 15 amino acids) from a naturally-occurring antigenic protein, but that nonetheless induce an immune response to the corresponding naturally-occurring antigenic protein; and fragments of antigenic proteins (e.g., fragments of from about 5 amino acids to about 100 amino acids, e.g., from about 5 to about 50 amino acids, which fragments comprises one or more antigenic epitopes), which fragments induce an immune response to the corresponding naturally-occurring antigenic protein.

In some embodiments, an immune response to an antigenic protein encoded by a subject rAAV vector will stimulate a protective immune response to a pathogenic organism that displays the antigenic protein or antigenic epitope (or a protein or an epitope that is cross-reactive with the rAAV-encoded antigenic protein or antigenic epitopes) in the mammalian host. In some embodiments, a cytotoxic T lymphocyte (CTL) response to the rAAV-encoded antigenic protein will be induced in the mammalian host. In other embodiments, a humoral response to the rAAV-encoded antigenic protein will be induced in the mammalian host, such that antibodies specific to the antigenic protein are generated. In many embodiments, a TH1 immune response to the rAAV-encoded antigenic protein will be induced in the mammalian host. Suitable antigenic proteins include tumor/cancer-associated antigens, viral antigens, bacterial antigens, and protozoal antigens; and antigenic fragments thereof. In some embodiments, the antigenic protein is derived from an intracellular pathogen. In other embodiments, the antigenic protein is a self-antigen. In yet other embodiments, the antigenic protein is an allergen.

Tumor/cancer-specific antigens include, but are not limited to, any of the various MAGEs (Melanoma-Associated Antigen E), including MAGE 1 (e.g., GenBank Accession No. M77481), MAGE 2 (e.g., GenBank Accession No. U03735), MAGE 3, MAGE 4, etc.; any of the various tyrosinases; mutant ras; mutant p53 (e.g., GenBank Accession No. X54156 and AA494311); and p97 melanoma antigen (e.g., GenBank Accession No. M12154). Other tumor/cancer-specific antigens include the Ras peptide and p53 peptide associated with advanced cancers, the HPV 16/18 and E6/E7 antigens associated with cervical cancers, MUCI1-KLH antigen associated with breast carcinoma (e.g., GenBank Accession No. J03651), CEA (carcinoembryonic antigen) associated with colorectal cancer (e.g., GenBank Accession No. X98311), gp100 (e.g., GenBank Accession No. 573003) or MART1 antigens associated with melanoma, and the PSA antigen associated with prostate cancer (e.g., GenBank Accession No. X14810). The p53 gene sequence is known (See e.g., Harris et al. (1986) Mol. Cell. Biol., 6:4650-4656) and is deposited with GenBank under Accession No. M14694. Thus, subject proteins, nucleic acids, and/or virions can be used as immunotherapeutics for cancers including, but not limited to, cervical, breast, colorectal, prostate, lung cancers, and for melanomas.

Viral antigens are derived from known causative agents responsible for diseases including, but not limited to, measles, mumps, rubella, poliomyelitis, hepatitis A, B (e.g., GenBank Accession No. E02707), and C (e.g., GenBank Accession No. E06890), as well as other hepatitis viruses, influenza, adenovirus (e.g., types 4 and 7), rabies (e.g., GenBank Accession No. M34678), yellow fever, Japanese encephalitis (e.g., GenBank Accession No. E07883), dengue (e.g., GenBank Accession No. M24444), hantavirus, and human immunodeficiency virus (e.g., GenBank Accession No. U18552).

Suitable bacterial and parasitic antigens include those derived from known causative agents responsible for diseases including, but not limited to, diphtheria, pertussis (e.g., GenBank Accession No. M35274), tetanus (e.g., GenBank Accession No. M64353), tuberculosis, bacterial and fungal pneumonias (e.g., Haemophilus influenzae, Pneumocystis carinii, etc.), cholera, typhoid, plague, shigellosis, salmonellosis (e.g., GenBank Accession No. L03833), Legionnaire's Disease, Lyme disease (e.g., GenBank Accession No. U59487), malaria (e.g., GenBank Accession No. X53832), hookworm, onchocerciasis (e.g., GenBank Accession No. M27807), schistosomiasis (e.g., GenBank Accession No. L08198), trypanosomiasis, leshmaniasis, giardiasis (e.g., GenBank Accession No. M33641), amoebiasis, filariasis (e.g., GenBank Accession No. J03266), borreliosis, and trichinosis.

Suitable heterologous nucleic acids that encode heterologous gene products include non-translated RNAs, such as an RNAi agent (as described in greater detail above) (e.g., an antisense RNA; an siRNA; an shRNA; a double stranded RNA (dsRNA); a CRISPR agent, e.g., a Cas9 or Cas9-like protein, a crRNA-like RNA, a tracrRNA-like RNA, a single guide RNA, and/or a donor polynucleotide; and the like), a ribozyme, etc. RNAi agents can be used to inhibit gene expression. Some RNAi agents provide a tool that can be subsequently used to inhibit gene expression (e.g., a CRISPR agent such as a cas9 or cas9-like protein).

Target genes include any gene encoding a target gene product (RNA or protein) that is deleterious (e.g., pathological), for example, a target gene product that is malfunctioning (e.g., due to a mutation in the encoded protein sequence, due to a mutation in the non-coding sequences that control the steady state level of the gene product, etc.). Target gene products include, but are not limited to, huntingtin; hepatitis C virus; human immunodeficiency virus; amyloid precursor protein; tau; a protein that includes a polyglutamine repeat; a herpes virus (e.g., varicella zoster); any pathological virus; and the like.

As such a subject rAAV that includes a heterologous nucleic acid encoding an RNAi agent is useful for treating a variety of disorders and conditions, including, but not limited to, neurodegenerative diseases, e.g., a trinucleotide-repeat disease, such as a disease associated with polyglutamine repeats, e.g., Huntington's disease, spinocerebellar ataxia, spinal and bulbar muscular atrophy (SBMA), dentatorubropallidoluysian atrophy (DRPLA), etc.; an acquired pathology (e.g., a disease or syndrome manifested by an abnormal physiological, biochemical, cellular, structural, or molecular biological state) such as a viral infection, e.g., hepatitis that occurs or may occur as a result of an HCV infection, acquired immunodeficiency syndrome, which occurs as a result of an HIV infection; cancer; and the like.

In many embodiments, a heterologous nucleic acid encoding an RNAi agent is operably linked to a promoter. Suitable promoters are known those skilled in the art and include the promoter of any protein-encoding gene, e.g., an endogenously regulated gene or a constitutively expressed gene. For example, the promoters of genes regulated by cellular physiological events, e.g., heat shock, oxygen levels and/or carbon monoxide levels, e.g., in hypoxia, may be operably linked to an siRNA-encoding nucleic acid.

The selected heterologous nucleotide sequence, such as EPO-encoding or nucleic acid of interest, is operably linked to control elements that direct the transcription or expression thereof in the nucleotide sequence in vivo. Such control elements can comprise control sequences normally associated with the selected gene (e.g., endogenous cellular control elements). Alternatively, heterologous control sequences can be employed. Useful heterologous control sequences generally include those derived from sequences encoding mammalian or viral genes. Examples include, but are not limited to, the SV40 early promoter, mouse mammary tumor virus long terminal repeat (LTR) promoter; adenovirus major late promoter (Ad MLP); a herpes simplex virus (HSV) promoter, an endogenous cellular promoter that is heterologous to the gene of interest, a cytomegalovirus (CMV) promoter such as the CMV immediate early promoter region (CMVIE), a rous sarcoma virus (RSV) promoter, synthetic promoters, hybrid promoters, and the like. In addition, sequences derived from nonviral genes, such as the murine metallothionein gene, will also find use herein. Such promoter sequences are commercially available from, e.g., Stratagene (San Diego, Calif.).

In some embodiments, cell type-specific or tissue-specific promoter will be operably linked to the heterologous nucleic acid encoding the heterologous gene product, such that the gene product is produced selectively or preferentially in a particular cell type(s) or tissue(s). In some embodiments, an inducible promoter will be operably linked to the heterologous nucleic acid.

For example, muscle-specific and inducible promoters, enhancers and the like, are useful for delivery of a gene product to a muscle cell. Such control elements include, but are not limited to, those derived from the actin and myosin gene families, such as from the myoD gene family; the myocyte-specific enhancer binding factor MEF-2; control elements derived from the human skeletal actin gene and the cardiac actin gene; muscle creatine kinase sequence elements and the murine creatine kinase enhancer (mCK) element; control elements derived from the skeletal fast-twitch troponin C gene, the slow-twitch cardiac troponin C gene and the slow-twitch troponin I gene; hypoxia-inducible nuclear factors; steroid-inducible elements and promoters, such as the glucocorticoid response element (GRE); the fusion consensus element for RU486 induction; and elements that provide for tetracycline regulated gene expression.

The AAV expression vector which harbors the DNA molecule of interest (the heterologous DNA) bounded by AAV ITRs, can be constructed by directly inserting the selected sequence(s) into an AAV genome which has had the major AAV open reading frames ("ORFs") excised therefrom. Other portions of the AAV genome can also be deleted, so long as a sufficient portion of the ITRs remain to allow for replication and packaging functions. Such constructs can be designed using techniques well known in the art. See, e.g., U.S. Pat. Nos. 5,173,414 and 5,139,941; International Publication Nos. WO 92/01070 (published Jan. 23, 1992) and WO 93/03769 (published Mar. 4, 1993); Lebkowski et al. (1988) Molec. Cell. Biol. 8:3988-3996; Vincent et al. (1990) Vaccines 90 (Cold Spring Harbor Laboratory Press); Carter, B. J. (1992) Current Opinion in Biotechnology 3:533-539; Muzyczka, N. (1992) Current Topics in Microbiol. and Immunol. 158:97-129; Kotin, R. M. (1994) Human Gene Therapy 5:793-801; Shelling and Smith (1994) Gene Therapy 1:165-169; and Zhou et al. (1994) J. Exp. Med. 179:1867-1875.

Alternatively, AAV ITRs can be excised from the viral genome or from an AAV vector containing the same and fused 5' and 3' of a selected nucleic acid construct that is present in another vector using any convenient method known to one of ordinary skill in the art. For example, one suitable approach uses standard ligation techniques, such as those described in Sambrook et al., supra. For example, ligations can be accomplished in 20 mM Tris-Cl pH 7.5, 10 mM $MgCl_2$, 10 mM DTT, 33 µg/ml BSA, 10 mM-50 mM NaCl, and either 40 µM ATP, 0.01-0.02 (Weiss) units T4 DNA ligase at 0° C. to 16° C. (for "sticky end" ligation) or 1 mM ATP, 0.3-0.6 (Weiss) units T4 DNA ligase at 14° C. (for "blunt end" ligation). Intermolecular "sticky end" ligations are usually performed at 30-100 µm/ml total DNA concentrations (5-100 nM total end concentration). AAV vectors which contain ITRs have been described in, e.g., U.S. Pat. No. 5,139,941. In particular, several AAV vectors are described therein which are available from the American Type Culture Collection ("ATCC") under Accession Numbers 53222, 53223, 53224, 53225 and 53226.

Additionally, chimeric genes can be produced synthetically to include AAV ITR sequences arranged 5' and 3' of one or more selected nucleic acid sequences. Preferred codons for expression of the chimeric gene sequence in mammalian muscle cells can be used. The complete chimeric sequence is assembled from overlapping oligonucleotides prepared by standard methods. See, e.g., Edge, Nature (1981) 292:756; Nambair et al. Science (1984) 223:1299; Jay et al. J. Biol. Chem. (1984) 259:6311.

Generation of Subject Infectious rAAV Virions

By way of introduction, it is typical to employ a host or "producer" cell for rAAV vector replication and packaging. Such a producer cell (usually a mammalian host cell) generally comprises or is modified to comprise several different types of components for rAAV production. The first component is a recombinant adeno-associated viral (rAAV) vector genome (or "rAAV pro-vector") that can be replicated and packaged into vector particles by the host packaging cell. The rAAV pro-vector will normally comprise a heterologous polynucleotide (or "transgene"), with which it is desired to genetically alter another cell in the context of gene therapy (since the packaging of such a transgene into rAAV vector particles can be effectively used to deliver the transgene to a variety of mammalian cells). The transgene is generally flanked by two AAV inverted terminal repeats (ITRs) which comprise sequences that are recognized during excision, replication and packaging of the AAV vector, as well as during integration of the vector into a host cell genome.

A second component is a helper virus that can provide helper functions for AAV replication. Although adenovirus is commonly employed, other helper viruses can also be used as is known in the art. Alternatively, the requisite helper virus functions can be isolated genetically from a helper virus and the encoding genes can be used to provide helper virus functions in trans. The AAV vector elements and the helper virus (or helper virus functions) can be introduced into the host cell either simultaneously or sequentially in any order.

The final components for AAV production to be provided in the producer cell are "AAV packaging genes" such as AAV rep and cap genes that provide replication and encapsidation proteins, respectively. Several different versions of AAV packaging genes can be provided (including rep-cap cassettes and separate rep and/or cap cassettes in which the rep and/or cap genes can be left under the control of the native promoters or operably linked to heterologous promoters. Such AAV packaging genes can be introduced either transiently or stably into the host packaging cell, as is known in the art and described in more detail below.

1. rAAV Vector

A subject rAAV virion, including the heterologous DNA of interest (where "heterologous DNA of interest" is also referred to herein as "heterologous nucleic acid"), can be produced using standard methodology, known to those of skill in the art. The methods generally involve the steps of (1) introducing a subject rAAV vector into a host cell; (2) introducing an AAV helper construct into the host cell, where the helper construct includes AAV coding regions capable of being expressed in the host cell to complement AAV helper functions missing from the AAV vector; (3)

introducing one or more helper viruses and/or accessory function vectors into the host cell, wherein the helper virus and/or accessory function vectors provide accessory functions capable of supporting efficient recombinant AAV ("rAAV") virion production in the host cell; and (4) culturing the host cell to produce rAAV virions. The AAV expression vector, AAV helper construct and the helper virus or accessory function vector(s) can be introduced into the host cell, either simultaneously or serially, using standard transfection techniques.

AAV expression vectors are constructed using known techniques to at least provide as operatively linked components in the direction of transcription, control elements including a transcriptional initiation region, the DNA of interest and a transcriptional termination region. The control elements are selected to be functional in a mammalian muscle cell. The resulting construct which contains the operatively linked components is bounded (5' and 3') with functional AAV ITR sequences.

The nucleotide sequences of AAV ITR regions are known. See, e.g., Kotin, R. M. (1994) Human Gene Therapy 5:793-801; Berns, K. I. "Parvoviridae and their Replication" in Fundamental Virology, 2nd Edition, (B. N. Fields and D. M. Knipe, eds.) for the AAV-2 sequence. AAV ITRs used in the vectors of the invention need not have a wild-type nucleotide sequence, and may be altered, e.g., by the insertion, deletion or substitution of nucleotides. Additionally, AAV ITRs may be derived from any of several AAV serotypes, including without limitation, AAV-1, AAV-2, AAV-3, AAV-4, AAV-5, AAV-7, etc. Furthermore, 5' and 3' ITRs which flank a selected nucleotide sequence in an AAV expression vector need not necessarily be identical or derived from the same AAV serotype or isolate, so long as they function as intended, i.e., to allow for excision and rescue of the sequence of interest from a host cell genome or vector, and to allow integration of the DNA molecule into the recipient cell genome when AAV Rep gene products are present in the cell. ITRs allow replication of the vector sequence in the presence of an appropriate mixture of Rep proteins. ITRs also allow for the incorporation of the vector sequence into the capsid to generate an AAV particle.

In order to produce rAAV virions, an AAV expression vector is introduced into a suitable host cell using known techniques, such as by transfection. A number of transfection techniques are generally known in the art. See, e.g., Graham et al. (1973) Virology, 52:456, Sambrook et al. (1989) Molecular Cloning, A Laboratory Manual, Cold Spring Harbor Laboratories, New York, Davis et al. (1986) Basic Methods in Molecular Biology, Elsevier, and Chu et al. (1981) Gene 13:197. Particularly suitable transfection methods include calcium phosphate co-precipitation (Graham et al. (1973) Virol. 52:456-467), direct micro-injection into cultured cells (Capecchi, M. R. (1980) Cell 22:479-488), electroporation (Shigekawa et al. (1988) BioTechnigues 6:742-751), liposome mediated gene transfer (Mannino et al. (1988) BioTechniques 6:682-690), lipid-mediated transduction (Felgner et al. (1987) Proc. Natl. Acad. Sci. USA 84:7413-7417), and nucleic acid delivery using high-velocity microprojectiles (Klein et al. (1987) Nature 327:70-73).

For the purposes of this disclosure, suitable host cells for producing rAAV virions include microorganisms, yeast cells, insect cells, and mammalian cells, that can be, or have been, used as recipients of a heterologous DNA molecule. The term includes the progeny of the original cell which has been transfected. Thus, a "host cell" for producing rAAV virions generally refers to a cell which has been transfected with an exogenous DNA sequence. Cells from the stable human cell line, 293 (readily available through, e.g., the American Type Culture Collection under Accession Number ATCC CRL1573) are used in many embodiments. Particularly, the human cell line 293 is a human embryonic kidney cell line that has been transformed with adenovirus type-5 DNA fragments (Graham et al. (1977) J. Gen. Virol. 36:59), and expresses the adenoviral E1a and E1b genes (Aiello et al. (1979) Virology 94:460). The 293 cell line is readily transfected, and provides a particularly convenient platform in which to produce rAAV virions.

2. AAV Helper Functions

Host cells containing the above-described AAV expression vectors must be rendered capable of providing AAV helper functions in order to replicate and encapsidate the nucleotide sequences flanked by the AAV ITRs to produce rAAV virions. AAV helper functions are generally AAV-derived coding sequences which can be expressed to provide AAV gene products that, in turn, function in trans for productive AAV replication. AAV helper functions are used herein to complement necessary AAV functions that are missing from the AAV expression vectors. Thus, AAV helper functions include one, or both of the major AAV ORFs, namely the rep and cap coding regions, or functional homologues thereof. In the context of the instant disclosure, the cap functions include one or more mutant capsid proteins, wherein at least one capsid protein comprises at least one mutation, as described above.

By "AAV rep coding region" is meant the art-recognized region of the AAV genome which encodes the replication proteins Rep 78, Rep 68, Rep 52 and Rep 40. These Rep expression products have been shown to possess many functions, including recognition, binding and nicking of the AAV origin of DNA replication, DNA helicase activity and modulation of transcription from AAV (or other heterologous) promoters. The Rep expression products are collectively required for replicating the AAV genome. For a description of the AAV rep coding region, see, e.g., Muzyczka, N. (1992) Current Topics in Microbiol. and Immunol. 158:97-129; and Kotin, R. M. (1994) Human Gene Therapy 5:793-801. Suitable homologues of the AAV rep coding region include the human herpesvirus 6 (HHV-6) rep gene which is also known to mediate AAV-2 DNA replication (Thomson et al. (1994) Virology 204:304-311).

AAV cap proteins include VP1, VP2, and VP3, wherein at least one of VP1, VP2, and VP3 comprises at least one mutation, as described above.

AAV helper functions are introduced into the host cell by transfecting the host cell with an AAV helper construct either prior to, or concurrently with, the transfection of the AAV expression vector. AAV helper constructs are thus used to provide at least transient expression of AAV rep and/or cap genes to complement missing AAV functions that are necessary for productive AAV infection. AAV helper constructs lack AAV ITRs and can neither replicate nor package themselves. These constructs can be in the form of a plasmid, phage, transposon, cosmid, virus, or virion. A number of AAV helper constructs have been described, such as the commonly used plasmids pAAV/Ad and pIM29+45 which encode both Rep and Cap expression products. See, e.g., Samulski et al. (1989) J. Virol. 63:3822-3828; and McCarty et al. (1991) J. Virol. 65:2936-2945. A number of other vectors have been described which encode Rep and/or Cap expression products. See, e.g., U.S. Pat. No. 5,139,941.

Both AAV expression vectors and AAV helper constructs can be constructed to contain one or more optional selectable markers. Suitable markers include genes which confer antibiotic resistance or sensitivity to, impart color to, or change the antigenic characteristics of those cells which have been transfected with a nucleic acid construct containing the selectable marker when the cells are grown in an appropriate selective medium. Several selectable marker genes that are useful in practicing methods of the disclosure include the hygromycin B resistance gene (encoding Aminoglycoside phosphotranferase (APH)) that allows selection in mammalian cells by conferring resistance to hygromycin; the neomycin phosphotranferase gene (encoding neomycin phosphotransferase) that allows selection in mammalian cells by conferring resistance to G418; and the like. Other suitable markers are known to those of skill in the art.

3. AAV Accessory Functions

The host cell (or packaging cell) must also be rendered capable of providing non AAV derived functions, or "accessory functions," in order to produce rAAV virions. Accessory functions are non AAV derived viral and/or cellular functions upon which AAV is dependent for its replication. Thus, accessory functions include at least those non AAV proteins and RNAs that are required in AAV replication, including those involved in activation of AAV gene transcription, stage specific AAV mRNA splicing, AAV DNA replication, synthesis of Cap expression products and AAV capsid assembly. Viral-based accessory functions can be derived from any of the known helper viruses.

Particularly, accessory functions can be introduced into and then expressed in host cells using methods known to those of skill in the art. Commonly, accessory functions are provided by infection of the host cells with an unrelated helper virus. A number of suitable helper viruses are known, including adenoviruses; herpesviruses such as herpes simplex virus types 1 and 2; and vaccinia viruses. Nonviral accessory functions will also find use herein, such as those provided by cell synchronization using any of various known agents. See, e.g., Buller et al. (1981) J. Virol. 40:241-247; McPherson et al. (1985) Virology 147:217-222; Schlehofer et al. (1986) Virology 152:110-117.

Alternatively, accessory functions can be provided using an accessory function vector. Accessory function vectors include nucleotide sequences that provide one or more accessory functions. An accessory function vector is capable of being introduced into a suitable host cell in order to support efficient AAV virion production in the host cell. Accessory function vectors can be in the form of a plasmid, phage, transposon, cosmid, or another virus. Accessory vectors can also be in the form of one or more linearized DNA or RNA fragments which, when associated with the appropriate control elements and enzymes, can be transcribed or expressed in a host cell to provide accessory functions.

Nucleic acid sequences providing the accessory functions can be obtained from natural sources, such as from the genome of an adenovirus particle, or constructed using recombinant or synthetic methods known in the art. In this regard, adenovirus-derived accessory functions have been widely studied, and a number of adenovirus genes involved in accessory functions have been identified and partially characterized. See, e.g., Carter, B. J. (1990) "Adeno-Associated Virus Helper Functions," in CRC Handbook of Parvoviruses, vol. I (P. Tijssen, ed.), and Muzyczka, N. (1992) Curr. Topics. Microbiol. and Immun. 158:97-129. Specifically, early adenoviral gene regions E1a, E2a, E4, VAI RNA and, possibly, E1b are thought to participate in the accessory process. Janik et al. (1981) Proc. Natl. Acad. Sci. USA 78:1925-1929. Herpesvirus-derived accessory functions have been described. See, e.g., Young et al. (1979) Prog. Med. Virol. 25:113. Vaccinia virus-derived accessory functions have also been described. See, e.g., Carter, B. J. (1990), supra., Schlehofer et al. (1986) Virology 152:110-117.

As a consequence of the infection of the host cell with a helper virus, or transfection of the host cell with an accessory function vector, accessory functions are expressed which transactivate the AAV helper construct to produce AAV Rep and/or Cap proteins. The Rep expression products excise the recombinant DNA (including the DNA of interest, e.g., the heterologous nucleic acid) from the AAV expression vector. The Rep proteins also serve to duplicate the AAV genome. The expressed Cap proteins assemble into capsids, and the recombinant AAV genome is packaged into the capsids. Thus, productive AAV replication ensues, and the DNA is packaged into rAAV virions.

Following recombinant AAV replication, rAAV virions can be purified from the host cell using a variety of conventional purification methods, such as CsCl gradients. Further, if infection is employed to express the accessory functions, residual helper virus can be inactivated, using known methods. For example, adenovirus can be inactivated by heating to temperatures of approximately 60° C. for, e.g., 20 minutes or more. This treatment effectively inactivates only the helper virus since AAV is extremely heat stable while the helper adenovirus is heat labile.

The resulting rAAV virions are then ready for use for DNA delivery, such as in gene therapy applications, or for the delivery of a gene product to a mammalian host.

Delivering a Heterologous Nucleic Acid

The present disclosure further provides methods of delivering a heterologous nucleic acid to a target cell and/or to an individual in need thereof. In some embodiments, an individual in need thereof is a human who has previously been naturally exposed to AAV and as a result harbors anti-AAV antibodies (i.e., AAV neutralizing antibodies). Based on positive results in clinical trials involving AAV gene delivery to, for example, liver, muscle, and retina—all tissues affected by neutralizing antibodies against this vehicle—there are many such therapeutic applications/disease targets.

A subject method generally involves: (i) administering an effective amount of a subject rAAV virion to an individual, and/or (ii) contacting a target cell with a subject virion. Generally, rAAV virions are administered to a subject using either in vivo ("direct") or in vitro ("indirect") transduction techniques. If transduced in vitro ("indirectly"), a desired recipient cell (i.e., "target cell") can be removed from the individual, transduced with rAAV virions and reintroduced into the individual. Alternatively, syngeneic or xenogeneic cells can be used where those cells will not generate an inappropriate immune response in the individual.

Suitable methods for the delivery and introduction of transduced target cells into an individual have been described. For example, cells can be transduced in vitro by combining recombinant AAV virions with cells e.g., in appropriate media, and screening for those cells harboring the DNA of interest using conventional techniques such as Southern blots and/or PCR, or by using selectable markers. Transduced cells can then be formulated into pharmaceutical compositions, described more fully below, and the composition introduced into the subject by various techniques, such as by intramuscular, intravenous, subcutaneous and intraperitoneal injection.

For in vivo (i.e., "direct") delivery, the rAAV virions will be formulated into pharmaceutical compositions and will generally be administered parenterally (e.g., administered via an intramuscular, subcutaneous, intratumoral, transdermal, intrathecal, intravenous, etc.) route of administration.

Pharmaceutical compositions will comprise sufficient genetic material to produce a therapeutically effective amount of the gene expression product of interest, i.e., an amount sufficient to reduce or ameliorate symptoms of the disease state in question or an amount sufficient to confer the desired benefit. The pharmaceutical compositions will also contain a pharmaceutically acceptable excipient. Such excipients include any pharmaceutical agent that does not itself induce the production of antibodies harmful to the individual receiving the composition, and which may be administered without undue toxicity. Pharmaceutically acceptable excipients include, but are not limited to, liquids such as water, saline, glycerol and ethanol. Pharmaceutically acceptable salts can be included therein, for example, mineral acid salts such as hydrochlorides, hydrobromides, phosphates, sulfates, and the like; and the salts of organic acids such as acetates, propionates, malonates, benzoates, and the like. Additionally, auxiliary substances, such as wetting or emulsifying agents, pH buffering substances, and the like, may be present in such vehicles. A wide variety of pharmaceutically acceptable excipients are known in the art and need not be discussed in detail herein. Pharmaceutically acceptable excipients have been amply described in a variety of publications, including, for example, A. Gennaro (2000) "Remington: The Science and Practice of Pharmacy," 20th edition, Lippincott, Williams, & Wilkins; Pharmaceutical Dosage Forms and Drug Delivery Systems (1999) H. C. Ansel et al., eds., $7^{th}$ ed., Lippincott, Williams, & Wilkins; and Handbook of Pharmaceutical Excipients (2000) A. H. Kibbe et al., eds., $3^{rd}$ ed. Amer. Pharmaceutical Assoc.

Appropriate doses will depend on the mammal being treated (e.g., human or nonhuman primate or other mammal), age and general condition of the subject to be treated, the severity of the condition being treated, the particular therapeutic protein in question, its mode of administration, among other factors. An appropriate effective amount can be readily determined by one of skill in the art.

Thus, a "therapeutically effective amount" will fall in a relatively broad range that can be determined through clinical trials. For example, for in vivo injection, i.e., injection directly to skeletal or cardiac muscle, a therapeutically effective dose will be on the order of from about $10^6$ to about $10^{15}$ of the rAAV virions, e.g., from about $10^8$ to $10^{12}$ rAAV virions. For in vitro transduction, an effective amount of rAAV virions to be delivered to cells will be on the order of from about $10^8$ to about $10^{13}$ of the rAAV virions. Other effective dosages can be readily established by one of ordinary skill in the art through routine trials establishing dose response curves.

Dosage treatment may be a single dose schedule or a multiple dose schedule. Moreover, the subject may be administered as many doses as appropriate. One of skill in the art can readily determine an appropriate number of doses.

The cells of interest (i.e., "target cells") are typically mammalian, where the term refers to any animal classified as a mammal, including humans, domestic and farm animals, and zoo, laboratory, sports, or pet animals, such as dogs, horses, cats, cows, mice, rats, rabbits, etc. In some embodiments, the target cell is a human cell.

Target cells of interest include any cell susceptible to infection by a subject rAAV virion. In some cases, e.g., when the method is a method of delivering a heterologous nucleic acid to a target cell, the target cell can be a cell removed from an individual (e.g., a "primary" cell), or the target cell can be a tissue culture cell (e.g., from an established cell line).

Exemplary target cells include, but are not limited to, liver cells, pancreatic cells (e.g., islet cells: alpha cells, beta cells, delta cells, gamma cells, and/or epsilon cells), skeletal muscle cells, heart muscle cells, fibroblasts, retinal cells, synovial joint cells, lung cells, T cells, neurons, glial cells, stem cells, hematopoietic progenitor cells, neural progenitor cells, endothelial cells, and cancer cells. Exemplary stem cell target cells include, but are not limited to, hematopoietic stem cells, neural stem cells, neural crest stem cells, embryonic stem cells, induced pluripotent stem cells (iPS cells), mesenchymal stem cells, mesodermal stem cells, liver stem cells, pancreatic stem cells, muscle stem cells, and retinal stem cells.

The term "stem cell" is used herein to refer to a mammalian cell that has the ability both to self-renew, and to generate differentiated progeny (see, e.g., Morrison et al. (1997) Cell 88:287-298). Generally, stem cells also have one or more of the following properties: an ability to undergo asynchronous, or symmetric replication, that is where the two daughter cells after division can have different phenotypes; extensive self-renewal capacity; capacity for existence in a mitotically quiescent form; and clonal regeneration of all the tissue in which they exist, for example the ability of hematopoietic stem cells to reconstitute all hematopoietic lineages. As is appreciated by one of ordinary skill in the art, "progenitor cells" differ from stem cells in that they typically do not have the extensive self-renewal capacity, and often can generate a more restricted subset of the lineages in the tissue from which they derive, for example only lymphoid, or erythroid lineages in a hematopoietic setting. As used herein, the term "stem cell" encompasses both "stem cells" and "progenitor cells" as defined above.

Stem cells may be characterized by both the presence of markers associated with specific epitopes identified by antibodies and the absence of certain markers as identified by the lack of binding of specific antibodies. Stem cells may also be identified by functional assays both in vitro and in vivo, particularly assays relating to the ability of stem cells to give rise to multiple differentiated progeny.

Suitable stem cells of interest include, but are not limited to: hematopoietic stem cells and progenitor cells derived therefrom (U.S. Pat. No. 5,061,620); neural crest stem cells (see Morrison et al. (1999) Cell 96:737-749); neural stem cells and neural progenitor cells; embryonic stem cells; mesenchymal stem cells; mesodermal stem cells; liver stem cells, muscle stem cells, retinal stem cells, induced pluripotent stem cells (iPS cells), etc. Other hematopoietic "progenitor" cells of interest include cells dedicated to lymphoid lineages, e.g. immature T cell and B cell populations.

Purified populations of stem or progenitor cells may be used. For example, human hematopoietic stem cells may be positively selected using antibodies specific for CD34, thy-1; or negatively selected using lineage specific markers which may include glycophorin A, CD3, CD24, CD16, CD14, CD38, CD45RA, CD36, CD2, CD19, CD56, CD66a, and CD66b; T cell specific markers, tumor/cancer specific markers, etc. Markers useful for the separation of mesodermal stem cells include FcγRII, FcγRIII, Thy-1, CD44, VLA-4α, LFA-1β, HSA, ICAM-1, CD45, Aa4.1, Sca-1, etc. Neural crest stem cells may be positively selected with antibodies specific for low-affinity nerve growth factor receptor (LNGFR), and negatively selected for the markers sulfatide, glial fibrillary acidic protein (GFAP), myelin protein $P_o$, peripherin and neurofilament. Human mesenchymal stem cells may be positively separated using the markers SH2, SH3 and SH4.

Target cells which are employed may be fresh, frozen, or have been subject to prior culture. They may be fetal, neonate, adult. Hematopoietic cells may be obtained from fetal liver, bone marrow, blood, particularly G-CSF or GM-CSF mobilized peripheral blood, or any other conventional source. The manner in which stem cells are separated from other cells of the hematopoietic or other lineage is not critical to this disclosure. As described above, a substantially homogeneous population of stem or progenitor cells may be obtained by selective isolation of cells free of markers associated with differentiated cells, while displaying epitopic characteristics associated with the stem cells.

Nucleic acids that can be delivered to an individual include any of the above defined heterologous nucleic acids. Proteins that can be delivered using a subject method also include a functional fragment of any of the aforementioned proteins; and functional variants of any of the aforementioned proteins.

In some embodiments, a therapeutically effective amount of a protein is produced in the mammalian host. Whether a therapeutically effective amount of a particular protein is produced in the mammalian host using a subject method is readily determined using assays appropriate to the particular protein. For example, where the protein is EPO, hematocrit is measured.

Where the rAAV encodes an antigenic protein, suitable antigenic proteins that can be delivered to an individual using a subject method include, but are not limited to, tumor/cancer-associated antigens, autoantigens ("self" antigens), viral antigens, bacterial antigens, protozoal antigens, and allergens; and antigenic fragments thereof. In some embodiments, a cytotoxic T lymphocyte (CTL) response to the rAAV-encoded antigenic protein will be induced in the mammalian host. In other embodiments, a humoral response to the rAAV-encoded antigenic protein will be induced in the mammalian host, such that antibodies specific to the antigenic protein are generated. In many embodiments, a TH1 immune response to the rAAV-encoded antigenic protein will be induced in the mammalian host. Whether an immune response to the antigenic protein has been generated is readily determined using well-established methods. For example, an enzyme-linked immunosorbent assay can be used to determine whether antibody to an antigenic protein has been generated. Methods of detecting antigen-specific CTL are well known in the art. For example, a detectably labeled target cell expressing the antigenic protein on its surface is used to assay for the presence of antigen-specific CTL in a blood sample.

Whether a therapeutically effective amount of a heterologous nucleic acid (e.g., a nucleic acid encoding a polypeptide, an RNAi agent, etc.) has been delivered to a mammalian host using a subject method is readily determined using any appropriate assay. For example, where the gene product is an RNAi agent that inhibits HIV, viral load can be measured.

Methods of Generating and Identifying Modified rAAV Virions

The present disclosure provides a method of generating and identifying a modified infectious recombinant adeno-associated virus (rAAV) virion that comprises a variant capsid protein comprising an amino acid sequence with at least one amino acid substitution (including deletions, insertions, etc.) compared to a starter AAV capsid protein. A starter AAV capsid protein comprises an amino acid sequence set forth in one of SEQ ID NOs: 10-13 and 26-33.

The method generally involves generating a mutant rAAV virion library; and selecting the library for modified rAAV virions with altered properties relative to a starter rAAV virion. The starter rAAV virion comprises a variant AAV capsid protein that comprises an amino acid sequence set forth in one of SEQ ID NOs: 10-13 and 26-33. The present disclosure further provides libraries and compositions comprising the libraries.

In some embodiments, a given selection step is repeated two, three, four, or more times to enrich a subject AAV library for altered virion properties. In some embodiments, following selection of an AAV library, individual clones are isolated and sequenced.

Generation of a Mutant AAV Library

A mutant AAV library is generated that comprises one or more mutations relative to a starter AAV cap gene. A starter cap gene is a cap comprising a nucleotide sequence that encodes a variant AAV capsid protein that comprises an amino acid sequence set forth in one of SEQ ID NOs: 10-13 and 26-33. Mutations in the rAAV cap gene are generated using any known method. Suitable methods for mutagenesis of a starter AAV cap gene include, but are not limited to, a polymerase chain reaction (PCR)-based method, oligonucleotide-directed mutagenesis, saturation mutagenesis, loop-swapping mutagenesis, fragment shuffling mutagenesis (i.e., DNA shuffling), and the like. Methods for generating mutations are well described in the art. See, e.g., Zhao et al. Nat Biotechnol. 1998 March; 16(3):234-5; Koerber et. al.; Mol Ther. 2008 October; 16(10):1703-9; Koerber et. al.; Mol Ther. 2009 December; 17(12):2088-95; U.S. Pat. Nos. 6,579,678; 6,573,098; and 6,582,914; all of which are hereby incorporated by reference for their teachings related to mutagenesis.

In some embodiments, a mutant AAV library comprising mutations in the cap gene will be generated using a staggered extension process. The staggered extension process involves amplification of the cap gene using a PCR-based method. The template cap gene is primed using specific PCR primers, followed by repeated cycles of denaturation and very short annealing/polymerase-catalyzed extension. In each cycle, the growing fragments anneal to different templates based on sequence complementarity and extend further. The cycles of denaturation, annealing, and extension are repeated until full-length sequences form. The resulting full-length sequences include at least one mutation in the cap gene compared to a wild-type AAV cap gene.

The PCR products comprising AAV cap sequences that include one or more mutations are inserted into a plasmid containing a wild-type AAV genome. The result is a library of AAV cap mutants. Thus, the present disclosure provides a mutant AAV cap gene library comprising from about 10 to about $10^{10}$ members, and comprising mutations in the AAV cap gene. A given member of the library has from about one to about 50 mutations in the AAV cap gene. A subject library comprises from 10 to about $10^9$ distinct members, each having a different mutation(s) in the AAV cap gene.

Once a cap mutant library is generated, viral particles are produced that can then be selected on the basis of altered capsid properties. Library plasmid DNA is transfected into a suitable host cell (e.g., 293 cells), followed by introduction into the cell of helper virus. Viral particles produced by the transfected host cells (rAAV library particles) are collected.

Library Selection

Once a library is generated, it is selected for a particular virion property (i.e., an altered property of infection). Viral particles are generated as discussed above (thus producing a library of modified rAAV virions), and subjected to one or more selection steps to identify a modified rAAV virion with an altered property of infection (relative to an infectious rAAV virion comprising a variant capsid protein that comprises an amino acid sequence set forth in one of SEQ ID NOs: 10-13 and 26-33). Properties of infection that are selected for can include, but are not limited to: 1) altered binding (e.g., decreased binding) to AAV neutralizing antibodies; 2) increased evasion of AAV neutralizing antibodies; 3) increased infectivity of a cell that is resistant to infection with AAV; and 4) altered heparin binding.

1. Selection for Reduced Binding to AAV Neutralizing Antibodies

In some embodiments, a subject AAV library is selected for altered (e.g., reduced) binding to neutralizing antibodies that bind to and neutralize wild-type AAV virions, compared to the binding of such antibodies to wild-type AAV virions and neutralization of wild-type AAV virions (or relative to an infectious rAAV virion comprising a variant capsid protein that comprises an amino acid sequence set forth in one of SEQ ID NOs: 10-13 and 26-33). AAV library particles (AAV library virion) are contacted with neutralizing antibodies and the ability of the AAV library particles to infect a permissive host cell is tested. Typically, AAV library particles are contacted with various concentrations of neutralizing antibodies. The higher the concentration of neutralizing antibodies that is required to reduce infectivity of the AAV library particles, the more resistant the AAV particles are to neutralization. Any convenient assay known to one of ordinary skill in the art may be used to directly measure the binding (e.g., measure the binding affinity) of an AAV library virion to neutralizing anti-AAV antibodies.

2. Selection for Increased Evasion of AAV Neutralizing Antibodies

In some embodiments, a subject AAV library is selected for increased evasion of neutralizing antibodies (i.e. increased resistance to human neutralizing AAV antibodies) relative to an infectious rAAV virion comprising a variant capsid protein that comprises an amino acid sequence set forth in one of SEQ ID NOs: 10-13 and 26-33. AAV library particles are contacted with targets cells in the presence of neutralizing AAV antibodies (usually human neutralizing anti-AAV antibodies). After a suitable amount of time to allow for infection of the cells with AAV library particles, helper virus is added, and AAV library particles that successfully infected the cell(s) are harvested. In some embodiments, infectivity is measured (e.g., as described above) for those virions exhibiting successful infection. In some embodiments, the cycle of infection, addition of helper virus, and harvesting of AAV particles is repeated one, two, three, or more times. The selection can occur with varying amounts (concentrations) of neutralizing AAV antibodies to select for various degrees of evasion (e.g., each repeated round can utilize an increased concentration of antibodies relative to the previous round).

3. Selection for Increased Infectivity of Non-Permissive Cells

In some embodiments, a subject AAV library is selected for increased infectivity of non-permissive cells (relative to an infectious rAAV virion comprising a variant capsid protein that comprises an amino acid sequence set forth in one of SEQ ID NOs: 10-13 and 26-33). AAV library particles are contacted with a non-permissive cell (e.g., a population of non-permissive cells). After a suitable amount of time to allow for infection of the cells with AAV library particles, helper virus is added, and AAV library particles that successfully infected the non-permissive cell(s) are harvested. In some embodiments, the cycle of infection, addition of helper virus, and harvesting of AAV particles is repeated one, two, three, or more times.

4. Selection for Altered Heparin Binding

In some embodiments, a subject library is selected for altered heparin binding, including increased heparin binding and decreased heparin binding relative to wild-type AAV virion heparin binding (or relative to an infectious rAAV virion comprising a variant capsid protein that comprises an amino acid sequence set forth in one of SEQ ID NOs: 10-13 and 26-33). AAV library particles are contacted with a heparin affinity matrix. For example, AAV library particles are loaded onto a heparin affinity column under conditions that permit binding of the AAV library particles to the heparin. Exemplary conditions include equilibration of the column with 0.15 M NaCl and 50 mM Tris at pH 7.5. After allowing the AAV library particle to bind to the heparin affinity matrix, the AAV library particle/heparin affinity matrix complex is washed with volumes of buffer containing progressively increasing concentrations of NaCl, and at each NaCl concentration, eluted AAV library particles are collected. For example, after binding the AAV library particle/heparin affinity matrix complex is washed with a volume of 50 mM Tris buffer, pH 7.5, containing 200 mM NaCl, and eluted AAV library particles are collected. The elution step is repeated with a 50 mM Tris buffer, pH 7.5, containing about 250 mM NaCl, about 300 mM NaCl, about 350 mM, about 400 mM NaCl, about 450 mM NaCl, about 500 mM NaCl, about 550 mM NaCl, about 600 mM NaCl, about 650 mM NaCl, about 700 mM NaCl, or about 750 mM NaCl.

AAV library particles that elute at NaCl concentrations lower than about 450 mM NaCl exhibit decreased heparin binding properties relative to wild-type AAV. AAV library particles that elute at NaCl concentrations higher than about 550 mM NaCl exhibit increased heparin binding properties relative to wild-type AAV.

In some embodiments, eluted AAV library particles are amplified by co-infection of permissive cells with a helper virus, and are re-fractionated on heparin affinity matrix. This step can be repeated a number of times to enrich for AAV library particles with altered heparin binding properties.

In the present methods, one or more selection steps may follow generation of AAV library particles. For example, in some embodiments, the method comprises selecting for increased heparin binding, followed by selecting for decreased binding to neutralizing antibodies. In other embodiments, the method comprises selecting for decreased binding to neutralizing antibodies, followed by selecting for increased heparin binding. In other embodiments, the method comprises selecting for decreased heparin binding, followed by selecting for decreased binding to neutralizing antibodies. In other embodiments, the method comprises selecting for decreased binding to neutralizing antibodies, followed by selecting for decreased heparin binding. In other embodiments, the method comprises selecting for decreased binding to neutralizing antibodies, followed by selecting for increased infectivity of a stem cell. In other embodiments, the method comprises selecting for decreased binding to neutralizing antibodies, followed by selecting for increased evasion of neutralizing antibodies. In other embodiments, the method comprises selecting for increased evasion of neutralizing antibodies, followed by selecting for decreased binding to neutralizing antibodies.

Thus, the present disclosure provides an adeno-associated virus (AAV) library that includes a plurality of nucleic acids, each of which nucleic acid includes a nucleotide sequence that encodes a variant AAV capsid protein. The encoded variant AAV capsid protein includes at least one amino acid substitution relative to a sequence set forth in one of SEQ ID NOs: 10-13 and 26-33. The present disclosure provides a library of mutant adeno-associated virus (AAV) particles, including a plurality of AAV particles each of which includes an AAV capsid protein that includes at least one amino acid substitution relative to a sequence set forth in one of SEQ ID NOs: 10-13 and 26-33. Nucleic acids encoding mutant AAV capsid proteins are described above, as are the properties of the encoded mutant AAV capsid proteins.

The present disclosure further provides a library comprising at least one of: (i) two or more infectious rAAV virions, each comprising a variant adeno-associated virus (AAV) capsid protein and a heterologous nucleic acid; (ii) two or more isolated nucleic acids, each comprising a nucleotide sequence that encodes a variant AAV capsid protein; (iii) two or more host cells, each comprising a nucleic acid that comprises a nucleotide sequence that encodes a variant AAV capsid protein; and (iv) two or more variant AAV capsid proteins; where the variant AAV capsid protein of at least one member of the library comprises an amino acid sequence having at least one amino acid substitution relative to the amino acid sequence set forth in one of SEQ ID NOs: 10-13 and 26-33.

Compositions and Kits

Also provided are compositions and kits for use in the methods of the present disclosure. The subject compositions and kits include at least one of: a subject infectious rAAV virion, a subject rAAV vector, a subject nucleotide acid comprising a nucleotide sequence encoding a subject variant AAV capsid protein, an isolated host cell comprising a subject nucleic acid (i.e., a subject genetically modified host cell comprising a nucleic acid that comprises a nucleotide sequence encoding a subject variant AAV capsid protein); a subject library (e.g., any of the above described libraries); and a subject variant AAV capsid protein. A composition or kit can include any convenient combination of the above. A composition or kit can also include helper virus and/or a nucleic acid comprising a nucleotide sequence that encodes a helper virus. A kit may also include reagents for the generation of nucleic acids (i.e., "mutant" nucleic acids) encoding modified variant AAV capsid proteins.

In addition to the above components, the subject kits may further include (in certain embodiments) instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, and the like. Yet another form of these instructions is a computer readable medium, e.g., diskette, compact disk (CD), flash drive, and the like, on which the information has been recorded. Yet another form of these instructions that may be present is a website address which may be used via the internet to access the information at a removed site.

The invention now being fully described, it will be apparent to one of ordinary skill in the art that various changes and modifications can be made without departing from the spirit or scope of the invention.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); ml, milliliter(s); µl, microliter(s); nl, nanoliter(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); i.v., intravenous(ly); and the like.

Example 1

Adeno-associated virus (AAV) gene therapy vectors have demonstrated considerable promise in several clinical trials to date. However, circulating anti-AAV antibodies, resulting from childhood exposure or prior administration of an AAV vector, have prevented the implementation of AAV gene therapy for many potential patients. We have isolated novel AAV variants that are capable of enhanced anti-AAV antibody evasion, both in vitro and in vivo. The stringent pressure resulting from selections using low and high potency human sera pools and human IVIG evolved AAV variants capable of evasion of antibody neutralization from individual human sera, human IVIG, and mouse sera, the most broadly evasive variants to date.

Materials and Methods

Cell Lines

Cell lines were cultured at 37° C. and 5% $CO_2$, and unless otherwise mentioned, were obtained from the American Type Culture Collection (Manassas, Va.). HEK293T, HeLa, and HT1080 cells were cultured in Dulbecco's modified Eagle's medium supplemented with 10% fetal bovine serum (Gibco, Carlsbad, Calif.) and 1% penicillin/streptomycin (Invitrogen, Carlsbad, Calif.). CHO K1 and CHO pgsA cells were cultured in F-12K medium (ATCC) supplemented with 10% fetal bovine serum (Gibco) and 1% penicillin/streptomycin (Invitrogen). Pro5 and Lec1 cells were cultured in MEM-alpha medium (Gibco) supplemented with 10% fetal bovine serum (Gibco) and 1% penicillin/streptomycin (Invitrogen).

Human Sera Pools for Selection

Eighteen individual human serum samples were obtained from Innovative Research, Inc. (Southfield, Mich.) and the neutralizing antibody titer for wild type AAV2 was determined for each sample (Table 2). Since individual samples likely possess variations in both the affinities and epitope specificities of the antibodies, three potent sera pools (α=A+F+G, β=B+H+M, and γ=I+J+N) were generated by mixing equal volumes of individual serum samples. Selection in the presence of these variations of antibodies should result in a general enhancement of resistance to many pre-existing human antibodies. Later selections were performed in the presence of Gamimune N, 10% Human IVIG (Bayer, Elkhart Ind.) to select for resistance to an even broader range of antibodies.

Table 2: Neutralizing Antibody Titers of Individual Human Serum Samples

Neutralizing antibody (NAb) titers for each sample are reported as the reciprocal of the volume fraction of serum necessary to reduce infectivity to 37% of the value measured in the absence of serum. Three sera pools (α=A+F+G, β=B+H+M, and γ=I+J+N) were then generated by mixing equivolume amounts of three individual serum samples.

TABLE 2

| Human Serum Sample | ~NAB titer |
|---|---|
| A | 500 |
| B | 275 |
| C | 200 |
| D | <75 |
| E | <75 |
| F | 350 |
| G | 425 |
| H | 450 |
| I | 200 |
| J | 500 |
| K | 172 |
| L | <75 |
| M | 2200 |
| N | 5000 |
| O | <75 |
| P | <75 |
| Q | <75 |
| R | 120 |

Library Generation and Viral Production

To create the saturation mutagenesis library, an AAV2 cap library was generated by error-prone PCR followed by the staggered extension process described by Zhao et al. using 5'-GCGGAAGCTTCGATCAACTACGC-3' (SEQ ID NO: 14) and 5'-GGGGCGGCCGCAATTACAGATTACGAGTCAGGTATCTGGTG-3' (SEQ ID NO: 15) as forward and reverse primers, respectively. Selections using pooled individual human sera revealed a variant containing four point mutations (described in the results section) that served as the basis for the saturation mutagenesis library. The cap gene for this variant was subjected to further mutagenesis by changing the amino acids at specific sites. Primer 5'-cattNNKgaccagtctaggaactgg-3'(SEQ ID NO: 16) and the corresponding reverse complement primer were used to mutagenize the R471 amino acid site. Primer 5'-gc-cacaaggacgatgaagaaNNKttttttcctcagagcggggttctcatctttgggaagcaaggctcaNNKaaaacaagt gtggacattg-3'(SEQ ID NO: 17) and the corresponding reverse complement primer were used to mutagenize the K532 and E548 amino acid sites. Primer 5'-ccaacctccagagaggcNNKagacaagcagctacc-3'(SEQ ID NO: 18) and the corresponding reverse complement primer were used to mutagenize the N587 amino acid site. Primer 5'-ccaactacaacaagtctNNKaatgtggactttactgtggacNNKaatggcgtgtatt-3'(SEQ ID NO: 19) and the corresponding reverse complement primer were used to mutagenize the V708 and T716 amino acid sites. A library consisting of AAV2 containing randomized cap loop regions and a library containing shuffled DNA from the wild type AAV1, AAV2, AAV4, AAV5, AAV6, AAV8, AAV9 cap genes were packaged and pooled for initial selection steps (Koerber et. al.; Mol Ther. 2008 October; 16(10):1703-9; and Koerber et. al.; Mol Ther. 2009 December; 17(12):2088-95; both of which are hereby incorporated by reference in their entirety).

For the second and third rounds of evolution, random mutagenesis libraries were generated by subjecting cap genes from the Loop-Swap/Shuffle library and the Saturation Mutagenesis library to error-prone PCR using 5'-CATGGGAAAGGTGCCAGACG-3'(SEQ ID NO: 20) and 5'-ACCATCGGCAGCCATACCTG-3'(SEQ ID NO: 21) as forward and reverse primers, respectively, as previously described. The replication competent AAV libraries and recombinant AAV vectors expressing GFP under the control of a CMV promoter were packaged using HEK293T cells (ATCC) using the calcium phosphate transfection method, and the viruses were purified by iodixonal gradient centrifugation. Recombinant AAV vectors expressing GFP or luciferase under the control of a CMV promoter for use in vivo were further purified by Amicon filtration. DNase-resistant genomic titers were determined via quantitative PCR. (Excoffon et. al, Proc Natl Acad Sci USA. 2009 Mar. 10; 106(10):3865-70; and Maheshri et al., Nat Biotechnol. 2006 February; 24(2):198-204; both of which are hereby incorporated by reference in their entirety).

Library Selection and Evolution

One round of selection is defined as HEK293T cell infection using the AAV starting library (incubated for 30 minutes at room temperature for the pooled individual human sera or for 1 hour at 37° C. with heat inactivated IVIG prior to infection), followed by adenovirus rescue and harvest of successful variants. Each round of evolution consists of mutagenesis of the cap gene to create the starting library and three rounds of selection. Three rounds of evolution were performed with each library, with clonal analysis performed between each round of evolution. The starting libraries for each round of evolution were generated as described above. Following the third round of selection, AAV cap genes were isolated from the pool of successful AAV variants and amplified via PCR. Cap genes were inserted into the pXX2 recombinant AAV packaging plasmid using NotI and HindIII. Cap genes were then sequenced at the University of California, Berkeley DNA sequencing facility, and analyzed using Geneious software (Biomatters, Auckland, New Zealand). Three-dimensional models of the AAV2 capsid (Protein Databank accession number 1LP3) were rendered in Pymol (DeLano Scientific, San Carlos, Calif.).

In Vitro Transduction Analysis of Antibody-Evading Variants

HEK293T were plated at a density of $3 \times 10^4$ cells/well 24 hours prior to infection. Variants were incubated at 37° C. for 1 hour with heat inactivated IVIG, individual human sera, or individual mouse sera prior to infection, and cells were then infected with rAAV-GFP at a genomic MOI of 2000. The percentage of GFP positive cells was assessed 48 hours post infection using an ImageXpress Micro Cellular Imaging and Analysis System (Molecular Devices, Sunnyvale, Calif.) and MetaXpress Image Analysis Software, version 3.1.0, Multi Wavelength Cell Scoring Application Module (Molecular Devices).

In Vitro Transduction Analysis

To determine the relative transduction efficiencies the selected mutants compared to parental wild-type AAV serotypes, HEK293T, CHO K1, CHO pgsA (lacking all surface glycosaminoglycans), CHO Pro5 (the parental line for several glycosylation mutants, including Lec1 cells), CHO Lec1 (glycosylation defective), HeLa, and HT1080 cells (a human fibrosarcoma cell line) were plated at a density of $2.5 \times 10^4$ cells per well 24 hours prior to infection. Cells were infected with rAAV1-GFP, rAAV2-GFP, rAAV6-GFP, Shuffle 100.1-GFP, Shuffle 100.3-GFP, SM 10.2-GFP, or Shuffle 100.7-GFP at a range of MOI of 100-1000. The percentage of GFP positive cells was assessed 48 hours post infection using a Beckman-Coulter Cytomics FC500 flow cytometer (Beckman-Coulter, Brea, Calif.).

In Vivo Analysis of Antibody-Evading Variants

For analysis of gene expression in vivo, eight week old, female, Balb/c mice were primed with 4 mg IVIG per mouse or phosphate buffered saline (for control mice) via tail vein injection 24 hours prior to administration of recombinant Shuffle 100-3 (see SEQ ID NO: 12), SM 10-2 (see SEQ ID NO: 10), or AAV2 vectors. Mice were infected with $10^{11}$ viral genomes of recombinant AAV vectors encoding luciferase under the control of a CMV promoter via tail vein injection. For bioluminescence imaging, mice were anesthetized with 2% isofluorane and oxygen. D-luciferin substrate (GOLD Biotechnology, St. Louis, Mo.) was injected intraperitoneally, at a dose of 500 µg/g of body weight. Images were generated using a VivoVision IVIS Lumina imager (Xenogen, Alameda, Calif.). For each mouse, ventral images were taken 7-10 minutes after the substrate injection, every week for four weeks. Five weeks post-infection, serum was collected via cardiac puncture and mice were then perfused with 0.9% saline solution. Heart, liver, lungs, kidney, spleen, brain, spinal cord, and hind limb muscle were harvested and frozen. Frozen tissue samples were homogenized and resuspended in reporter lysis buffer (Promega, Mannheim, Germany) for in vitro luciferase analysis. Lysate containing luciferase was clarified by centrifugation for 10 minutes at 10,000 g. To assay the samples, 20 µL of the lysate was added to 100 µL of the luciferase assay buffer, mixed, incubated for 5 minutes, and placed in the luminometer. The signal was integrated for 30 seconds with a 2 second delay and was reported in Relative Light Units (RLU) detected by a TD 20/20 luminometer (Turner Designs, Sunnyvale, Calif.). The luciferase signal was normalized to the total protein content determined by a bicinchoninic acid assay (Pierce).

Results

Our results demonstrate that AAV can evolve to significantly overcome neutralization by anti-AAV antibodies, both in vitro and in vivo. Novel AAV variants were isolated that required 2- to 35-fold higher neutralizing antibody titers (using human IVIG) than wild-type AAV in vitro. The antibody neutralization properties also translated to enhanced transduction in vivo in the presence of neutralizing antibodies. The isolation of such novel clones resistant to anti-AAV antibodies allows for the broader implementation of treatments based on AAV as a nucleic acid delivery vector (including individuals with high antibody titers that are currently ineligible for AAV gene therapy).

AAV Library Generation and Selection Through Directed Evolution

FIG. 1a shows a schematic of the directed evolution approach used to isolate novel AAV variants capable of evading human antibody neutralization. Libraries of viruses were created using the DNA mutagenesis techniques described in the following paragraphs (FIG. 1a, steps 1 and 2). During initial selections, pools of viral libraries developed from error-prone PCR mutations to AAV2 cap genes were incubated with various dilutions of the low potency α human sera pool for 30 minutes at room temperature prior to infection of HEK293T cells (step 3). Following three rounds of selection against the low potency α human sera pool (FIG. 1a, steps 4 and 5), several variants with enhanced resistance to this neutralizing sera pool were obtained (FIG. 1a, step 6, FIG. 7a). Variant 1.45, contained two point mutations (N312K, N449D), which resulted in >10-fold more resistance to neutralization by the α pool compared to wild type AAV2.

The cap gene from variant 1.45 was subjected to additional random mutagenesis and the resulting library was selected for three additional rounds of selection against the β and γ pools, in parallel. As only minor improvements in antibody evasion were observed (data not shown), the recovered cap genes were pooled and subjected to additional diversification via DNA shuffling and EP PCR. Three more rounds of selection against increasing amounts of sera from both the β and γ pools resulted in substantial enrichment in the amount of recovered virus from the viral library compared to wild type AAV2 (FIG. 7b, c). Sequencing of the successful cap genes from both pools revealed several low frequency mutants and a single dominant mutant, variant γ4.3, which contained four point mutations (N312K, N449D, N551S, and I698V), present within both libraries. In the presence of human IVIG, variant 1.45 demonstrated a modest 1.2-fold enhanced resistance to neutralization, whereas γ4.3 demonstrated 3.1-fold enhanced resistance to neutralization (FIG. 7d). This observation confirms the hypothesis that pools of individual human sera can be used to isolate AAV variants capable of enhanced evasion of antibodies present in the general human population.

Figure 1B:
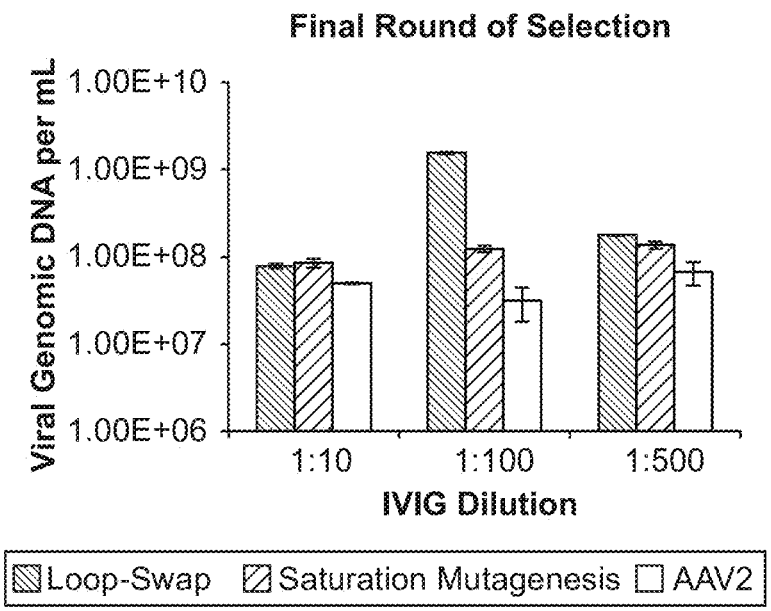
Figure 2A:
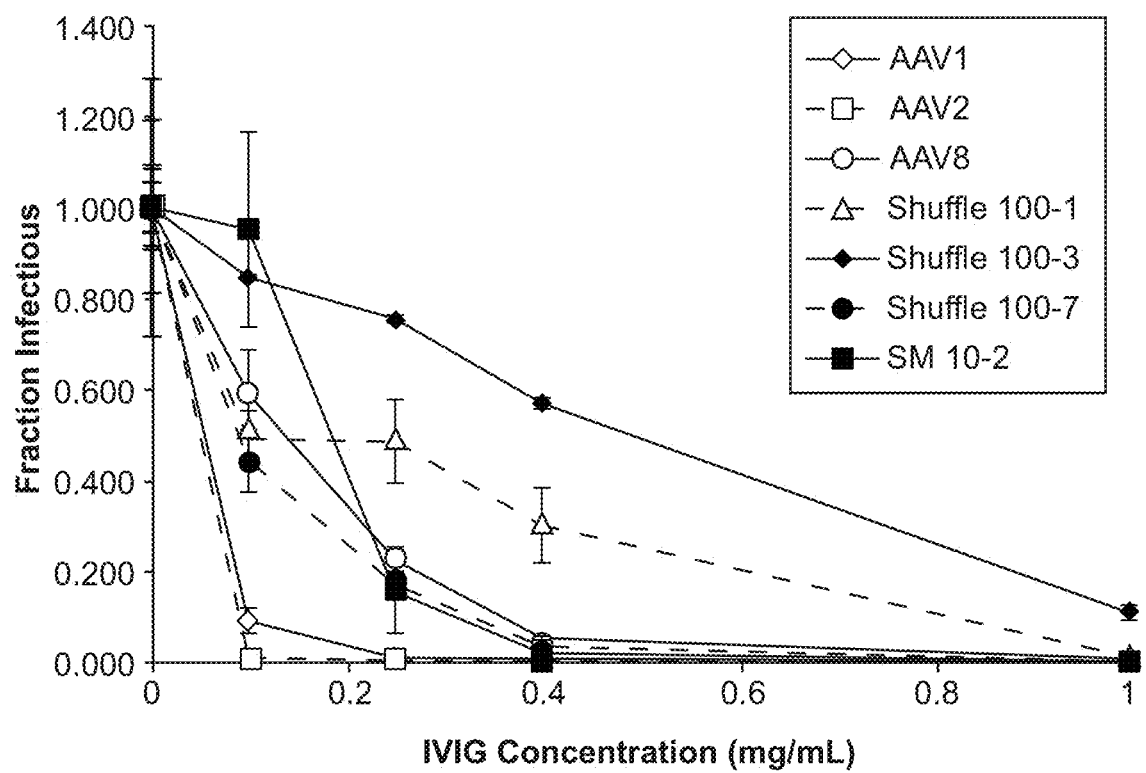
Figure 3A:
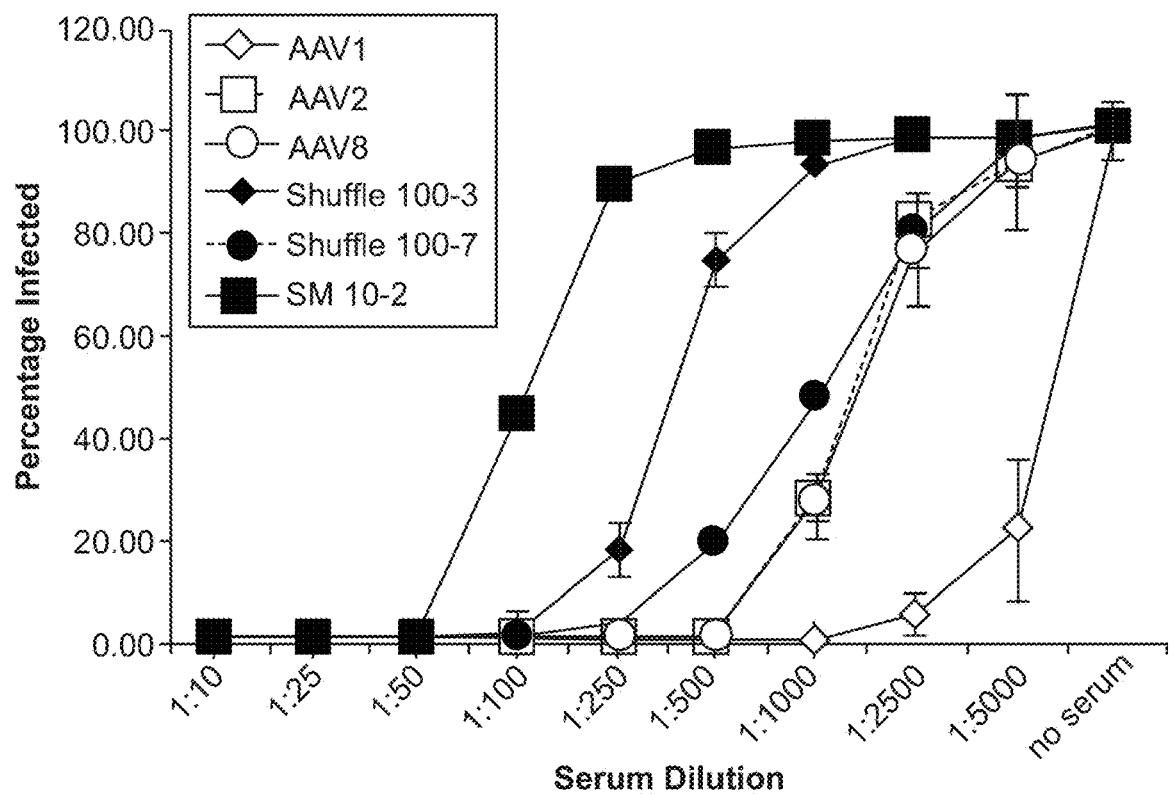
Figure 3B:
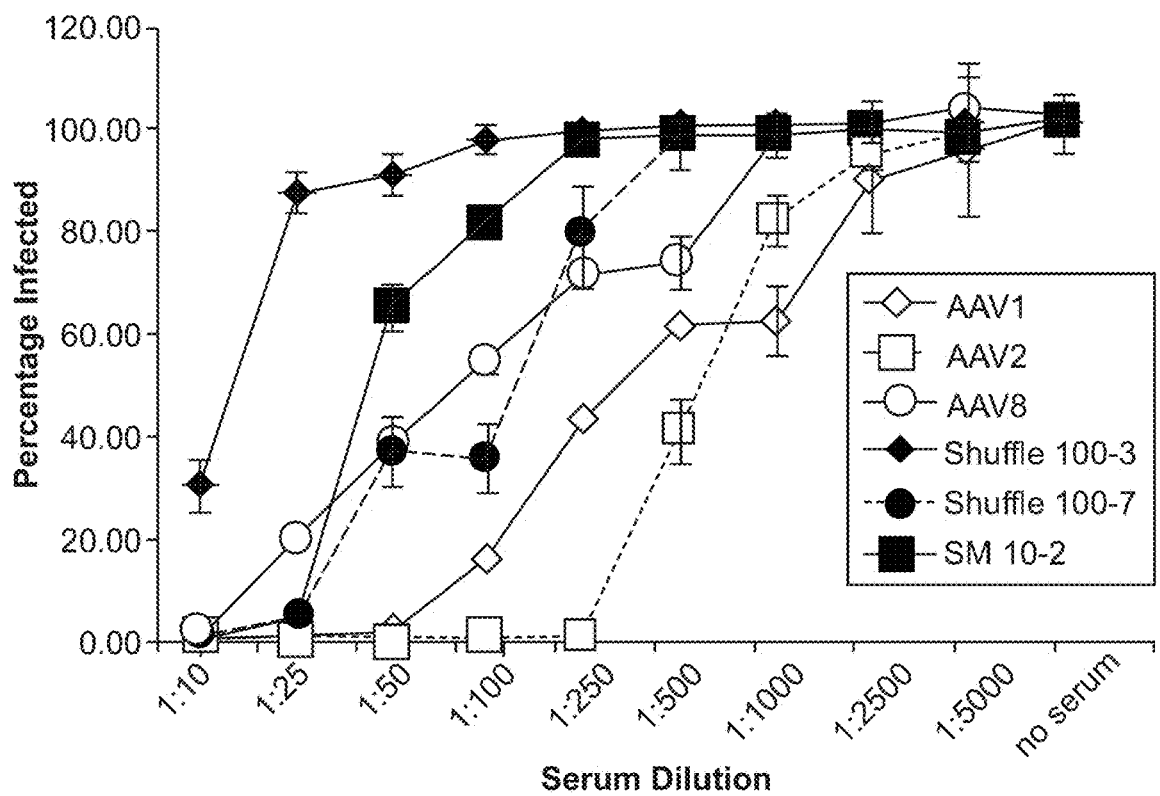
Figure 3C:
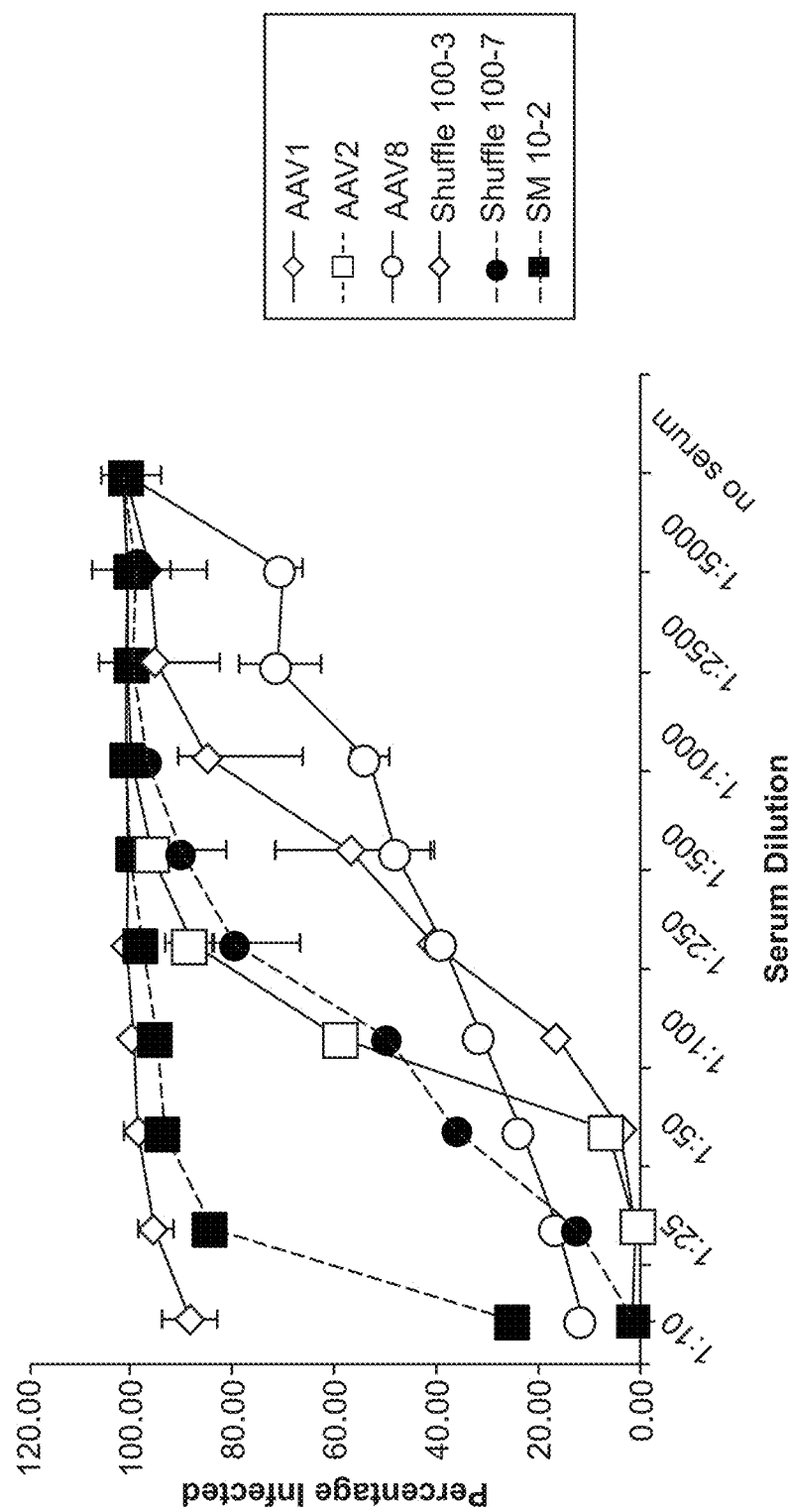

The moderate success of variant γ4.3 in resisting neutralization by anti-AAV antibodies prompted the development of a library based on the γ4.3 cap gene. Amino acid sites R471, K532, E548, N587, V708, T716, previously determined to be immunogenic sites on the AAV2 capsid, were subjected to saturation mutagenesis in an attempt to find amino acid mutations that may improve upon the antibody resistance of γ4.3. This "saturation mutagenesis" library, along with a "shuffled" library composed of random cap chimeras of 7 parent AAV serotypes and a "loop-swap" library composed of AAV2 cap with substituted loop regions were subjected to three additional rounds of selection, in which the pools of viral libraries were incubated with various dilutions of human IVIG for one hour at 37° C. prior to infection of HEK293T cells. Following infection with AAV libraries, and amplification of the infectious AAV variants through adenovirus superinfection, the number of viral genomes, or viral titer, from each library condition was quantified and compared to titers of wild-type AAV2 as a method for determining the success of the selection (FIG. 1b). For each round of selection using the saturation mutagenesis and loop-swap/shuffled libraries, viral pools from the 1:10 and 1:100 IVIG dilution conditions that produced higher viral titers than wild-type AAV2 were used as the starting point for the subsequent round of selection. After three rounds of selection, the successful viral cap genes were isolated and tested individually to determine the virus with the most efficient gene delivery. In addition, the cap genes isolated from the third round of selection were subjected to additional rounds of error-prone PCR mutagenesis, and the process was repeated to iteratively increase the fitness of the virus.

FIG. 1 depicts directed Evolution of AAV for Enhanced Antibody Evasion. (a) Schematic of Directed Evolution. 1) A viral library is created by genetically diversifying the cap gene using several complementary approaches. 2) Viruses are packaged in HEK293T cells using plasmid transfection, then harvested and purified. 3) The viral library is incubated with human IVIG at several concentrations and introduced to HEK293T cells in vitro. 4) Successful viruses are amplified and recovered via adenovirus superinfection. 5) Successful clones are enriched through repeated selections at lower MOIs. 6) Isolated viral DNA reveals successful cap genes. 7) Successful cap genes are mutated again to serve as a new starting point for selection. (b) Selection of Antibody Evading Mutants from Loop-Swap/Shuffled, and Saturation Mutagenesis libraries. HEK293T cells were infected with viral libraries for 24 hours. Viral particles that productively infected cells were amplified by adenovirus infection, and the rescued AAV was quantified by qPCR. A 1:10 dilution of IVIG corresponds to a concentration of 10 mg IVIG/mL. Error bars indicate the standard deviation (n=3).

FIG. 7 demonstrates the generation of human antibody evaders based on AAV2. (a) Four viral clones selected after three rounds of selection against the low stringency α pool demonstrate enhanced resistance to 1 µL of α serum at MOI of 1. Two additional rounds of diversification (i.e. mutagenesis and DNA shuffling) and selection (3 rounds of increasing serum amounts) resulted in significantly enhanced viral recovery in the presence of large amounts of highly potent (b) β and (c) γ pools. (d) Additionally, two viral clones (1.45 and γ4.3) demonstrate 1.23- and 3.10-fold enhanced resistances to a highly diverse pool of pre-existing antibodies present with pooled human intravenous immunoglobulin (IVIg) from ~100,000 individuals compared to wild-type AAV2.

Increased Antibody Evasion of the Novel Evolved AAV Variants In Vitro

Of the twelve clones selected and packaged for individual analysis from the saturation mutagenesis and loop-swap/shuffled libraries after nine rounds screening against human IVIG, all twelve required higher neutralizing antibody titers than both wild-type AAV1 and AAV2 (FIG. 2*a* and Table 1). Variant Shuffle 100-3 (see SEQ ID NO: 12), which required a 35-fold higher in vitro IVIG concentration for neutralization than wild-type AAV2, was still capable of transducing approximately 10% of cells in the presence of 1 mg/mL IVIG (FIG. 2*b*). In addition, variant SM 10-2 from the AAV2 saturation mutagenesis library required a 7.5-fold higher in vitro WIG concentration for neutralization than wild-type AAV2. Furthermore, variants Shuffle 100-3 and SM 10-2 (see SEQ ID NO: 10) showed enhanced transduction in the presence of sera samples from individual patients excluded from a hemophilia B clinical trial (FIG. 3) (Nathwani et al., N Engl J Med. 2011 Dec. 22; 365(25):2357-65).

FIG. 2 depicts the neutralization profiles of antibody evading variants. The cap genes of antibody evading mutants isolated after three rounds of evolution were used to package recombinant AAV encoding GFP and incubated with human IVIG before infection of HEK293T cells. The fraction of remaining infectious particles was determined using high content fluorescence imaging and normalized to the infectious titer in the absence of IVIG. Two clones from each library with resistance to IVIG are shown. Data for the other clones analyzed are displayed in Table 1. (a) Neutralization curves. Error bars indicate the standard deviation (n=3). (b) Representative fluorescence images from several IVIG dilutions show that mutants are capable of HEK293T transduction in the presence of high concentrations of neutralizing antibodies.

FIG. 3 depicts the neutralization profiles of antibody evading variants. Human sera were acquired from individuals that were excluded from hemophilia B clinical trials due to the presence of high neutralizing antibody titers against AAV. Recombinant AAV encoding GFP was incubated with individual human serum samples before infection of HEK293T cells. The fraction of remaining infectious particles was determined using fluorescence microscopy and normalized to the infectious titer in the absence of human sera. Error bars indicate the standard deviation (n=3).

Sequence analysis of the twelve clones revealed that the two variants with the highest neutralizing antibody resistance, Shuffle 100-3 (see SEQ ID NO: 12) and Shuffle 100-1 (see SEQ ID NO: 11), are almost identical shuffled capsids containing fragments of AAV1-4, AAV6, and AAV9 (FIG. 4). Differences in amino acids 469 (AAV6 residue to AAV7 residue) and 598 (AAV6 residue to AAV1 residue) between the two variants translate to almost a 3-fold increase in neutralizing antibody titer for Shuffle 100-3 (see SEQ ID NO: 12) (Table 1). Variant Shuffle 100-7 (see SEQ ID NO: 13), which had the fourth highest neutralizing antibody resistance (Table 1), is also a shuffled capsid containing fragments of AAV1, AAV6, and AAV8 (FIG. 4), which agrees well with reported data showing that wild-type AAV1 and AAV8 are effective at evading anti-AAV2 antibodies. Interestingly, variant SM 10-2 (SEE SEQ ID NO: 10) retained the point mutations acquired by variant γ4.3 and also retained wild type residues at the saturation mutagenesis sites. Variant SM 10-2 (SEE SEQ ID NO: 10) did acquire additional point mutations at surface residue D472N and internal residue L735Q. FIG. 4 depicts the amino acid sequences of loop-swap/shuffle and saturation mutagenesis clones. (a) Schematics of the capsid protein are shown for the two clones from each library with the highest neutralizing IVIG concentrations. Each region is shaded according to the parent serotype from which it is derived. Black arrows denote (from left to right) the start codons of VP1, VP2, and VP3 capsid proteins. Gray arrows denote (from left to right) surface loop regions I, II, III, IV, and V based on the AAV2 capsid. (b) Molecular models of the full AAV2 capsid, based on the solved structure, are shown for the two clones from each library with the highest neutralizing IVIG concentrations. Each region is shaded according to the parent serotype from which it is derived. For variant Shuffle 100-3 (see SEQ ID NO: 12), black arrows indicate differences from variant Shuffle 100-1 (see SEQ ID NO: 11). For variant SM 10-2 (SEE SEQ ID NO: 10), mutations N449D, D472N, N551S, and I698V are surface mutations (black).

Table 1: IVIG Neutralizing Antibody Titers of Library Clones and Parent Serotypes Human IVIG was used to neutralize recombinant AAV-GFP vectors with capsids from wild-type AAV1, AAV2, AAV8, and variants recovered from the loop-swap/shuffled and saturation mutagenesis libraries. The IVIG concentration (mg/mL) required to reduce gene delivery efficiency to 50% of that in the absence of IVIG is shown, and compared to the concentration required to reduce delivery of AAV2. All variants analyzed required higher concentrations of IVIG than wild-type AAV1 and AAV2. The neutralizing antibody titer was determined by fitting the curves in FIG. 2 to an exponential curve. SEQ ID NOs are listed as "amino acid, nucleotide."

TABLE 1

| Clone | SEQ ID NO: | Neutralizing IVIG concentration mg/ml | Fold Resistance Relative to AAV2 |
|---|---|---|---|
| AAV1 | 1 | 0.026 | 1.757 |
| AAV2 | 2 | 0.015 | 1.000 |
| AAV8 | 8 | 0.092 | 6.113 |
| Shuffle 10-2 | 26, 34 | 0.037 | 2.443 |
| Shuffle 10-6 | 27, 35 | 0.028 | 1.842 |
| Shuffle 10-8 | 28, 36 | 0.084 | 5.583 |
| Shuffle 100-1 | 11, 23 | 0.183 | 12.178 |
| Shuffle 100-2 | 29, 37 | 0.073 | 4.831 |
| Shuffle 100-3 | 12, 24 | 0.529 | 35.227 |
| Shuffle 100-7 | 13, 25 | 0.090 | 6.025 |
| SM 10-1 | 30, 38 | 0.071 | 4.732 |
| SM 10-2 | 10, 22 | 0.113 | 7.519 |
| SM 10-8 | 31, 39 | 0.051 | 3.409 |
| SM 100-3 | 32, 40 | 0.074 | 4.941 |
| SM 100-10 | 33, 41 | 0.066 | 4.393 |

Variants Shuffle 100-3 (see SEQ ID NO: 12), Shuffle 100-1 (see SEQ ID NO: 11), and Shuffle 100-7 (see SEQ ID NO: 13) have transduction profiles that mimic the transduction profiles of parent serotypes AAV1 and AAV6 (FIG. 5). In addition, the mutations in SM 10-2 (see SEQ ID NO: 10) do not prevent a heparin dependence (as seen in parent serotype AAV2) leading to a profile similar to AAV2 (FIG. 5).

Figure 5:
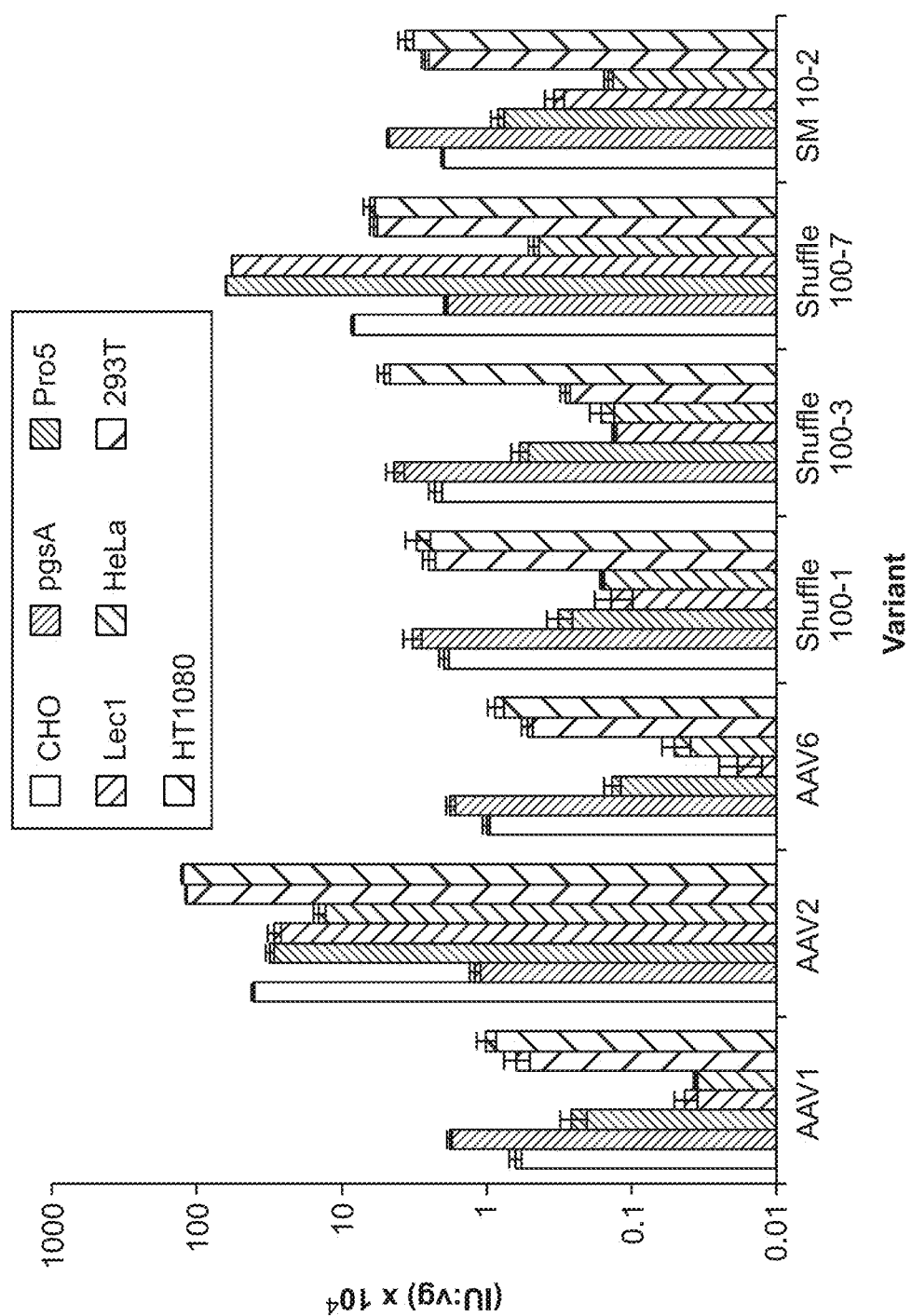

FIG. 5 demonstrates the in vitro tropism of novel aav variants. Recombinant AAV vectors expressing green fluorescent protein were used to transduce a panel of cell lines: CHO, pgsA (lacking all surface glycosaminoglycans), Pro5, Lec1 (lacking sialic acid), HEK293T, HeLa, and HT1080 (human fibrosarcoma cell line) to profile the transduction properties of the new AAV variants. Error bars indicate the standard deviation (n=3).

Increased Antibody Evasion of the Novel Evolved AAV Variants In Vivo

Figure 6A:
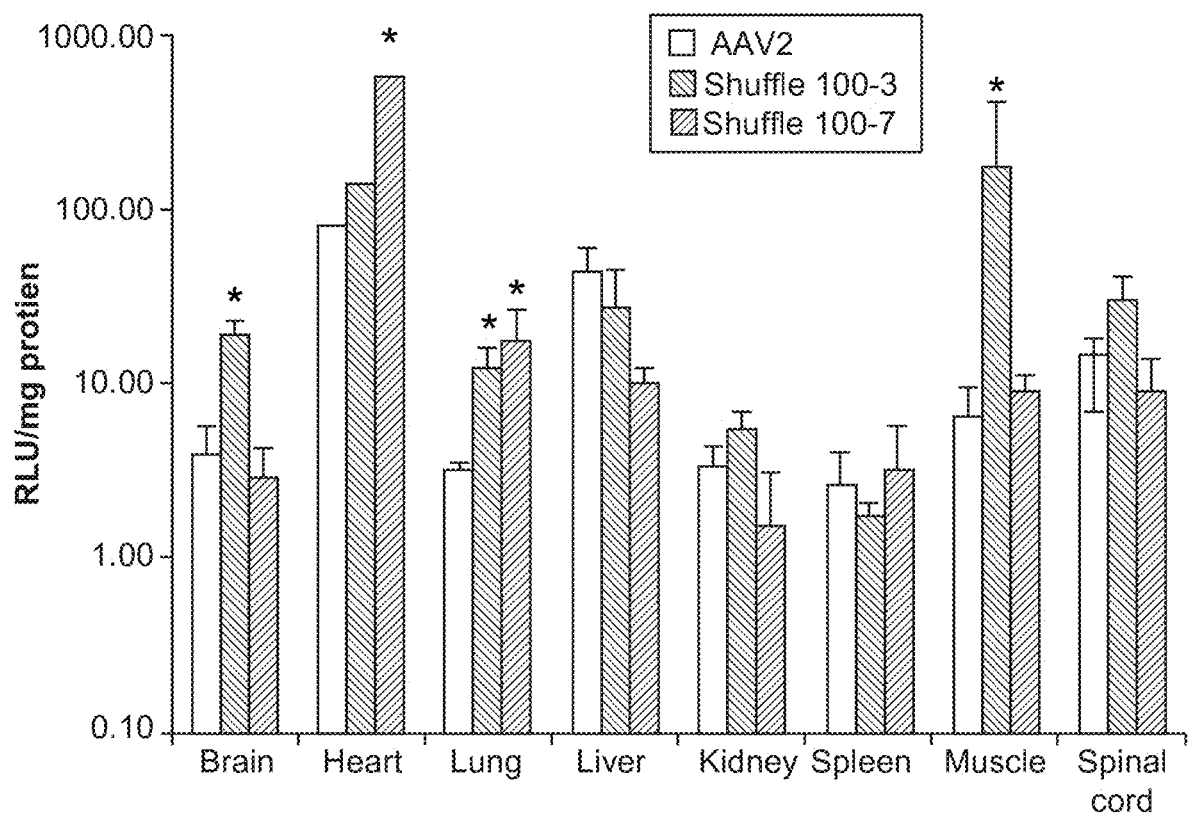

To determine the localization pattern of variants Shuffle 100-3 and Shuffle 100-7, luciferase enzyme activity was examined in various tissues of naïve mice injected with AAV2, Shuffle 100-3, or Shuffle 100-7 (FIG. 6a). Variant Shuffle 100-7 displayed similar in vivo tropism to AAV2, except for 7-fold higher transduction of the heart, 5-fold higher transduction of the lungs, and 4.5-fold lower transduction of the liver. The Shuffle 100-3 variant exhibited over 4-fold higher transduction of the brain, over 3-fold higher transduction of the lungs, and 27-fold higher transduction of muscle than AAV2. Analysis of the serum from these mice showed that variant Shuffle 100-3 required equal or higher in vitro serum concentrations for neutralization than AAV1 and AAV8 for serum from mice given AAV1, AAV2, AAV8 or Shuffle 100-3 gene delivery vectors (FIG. 11). Shuffle 100-7 required equal or higher in vitro serum concentrations for neutralization than AAV1 for serum from mice given AAV1, AAV2, AAV8, Shuffle 100-3, or SM 10-2 gene delivery vectors (FIG. 11). Furthermore, both variants were less neutralized by serum from mice given AAV2 gene delivery vectors than all wild-type AAV serotypes tested. Interestingly, variant Shuffle 100-3 was also less neutralized by serum of mice immunized against it than any of the other serotypes or variants tested (FIG. 11). This data illustrates the possibility that these variants could be used in combination with wild-type AAV serotypes or the other variant in applications requiring multiple vector administrations.

FIG. 11 shows the neutralizing antibody titers of library clones and parent serotypes in immunized mouse sera. Sera from mice administered library clones or wild-type AAV was used to neutralize recombinant AAV-GFP vectors with capsids from wild-type AAV1, AAV2, AAV8, and variants recovered from the loop-swap/shuffled and saturation mutagenesis libraries. The serum dilution required to reduce gene delivery efficiency to 50% of that in the absence of serum is shown.

Figure 6B:
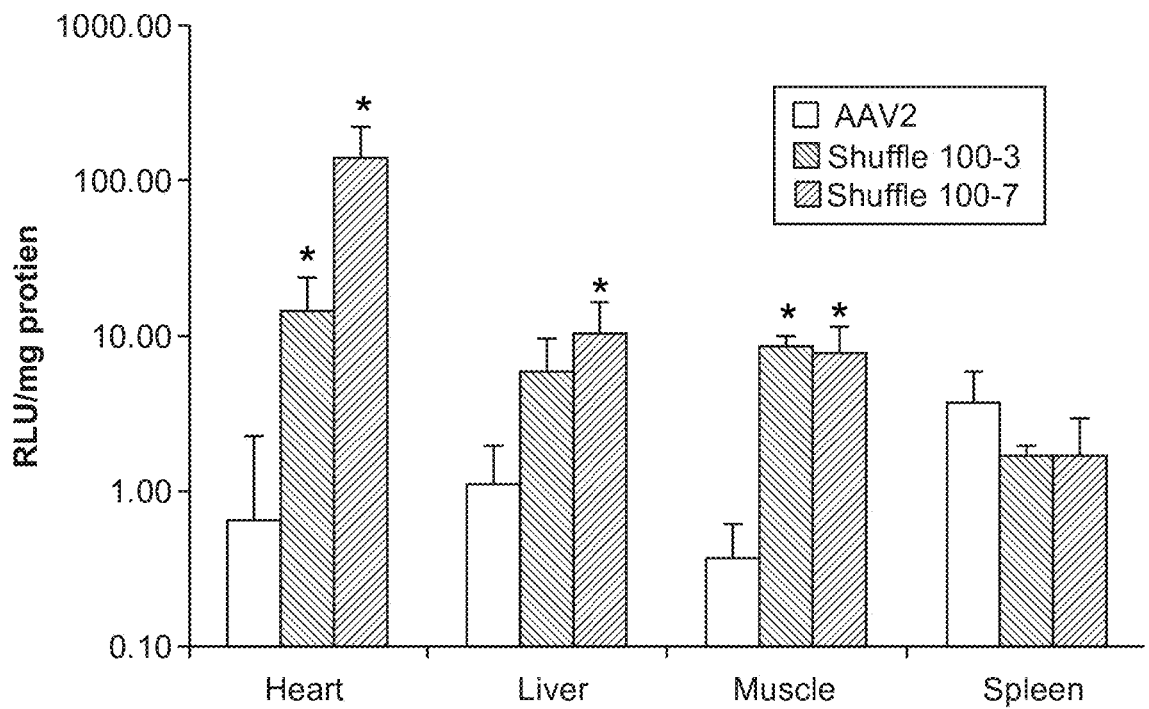

To determine the ability of variants Shuffle 100-7 and Shuffle 100-3 to evade antibody neutralization in vivo, mice were passively immunized with human IVIG prior to AAV injection. Variant Shuffle 100-7 had significantly higher heart, liver, and muscle transduction than AAV2, as measured by luciferase enzyme activity (FIG. 6b). Variant Shuffle 100-3 had significantly higher heart and muscle transduction compared to AAV2 (FIG. 6b).

FIG. 6 shows the in vivo localization and neutralization of novel AAV variants. (a) Recombinant AAV vectors encoding luciferase were administered via tail vein injection to female BALB/c mice. After 5 weeks, levels of luciferase activity were determined and normalized to total protein for each sample analyzed. (b) Recombinant AAV vectors expressing luciferase were administered via tail vein injection to female BALB/c mice 24 hours after tail vein injection of 4 mg of human IVIG. After 5 weeks, levels of luciferase expression were normalized to total protein for each sample analyzed. Error bars indicate the standard deviation (n=3), *=p<0.05. RLU, relative luciferase unit.

Figure 4A:
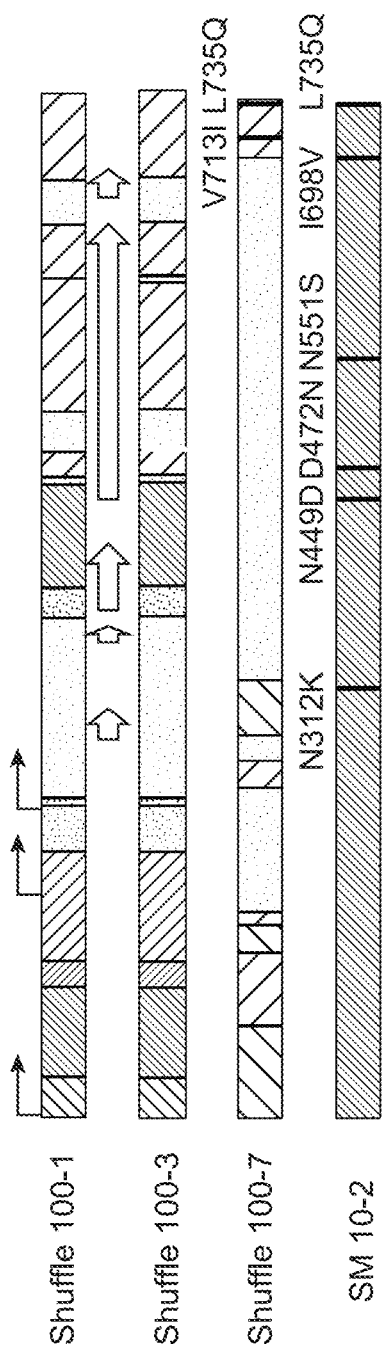
Figure 4B:
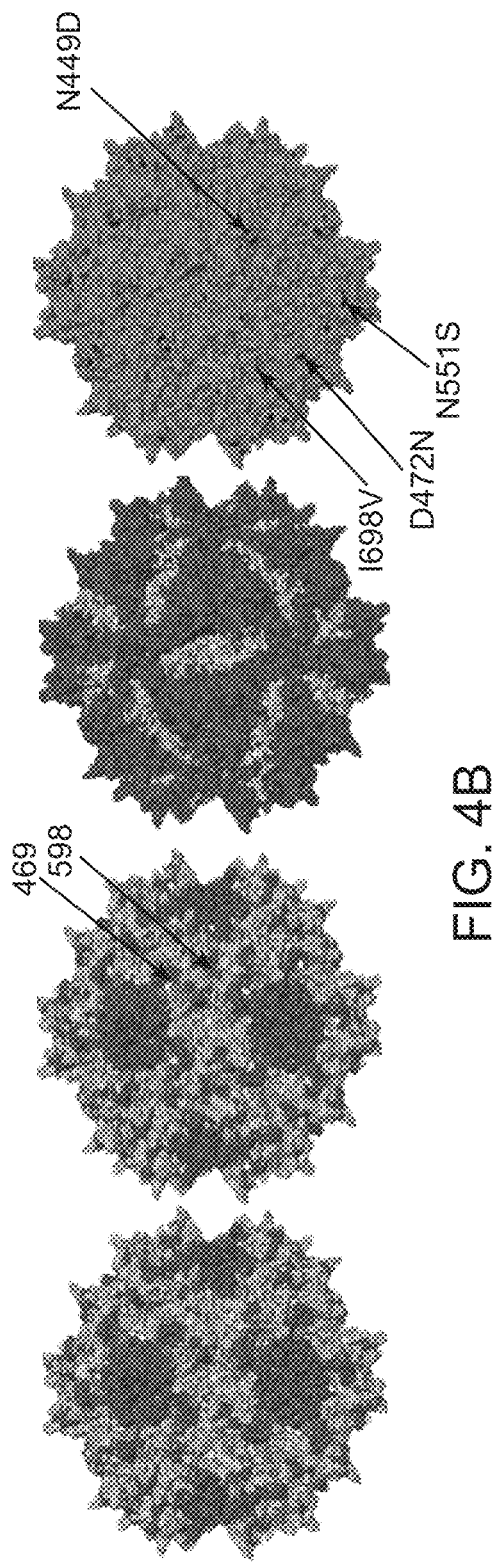

Variant γ4.3, isolated from an AAV2-based error-prone library selected against a pool of individual human sera, contained four point mutations (N312K, N449D, N551S, and I698V). Interestingly, two of these positions (N449 and N551) were previously identified as immunogenic residues using other pools of human serum, demonstrating that antigenic epitopes involving these sites are targeted by many different neutralizing antibodies. Thus, these sites are interesting and valuable targets for mutation. Pairing directed evolution and rational design in the saturation mutagenesis library resulted in the isolation of variant SM 10-2, which was capable of higher antibody resistance than both AAV1 and AAV2 in vitro. Variant SM 10-2 incorporates two additional point mutations (D472N and L735Q) to those found on variant γ4.3. The D472N mutation was previously shown to increase the level of capsid synthesis in HEK293 cells. Similarly, the replacement of the positively charged lysine side chain at amino acid position 735 with the uncharged glutamine side chain may function to stabilize the capsid, as it is also present in variant Shuffle 100-7 despite being located within the interior of the assembled capsid (FIG. 4).

The creation of chimeric AAV capsids allows for the creation of viral variants that can merge desirable properties from multiple AAV serotypes. Although AAV8 and AAV9 have also been shown to be much more resistant to neutralization by IVIG than AAV2, amino acids specific to these capsids were only present in small spans on the surface of the shuffled variants isolated during our selections (FIG. 4). The variant displaying the more efficient evasion of antibody neutralization in vitro, Shuffle 100-3, displayed similar in vitro tropism to its parental serotypes AAV1 and AAV6, but at a higher rate of infectivity than either wild-type serotype. Differences in amino acids 469 and 598 between variants Shuffle 100-1 and Shuffle 100-3 translate to almost a 3-fold increase in neutralizing antibody titer for Shuffle 100-3. A study by Lochrie et al. reported that the immunogenic residues recognized by human sera and IVIG are different, suggesting that different humans can produce various neutralizing antibodies to different sets of epitopes on the AAV capsid and complete escape from neutralization is not easy (Lochrie et al., J Virol. 2006 January; 80(2):821-34). Our work demonstrates that the use of multiple rounds of directed evolution using several different serum pools containing various amounts and potencies of anti-AAV antibodies will result in the isolation of novel AAV variants that are capable of enhanced cellular transduction, both in vitro and in vivo, in the presence of multiple anti-AAV antibody pools.

Adaptive immune responses to AAV vector components in animals and humans often prevent re-administration of AAV vectors of the same serotype, making gene delivery applications requiring multiple vector administrations difficult. In vitro neutralization assays using the serum from the mice used in the biodistribution studies demonstrate that the variants are less neutralized by these sera than wild-type AAV (FIG. 11), which may be useful for gene therapy strategies in which vector readministration is necessary. For example, Shuffle 100-3 was not neutralized by serum from mice injected with AAV2, and AAV2 was not neutralized by serum from mice injected with Shuffle 100-3, suggesting this variant can be used in combination with wild-type AAV serotypes or in applications requiring multiple vector administrations. In conclusion, we have used directed evolution to isolate novel AAV variants that are capable of reduced neutralization by anti-AAV antibodies derived from individual human patients, pooled human serum, and mouse serum, both in vitro and in vivo.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

```

What is claimed is:

1. A recombinant adeno-associated virus (rAAV) comprising:
   (a) a variant capsid protein having an amino acid sequence comprising:
      at least 95% amino acid sequence identity to amino acids 203-736 of the amino acid sequence set forth in SEQ ID NO:12, and
      a Thr at amino acid 469 and an Ala at amino acid 598 based on the amino acid numbering set forth in SEQ ID NO:12; and
   (b) a heterologous nucleic acid;
   wherein the rAAV exhibits at least 5-fold greater resistance to human neutralizing antibodies compared to the resistance to the antibodies exhibited by AAV2.

2. The rAAV of claim 1, wherein the amino acid sequence comprises at least 96% amino acid sequence identity to amino acids 203-736 of the amino acid sequence set forth in SEQ ID NO:12.

3. The rAAV of claim 1, wherein the amino acid sequence comprises at least 97% amino acid sequence identity to amino acids 203-736 of the amino acid sequence set forth in SEQ ID NO:12.

4. The rAAV of claim 1, wherein the amino acid sequence comprises at least 98% amino acid sequence identity to amino acids 203-736 of the amino acid sequence set forth in SEQ ID NO:12.

5. The rAAV of claim 1, wherein the amino acid sequence comprises at least 99% amino acid sequence identity to amino acids 203-736 of the amino acid sequence set forth in SEQ ID NO:12.

6. The rAAV of claim 1, wherein the rAAV exhibits at least 10-fold greater resistance to human neutralizing antibodies than the resistance exhibited by AAV2.

7. The rAAV of claim 1, wherein the rAAV exhibits at least 15-fold greater resistance to human neutralizing antibodies than the resistance exhibited by AAV2.

8. The rAAV of claim 1, wherein the rAAV exhibits at least 20-fold greater resistance to human neutralizing antibodies than the resistance exhibited by AAV2.

9. The rAAV of claim 1, wherein the rAAV exhibits at least 25-fold greater resistance to human neutralizing antibodies than the resistance exhibited by AAV2.

10. The rAAV of claim 1, wherein the rAAV exhibits at least 30-fold greater resistance to human neutralizing antibodies than the resistance exhibited by AAV2.

11. The rAAV of claim 1, wherein the rAAV exhibits at least 35-fold greater resistance to human neutralizing antibodies than the resistance exhibited by AAV2.

12. The rAAV of claim 1, wherein the rAAV exhibits increased transduction of mammalian cells in the presence of human neutralizing antibodies compared to the transduction of mammalian cells exhibited by wild type AAV serotype 2 (AAV2).

13. The rAAV of claim 12, wherein the mammalian cells are liver cells, pancreatic cells, skeletal muscle cells, heart muscle cells, fibroblasts, retinal cells, synovial joint cells, lung cells, T cells, neurons, glial cells, stem cells, endothelial cells, or cancer cells.

14. The rAAV of claim 13, wherein the stem cells are hematopoietic stem cells, hematopoietic progenitor cells, neural stem cells, neural progenitor cells, neural crest stem cells, embryonic stem cells, induced pluripotent stem cells (iPS cells), mesenchymal stem cells, mesodermal stem cells, liver stem cells, pancreatic stem cells, pancreatic progenitor cells, muscle stem cells, or retinal stem cells.

15. The rAAV of claim 1, wherein the heterologous nucleic acid comprises an interfering RNA.

16. The rAAV of claim 1, wherein the heterologous nucleic acid comprises a nucleotide sequence encoding a polypeptide.

17. A pharmaceutical composition comprising:
   a) the rAAV virion according to claim 1; and
   b) a pharmaceutically acceptable excipient.

18. The pharmaceutical composition of claim 17, comprising from $10^6$ to $10^{15}$ rAAV virions.

19. An isolated nucleic acid comprising a nucleotide sequence that encodes the variant adeno-associated virus (AAV) capsid protein according to claim 1.

20. An isolated host cell comprising the nucleic acid of claim 19.

* * * * *